United States Patent
Chang et al.

(10) Patent No.: US 7,981,904 B2
(45) Date of Patent: Jul. 19, 2011

(54) ACETYL COA CARBOXYLASE INHIBITORS

(75) Inventors: Edcon Chang, San Diego, CA (US);
Tracy Duong, San Diego, CA (US);
Angie Vassar, San Diego, CA (US)

(73) Assignee: Takeda Pharmaceutical Company Limited, Osaka (JP)

( * ) Notice: Subject to any disclaimer, the term of this patent is extended or adjusted under 35 U.S.C. 154(b) by 253 days.

(21) Appl. No.: 12/407,694

(22) Filed: Mar. 19, 2009

(65) Prior Publication Data
US 2009/0253725 A1      Oct. 8, 2009

Related U.S. Application Data

(60) Provisional application No. 61/038,388, filed on Mar. 20, 2008.

(51) Int. Cl.
*A61K 31/438* (2006.01)
*C07D 471/10* (2006.01)
(52) U.S. Cl. .......................... 514/278; 546/20
(58) Field of Classification Search ............... 514/278; 546/20
See application file for complete search history.

(56) References Cited

U.S. PATENT DOCUMENTS

| | | |
|---|---|---|
| 2002/0006932 A1 | 1/2002 | Galley et al. |
| 2005/0107373 A1 | 5/2005 | Ceccarelli et al. |
| 2006/0167247 A1 | 7/2006 | Michelotti et al. |
| 2006/0178400 A1 | 8/2006 | Beutel et al. |
| 2010/0113418 A1 * | 5/2010 | Fukatsu et al. ........... 514/212.02 |

FOREIGN PATENT DOCUMENTS

WO          W003/072197 A1      9/2003

* cited by examiner

*Primary Examiner* — D Seaman
*Assistant Examiner* — Niloofar Rahmani
(74) *Attorney, Agent, or Firm* — Mitchell R. Brustein

(57) ABSTRACT

The present invention relates to acetyl coenzyme-A carboxylase ("ACC") inhibiting compounds of the formula

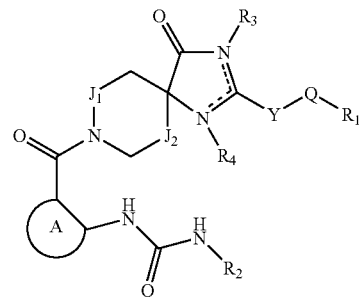

wherein the variables are as defined herein. In particular, the present invention relates to ACC1 and/or ACC2 inhibitors, compositions of matter, kits and articles of manufacture comprising these compounds, methods for inhibiting ACC1 and/or ACC2, and methods of making the inhibitors.

37 Claims, 1 Drawing Sheet

FIGURE 1

DNA Sequence Encoding First PCR Primer [SEQ ID NO: 1]

aaaagtcgac ccaccatgga tgaaccttct cccttggccc

DNA Sequence Encoding Second PCR Primer [SEQ ID NO: 2]

aaaagcggcc gcctacgtag aaggggagtc catagtg

DNA Sequence Encoding Third PCR Primer [SEQ ID NO: 3]

ccaggtcgac ccgccaacgg gactgggaca caagg

DNA Sequence Encoding Fourth PCR Primer [SEQ ID NO: 4]

cgcactctca gtttcccgga ttccc

ACETYL COA CARBOXYLASE INHIBITORS

RELATED APPLICATION

This application claims the benefit of U.S. Provisional Application No. 61/038,388, filed Mar. 20, 2008, which incorporated herein by reference.

FIELD OF THE INVENTION

The present invention relates to compounds that may be used to inhibit acetyl coenzyme-A carboxylase ("ACC"), as well as compositions of matter, kits and articles of manufacture comprising these compounds. The invention also relates to methods for inhibiting ACC and methods of using compounds according to the present invention to treat, for example, metabolic syndrome, diabetes, obesity, atherosclerosis, and cardiovascular disease in mammals, including humans. In addition, the invention relates to methods of making the compounds of the present invention, as well as intermediates useful in such methods. In particular, the present invention relates to ACC1 and/or ACC2 inhibitors, compositions of matter, kits and articles of manufacture comprising these compounds, methods for inhibiting ACC1 and/or ACC2, and methods of making the inhibitors.

BACKGROUND OF THE INVENTION

Acetyl coenzyme-A carboxylases (ACC) catalyze the rate limiting reaction in fatty acid biosynthesis in plants and animals. ACC is a biotin containing enzyme which catalyzes the carboxylation of acetyl CoA to form malonyl CoA in a two-step reaction. Beaty and Lane, *J. Biol. Chem.* 1982, 257:924 929. The first step is the ATP-dependent carboxylation of biotin covalently linked to the enzyme. In the second step, a carboxyltransferase step, the carboxyl group is transferred to the substrate, acetyl CoA, to form malonyl CoA.

Malonyl-CoA is an intermediate substrate that plays an important role in the overall fatty acid metabolism: malonyl-CoA is utilized (as C2 donor) by fatty acid synthase for de novo synthesis of long chain fatty acids, and also acts as a potent allosteric inhibitor of carnitine palmitoyltransferase 1 (CPT1), a mitochondrial membrane protein that shuttles long chain fatty acyl CoAs into the mitochondria where they are oxidized. Ruderman N. and Prentki M, *Nat Rev Drug Discov.* 2004; 3:340-51. An inhibitor of ACC would thus limit de novo lipid synthesis, de-inhibit CPT1 and subsequently increase fat oxidation.

In mammals, there are two known isoforms of acetyl CoA carboxylase (ACC) that are encoded by distinct genes and share approximately 70% amino acids identity. ACC1 (ACCα), a 265 KD protein, is highly expressed in the cytosol of lipogenic tissues such as liver and adipose tissue, where fatty acids are synthesized. ACC2 (ACCβ), a 280 KD protein, is expressed mainly in oxidative, non-lipogenic, tissues, such as skeletal muscle and heart muscle, although some is also found in liver. Mao J. et al., *Proc Natl Acad Sci USA*, 2003, 100:7515-20; Abu-Elheiga L. et al., *J Biol Chem* 1997; 272: 10669-77. Malonyl CoA produced by ACC1 is preferentially converted into fatty acids by fatty acid synthase. Abu-Elheiga L. et al., *Proc Natl Acad Sci USA* 2000; 97:1444-9.

The malonyl CoA postulated to be formed by ACC2 locally on the mitochondrial surface regulates the palmitoyl CoA shuttle system. Abu-Elheiga L. et al., *Proc Natl Acad Sci USA* 2000; 97:1444-9. Malonyl CoA is a potent inhibitor of carnitine palmitoyl transferase 1 (CPT-1), and as a consequence, it decreases the fatty acid flux into the mitochondria. Thus, reduction of ACC2 activity would reduce local malonyl CoA levels and increase fatty acid β-oxidation concomitantly reducing triacylglycerol (TAG) synthesis. Munday, *Biochem Soc Trans.* 2001 30:1059-64; Yamauchi T. et al. *Nat Med* 2001; 7:941-6.

ACC is a potential target in metabolic diseases, such as metabolic syndrome, obesity, insulin resistance, dyslipidemia, diabetes, atherosclerosis, and cardiovascular diseases, which are mediated by abnormal fatty acid metabolism. An inhibitor of ACC would potentially limit de novo lipid synthesis, de-inhibit CPT1 and subsequently increase fat oxidation. Increased rates of muscle fatty acid oxidation, a reduced fat content and a reduction in total body fat were observed in ACC-2 knock-out mice (Abu-Elheiga et al., *Science* 2001, 291:2613 2616; Abu-Elheiga et al., *Proc. Natl. Acad. Sci. USA,* 2003 100:10207 10212). Harwood et al. reported that ACC inhibitors caused reduction in fatty acid synthesis, increase in fatty acid oxidation, and reduction of respiratory quotient in rats. Harwood et al., *J. Biol. Chem.* 2003, 278: 37099 37111. Chronic dosing of these compounds resulted in the reduction of whole body fat mass and improvement of insulin sensitivity. Harwood et al., *J. Biol. Chem.* 2003, 278: 37099 37111. These observations further validated the enzyme as a drug target.

Several non-natural product small molecule have been identified which target ACC for the prophylaxis or treatment of metabolic syndrome, atherosclerosis, diabetes, and obesity, see, U.S. Pat. No. 6,979,741, US Applications No. 2007/0219258, No. 2007/0219251, and No. 2003/0187254. There is a continuing need and a continuing search in this field of art for more potent therapeutic agents.

SUMMARY OF THE INVENTION

The present invention relates to compounds that inhibit ACC. The present invention also provides compositions, articles of manufacture and kits comprising these compounds. The invention further provides methods of using, and methods of preparing the compounds of the invention.

In one aspect, the invention relates to compounds of the formula:

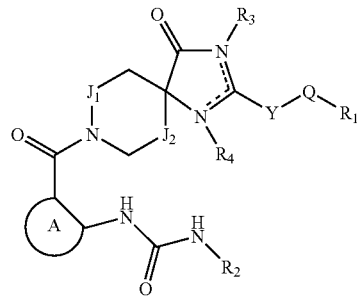

or a hydrate, solvate, ester, tautomer, enantiomer, or pharmaceutically acceptable salt thereof;

wherein $J_1$ and $J_2$ are each independently selected from the group consisting of —(CH$_2$)— and —(CH$_2$)$_2$—, provided that $J_1$ and $J_2$ cannot both be —(CH$_2$)$_2$—;

Y is selected from the group consisting of a bond, —CH$_2$—, —(CH$_2$)$_2$—, —NH—CH$_2$—, and —CH$_2$—NH—;

Q is selected from the group consisting of a bond, —C(O)—, —C(O)O—, —NH—, —O—, —S—, —S(O)—, -and S(O)$_2$—;

A is selected from the group consisting of five or six membered, substituted or unsubstituted aryl and heteroaryl, where the substituents on adjacent ring atoms of the aryl or heteroaryl may be taken together to form five or six membered, substituted or unsubstituted, saturated, unsaturated or aromatic ring;

$R_1$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, $(C_{3-12})$cycloalkyloxy, hetero$(C_{3-12})$cycloalkyloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-2})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted;

$R_2$ is substituted or unsubstituted alkyl;

$R_3$ and $R_4$ are each independently selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-2})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, and provided that one of $R_3$ and $R_4$ is absent, and where $R_3$ is absent, the nitrogen on which $R_3$ is drawn is part of a double bond, and where $R_4$ is absent, the nitrogen on which $R_4$ is drawn is part of a double bond.

In another aspect, the invention relates to pharmaceutical compositions that comprise an ACC inhibitor according to the present invention as an active ingredient. In one embodiment, the ACC inhibitor is a member selected from an ACC1 inhibitor and an ACC2 inhibitor. Pharmaceutical compositions according to the invention may optionally comprise 0.001%-100% of one or more inhibitors of this invention. These pharmaceutical compositions may be administered or coadministered by a wide variety of routes, including for example, orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, or intrathecally. The compositions may also be administered or coadministered in slow release dosage forms.

In another aspect, the invention is related to kits and other articles of manufacture for treating disease states associated with ACC.

In one embodiment, a kit is provided that comprises a composition comprising at least one ACC inhibitor of the present invention in combination with instructions. In one embodiment, the ACC inhibitor is a member selected from an ACC1 inhibitor and an ACC2 inhibitor. The instructions may indicate the disease state for which the composition is to be administered, storage information, dosing information and/or instructions regarding how to administer the composition. The kit may also comprise packaging materials. The packaging material may comprise a container for housing the composition. The kit may also optionally comprise additional components, such as syringes for administration of the composition. The kit may comprise the composition in single or multiple dose forms.

In another embodiment, an article of manufacture is provided that comprises a composition comprising at least one ACC inhibitor of the present invention in combination with packaging materials. In one embodiment, the ACC inhibitor is a member selected from an ACC1 inhibitor and an ACC2 inhibitor. The packaging material may comprise a container for housing the composition. The container may optionally comprise a label indicating the disease state for which the composition is to be administered, storage information, dosing information and/or instructions regarding how to administer the composition. The kit may also optionally comprise additional components, such as syringes for administration of the composition. The kit may comprise the composition in single or multiple dose forms.

Also provided are methods for preparing compounds, compositions and kits according to the present invention. For example, several synthetic schemes are provided herein for synthesizing compounds according to the present invention.

Also provided are methods for using compounds, compositions, kits and articles of manufacture according to the present invention.

In one embodiment, the compounds, compositions, kits and articles of manufacture are used to inhibit ACC. In one embodiment, ACC is a member selected from ACC1 and ACC2.

In another embodiment, the compounds, compositions, kits and articles of manufacture are used to treat a disease state for which ACC possesses activity that contributes to the pathology and/or symptomology of the disease state. In one embodiment, the disease is treated by inhibiting ACC1. In another embodiment, the disease is treated by inhibiting ACC2.

In another embodiment, a compound is administered to a subject wherein ACC activity within the subject is altered, preferably reduced. In one embodiment, the administered compound alters and preferably reduces the activity of ACC1 in a subject. In another embodiment, the administered compound alters and preferably reduces the activity of ACC2 in a subject.

In another embodiment, a prodrug of a compound is administered to a subject that is converted to the compound in vivo where it inhibits ACC. In one embodiment, the prodrug inhibits ACC1. In another embodiment, the prodrug inhibits ACC2.

In another embodiment, a method of inhibiting ACC is provided that comprises contacting an ACC with a compound according to the present invention. In one embodiment, the invention provides a method of inhibiting ACC1 that comprises contacting ACC1 with a compound according to the present invention. In another embodiment, the invention provides a method of inhibiting ACC2 that comprises contacting ACC2 with a compound according to the present invention.

In another embodiment, a method of inhibiting ACC is provided that comprises causing a compound according to the present invention to be present in a subject in order to inhibit ACC in vivo. In one embodiment, the invention provides a method of inhibiting ACC1 that comprises causing a compound according to the present invention to be present in a subject in order to inhibit ACC1 in vivo. In another embodiment, the invention provides a method of inhibiting ACC2 that comprises causing a compound according to the present invention to be present in a subject in order to inhibit ACC2 in vivo.

It is further noted that prodrugs may also be administered which are altered in vivo and become a compound according to the present invention. The various methods of using the compounds of the present invention are intended, regardless of whether prodrug delivery is specified, to encompass the administration of a prodrug that is converted in vivo to a compound according to the present invention. It is also noted that certain compounds of the present invention may be altered in vivo prior to inhibit ACC and thus may themselves be prodrugs for another compound. Such prodrugs of another compound may or may not themselves individually have ACC inhibitory activity.

BRIEF DESCRIPTION OF THE FIGURES

FIG. 1 illustrates SEQ ID NO: 1, SEQ ID NO: 2, SEQ ID NO: 3, and SEQ ID NO: 4, referred to in this application.

DEFINITIONS

Unless otherwise stated, the following terms used in the specification and claims shall have the following meanings for the purposes of this application.

It is noted that, as used in the specification and the appended claims, the singular forms "a," "an" and "the" include plural referents unless the context clearly dictates otherwise. Further, definitions of standard chemistry terms may be found in reference works, including Carey and Sundberg "ADVANCED ORGANIC CHEMISTRY $5^{th}$ ED." Vols. A (2007) and B (2007), Springer Science and Business Media, New York. Also, unless otherwise indicated, conventional methods of mass spectroscopy, NMR, HPLC, protein chemistry, biochemistry, recombinant DNA techniques and pharmacology, within the skill of the art are employed.

"Alicyclic" means a moiety comprising a non-aromatic ring structure. Alicyclic moieties may be saturated or partially unsaturated with one, two or more double or triple bonds. Alicyclic moieties may also optionally comprise heteroatoms such as nitrogen, oxygen and sulfur. The nitrogen atoms can be optionally quaternerized or oxidized and the sulfur atoms can be optionally oxidized. Examples of alicyclic moieties include, but are not limited to moieties with ($C_{3-8}$) rings such as cyclopropyl, cyclohexane, cyclopentane, cyclopentene, cyclopentadiene, cyclohexane, cyclohexene, cyclohexadiene, cycloheptane, cycloheptene, cycloheptadiene, cyclooctane, cyclooctene, and cyclooctadiene.

"Aliphatic" means a moiety characterized by a straight or branched chain arrangement of constituent carbon atoms and may be saturated or partially unsaturated with one, two or more double or triple bonds.

"Alkenyl" means a straight or branched, carbon chain that contains at least one carbon-carbon double bond (—CR=CR'— or —CR=CR'R", wherein R, R' and R" are each independently hydrogen or further substituents). Examples of alkenyl include vinyl, allyl, isopropenyl, pentenyl, hexenyl, heptenyl, 1-propenyl, 2-butenyl, 2-methyl-2-butenyl, and the like. In particular embodiments, "alkenyl," either alone or represented along with another radical, can be a ($C_{2-20}$)alkenyl, a ($C_{2-15}$)alkenyl, a ($C_{2-10}$)alkenyl, a ($C_{2-5}$)alkenyl or a ($C_{2-3}$)alkenyl. Alternatively, "alkenyl," either alone or represented along with another radical, can be a ($C_2$)alkenyl, a ($C_3$)alkenyl or a ($C_4$)alkenyl.

"Alkenylene" means a straight or branched, divalent carbon chain having one or more carbon-carbon double bonds (—CR=CR'—, wherein R and R' are each independently hydrogen or further substituents). Examples of alkenylene include ethene-1,2-diyl, propene-1,3-diyl, methylene-1,1-diyl, and the like. In particular embodiments, "alkenylene," either alone or represented along with another radical, can be a ($C_{2-20}$) alkenylene, a ($C_{2-15}$) alkenylene, a ($C_{2-10}$) alkenylene, a ($C_{2-5}$) alkenylene or a ($C_{2-3}$) alkenylene. Alternatively, "alkenylene," either alone or represented along with another radical, can be a ($C_2$) alkenylene, a ($C_3$) alkenylene or a ($C_4$) alkenylene.

"Alkoxy" means an oxygen moiety having a further alkyl substituent. The alkoxy groups of the present invention can be optionally substituted.

"Alkyl" represented by itself means a straight or branched, saturated or unsaturated, aliphatic radical having a chain of carbon atoms, optionally with one or more of the carbon atoms being replaced with oxygen (See "oxaalkyl"), a carbonyl group (See "oxoalkyl"), sulfur (See "thioalkyl"), and/or nitrogen (See "azaalkyl"). ($C_X$)alkyl and ($C_{X-Y}$)alkyl are typically used where X and Y indicate the number of carbon atoms in the chain. For example, ($C_{1-6}$)alkyl includes alkyls that have a chain of between 1 and 6 carbons (e.g., methyl, ethyl, propyl, isopropyl, butyl, sec-butyl, isobutyl, tert-butyl, vinyl, allyl, 1-propenyl, isopropenyl, 1-butenyl, 2-butenyl, 3-butenyl, 2-methylallyl, ethynyl, 1-propynyl, 2-propynyl, and the like). Alkyl represented along with another radical (e.g., as in arylalkyl, heteroarylalkyl and the like) means a straight or branched, saturated or unsaturated aliphatic divalent radical having the number of atoms indicated or when no atoms are indicated means a bond (e.g., ($C_{6-10}$)aryl($C_{1-3}$)alkyl includes, benzyl, phenethyl, 1-phenylethyl, 3-phenylpropyl, 2-thienylmethyl, 2-pyridinylmethyl and the like). In particular embodiments, "alkyl," either alone or represented along with another radical, can be a ($C_{1-20}$)alkyl, a ($C_{1-15}$)alkyl, a ($C_{1-10}$)alkyl, a ($C_{1-5}$)alkyl or a ($C_{1-3}$)alkyl. Alternatively, "alkyl," either alone or represented along with another radical, can be a ($C_1$)alkyl, a ($C_2$)alkyl or a ($C_3$)alkyl.

"Alkylene", unless indicated otherwise, means a straight or branched, saturated or unsaturated, aliphatic, divalent radical. ($C_X$)alkylene and ($C_{X-Y}$)alkylene are typically used where X and Y indicate the number of carbon atoms in the chain. For example, ($C_{1-6}$)alkylene includes methylene (—CH$_2$—), ethylene (—CH$_2$CH$_2$—), trimethylene (—CH$_2$CH$_2$CH$_2$—), tetramethylene (—CH$_2$CH$_2$CH$_2$CH$_2$—), 2-butenylene (—CH$_2$CH=CHCH$_2$—), 2-methyltetramethylene (—CH$_2$CH(CH$_3$)CH$_2$CH$_2$—), pentamethylene (—CH$_2$CH$_2$CH$_2$CH$_2$CH$_2$—), and the like. In particular embodiments, "alkylene," either alone or represented along with another radical, can be a ($C_{1-20}$)alkylene, a ($C_{1-15}$)alkylene, a ($C_{1-10}$)alkylene, a ($C_{1-5}$)alkylene or a ($C_{1-3}$)alkylene. Alternatively, "alkylene," either alone or represented along with another radical, can be a ($C_1$)alkylene, a ($C_2$)alkylene or a ($C_3$)alkylene.

"Alkylidene" means a straight or branched, saturated or unsaturated, aliphatic radical connected to the parent molecule by a double bond. ($C_X$)alkylidene and ($C_{X-Y}$)alkylidene are typically used where X and Y indicate the number of carbon atoms in the chain. For example, ($C_{1-6}$)alkylidene includes methylene (=CH$_2$), ethylidene (=CHCH$_3$), isopropylidene (=C(CH$_3$)$_2$), propylidene (=CHCH$_2$CH$_3$), allylidene (=CH—CH=CH$_2$), and the like. In particular embodiments, "alkylidene," either alone or represented along with another radical, can be a ($C_{1-20}$)alkylidene, a ($C_{1-15}$)alkylidene, a ($C_{1-10}$)alkylidene, a ($C_{1-5}$)alkylidene or a ($C_{1-3}$)alkylidene. Alternatively, "alkylidene," either alone or represented along with another radical, can be a $(C_1)$alkylidene, a $(C_2)$alkylidene or a $(C_3)$alkylidene.

"Alkynyl" means a straight or branched, carbon chain that contains at least one carbon-carbon triple bond (—C≡C— or —C≡CR, wherein R is hydrogen or a further substituent). Examples of alkynyl include ethynyl, propargyl, 3-methyl-1-pentynyl, 2-heptynyl and the like. In particular embodiments, "alkynyl," either alone or represented along with another radical, can be a $(C_{2-20})$alkynyl, a $(C_{2-15})$alkynyl, a $(C_{2-10})$alkynyl, a $(C_{2-5})$alkynyl or a $(C_{2-3})$alkynyl. Alternatively, "alkynyl," either alone or represented along with another radical, can be a $(C_2)$alkynyl, a $(C_3)$alkynyl or a $(C_4)$alkynyl.

"Alkynylene" means a straight or branched, divalent carbon chain having one or more carbon-carbon triple bonds (—CR≡CR'—, wherein R and R' are each independently hydrogen or further substituents). Examples of alkynylene include ethyne-1,2-diyl, propyne-1,3-diyl, and the like. In particular embodiments, "alkynylene," either alone or represented along with another radical, can be a $(C_{2-20})$ alkynylene, a $(C_{2-15})$ alkynylene, a $(C_{2-10})$ alkynylene, a $(C_{2-5})$ alkynylene or a $(C_{2-3})$ alkynylene. Alternatively, "alkynylene," either alone or represented along with another radical, can be a $(C_2)$ alkynylene, a $(C_3)$ alkynylene or a $(C_4)$ alkynylene.

"Amido" means the radical —C(═O)—NR—, —C(═O)—NRR', —NR—C(═O)— and/or —NR—C(═O)R', wherein each R and R' are independently hydrogen or a further substituent.

"Amino" means a nitrogen moiety having two further substituents where, for example, a hydrogen or carbon atom is attached to the nitrogen. For example, representative amino groups include —NH$_2$, —NHCH$_3$, —N(CH$_3$)$_2$, —NH(($C_{1-10}$)alkyl), —N(($C_{1-10}$)alkyl)$_2$, —NH(aryl), —NH(heteroaryl), —N(aryl)$_2$, —N(heteroaryl)$_2$, and the like. Optionally, the two substituents together with the nitrogen may also form a ring. Unless indicated otherwise, the compounds of the invention containing amino moieties may include protected derivatives thereof. Suitable protecting groups for amino moieties include acetyl, tert-butoxycarbonyl, benzyloxycarbonyl, and the like.

"Animal" includes humans, non-human mammals (e.g., dogs, cats, rabbits, cattle, horses, sheep, goats, swine, deer, and the like) and non-mammals (e.g., birds, and the like).

"Aromatic" means a moiety wherein the constituent atoms make up an unsaturated ring system, all atoms in the ring system are sp$^2$ hybridized and the total number of pi electrons is equal to 4n+2. An aromatic ring may be such that the ring atoms are only carbon atoms or may include carbon and non-carbon atoms (See "heteroaryl").

"Aryl" means a monocyclic or polycyclic ring assembly wherein each ring is aromatic or when fused with one or more rings forms an aromatic ring assembly. If one or more ring atoms is not carbon (e.g., N, S), the aryl is a heteroaryl. $(C_X)$aryl and $(C_{X-Y})$aryl are typically used where X and Y indicate the number of carbon atoms in the ring. In particular embodiments, "aryl," either alone or represented along with another radical, can be a $(C_{3-14})$aryl, a $(C_{3-10})$aryl, a $(C_{3-7})$aryl, a $(C_{8-10})$aryl or a $(C_{5-7})$aryl. Alternatively, "aryl," either alone or represented along with another radical, can be a $(C_5)$aryl, a $(C_6)$aryl, a $(C_7)$aryl, a $(C_8)$aryl, a $(C_9)$aryl or a $(C_{10})$aryl.

"Azaalkyl" means an alkyl, as defined above, except where one or more of the carbon atoms forming the alkyl chain are replaced with substituted or unsubstituted nitrogen atoms (—NR— or —NRR', wherein R and R' are each independently hydrogen or further substituents). For example, a $(C_{1-10})$azaalkyl refers to a chain comprising between 1 and 10 carbons and one or more nitrogen atoms.

"Bicycloalkyl" means a saturated or partially unsaturated fused, spiro or bridged bicyclic ring assembly. In particular embodiments, "bicycloalkyl," either alone or represented along with another radical, can be a $(C_{4-15})$bicycloalkyl, a $(C_{4-10})$bicycloalkyl, a $(C_{6-10})$bicycloalkyl or a $(C_{8-10})$bicycloalkyl. Alternatively, "bicycloalkyl," either alone or represented along with another radical, can be a $(C_8)$bicycloalkyl, a $(C_9)$bicycloalkyl or a $(C_{10})$bicycloalkyl.

"Bicycloaryl" means a fused, spiro or bridged bicyclic ring assembly wherein at least one of the rings comprising the assembly is aromatic. $(C_X)$bicycloaryl and $(C_{X-Y})$bicycloaryl are typically used where X and Y indicate the number of carbon atoms in the bicyclic ring assembly and directly attached to the ring. In particular embodiments, "bicycloaryl," either alone or represented along with another radical, can be a $(C_{4-15})$bicycloaryl, a $(C_{4-10})$bicycloaryl, a $(C_{6-10})$bicycloaryl, or a $(C_{8-10})$bicycloaryl. Alternatively, "bicycloalkyl," either alone or represented along with another radical, can be a $(C_8)$bicycloaryl, a $(C_9)$bicycloaryl or a $(C_{10})$bicycloaryl.

"Bridging ring" and "bridged ring" as used herein refer to a ring that is bonded to another ring to form a compound having a bicyclic or polycyclic structure where two ring atoms that are common to both rings are not directly bound to each other. Non-exclusive examples of common compounds having a bridging ring include borneol, norbornane, 7-oxabicyclo[2.2.1]heptane, and the like. One or both rings of the bicyclic system may also comprise heteroatoms.

"Carbamoyl" means the radical —OC(O)NRR', wherein R and R' are each independently hydrogen or further substituents.

"Carbocycle" means a ring consisting of carbon atoms.

"Carbonyl" means the radical —C(═O)— and/or —C(═O)R, wherein R is hydrogen or a further substituent. It is noted that the carbonyl radical may be further substituted with a variety of substituents to form different carbonyl groups including acids, acid halides, aldehydes, amides, esters, and ketones.

"Carboxy" means the radical —C(═O)—O— and/or —C(═O)—OR, wherein R is hydrogen or a further substituent. It is noted that compounds of the invention containing carboxy moieties may include protected derivatives thereof, i.e., where the oxygen is substituted with a protecting group. Suitable protecting groups for carboxy moieties include benzyl, tert-butyl, and the like.

"Cyano" means the radical —CN.

"Cycloalkyl" means a non-aromatic, saturated or partially unsaturated, monocyclic, bicyclic or polycyclic ring assembly. $(C_X)$cycloalkyl and $(C_{X-Y})$cycloalkyl are typically used where X and Y indicate the number of carbon atoms in the ring assembly. For example, $(C_{3-10})$cycloalkyl includes cyclopropyl, cyclobutyl, cyclopentyl, cyclohexyl, cyclohexenyl, 2,5-cyclohexadienyl, bicyclo[2.2.2]octyl, adamantan-1-yl, decahydronaphthyl, oxocyclohexyl, dioxocyclohexyl, thiocyclohexyl, 2-oxobicyclo[2.2.1]hept-1-yl, and the like. In particular embodiments, "cycloalkyl," either alone or represented along with another radical, can be a $(C_{3-14})$cycloalkyl, a $(C_{3-10})$cycloalkyl, a $(C_{3-7})$cycloalkyl, a $(C_{8-10})$cycloalkyl or a $(C_{5-7})$cycloalkyl. Alternatively, "cycloalkyl," either alone or represented along with another radical, can be a $(C_5)$cycloalkyl, a $(C_6)$cycloalkyl, a $(C_7)$cycloalkyl, a $(C_8)$cycloalkyl, a $(C_9)$cycloalkyl, or a $(C_{10})$cycloalkyl.

"Cycloalkylene" means a divalent, saturated or partially unsaturated, monocyclic, bicyclic or polycyclic ring assembly. $(C_X)$cycloalkylene and $(C_{X-Y})$cycloalkylene are typically used where X and Y indicate the number of carbon atoms in the ring assembly. In particular embodiments, "cycloalkylene," either alone or represented along with another radical, can be a $(C_{3-14})$cycloalkylene, a $(C_{3-10})$cycloalkylene, a $(C_{3-7})$cycloalkylene, a $(C_{8-10})$cycloalkylene or a $(C_{5-7})$cycloalkylene. Alternatively, "cycloalkylene," either alone or represented along with another radical, can be a $(C_5)$cycloalkylene, a $(C_6)$cycloalkylene, a $(C_7)$cycloalkylene, a $(C_8)$cycloalkylene, a $(C_9)$cycloalkylene, or a $(C_{10})$cycloalkylene.

"Disease" specifically includes any unhealthy condition of an animal or part thereof and includes an unhealthy condition that may be caused by, or incident to, medical or veterinary therapy applied to that animal, i.e., the "side effects" of such therapy.

"$EC_{50}$" means the molar concentration of an agonist that produces 50% of the maximal possible effect of that agonist. The action of the agonist may be stimulatory or inhibitory.

"Fused ring" as used herein refers to a ring that is bonded to another ring to form a compound having a bicyclic structure where the ring atoms that are common to both rings are directly bound to each other. Non-exclusive examples of common fused rings include decalin, naphthalene, anthracene, phenanthrene, indole, furan, benzofuran, quinoline, and the like. Compounds having fused ring systems may be saturated, partially saturated, carbocyclics, heterocyclics, aromatics, heteroaromatics, and the like.

"Halo" means fluoro, chloro, bromo or iodo.

"Heteroalicyclic" means an alicyclic moiety as defined in this application where at least one of the ring atoms is a heteroatom. The heteroalicyclic contemplated in this application includes, but are not limited to, pyrroline, pyrrolidine, dioxiane, imidazoline, imidazolidine, pyrazoline, pyrazolidine, pyran, poperidine, dioxane, morpholine, dithiane, thiomorpholine, piperazine, trithiane, indoline, quinuclidine, indene, norbornane, fluorine, norbornane, adamantane, and the like.

"Heteroalkyl" means alkyl, as defined in this application, provided that one or more of the atoms within the alkyl chain is a heteroatom. In particular embodiments, "heteroalkyl," either alone or represented along with another radical, can be a hetero$(C_{1-20})$alkyl, a hetero$(C_{1-15})$alkyl, a hetero$(C_{1-10})$alkyl, a hetero$(C_{1-5})$alkyl, a hetero$(C_{1-3})$alkyl or a hetero$(C_{1-2})$alkyl. Alternatively, "heteroalkyl," either alone or represented along with another radical, can be a hetero$(C_1)$alkyl, a hetero$(C_2)$alkyl or a hetero$(C_3)$alkyl.

"Heteroaryl" means a monocyclic, bicyclic or polycyclic aromatic group wherein at least one ring atom is a heteroatom and the remaining ring atoms are carbon. Monocyclic heteroaryl groups include, but are not limited to, cyclic aromatic groups having five or six ring atoms, wherein at least one ring atom is a heteroatom and the remaining ring atoms are carbon. The nitrogen atoms can be optionally quaternerized and the sulfur atoms can be optionally oxidized. Heteroaryl groups of this invention include, but are not limited to, those derived from furan, imidazole, isothiazole, isoxazole, oxadiazole, oxazole, 1,2,3-oxadiazole, pyrazine, pyrazole, pyridazine, pyridine, pyrimidine, pyrroline, thiazole, 1,3,4-thiadiazole, triazole and tetrazole. "Heteroaryl" also includes, but is not limited to, bicyclic or tricyclic rings, wherein the heteroaryl ring is fused to one or two rings independently selected from the group consisting of an aryl ring, a cycloalkyl ring, a cycloalkenyl ring, and another monocyclic heteroaryl or heterocycloalkyl ring. These bicyclic or tricyclic heteroaryls include, but are not limited to, those derived from benzo[b]furan, benzo[b]thiophene, benzimidazole, imidazo[4,5-c]pyridine, quinazoline, thieno[2,3-c]pyridine, thieno[3,2-b]pyridine, thieno[2,3-b]pyridine, indolizine, imidazo[1,2a]pyridine, quinoline, isoquinoline, phthalazine, quinoxaline, naphthyridine, quinolizine, indole, isoindole, indazole, indoline, benzoxazole, benzopyrazole, benzothiazole, imidazo[1,5-a]pyridine, pyrazolo[1,5-a]pyridine, imidazo[1,2-a]pyrimidine, imidazo[1,2-c]pyrimidine, imidazo[1,5-a]pyrimidine, imidazo[1,5-c]pyrimidine, pyrrolo[2,3-b]pyridine, pyrrolo[2,3-c]pyridine, pyrrolo[3,2-c]pyridine, pyrrolo[3,2-b]pyridine, pyrrolo[2,3-d]pyrimidine, pyrrolo[3,2-d]pyrimidine, pyrrolo[2,3-b]pyrazine, pyrazolo[1,5-a]pyridine, pyrrolo[1,2-b]pyridazine, pyrrolo[1,2-c]pyrimidine, pyrrolo[1,2-a]pyrimidine, pyrrolo[1,2-a]pyrazine, triazo[1,5-a]pyridine, pteridine, purine, carbazole, acridine, phenazine, phenothiazene, phenoxazine, 1,2-dihydropyrrolo[3,2,1-hi]indole, indolizine, pyrido[1,2-a]indole and 2(1H)-pyridinone. The bicyclic or tricyclic heteroaryl rings can be attached to the parent molecule through either the heteroaryl group itself or the aryl, cycloalkyl, cycloalkenyl or heterocycloalkyl group to which it is fused. The heteroaryl groups of this invention can be substituted or unsubstituted. In particular embodiments, "heteroaryl," either alone or represented along with another radical, can be a hetero$(C_{1-13})$aryl, a hetero$(C_{2-13})$aryl, a hetero$(C_{2-6})$aryl, a hetero$(C_{3-9})$aryl or a hetero$(C_{5-9})$aryl. Alternatively, "heteroaryl," either alone or represented along with another radical, can be a hetero$(C_3)$aryl, a hetero$(C_4)$aryl, a hetero$(C_5)$aryl, a hetero$(C_6)$aryl, a hetero$(C_7)$aryl, a hetero$(C_8)$aryl or a hetero$(C_9)$aryl.

"Heteroatom" refers to an atom that is not a carbon atom. Particular examples of heteroatoms include, but are not limited to, nitrogen, oxygen, and sulfur.

"Heteroatom moiety" includes a moiety where the atom by which the moiety is attached is not a carbon. Examples of heteroatom moieties include —NR—, —N$^+$(O$^-$)=, —O—, —S— or —S(O)$_2$—, wherein R is hydrogen or a further substituent.

"Heterobicycloalkyl" means bicycloalkyl, as defined in this application, provided that one or more of the atoms within the ring is a heteroatom. For example hetero$(C_{9-12})$bicycloalkyl as used in this application includes, but is not limited to, 3-aza-bicyclo[4.1.0]hept-3-yl, 2-aza-bicyclo[3.1.0]hex-2-yl, 3-aza-bicyclo[3.1.0]hex-3-yl, and the like. In particular embodiments, "heterobicycloalkyl," either alone or represented along with another radical, can be a hetero$(C_{1-14})$bicycloalkyl, a hetero$(C_{4-14})$bicycloalkyl, a hetero$(C_{4-9})$bicycloalkyl, or a hetero$(C_{5-9})$bicycloalkyl. Alternatively, "heterobicycloalkyl," either alone or represented along with another radical, can be a hetero$(C_5)$bicycloalkyl, hetero$(C_6)$bicycloalkyl, hetero$(C_7)$bicycloalkyl, hetero$(C_8)$bicycloalkyl, or a hetero$(C_9)$bicycloalkyl.

"Heterobicycloaryl" means bicycloaryl, as defined in this application, provided that one or more of the atoms within the ring is a heteroatom. For example, hetero$(C_{4-12})$bicycloaryl as used in this application includes, but is not limited to, 2-amino-4-oxo-3,4-dihydropteridin-6-yl, tetrahydroisoquinolinyl, and the like. In particular embodiments, "heterobicycloaryl," either alone or represented along with another radical, can be a hetero$(C_{1-14})$bicycloaryl, a hetero$(C_{4-14})$bicycloaryl, a hetero$(C_{4-9})$bicycloaryl or a hetero$(C_{5-9})$bicycloaryl. Alternatively, "heterobicycloaryl," either alone or represented along with another radical, can be a hetero$(C_5)$bicycloaryl, hetero$(C_6)$bicycloaryl, hetero$(C_7)$bicycloaryl, hetero$(C_8)$bicycloaryl, or a hetero$(C_9)$bicycloaryl.

"Heterocycloalkyl" means cycloalkyl, as defined in this application, provided that one or more of the atoms forming the ring is a heteroatom selected independently from N, O, or S. Non-exclusive examples of heterocycloalkyl include piperidyl, 4-morpholyl, 4-piperazinyl, pyrrolidinyl, perhydropyrrolizinyl, 1,4-diazaperhydroepinyl, 1,3-dioxanyl, 1,4-dioxanyl and the like. In particular embodiments, "heterocycloalkyl," either alone or represented along with another radical, can be a hetero($C_{1-13}$)cycloalkyl, a hetero($C_{1-9}$)cycloalkyl, a hetero($C_{1-6}$)cycloalkyl, a hetero($C_{5-9}$)cycloalkyl or a hetero($C_{2-6}$)cycloalkyl. Alternatively, "heterocycloalkyl," either alone or represented along with another radical, can be a hetero($C_2$)cycloalkyl, a hetero($C_3$)cycloalkyl, a hetero($C_4$)cycloalkyl, a hetero($C_5$)cycloalkyl, a hetero($C_6$)cycloalkyl, hetero($C_7$)cycloalkyl, hetero($C_8$)cycloalkyl, or a hetero($C_9$)cycloalkyl.

"Heterocycloalkylene" means cycloalkylene, as defined in this application, provided that one or more of the ring member carbon atoms is replaced by a heteroatom. In particular embodiments, "heterocycloalkylene," either alone or represented along with another radical, can be a hetero($C_{1-13}$)cycloalkylene, a hetero($C_{1-9}$)cycloalkylene, a hetero($C_{1-6}$)cycloalkylene, a hetero($C_{5-9}$)cycloalkylene, or a hetero($C_{2-6}$)cycloalkylene. Alternatively, "heterocycloalkylene," either alone or represented along with another radical, can be a hetero($C_2$)cycloalkylene, a hetero($C_3$)cycloalkylene, a hetero($C_4$)cycloalkylene, a hetero($C_5$)cycloalkylene, a hetero($C_6$)cycloalkylene, hetero($C_7$)cycloalkylene, hetero($C_8$)cycloalkylene, or a hetero($C_9$)cycloalkylene.

"Hydroxy" means the radical —OH.

"$IC_{50}$" means the molar concentration of an inhibitor that produces 50% inhibition of the target enzyme.

"Imino" means the radical —CR(=NR') and/or —C(=NR')—, wherein R and R' are each independently hydrogen or a further substituent.

"Iminoketone derivative" means a derivative comprising the moiety —C(NR)—, wherein R is hydrogen or a further substituent.

"Isomers" means compounds having identical molecular formulae but differing in the nature or sequence of bonding of their atoms or in the arrangement of their atoms in space. Isomers that differ in the arrangement of their atoms in space are termed "stereoisomers." Stereoisomers that are not mirror images of one another are termed "diastereomers" and stereoisomers that are nonsuperimposable mirror images are termed "enantiomers" or sometimes "optical isomers." A carbon atom bonded to four nonidentical substituents is termed a "chiral center." A compound with one chiral center has two enantiomeric forms of opposite chirality. A mixture of the two enantiomeric forms is termed a "racemic mixture." A compound that has more than one chiral center has $2^{n-1}$ enantiomeric pairs, where n is the number of chiral centers. Compounds with more than one chiral center may exist as ether an individual diastereomer or as a mixture of diastereomers, termed a "diastereomeric mixture." When one chiral center is present a stereoisomer may be characterized by the absolute configuration of that chiral center. Absolute configuration refers to the arrangement in space of the substituents attached to the chiral center. Enantiomers are characterized by the absolute configuration of their chiral centers and described by the R- and S-sequencing rules of Cahn, Ingold and Prelog. Conventions for stereochemical nomenclature, methods for the determination of stereochemistry and the separation of stereoisomers are well known in the art (e.g., see "Advanced Organic Chemistry", 5th edition, March, Jerry, John Wiley & Sons, New York, 2001).

"Leaving group" means the group with the meaning conventionally associated with it in synthetic organic chemistry, i.e., an atom or group displaceable under reaction (e.g., alkylating) conditions. Examples of leaving groups include, but are not limited to, halo (e.g., F, Cl, Br and I), alkyl (e.g., methyl and ethyl) and sulfonyloxy (e.g., mesyloxy, ethanesulfonyloxy, benzenesulfonyloxy and tosyloxy), thiomethyl, thienyloxy, dihalophosphinoyloxy, tetrahalophosphoxy, benzyloxy, isopropyloxy, acyloxy, and the like.

"Nitro" means the radical —$NO_2$.

"Oxaalkyl" means an alkyl, as defined above, except where one or more of the carbon atoms forming the alkyl chain are replaced with oxygen atoms (—O— or —OR, wherein R is hydrogen or a further substituent). For example, an oxa($C_{1-10}$)alkyl refers to a chain comprising between 1 and 10 carbons and one or more oxygen atoms.

"Oxoalkyl" means an alkyl, as defined above, except where one or more of the carbon atoms forming the alkyl chain are replaced with carbonyl groups (—C(=O)— or —C(=O)—R, wherein R is hydrogen or a further substituent). The carbonyl group may be an aldehyde, ketone, ester, amide, and acid or acid halide. For example, an oxo($C_{1-10}$)alkyl refers to a chain comprising between 1 and 10 carbon atoms and one or more carbonyl groups.

"Oxy" means the radical —O— or —OR, wherein R is hydrogen or a further substituent. Accordingly, it is noted that the oxy radical may be further substituted with a variety of substituents to form different oxy groups including hydroxy, alkoxy, aryloxy, heteroaryloxy or carbonyloxy.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzenesulfonic acid, p-chlorobenzenesulfonic acid, 2-naphthalenesulfonic acid, p-toluenesulfonic acid, camphorsulfonic acid, 4-methylbicyclo[2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like.

Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like.

"Polycyclic ring" includes bicyclic and multi-cyclic rings. The individual rings comprising the polycyclic ring can be fused, spiro or bridging rings.

"Prodrug" means a compound that is convertible in vivo metabolically into an inhibitor according to the present invention. The prodrug itself may or may not also have activity with respect to a given target protein. For example, a compound comprising a hydroxy group may be administered as an ester that is converted by hydrolysis in vivo to the hydroxy compound. Suitable esters that may be converted in vivo into hydroxy compounds include acetates, citrates, lactates, phosphates, tartrates, malonates, oxalates, salicylates, propionates, succinates, fumarates, maleates, methylene-bis-b-hydroxynaphthoates, gentisates, isethionates, di-p-toluoyltartrates, methanesulfonates, ethanesulfonates, benzenesulfonates, p-toluenesulfonates, cyclohexylsulfamates, quinates, esters of amino acids, and the like. Similarly, a compound comprising an amine group may be administered as an amide that is converted by hydrolysis in vivo to the amine compound.

"Protected derivatives" means derivatives of inhibitors in which a reactive site or sites are blocked with protecting groups. Protected derivatives are useful in the preparation of inhibitors or in themselves may be active as inhibitors. A comprehensive list of suitable protecting groups can be found in P. G. M. Wuts and T. W. Greene, "*Greene's Protecting Groups in Organic Synthesis,* 4th edition, John Wiley & Sons, Inc. 2007.

"Ring" and "ring assembly" means a carbocyclic or a heterocyclic system and includes aromatic and non-aromatic systems. The system can be monocyclic, bicyclic or polycyclic. In addition, for bicyclic and polycyclic systems, the individual rings comprising the polycyclic ring can be fused, spiro or bridging rings.

"Subject" and "patient" includes humans, non-human mammals (e.g., dogs, cats, rabbits, cattle, horses, sheep, goats, swine, deer, and the like) and non-mammals (e.g., birds, and the like).

"Substituted or unsubstituted" means that a given moiety may consist of only hydrogen substituents through available valencies (unsubstituted) or may further comprise one or more non-hydrogen substituents through available valencies (substituted) that are not otherwise specified by the name of the given moiety. For example, isopropyl is an example of an ethylene moiety that is substituted by —$CH_3$. In general, a non-hydrogen substituent may be any substituent that may be bound to an atom of the given moiety that is specified to be substituted. Examples of substituents include, but are not limited to, aldehyde, alicyclic, aliphatic, ($C_{1-10}$)alkyl, alkylene, alkylidene, amide, amino, aminoalkyl, aromatic, aryl, bicycloalkyl, bicycloaryl, carbamoyl, carbocyclyl, carboxyl, carbonyl group, cycloalkyl, cycloalkylene, ester, halo, heterobicycloalkyl, heterocycloalkylene, heteroaryl, heterobicycloaryl, heterocycloalkyl, oxo, hydroxy, iminoketone, ketone, nitro, oxaalkyl, and oxoalkyl moieties, each of which may optionally also be substituted or unsubstituted. In one particular embodiment, examples of substituents include, but are not limited to, hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, aminocarbonyl, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, ($C_{1-10}$)azaalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-2}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl. In addition, the substituent is itself optionally substituted by a further substituent. In one particular embodiment, examples of the further substituent include, but are not limited to, hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, aminocarbonyl, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, ($C_{1-10}$)azaalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-2}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl.

"Sulfinyl" means the radical —SO— and/or —SO—R, wherein R is hydrogen or a further substituent. It is noted that the sulfinyl radical may be further substituted with a variety of substituents to form different sulfinyl groups including sulfinic acids, sulfinamides, sulfinyl esters, and sulfoxides.

"Sulfonyl" means the radical —$SO_2$— and/or —$SO_2$—R, wherein R is hydrogen or a further substituent. It is noted that the sulfonyl radical may be further substituted with a variety of substituents to form different sulfonyl groups including sulfonic acids, sulfonamides, sulfonate esters, and sulfones.

"Therapeutically effective amount" means that amount which, when administered to an animal for treating a disease, is sufficient to effect such treatment for the disease.

"Thio" denotes replacement of an oxygen by a sulfur and includes, but is not limited to, —SR, —S— and =S containing groups.

"Thioalkyl" means an alkyl, as defined above, except where one or more of the carbon atoms forming the alkyl chain are replaced with sulfur atoms (—S— or —S—R, wherein R is hydrogen or a further substituent). For example, a thio($C_{1-10}$)alkyl refers to a chain comprising between 1 and 10 carbons and one or more sulfur atoms.

"Thiocarbonyl" means the radical —C(=S)— and/or —C(=S)—R, wherein R is hydrogen or a further substituent. It is noted that the thiocarbonyl radical may be further substituted with a variety of substituents to form different thiocarbonyl groups including thioacids, thioamides, thioesters, and thioketones.

"Treatment" or "treating" means any administration of a compound of the present invention and includes:

(1) preventing the disease from occurring in an animal which may be predisposed to the disease but does not yet experience or display the pathology or symptomatology of the disease, (2) inhibiting the disease in an animal that is experiencing or displaying the pathology or symptomatology of the diseased (i.e., arresting further development of the pathology and/or symptomatology), or (3) ameliorating the disease in an animal that is experiencing or displaying the pathology or symptomatology of the diseased (i.e., reversing the pathology and/or symptomatology).

It is noted in regard to all of the definitions provided herein that the definitions should be interpreted as being open ended in the sense that further substituents beyond those specified may be included. Hence, a $C_1$ alkyl indicates that there is one carbon atom but does not indicate what are the substituents on the carbon atom. Hence, a ($C_1$)alkyl comprises methyl (i.e., —$CH_3$) as well as —CRR'R" where R, R', and R" may each independently be hydrogen or a further substituent where the atom attached to the carbon is a heteroatom or cyano. Hence, $CF_3$, $CH_2OH$ and $CH_2CN$, for example, are all ($C_1$)alkyls. Similarly, terms such as alkylamino and the like comprise dialkylamino and the like.

A compound having a formula that is represented with a dashed bond is intended to include the formulae optionally having zero, one or more double bonds, as exemplified and shown below:

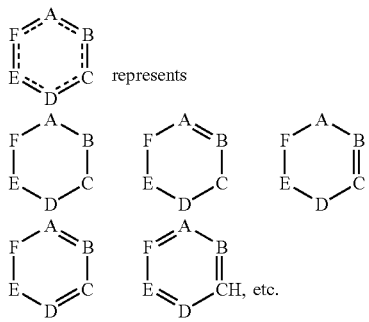

In addition, atoms making up the compounds of the present invention are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$.

DETAILED DESCRIPTION OF THE INVENTION

The present invention relates to compounds that may be used to inhibit acetyl-CoA carboxylase (ACC) and, in particular, ACC1 and/or ACC2. The present invention also relates to pharmaceutical compositions, kits and articles of manufacture comprising such compounds. In addition, the present invention relates to methods and intermediates useful for making the compounds. Further, the present invention relates to methods of using said compounds.

It is noted that the compounds of the present invention may also possess inhibitory activity for other ACC family members and thus may be used to address disease states associated with these other family members.

Compound of the Invention

In one of its aspects, the present invention relates to compounds that are useful as ACC inhibitors. In one embodiment, the compounds of the invention consist of the formula:

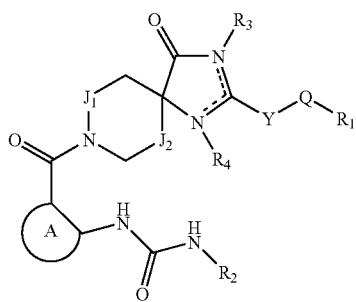

or a hydrate, solvate, ester, tautomer, enantiomer, or pharmaceutically acceptable salt thereof,
wherein
$J_1$ and $J_2$ are each independently selected from the group consisting of —$(CH_2)$— and —$(CH_2)_2$—, provided that $J_1$ and $J_2$ cannot both be —$(CH_2)_2$—;
Y is selected from the group consisting of a bond, —$CH_2$—, —$(CH_2)_2$—, —NH—$CH_2$—, and —$CH_2$—NH—;
Q is selected from the group consisting of a bond, —C(O)—, —C(O)O—, —NH—, —O—, —S—, —S(O)—, and —S(O)$_2$—;

A is selected from the group consisting of five or six membered, substituted or unsubstituted aryl and heteroaryl, where the substituents on adjacent ring atoms of the aryl or heteroaryl may be taken together to form five or six membered, substituted or unsubstituted, saturated, unsaturated or aromatic ring;
$R_1$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, $(C_{3-12})$cycloalkyloxy, hetero$(C_{3-12})$cycloalkyloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-2})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted;
$R_2$ is substituted or unsubstituted alkyl;
$R_3$ and $R_4$ are each independently selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted; and
provided that one of $R_3$ and $R_4$ is absent, and where $R_3$ is absent, the nitrogen on which $R_3$ is drawn is part of a double bond, and where $R_4$ is absent, the nitrogen on which $R_4$ is drawn is part of a double bond.

In another embodiment, the compounds of the invention consist of the formula:

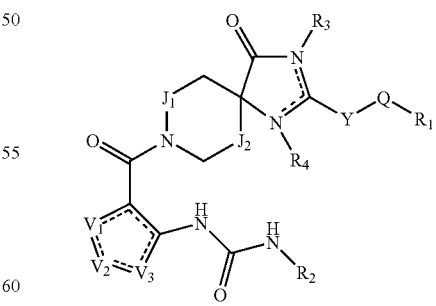

or a hydrate, solvate, ester, tautomer, enantiomer, or pharmaceutically acceptable salt thereof, wherein
$J_1$ and $J_2$ are each independently selected from the group consisting of —$(CH_2)$— and —$(CH_2)_2$—, provided that $J_1$ and $J_2$ cannot both be —$(CH_2)_2$—;

Y is selected from the group consisting of a bond, —CH$_2$—, —(CH$_2$)$_2$—, —NH—CH$_2$—, and —CH$_2$—NH—;

Q is selected from the group consisting of a bond, —C(O)—, —C(O)O—, —NH—, —O—, —S—, —S(O)—, and —S(O)$_2$—;

the ring comprising V$_1$, V$_2$ and V$_3$ is selected from the group consisting of substituted or unsubstituted aryl and substituted or unsubstituted heteroaryl;

V$_1$ is CR$_{11}$, NR$_{11}$, N, O, or S;
V$_2$ is CR$_{12}$, NR$_{12}$, N, O, or S;
V$_3$ is CR$_{13}$, NR$_{13}$, N, O, or S;

R$_1$ is selected from the group consisting of hydrogen, halo, nitro, cyano, thio, oxy, hydroxy, carbonyloxy, (C$_{1-10}$)alkoxy, (C$_{4-12}$)aryloxy, hetero(C$_{1-10}$)aryloxy, (C$_{3-12}$)cycloalkyloxy, hetero(C$_{3-12}$)cycloalkyloxy, carbonyl, oxycarbonyl, aminocarbonyl, amino, (C$_{1-10}$)alkylamino, sulfonamido, imino, sulfonyl, sulfinyl, (C$_{1-10}$)alkyl, halo(C$_{1-10}$)alkyl, hydroxy(C$_{1-10}$)alkyl, carbonyl(C$_{1-10}$)alkyl, thiocarbonyl(C$_{1-10}$)alkyl, sulfonyl(C$_{1-10}$)alkyl, sulfinyl(C$_{1-10}$)alkyl, aza(C$_{1-10}$)alkyl, (C$_{1-10}$)Oxaalkyl, (C$_{1-10}$)Oxoalkyl, imino(C$_{1-10}$)alkyl, (C$_{3-12}$)cycloalkyl(C$_{1-5}$)alkyl, hetero(C$_{3-12}$)cycloalkyl(C$_{1-10}$)alkyl, aryl(C$_{1-10}$)alkyl, hetero(C$_{1-10}$)aryl(C$_{1-5}$)alkyl, (C$_{9-12}$)bicycloaryl(C$_{1-5}$)alkyl, hetero(C$_{8-12}$)bicycloaryl(C$_{1-5}$)alkyl, hetero(C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{1-10}$)aryl, (C$_{9-12}$)bicycloaryl and hetero(C$_{4-12}$)bicycloaryl, each substituted or unsubstituted;

R$_2$ is substituted or unsubstituted alkyl;

R$_3$ and R$_4$ are each independently selected from the group consisting of hydrogen, halo, nitro, cyano, thio, oxy, hydroxy, carbonyloxy, (C$_{1-10}$)alkoxy, (C$_{4-12}$)aryloxy, hetero(C$_{1-10}$)aryloxy, carbonyl, oxycarbonyl, aminocarbonyl, amino, (C$_{1-10}$)alkylamino, sulfonamido, imino, sulfonyl, sulfinyl, (C$_{1-10}$)alkyl, halo(C$_{1-10}$)alkyl, hydroxy(C$_{1-10}$)alkyl, carbonyl(C$_{1-10}$)alkyl, thiocarbonyl(C$_{1-10}$)alkyl, sulfonyl(C$_{1-10}$)alkyl, sulfinyl(C$_{1-10}$)alkyl, aza(C$_{1-10}$)alkyl, (C$_{1-10}$)oxaalkyl, (C$_{1-10}$)oxoalkyl, imino(C$_{1-10}$)alkyl, (C$_{3-12}$)cycloalkyl(C$_{1-5}$)alkyl, hetero(C$_{3-12}$)cycloalkyl(C$_{1-10}$)alkyl, aryl(C$_{1-10}$)alkyl, hetero(C$_{1-10}$)aryl(C$_{1-5}$)alkyl, (C$_{9-12}$)bicycloaryl(C$_{1-5}$)alkyl, hetero(C$_{8-2}$)bicycloaryl(C$_{1-5}$)alkyl, hetero(C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{1-10}$)aryl, (C$_{9-12}$)bicycloaryl, and hetero(C$_{4-12}$)bicycloaryl, each substituted or unsubstituted;

R$_{11}$, R$_{12}$ and R$_{13}$ are each independently selected from the group consisting of H, halo, nitro, cyano, thio, oxy, hydroxy, carbonyloxy, (C$_{1-10}$)alkoxy, (C$_{4-12}$)aryloxy, hetero(C$_{1-10}$)aryloxy, carbonyl, oxycarbonyl, aminocarbonyl, amino, (C$_{1-10}$)alkylamino, sulfonamido, imino, sulfonyl, sulfinyl, (C$_{1-10}$)alkyl, halo(C$_{1-10}$)alkyl, hydroxy(C$_{1-10}$)alkyl, carbonyl(C$_{1-10}$)alkyl, thiocarbonyl(C$_{1-10}$)alkyl, sulfonyl(C$_{1-10}$)alkyl, sulfinyl(C$_{1-10}$)alkyl, aza(C$_{1-10}$)alkyl, (C$_{1-10}$)oxaalkyl, (C$_{1-10}$)oxoalkyl, imino(C$_{1-10}$)alkyl, (C$_{3-12}$)cycloalkyl(C$_{1-5}$)alkyl, hetero(C$_{3-12}$)cycloalkyl(C$_{1-10}$)alkyl, aryl(C$_{1-10}$)alkyl, hetero(C$_{1-10}$)aryl(C$_{1-5}$)alkyl, (C$_{9-12}$)bicycloaryl(C$_{1-5}$)alkyl, hetero(C$_{8-12}$)bicycloaryl(C$_{1-5}$)alkyl, hetero(C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{1-10}$)aryl, (C$_{9-12}$)bicycloaryl, and hetero(C$_{4-12}$)bicycloaryl, each substituted or unsubstituted; or R$_{11}$ and R$_{12}$, or R$_{12}$ and R$_{13}$, are taken together to form a ring selected from the group consisting of substituted or unsubstituted cycloalkyl, substituted or unsubstituted heterocycloalkyl, substituted or unsubstituted aryl, and substituted or unsubstituted heteroaryl; and provided that one of R$_3$ and R$_4$ is absent, and where R$_3$ is absent, the nitrogen on which R$_3$ is drawn is part of a double bond, and where R$_4$ is absent, the nitrogen on which R$_4$ is drawn is part of a double bond.

In another embodiment, the compounds of the invention consist of the formula:

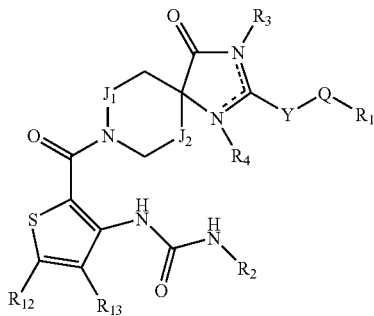

or a hydrate, solvate, ester, tautomer, enantiomer, or pharmaceutically acceptable salt thereof, wherein J$_1$ and J$_2$ are each independently selected from the group consisting of —(CH$_2$)— and —(CH$_2$)$_2$—, provided that J$_1$ and J$_2$ cannot both be —(CH$_2$)$_2$—;

Y is selected from the group consisting of a bond, —CH$_2$—, —(CH$_2$)$_2$—, —NH—CH$_2$—, and —CH$_2$—NH—;

Q is selected from the group consisting of a bond, —C(O)—, —C(O)O—, —NH—, —O—, —S—, —S(O)—, and —S(O)$_2$—;

R$_1$ is selected from the group consisting of hydrogen, halo, nitro, cyano, thio, oxy, hydroxy, carbonyloxy, (C$_{1-10}$)alkoxy, (C$_{4-12}$)aryloxy, hetero(C$_{1-10}$)aryloxy, (C$_{3-12}$)cycloalkyloxy, hetero(C$_{3-12}$)cycloalkyloxy, carbonyl, oxycarbonyl, aminocarbonyl, amino, (C$_{1-10}$)alkylamino, sulfonamido, imino, sulfonyl, sulfinyl, (C$_{1-10}$)alkyl, halo(C$_{1-10}$)alkyl, hydroxy(C$_{1-10}$)alkyl, carbonyl(C$_{1-10}$)alkyl, thiocarbonyl(C$_{1-10}$)alkyl, sulfonyl(C$_{1-10}$)alkyl, sulfinyl(C$_{1-10}$)alkyl, aza(C$_{1-10}$)alkyl, (C$_{1-10}$)oxaalkyl, (C$_{1-10}$)oxoalkyl, imino(C$_{1-10}$)alkyl, (C$_{3-12}$)cycloalkyl(C$_{1-5}$)alkyl, hetero(C$_{3-12}$)cycloalkyl(C$_{1-10}$)alkyl, aryl(C$_{1-10}$)alkyl, hetero(C$_{1-10}$)aryl(C$_{1-5}$)alkyl, (C$_{9-12}$)bicycloaryl(C$_{1-5}$)alkyl, hetero(C$_{8-2}$)bicycloaryl(C$_{1-5}$)alkyl, hetero(C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{1-10}$)aryl, (C$_{9-12}$)bicycloaryl, and hetero(C$_{4-12}$)bicycloaryl, each substituted or unsubstituted;

R$_2$ is substituted or unsubstituted alkyl;

R$_3$ and R$_4$ are each independently selected from the group consisting of hydrogen, halo, nitro, cyano, thio, oxy, hydroxy, carbonyloxy, (C$_{1-10}$)alkoxy, (C$_{4-12}$)aryloxy, hetero(C$_{1-10}$)aryloxy, carbonyl, oxycarbonyl, aminocarbonyl, amino, (C$_{1-10}$)alkylamino, sulfonamido, imino, sulfonyl, sulfinyl, (C$_{1-10}$)alkyl, halo(C$_{1-10}$)alkyl, hydroxy(C$_{1-10}$)alkyl, carbonyl(C$_{1-10}$)alkyl, thiocarbonyl(C$_{1-10}$)alkyl, sulfonyl(C$_{1-10}$)alkyl, sulfinyl(C$_{1-10}$)alkyl, aza(C$_{1-10}$)alkyl, (C$_{1-10}$)oxaalkyl, (C$_{1-10}$)oxoalkyl, imino(C$_{1-10}$)alkyl, (C$_{3-12}$)cycloalkyl(C$_{1-5}$)alkyl, hetero(C$_{3-12}$)cycloalkyl(C$_{1-10}$)alkyl, aryl(C$_{1-10}$)alkyl, hetero(C$_{1-10}$)aryl(C$_{1-5}$)alkyl, (C$_{9-12}$)bicycloaryl(C$_{1-5}$)alkyl, hetero(C$_{8-2}$)bicycloaryl(C$_{1-5}$)alkyl, hetero(C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{1-10}$)aryl, (C$_{9-12}$)bicycloaryl, and hetero(C$_{4-12}$)bicycloaryl, each substituted or unsubstituted;

R$_{12}$ and R$_{13}$ are each independently selected from the group consisting of H, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl $(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-2})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl, and hetero$(C_{4-12})$bicycloaryl, each substituted or unsubstituted; or $R_{12}$ and $R_{13}$ may be taken together to form a ring selected from the group consisting of substituted or unsubstituted cycloalkyl, substituted or unsubstituted heterocycloalkyl, substituted or unsubstituted aryl, and substituted or unsubstituted heteroaryl; and provided that one of $R_3$ and $R_4$ is absent, and where $R_3$ is absent, the nitrogen on which $R_3$ is drawn is part of a double bond, and where $R_4$ is absent, the nitrogen on which $R_4$ is drawn is part of a double bond.

In another embodiment, the compounds of the invention consist of the formula:

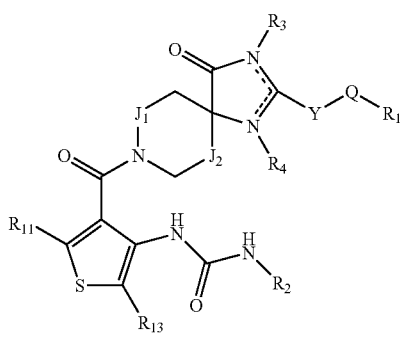

or a hydrate, solvate, ester, tautomer, enantiomer, or pharmaceutically acceptable salt thereof,
wherein
$J_1$ and $J_2$ are each independently selected from the group consisting of —$(CH_2)$— and —$(CH_2)_2$—, provided that $J_1$ and $J_2$ cannot both be —$(CH_2)_2$—;

Y is selected from the group consisting of a bond, —$CH_2$—, —$(CH_2)_2$—, —NH—$CH_2$—, and —$CH_2$—NH—;

Q is selected from the group consisting of a bond, —C(O)—, —C(O)O—, —NH—, —O—, —S—, —S(O)—, and —S(O)$_2$—;

$R_1$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, $(C_{3-12})$cycloalkyloxy, hetero$(C_{3-12})$cycloalkyloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-2})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl, and hetero$(C_{4-12})$bicycloaryl, each substituted or unsubstituted;

$R_2$ is substituted or unsubstituted alkyl;

$R_3$ and $R_4$ are each independently selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl $(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-2})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl, and hetero$(C_{4-12})$bicycloaryl, each substituted or unsubstituted;

$R_{11}$ and $R_{13}$ are each independently selected from the group consisting of H, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl $(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl, and hetero$(C_{4-12})$bicycloaryl, each substituted or unsubstituted; and provided that one of $R_3$ and $R_4$ is absent, and where $R_3$ is absent, the nitrogen on which $R_3$ is drawn is part of a double bond, and where $R_4$ is absent, the nitrogen on which $R_4$ is drawn is part of a double bond.

In another embodiment, the compounds of the invention consists of the formula:

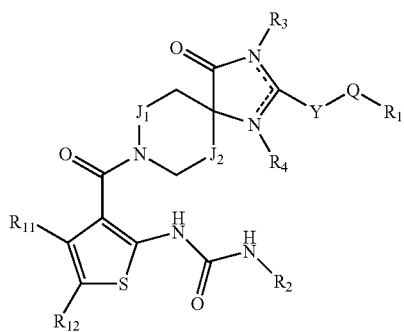

or a hydrate, solvate, ester, tautomer, enantiomer, or pharmaceutically acceptable salt thereof,
wherein
$J_1$ and $J_2$ are each independently selected from the group consisting of —$(CH_2)$— and —$(CH_2)_2$—, provided that $J_1$ and $J_2$ cannot both be —$(CH_2)_2$—;

Y is selected from the group consisting of a bond, —$CH_2$—, —$(CH_2)_2$—, —NH—$CH_2$—, and —$CH_2$—NH—;

Q is selected from the group consisting of a bond, —C(O)—, —C(O)O—, —NH—, —O—, —S—, —S(O)—, and —S(O)$_2$—;

R$_1$ is selected from the group consisting of hydrogen, halo, nitro, cyano, thio, oxy, hydroxy, carbonyloxy, (C$_{1-10}$)alkoxy, (C$_{4-12}$)aryloxy, hetero(C$_{1-10}$)aryloxy, (C$_{3-12}$)cycloalkyloxy, hetero(C$_{3-12}$)cycloalkyloxy, carbonyl, oxycarbonyl, aminocarbonyl, amino, (C$_{1-10}$)alkylamino, sulfonamido, imino, sulfonyl, sulfinyl, (C$_{1-10}$)alkyl, halo(C$_{1-10}$)alkyl, hydroxy(C$_{1-10}$)alkyl, carbonyl(C$_{1-10}$)alkyl, thiocarbonyl(C$_{1-10}$)alkyl, sulfonyl(C$_{1-10}$)alkyl, sulfinyl(C$_{1-10}$)alkyl, aza(C$_{1-10}$)alkyl, (C$_{1-10}$)oxaalkyl, (C$_{1-10}$)oxoalkyl, imino(C$_{1-10}$)alkyl, (C$_{3-12}$)cycloalkyl(C$_{1-5}$)alkyl, hetero(C$_{3-12}$)cycloalkyl(C$_{1-10}$)alkyl, aryl(C$_{1-10}$)alkyl, hetero(C$_{1-10}$)aryl(C$_{1-5}$)alkyl, (C$_{9-12}$)bicycloaryl(C$_{1-5}$)alkyl, hetero(C$_{8-12}$)bicycloaryl(C$_{1-5}$)alkyl, hetero(C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{1-10}$)aryl, (C$_{9-12}$)bicycloaryl, and hetero(C$_{4-12}$)bicycloaryl, each substituted or unsubstituted;

R$_2$ is substituted or unsubstituted alkyl;

R$_3$ and R$_4$ are each independently selected from the group consisting of hydrogen, halo, nitro, cyano, thio, oxy, hydroxy, carbonyloxy, (C$_{1-10}$)alkoxy, (C$_{4-12}$)aryloxy, hetero(C$_{1-10}$)aryloxy, carbonyl, oxycarbonyl, aminocarbonyl, amino, (C$_{1-10}$)alkylamino, sulfonamido, imino, sulfonyl, sulfinyl, (C$_{1-10}$)alkyl, halo(C$_{1-10}$)alkyl, hydroxy(C$_{1-10}$)alkyl, carbonyl(C$_{1-10}$)alkyl, thiocarbonyl(C$_{1-10}$)alkyl, sulfonyl(C$_{1-10}$)alkyl, sulfinyl(C$_{1-10}$)alkyl, aza(C$_{1-10}$)alkyl, (C$_{1-10}$)Oxaalkyl, (C$_{1-10}$)Oxoalkyl, imino(C$_{1-10}$)alkyl, (C$_{3-12}$)cycloalkyl(C$_{1-5}$)alkyl, hetero(C$_{3-12}$)cycloalkyl(C$_{1-10}$)alkyl, aryl(C$_{1-10}$)alkyl, hetero(C$_{1-10}$)aryl(C$_{1-5}$)alkyl, (C$_{9-12}$)bicycloaryl(C$_{1-5}$)alkyl, hetero(C$_{8-2}$)bicycloaryl(C$_{1-5}$)alkyl, hetero(C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{1-10}$)aryl, (C$_{9-12}$)bicycloaryl, and hetero(C$_{4-12}$)bicycloaryl, each substituted or unsubstituted;

R$_{11}$ and R$_{12}$ are each independently selected from the group consisting of H, halo, nitro, cyano, thio, oxy, hydroxy, carbonyloxy, (C$_{1-10}$)alkoxy, (C$_{4-12}$)aryloxy, hetero(C$_{1-10}$)aryloxy, carbonyl, oxycarbonyl, aminocarbonyl, amino, (C$_{1-10}$)alkylamino, sulfonamido, imino, sulfonyl, sulfinyl, (C$_{1-10}$)alkyl, halo(C$_{1-10}$)alkyl, hydroxy(C$_{1-10}$)alkyl, carbonyl(C$_{1-10}$)alkyl, thiocarbonyl(C$_{1-10}$)alkyl, sulfonyl(C$_{1-10}$)alkyl, sulfinyl(C$_{1-10}$)alkyl, aza(C$_{1-10}$)alkyl, (C$_{1-10}$)oxaalkyl, (C$_{1-10}$)oxoalkyl, imino(C$_{1-10}$)alkyl, (C$_{3-12}$)cycloalkyl(C$_{1-5}$)alkyl, hetero(C$_{3-12}$)cycloalkyl(C$_{1-10}$)alkyl, aryl(C$_{1-10}$)alkyl, hetero(C$_{1-10}$)aryl(C$_{1-5}$)alkyl, (C$_{9-12}$)bicycloaryl(C$_{1-5}$)alkyl, hetero(C$_{8-2}$)bicycloaryl(C$_{1-5}$)alkyl, hetero(C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{1-10}$)aryl, (C$_{9-12}$)bicycloaryl, and hetero(C$_{4-12}$)bicycloaryl, each substituted or unsubstituted; or R$_{11}$ and R$_{12}$ are taken together to form a ring selected from the group consisting of substituted or unsubstituted cycloalkyl, substituted or unsubstituted heterocycloalkyl, substituted or unsubstituted aryl, and substituted or unsubstituted heteroaryl; and provided that one of R$_3$ and R$_4$ is absent, and where R$_3$ is absent, the nitrogen on which R$_3$ is drawn is part of a double bond, and where R$_4$ is absent, the nitrogen on which R$_4$ is drawn is part of a double bond.

In some variations of the preceding embodiments, R$_{11}$, R$_{12}$ and R$_1$, when present, are each independently selected from the group consisting of H, (C$_{1-6}$)alkoxy, (C$_{4-6}$)aryloxy, hetero(C$_{1-5}$)aryloxy, carbonyl, oxycarbonyl, aminocarbonyl, amino, (C$_{1-6}$)alkylamino, (C$_{1-6}$)alkyl, halo(C$_{1-6}$)alkyl, hydroxy(C$_{1-6}$)alkyl, carbonyl(C$_{1-6}$)alkyl, thiocarbonyl(C$_{1-6}$)alkyl, sulfonyl(C$_{1-6}$)alkyl, sulfinyl(C$_{1-6}$)alkyl, (C$_{1-6}$)aza alkyl, (C$_{1-6}$)oxaalkyl, (C$_{3-6}$)cycloalkyl(C$_{1-5}$)alkyl, hetero(C$_{1-5}$)cycloalkyl(C$_{1-6}$)alkyl, (C$_{4-6}$)aryl(C$_{1-6}$)alkyl, hetero(C$_{1-5}$)aryl(C$_{1-5}$)alkyl, hetero(C$_{1-6}$)alkyl, (C$_{3-6}$)cycloalkyl, hetero(C$_{1-5}$)cycloalkyl, (C$_{4-6}$)aryl, and hetero(C$_{1-15}$)aryl, each substituted or unsubstituted; or R$_{11}$ and R$_{12}$, or R$_{12}$ and R$_{13}$, are taken together to form a ring selected from the group consisting of substituted or unsubstituted (C$_{3-6}$)cycloalkyl, substituted or unsubstituted hetero(C$_{1-5}$)cycloalkyl, substituted or unsubstituted (C$_{4-6}$)aryl and substituted or unsubstituted hetero(C$_{1-5}$)aryl.

In other variations, R$_{11}$ and R$_{12}$ are taken together to form a ring selected from the group consisting of substituted or unsubstituted cycloalkyl, substituted or unsubstituted heterocycloalkyl, substituted or unsubstituted aryl, and substituted or unsubstituted heteroaryl.

In another embodiment, the compounds of the invention consist of the formula:

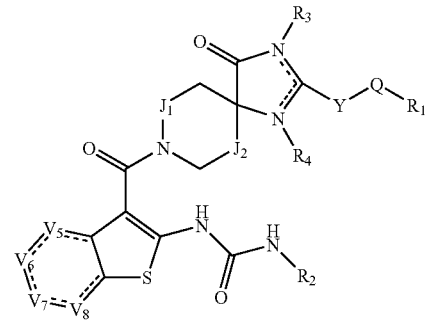

or a hydrate, solvate, ester, tautomer, enantiomer, or pharmaceutically acceptable salt thereof, wherein J$_1$ and J$_2$ are each independently selected from the group consisting of —(CH$_2$)— and —(CH$_2$)$_2$—, provided that J$_1$ and J$_2$ cannot both be —(CH$_2$)$_2$—;

Y is selected from the group consisting of a bond, —CH$_2$—, —(CH$_2$)$_2$—, —NH—CH$_2$—, and —CH$_2$—NH—;

Q is selected from the group consisting of a bond, —C(O)—, —C(O)O—, —NH—, —O—, —S—, —S(O)—, and —S(O)$_2$—;

V$_5$ is CR$_{15}$R$_{15'}$, NR$_{15'}$, O, or S;
V$_6$ is CR$_{16}$R$_{16'}$, NR$_{16'}$, O, or S;
V$_7$ is CR$_{17}$R$_{17'}$, NR$_{17'}$, O, or S;
V$_8$ is CR$_{18}$R$_{18'}$, NR$_{18'}$, O, or S;

R$_1$ is selected from the group consisting of hydrogen, halo, nitro, cyano, thio, oxy, hydroxy, carbonyloxy, (C$_{1-10}$)alkoxy, (C$_{4-12}$)aryloxy, hetero(C$_{1-10}$)aryloxy, (C$_{3-12}$)cycloalkyloxy, hetero(C$_{3-12}$)cycloalkyloxy, carbonyl, oxycarbonyl, aminocarbonyl, amino, (C$_{1-10}$)alkylamino, sulfonamido, imino, sulfonyl, sulfinyl, (C$_{1-10}$)alkyl, halo(C$_{1-10}$)alkyl, hydroxy(C$_{1-10}$)alkyl, carbonyl(C$_{1-10}$)alkyl, thiocarbonyl(C$_{1-10}$)alkyl, sulfonyl(C$_{1-10}$)alkyl, sulfinyl(C$_{1-10}$)alkyl, aza(C$_{1-10}$)alkyl, (C$_{1-10}$)oxaalkyl, (C$_{1-10}$)oxoalkyl, imino(C$_{1-10}$)alkyl, (C$_{3-12}$)cycloalkyl(C$_{1-5}$)alkyl, hetero(C$_{3-12}$)cycloalkyl(C$_{1-10}$)alkyl, aryl(C$_{1-10}$)alkyl, hetero(C$_{1-10}$)aryl(C$_{1-5}$)alkyl, (C$_{9-12}$)bicycloaryl(C$_{1-5}$)alkyl, hetero(C$_{8-12}$)bicycloaryl(C$_{1-5}$)alkyl, hetero(C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{1-10}$)aryl, (C$_{9-12}$)bicycloaryl, and hetero(C$_{4-12}$)bicycloaryl, each substituted or unsubstituted;

R$_2$ is substituted or unsubstituted alkyl;

$R_3$ and $R_4$ are each independently selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl $(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero $(C_{1-10})$aryl$(C_{1-5})$alkyl, $(C_{9-12})$bicycloaryl$(C_{1-5})$alkyl, hetero $(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero $(C_{3-12})$bicycloalkyl, $(C_{4-12})$aryl, hetero$(C_{1-10})$aryl, $(C_{9-12})$bicycloaryl, and hetero$(C_{4-12})$bicycloaryl, each substituted or unsubstituted;

$R_{15}$, $R_{15'}$, $R_{16}$, $R_{16'}$, $R_{17}$, $R_{17'}$, $R_{18}$ and $R_{18'}$ are each independently selected from the group consisting of H, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl $(C_{1-10})$alkyl, sulfonyl$(C_{1-10})$alkyl, sulfinyl$(C_{1-10})$alkyl, aza $(C_{1-10})$alkyl, $(C_{1-10})$oxaalkyl, $(C_{1-10})$Oxoalkyl, imino$(C_{1-10})$alkyl, $(C_{3-12})$cycloalkyl$(C_{1-5})$alkyl, hetero$(C_{3-12})$cycloalkyl $(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl $(C_{1-5})$alkyl, hetero$(C_{1-10})$alkyl, $(C_{3-12})$cycloalkyl, hetero $(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl, and hetero$(C_{4-12})$bicycloaryl, each substituted or unsubstituted, or $R_{15'}$, $R_{16'}$, $R_{17'}$, and $R_{18'}$ are each independently absent when the atom to which it is bound forms part of a double bond; and provided that one of $R_3$ and $R_4$ is absent, and where $R_3$ is absent, the nitrogen on which $R_3$ is drawn is part of a double bond, and where $R_4$ is absent, the nitrogen on which $R_4$ is drawn is part of a double bond.

In another embodiment, the compounds of the invention consist of the formula:

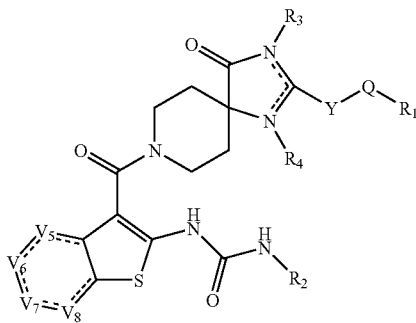

or a hydrate, solvate, ester, tautomer, enantiomer, or pharmaceutically acceptable salt thereof, wherein Y is selected from the group consisting of a bond, —$CH_2$—, —$(CH_2)_2$—, —NH—$CH_2$—, and —$CH_2$—NH—;

Q is selected from the group consisting of a bond, —C(O)—, —C(O)O—, —NH—, —O—, —S—, —S(O)—, and —$S(O)_2$—;

$V_5$ is $CR_{15}R_{15'}$, $NR_{15'}$, O, or S;
$V_6$ is $CR_{16}R_{16'}$, $NR_{16'}$, O, or S;
$V_7$ is $CR_{17}R_{17'}$, $NR_{17'}$, O, or S;
$V_8$ is $CR_{18}R_{18'}$, $NR_{18'}$, O, or S;

$R_1$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, $(C_{3-12})$cycloalkyloxy, hetero$(C_{3-12})$cycloalkyloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy $(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl, and hetero$(C_{4-12})$bicycloaryl, each substituted or unsubstituted;

$R_2$ is substituted or unsubstituted alkyl;

$R_3$ and $R_4$ are each independently selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl $(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero $(C_{1-10})$aryl$(C_{1-5})$alkyl, $(C_{9-12})$bicycloaryl$(C_{1-5})$alkyl, hetero $(C_{8-2})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero $(C_{3-12})$bicycloalkyl, $(C_{4-12})$aryl, hetero$(C_{1-10})$aryl, $(C_{9-12})$bicycloaryl, and hetero$(C_{4-12})$bicycloaryl, each substituted or unsubstituted;

$R_{15}$, $R_{15'}$, $R_{16}$, $R_{16'}$, $R_{17}$, $R_{17'}$, $R_{18}$ and $R_{18'}$ are each independently selected from the group consisting of H, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl $(C_{1-10})$alkyl, sulfonyl$(C_{1-10})$alkyl, sulfinyl$(C_{1-10})$alkyl, aza $(C_{1-10})$alkyl, $(C_{1-10})$Oxaalkyl, $(C_{1-10})$Oxoalkyl, imino$(C_{1-10})$alkyl, $(C_{3-12})$cycloalkyl$(C_{1-5})$alkyl, hetero$(C_{3-12})$cycloalkyl $(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-2})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl, and hetero $(C_{4-12})$bicycloaryl, each substituted or unsubstituted, or $R_{15'}$, $R_{16'}$, $R_{17'}$, and $R_{18'}$ are each independently absent when the atom to which it is bound forms part of a double bond; and provided that one of $R_3$ and $R_4$ is absent, and where $R_3$ is absent, the nitrogen on which $R_3$ is drawn is part of a double bond, and where $R_4$ is absent, the nitrogen on which $R_4$ is drawn is part of a double bond.

In another embodiment, the compounds of the invention consist of the formula:

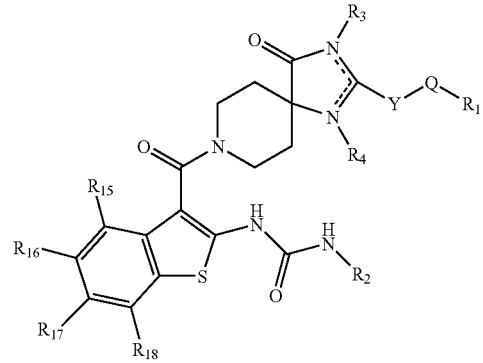

or a hydrate, solvate, ester, tautomer, enantiomer, or pharmaceutically acceptable salt thereof, wherein Y is selected from the group consisting of a bond, —CH$_2$—, —(CH$_2$)$_2$—, —NH—CH$_2$—, and —CH$_2$—NH—;

Q is selected from the group consisting of a bond, —C(O)—, —C(O)O—, —NH—, —O—, —S—, —S(O)—, and —S(O)$_2$—, R$_1$ is selected from the group consisting of hydrogen, halo, nitro, cyano, thio, oxy, hydroxy, carbonyloxy, (C$_{1-10}$)alkoxy, (C$_{4-12}$)aryloxy, hetero(C$_{1-10}$)aryloxy, (C$_{3-12}$)cycloalkyloxy, hetero(C$_{3-12}$)cycloalkyloxy, carbonyl, oxycarbonyl, aminocarbonyl, amino, (C$_{1-10}$)alkylamino, sulfonamido, imino, sulfonyl, sulfinyl, (C$_{1-10}$)alkyl, halo(C$_{1-10}$)alkyl, hydroxy (C$_{1-10}$)alkyl, carbonyl(C$_{1-10}$)alkyl, thiocarbonyl(C$_{1-10}$)alkyl, sulfonyl(C$_{1-10}$)alkyl, sulfinyl(C$_{1-10}$)alkyl, aza(C$_{1-10}$)alkyl, (C$_{1-10}$)oxaalkyl, (C$_{1-10}$)oxoalkyl, imino(C$_{1-10}$)alkyl, (C$_{3-12}$) cycloalkyl(C$_{1-5}$)alkyl, hetero(C$_{3-12}$)cycloalkyl(C$_{1-10}$)alkyl, aryl(C$_{1-10}$)alkyl, hetero(C$_{1-10}$)aryl(C$_{1-5}$)alkyl, (C$_{9-12}$)bicycloaryl(C$_{1-5}$)alkyl, hetero(C$_{8-2}$)bicycloaryl(C$_{1-5}$)alkyl, hetero(C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{1-10}$)aryl, (C$_{9-12}$)bicycloaryl, and hetero(C$_{4-12}$)bicycloaryl, each substituted or unsubstituted;

R$_2$ is substituted or unsubstituted alkyl;

R$_3$ and R$_4$ are each independently selected from the group consisting of hydrogen, halo, nitro, cyano, thio, oxy, hydroxy, carbonyloxy, (C$_{1-10}$)alkoxy, (C$_{4-12}$)aryloxy, hetero(C$_{1-10}$)aryloxy, carbonyl, oxycarbonyl, aminocarbonyl, amino, (C$_{1-10}$)alkylamino, sulfonamido, imino, sulfonyl, sulfinyl, (C$_{1-10}$)alkyl, halo(C$_{1-10}$)alkyl, hydroxy(C$_{1-10}$)alkyl, carbonyl (C$_{1-10}$)alkyl, thiocarbonyl(C$_{1-10}$)alkyl, sulfonyl(C$_{1-10}$)alkyl, sulfinyl(C$_{1-10}$)alkyl, aza(C$_{1-10}$)alkyl, (C$_{1-10}$)oxaalkyl, (C$_{1-10}$) oxoalkyl, imino(C$_{1-10}$)alkyl, (C$_{3-12}$)cycloalkyl(C$_{1-5}$)alkyl, hetero(C$_{3-12}$)cycloalkyl(C$_{1-10}$)alkyl, aryl(C$_{1-10}$)alkyl, hetero (C$_{1-10}$)aryl(C$_{1-5}$)alkyl, (C$_{9-12}$)bicycloaryl(C$_{1-5}$)alkyl, hetero (C$_{8-12}$)bicycloaryl(C$_{1-5}$)alkyl, hetero(C$_{1-10}$)alkyl, (C$_{3-12}$)cycloalkyl, hetero(C$_{3-12}$)cycloalkyl, (C$_{9-12}$)bicycloalkyl, hetero (C$_{3-12}$)bicycloalkyl, (C$_{4-12}$)aryl, hetero(C$_{1-10}$)aryl, (C$_{9-12}$) bicycloaryl, and hetero(C$_{4-12}$)bicycloaryl, each substituted or unsubstituted; and R$_{15}$, R$_{16}$, R$_{17}$, and R$_{18}$ are each independently selected from the group consisting of H, halo, nitro, cyano, thio, oxy, hydroxy, carbonyloxy, (C$_{1-10}$)alkoxy, (C$_{4-12}$)aryloxy, hetero (C$_{1-10}$)aryloxy, carbonyl, oxycarbonyl, aminocarbonyl, amino, (C$_{1-10}$)alkylamino, sulfonamido, imino, sulfonyl, sulfinyl, (C$_{1-10}$)alkyl, halo(C$_{1-10}$)alkyl, hydroxy(C$_{1-10}$)alkyl, carbonyl(C$_{1-10}$)alkyl, thiocarbonyl(C$_{1-10}$)alkyl, sulfonyl (C$_{1-10}$)alkyl, sulfinyl(C$_{1-10}$)alkyl, aza(C$_{1-10}$)alkyl, (C$_{1-10}$)oxaalkyl, (C$_{1-10}$)oxoalkyl, imino(C$_{1-10}$)alkyl, (C$_{3-12}$)cycloalkyl (C$_{1-5}$)alkyl, hetero(C$_{3-12}$)cycloalkyl(C$_{1-10}$)alkyl, aryl(C$_{1-10}$) alkyl, hetero(C$_{1-10}$)aryl(C$_{1-5}$)alkyl, (C$_{9-12}$)bicycloaryl(C$_{1-5}$) alkyl, hetero(C$_{8-2}$)bicycloaryl(C$_{1-5}$)alkyl, hetero(C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero (C$_{1-10}$)aryl, (C$_{9-12}$)bicycloaryl, and hetero(C$_{4-12}$)bicycloaryl, each substituted or unsubstituted.

In another embodiment, the compounds of the invention consist of the formula:

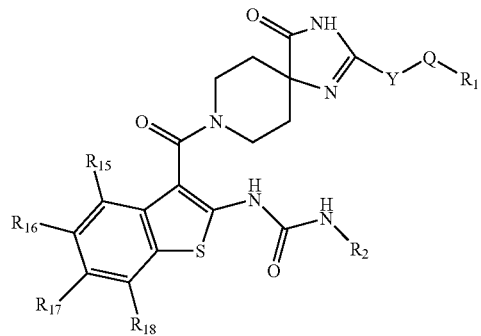

or a hydrate, solvate, ester, tautomer, enantiomer, or pharmaceutically acceptable salt thereof, wherein Y is selected from the group consisting of a bond, —CH$_2$—, —(CH$_2$)$_2$—, —NH—CH$_2$—, and —CH$_2$—NH—;

Q is selected from the group consisting of a bond, —C(O)—, —C(O)O—, —NH—, —O—, —S—, —S(O)—, and —S(O)$_2$—, R$_1$ is selected from the group consisting of hydrogen, halo, nitro, cyano, thio, oxy, hydroxy, carbonyloxy, (C$_{1-10}$)alkoxy, (C$_{4-12}$)aryloxy, hetero(C$_{1-10}$)aryloxy, (C$_{3-12}$)cycloalkyloxy, hetero(C$_{3-12}$)cycloalkyloxy, carbonyl, oxycarbonyl, aminocarbonyl, amino, (C$_{1-10}$)alkylamino, sulfonamido, imino, sulfonyl, sulfinyl, (C$_{1-10}$)alkyl, halo(C$_{1-10}$)alkyl, hydroxy (C$_{1-10}$)alkyl, carbonyl(C$_{1-10}$)alkyl, thiocarbonyl(C$_{1-10}$)alkyl, sulfonyl(C$_{1-10}$)alkyl, sulfinyl(C$_{1-10}$)alkyl, aza(C$_{1-10}$)alkyl, (C$_{1-10}$)oxaalkyl, (C$_{1-10}$)oxoalkyl, imino(C$_{1-10}$)alkyl, (C$_{3-12}$) cycloalkyl(C$_{1-5}$)alkyl, hetero(C$_{3-12}$)cycloalkyl(C$_{1-10}$)alkyl, aryl(C$_{1-10}$)alkyl, hetero(C$_{1-10}$)aryl(C$_{1-5}$)alkyl, (C$_{9-12}$)bicycloaryl(C$_{1-5}$)alkyl, hetero(C$_{8-12}$)bicycloaryl(C$_{1-5}$)alkyl, hetero(C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{1-10}$)aryl, (C$_{9-12}$)bicycloaryl, and hetero(C$_{4-12}$)bicycloaryl, each substituted or unsubstituted;

R$_2$ is substituted or unsubstituted alkyl; and

R$_{15}$, R$_{16}$, R$_{17}$, and R$_{18}$ are each independently selected from the group consisting of H, halo, nitro, cyano, thio, oxy, hydroxy, carbonyloxy, (C$_{1-10}$)alkoxy, (C$_{4-12}$)aryloxy, hetero (C$_{1-10}$)aryloxy, carbonyl, oxycarbonyl, aminocarbonyl, amino, (C$_{1-10}$)alkylamino, sulfonamido, imino, sulfonyl, sulfinyl, (C$_{1-10}$)alkyl, halo(C$_{1-10}$)alkyl, hydroxy(C$_{1-10}$)alkyl, carbonyl(C$_{1-10}$)alkyl, thiocarbonyl(C$_{1-10}$)alkyl, sulfonyl (C$_{1-10}$)alkyl, sulfinyl(C$_{1-10}$)alkyl, aza(C$_{1-10}$)alkyl, (C$_{1-10}$)oxaalkyl, (C$_{1-10}$)oxoalkyl, imino(C$_{1-10}$)alkyl, (C$_{3-12}$)cycloalkyl (C$_{1-5}$)alkyl, hetero(C$_{3-12}$)cycloalkyl(C$_{1-10}$)alkyl, aryl(C$_{1-10}$) alkyl, hetero(C$_{1-10}$)aryl(C$_{1-5}$)alkyl, (C$_{9-12}$)bicycloaryl(C$_{1-5}$) alkyl, hetero(C$_{8-12}$)bicycloaryl(C$_{1-5}$)alkyl, hetero(C$_{1-10}$) alkyl, (C$_{3-12}$)cycloalkyl, hetero(C$_{3-12}$)cycloalkyl, (C$_{9-12}$) bicycloalkyl, hetero(C$_{3-12}$)bicycloalkyl, (C$_{4-12}$)aryl, hetero (C$_{1-10}$)aryl, (C$_{9-2}$)bicycloaryl, and hetero(C$_{4-12}$)bicycloaryl, each substituted or unsubstituted.

In another embodiment, the compounds of the invention consist of the formula:

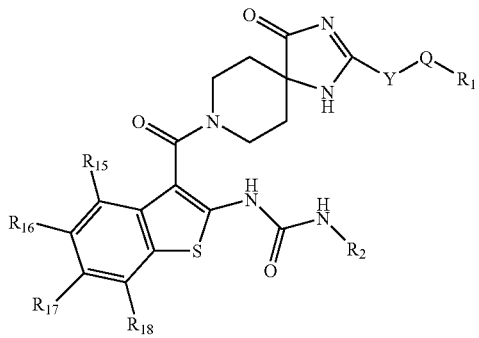

or a hydrate, solvate, ester, tautomer, enantiomer, or pharmaceutically acceptable salt thereof, wherein Y is selected from the group consisting of a bond, —$CH_2$—, —$(CH_2)_2$—, —NH—$CH_2$—, and —$CH_2$—NH—;

Q is selected from the group consisting of a bond, —C(O)—, —C(O)O—, —NH—, —O—, —S—, —S(O)—, and —$S(O)_2$—;

$R_1$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, ($C_{3-12}$)cycloalkyloxy, hetero($C_{3-12}$)cycloalkyloxy, carbonyl, oxycarbonyl, aminocarbonyl, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)Oxaalkyl, ($C_{1-10}$)Oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl, and hetero($C_{4-12}$)bicycloaryl, each substituted or unsubstituted;

$R_2$ is substituted or unsubstituted alkyl; and $R_{15}$, $R_{15'}$, $R_{16}$, $R_{16'}$, $R_{17}$, $R_{17'}$, $R_{18}$ and $R_{18'}$ are each independently selected from the group consisting of H, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, aminocarbonyl, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl, and hetero($C_{4-12}$)bicycloaryl, each substituted or unsubstituted, or $R_{15'}$, $R_{16'}$, $R_{17'}$, and $R_{18'}$ are each independently absent when the atom to which it is bound forms part of a double bond.

In another embodiment, the compounds of the invention consist of the formula:

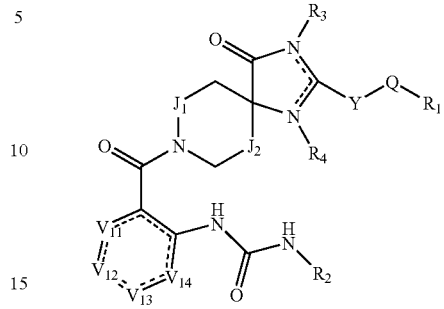

or a hydrate, solvate, ester, tautomer, enantiomer, or pharmaceutically acceptable salt thereof, wherein $J_1$ and $J_2$ are each independently selected from the group consisting of —($CH_2$)— and —$(CH_2)_2$—, provided that $J_1$ and $J_2$ cannot both be —$(CH_2)_2$—;

Y is selected from the group consisting of a bond, —$CH_2$—, —$(CH_2)_2$—, —NH—$CH_2$—, and —$CH_2$—NH—;

Q is selected from the group consisting of a bond, —C(O)—, —C(O)O—, —NH—, —O—, —S—, —S(O)—, and —$S(O)_2$—;

the ring comprising $V_{11}$, $V_{12}$, $V_{13}$ and $V_{14}$ is selected from the group of substituted or unsubstituted aryl and substituted or unsubstituted heteroaryl;

$V_{11}$ is $CR_{21}$ or N;
$V_{12}$ is $CR_{22}$ or N;
$V_{13}$ is $CR_{23}$ or N;
$V_{14}$ is $CR_{24}$ or N;

$R_1$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, ($C_{3-12}$)cycloalkyloxy, hetero($C_{3-12}$)cycloalkyloxy, carbonyl, oxycarbonyl, aminocarbonyl, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl, and hetero($C_{4-12}$)bicycloaryl, each substituted or unsubstituted;

$R_2$ is substituted or unsubstituted alkyl;

$R_3$ and $R_4$ are each independently selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, aminocarbonyl, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl, and hetero($C_{4-12}$)bicycloaryl, each substituted or unsubstituted;

$R_{21}$, $R_{22}$, $R_{23}$ and $R_{24}$ are each independently selected from the group consisting of H, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl, and hetero$(C_{4-12})$bicycloaryl, each substituted or unsubstituted; or $R_{21}$ and $R_{22}$, or $R_{22}$ and $R_{23}$, or $R_{23}$ and $R_{24}$, are taken together to form a ring selected from the group consisting of substituted or unsubstituted cycloalkyl, substituted or unsubstituted heterocycloalkyl, substituted or unsubstituted aryl, and substituted or unsubstituted heteroaryl; and provided that one of $R_3$ and $R_4$ is absent, and where $R_3$ is absent, the nitrogen on which $R_3$ is drawn is part of a double bond, and where $R_4$ is absent, the nitrogen on which $R_4$ is drawn is part of a double bond.

In another embodiment, the compounds of the invention consist of the formula:

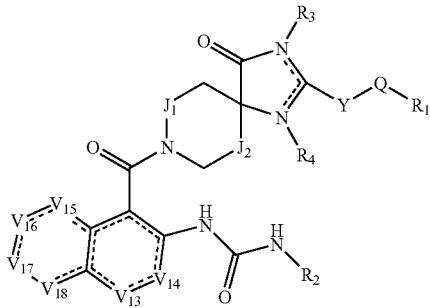

or a hydrate, solvate, ester, tautomer, enantiomer, or pharmaceutically acceptable salt thereof, wherein $J_1$ and $J_2$ are each independently selected from the group consisting of —(CH$_2$)— and —(CH$_2$)$_2$—, provided that $J_1$ and $J_2$ cannot both be —(CH$_2$)$_2$—;

Y is selected from the group consisting of a bond, —CH$_2$—, —(CH$_2$)$_2$—, —NH—CH$_2$—, and —CH$_2$—NH—;

Q is selected from the group consisting of a bond, —C(O)—, —C(O)O—, —NH—, —O—, —S—, —S(O)—, and —S(O)$_2$—;

the ring comprising $V_{13}$ and $V_{14}$ is selected from the group of substituted or unsubstituted aryl and substituted or unsubstituted heteroaryl;

$V_{13}$ is $CR_{23}$ or N;

$V_{14}$ is $CR_{24}$ or N;

$V_{15}$ is $CR_{25}R_{25'}$, $NR_{25'}$, O, or S;

$V_{16}$ is $CR_{26}R_{26'}$, $NR_{26'}$, O, or S;

$V_{17}$ is $CR_{27}R_{27'}$, $NR_{27'}$, O, or S;

$V_{18}$ is $CR_{28}R_{28'}$, $NR_{28'}$, O, or S;

$R_1$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, $(C_{3-12})$cycloalkyloxy, hetero$(C_{3-12})$cycloalkyloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$Oxaalkyl, $(C_{1-10})$Oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-2})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl, and hetero$(C_{4-12})$bicycloaryl, each substituted or unsubstituted;

$R_2$ is substituted or unsubstituted alkyl;

$R_3$ and $R_4$ are each independently selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-2})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl, and hetero$(C_{4-12})$bicycloaryl, each substituted or unsubstituted;

$R_{23}$, $R_{24}$, $R_{25}$, $R_{25'}$, $R_{26}$, $R_{26'}$, $R_{27}$, $R_{27'}$, $R_{28}$ and $R_{28'}$ are each independently selected from the group consisting of H, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-2})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl, and hetero$(C_{4-12})$bicycloaryl, each substituted or unsubstituted, or $R_{25'}$, $R_{26'}$, $R_{27'}$, and $R_{28'}$ are each independently absent when the atom to which it is bound forms part of a double bond; and provided that one of $R_3$ and $R_4$ is absent, and where $R_3$ is absent, the nitrogen on which $R_3$ is drawn is part of a double bond, and where $R_4$ is absent, the nitrogen on which $R_4$ is drawn is part of a double bond.

In another embodiment, the compounds of the invention consist of the formula:

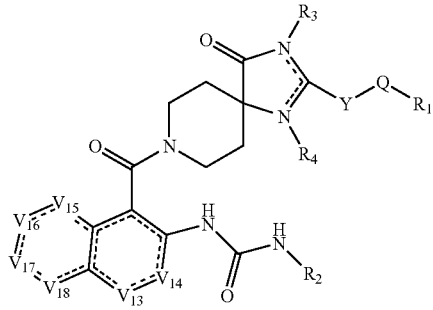

or a hydrate, solvate, ester, tautomer, enantiomer, or pharmaceutically acceptable salt thereof, wherein Y is selected from the group consisting of a bond, —$CH_2$—, —$(CH_2)_2$—, —NH—$CH_2$—, and —$CH_2$—NH—;

Q is selected from the group consisting of a bond, —C(O)—, —C(O)O—, —NH—, —O—, —S—, —S(O)—, and —$S(O)_2$—;

the ring comprising $V_{13}$ and $V_{14}$ is selected from the group of substituted or unsubstituted aryl and substituted or unsubstituted heteroaryl;

$V_{13}$ is $CR_{23}$ or N, $V_{14}$ is $CR_{24}$ or N, $V_{15}$ is $CR_{25}R_{25'}$, $NR_{25'}$, O, or S;

$V_{16}$ is $CR_{26}R_{26'}$, $NR_{26'}$, O, or S;

$V_{17}$ is $CR_{27}R_{27'}$, $NR_{27'}$, O, or S;

$V_{18}$ is $CR_{28}R_{28'}$, $NR_{28'}$, O, or S;

$R_1$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, $(C_{3-12})$cycloalkyloxy, hetero$(C_{3-12})$cycloalkyloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-2})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl, and hetero$(C_{4-12})$bicycloaryl, each substituted or unsubstituted;

$R_2$ is substituted or unsubstituted alkyl;

$R_3$ and $R_4$ are each independently selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-2})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl, and hetero$(C_{4-12})$bicycloaryl, each substituted or unsubstituted;

$R_{23}$, $R_{24}$, $R_{25}$, $R_{25'}$, $R_{26}$, $R_{26'}$, $R_{27}$, $R_{27'}$, $R_{28}$ and $R_{28'}$ are each independently selected from the group consisting of H, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl, and hetero$(C_{4-12})$bicycloaryl, each substituted or unsubstituted, or $R_{25'}$, $R_{26'}$, $R_{27'}$, and $R_{28'}$ are each independently absent when the atom to which it is bound forms part of a double bond; and provided that one of $R_3$ and $R_4$ is absent, and where $R_3$ is absent, the nitrogen on which $R_3$ is drawn is part of a double bond, and where $R_4$ is absent, the nitrogen on which $R_4$ is drawn is part of a double bond.

In another embodiment, the compounds of the invention consist of the formula:

or a hydrate, solvate, ester, tautomer, enantiomer, or pharmaceutically acceptable salt thereof, wherein Y is selected from the group consisting of a bond, —$CH_2$—, —$(CH_2)_2$—, —NH—$CH_2$—, and —$CH_2$—NH—;

Q is selected from the group consisting of a bond, —C(O)—, —C(O)O—, —NH—, —O—, —S—, —S(O)—, and —$S(O)_2$—;

$V_{15}$ is $CR_{25}R_{25'}$, $NR_{25'}$, O, or S;

$V_{16}$ is $CR_{26}R_{26'}$, $NR_{26'}$, O, or S;

$V_{17}$ is $CR_{27}R_{27'}$, $NR_{27'}$, O, or S;

$V_{18}$ is $CR_{28}R_{28'}$, $NR_{28'}$, O, or S;

$R_1$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, $(C_{3-12})$cycloalkyloxy, hetero$(C_{3-12})$cycloalkyloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-2})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl, and hetero$(C_{4-12})$bicycloaryl, each substituted or unsubstituted;

$R_2$ is substituted or unsubstituted alkyl;

$R_3$ and $R_4$ are each independently selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-2})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero ($C_{3-12}$)bicycloalkyl, ($C_{4-12}$)aryl, hetero($C_{1-10}$)aryl, ($C_{9-12}$)bicycloaryl, and hetero($C_{4-12}$)bicycloaryl, each substituted or unsubstituted;

$R_{25}$, $R_{25'}$, $R_{26}$, $R_{26'}$, $R_{27}$, $R_{27'}$, $R_{28}$ and $R_{28'}$ are each independently selected from the group consisting of H, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, aminocarbonyl, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)Oxaalkyl, ($C_{1-10}$)Oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-2}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl, and hetero($C_{4-12}$)bicycloaryl, each substituted or unsubstituted, or $R_{25'}$, $R_{26'}$, $R_{27'}$, and $R_{28'}$ are each independently absent when the atom to which it is bound forms part of a double bond; and provided that one of $R_3$ and $R_4$ is absent, and where $R_3$ is absent, the nitrogen on which $R_3$ is drawn is part of a double bond, and where $R_4$ is absent, the nitrogen on which $R_4$ is drawn is part of a double bond.

In another embodiment, the compounds of the invention consist of the formula:

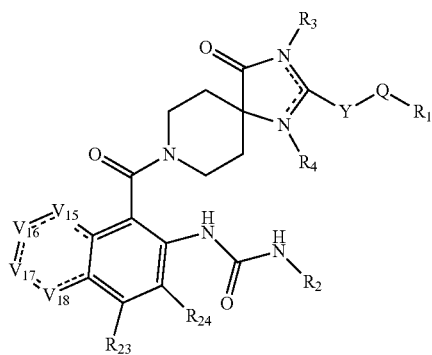

or a hydrate, solvate, ester, tautomer, enantiomer, or pharmaceutically acceptable salt thereof, wherein Y is selected from the group consisting of a bond, —CH$_2$—, —(CH$_2$)$_2$—, —NH—CH$_2$—, and —CH$_2$—NH—;

Q is selected from the group consisting of a bond, —C(O)—, —C(O)O—, —NH—, —O—, —S—, —S(O)—, and —S(O)$_2$—;

$V_{15}$ is $CR_{25}R_{25'}$, $NR_{25'}$, O, or S;
$V_{16}$ is $CR_{26}R_{26'}$, $NR_{26'}$, O, or S;
$V_{17}$ is $CR_{27}R_{27'}$, $NR_{27'}$, O, or S;
$V_{18}$ is $CR_{28}R_{28'}$, $NR_{28'}$, O, or S;

$R_1$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, ($C_{3-12}$)cycloalkyloxy, hetero($C_{3-12}$)cycloalkyloxy, carbonyl, oxycarbonyl, aminocarbonyl, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl, and hetero($C_{4-12}$)bicycloaryl, each substituted or unsubstituted;

$R_2$ is substituted or unsubstituted alkyl;

$R_3$ and $R_4$ are each independently selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, aminocarbonyl, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-2}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl, and hetero($C_{4-12}$)bicycloaryl, each substituted or unsubstituted;

$R_{23}$, $R_{24}$, $R_{25}$, $R_{25'}$, $R_{26}$, $R_{26'}$, $R_{27}$, $R_{27'}$, $R_{28}$ and $R_{28'}$ are each independently selected from the group consisting of H, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, aminocarbonyl, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl, and hetero($C_{4-12}$)bicycloaryl, each substituted or unsubstituted, or $R_{25'}$, $R_{26'}$, $R_{27'}$, and $R_{28'}$ are each independently absent when the atom to which it is bound forms part of a double bond; and provided that one of $R_3$ and $R_4$ is absent, and where $R_3$ is absent, the nitrogen on which $R_3$ is drawn is part of a double bond, and where $R_4$ is absent, the nitrogen on which $R_4$ is drawn is part of a double bond.

In another embodiment, the compounds of the invention consist of the formula:

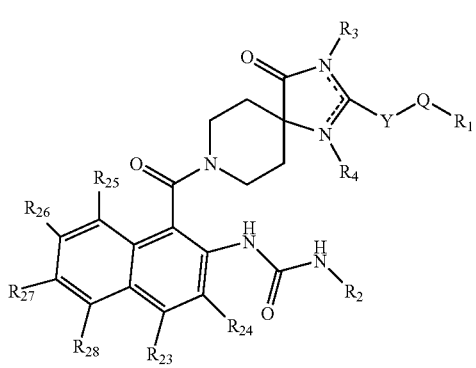

or a hydrate, solvate, ester, tautomer, enantiomer, or pharmaceutically acceptable salt thereof, wherein Y is selected from the group consisting of a bond, —CH$_2$—, —(CH$_2$)$_2$—, —NH—CH$_2$—, and —CH$_2$—NH—;

Q is selected from the group consisting of a bond, —C(O)—, —C(O)O—, —NH—, —O—, —S—, —S(O)—, and —S(O)$_2$—;

R$_1$ is selected from the group consisting of hydrogen, halo, nitro, cyano, thio, oxy, hydroxy, carbonyloxy, (C$_{1-10}$)alkoxy, (C$_{4-12}$)aryloxy, hetero(C$_{1-10}$)aryloxy, (C$_{3-12}$)cycloalkyloxy, hetero(C$_{3-12}$)cycloalkyloxy, carbonyl, oxycarbonyl, aminocarbonyl, amino, (C$_{1-10}$)alkylamino, sulfonamido, imino, sulfonyl, sulfinyl, (C$_{1-10}$)alkyl, halo(C$_{1-10}$)alkyl, hydroxy(C$_{1-10}$)alkyl, carbonyl(C$_{1-10}$)alkyl, thiocarbonyl(C$_{1-10}$)alkyl, sulfonyl(C$_{1-10}$)alkyl, sulfinyl(C$_{1-10}$)alkyl, aza(C$_{1-10}$)alkyl, (C$_{1-10}$)Oxaalkyl, (C$_{1-10}$)Oxoalkyl, imino(C$_{1-10}$)alkyl, (C$_{3-12}$)cycloalkyl(C$_{1-5}$)alkyl, hetero(C$_{3-12}$)cycloalkyl(C$_{1-10}$)alkyl, aryl(C$_{1-10}$)alkyl, hetero(C$_{1-10}$)aryl(C$_{1-5}$)alkyl, (C$_{9-12}$)bicycloaryl(C$_{1-5}$)alkyl, hetero(C$_{8-12}$)bicycloaryl(C$_{1-5}$)alkyl, hetero(C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{1-10}$)aryl, (C$_{9-12}$)bicycloaryl, and hetero(C$_{4-12}$)bicycloaryl, each substituted or unsubstituted;

R$_2$ is substituted or unsubstituted alkyl;

R$_3$ and R$_4$ are each independently selected from the group consisting of hydrogen, halo, nitro, cyano, thio, oxy, hydroxy, carbonyloxy, (C$_{1-10}$)alkoxy, (C$_{4-12}$)aryloxy, hetero(C$_{1-10}$)aryloxy, carbonyl, oxycarbonyl, aminocarbonyl, amino, (C$_{1-10}$)alkylamino, sulfonamido, imino, sulfonyl, sulfinyl, (C$_{1-10}$)alkyl, halo(C$_{1-10}$)alkyl, hydroxy(C$_{1-10}$)alkyl, carbonyl(C$_{1-10}$)alkyl, thiocarbonyl(C$_{1-10}$)alkyl, sulfonyl(C$_{1-10}$)alkyl, sulfinyl(C$_{1-10}$)alkyl, aza(C$_{1-10}$)alkyl, (C$_{1-10}$)oxaalkyl, (C$_{1-10}$)oxoalkyl, imino(C$_{1-10}$)alkyl, (C$_{3-12}$)cycloalkyl(C$_{1-5}$)alkyl, hetero(C$_{3-12}$)cycloalkyl(C$_{1-10}$)alkyl, aryl(C$_{1-10}$)alkyl, hetero(C$_{1-10}$)aryl(C$_{1-5}$)alkyl, (C$_{9-12}$)bicycloaryl(C$_{1-5}$)alkyl, hetero(C$_{8-2}$)bicycloaryl(C$_{1-5}$)alkyl, hetero(C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{1-10}$)aryl, (C$_{9-12}$)bicycloaryl, and hetero(C$_{4-12}$)bicycloaryl, each substituted or unsubstituted;

R$_{23}$, R$_{24}$ R$_{25}$, R$_{26}$, R$_{27}$, and R$_{28}$ are each independently selected from the group consisting of H, halo, nitro, cyano, thio, oxy, hydroxy, carbonyloxy, (C$_{1-10}$)alkoxy, (C$_{4-12}$)aryloxy, hetero(C$_{1-10}$)aryloxy, carbonyl, oxycarbonyl, aminocarbonyl, amino, (C$_{1-10}$)alkylamino, sulfonamido, imino, sulfonyl, sulfinyl, (C$_{1-10}$)alkyl, halo(C$_{1-10}$)alkyl, hydroxy(C$_{1-10}$)alkyl, carbonyl(C$_{1-10}$)alkyl, thiocarbonyl(C$_{1-10}$)alkyl, sulfonyl(C$_{1-10}$)alkyl, sulfinyl(C$_{1-10}$)alkyl, aza(C$_{1-10}$)alkyl, (C$_{1-10}$)oxaalkyl, (C$_{1-10}$)oxoalkyl, imino(C$_{1-10}$)alkyl, (C$_{3-12}$)cycloalkyl(C$_{1-5}$)alkyl, hetero(C$_{3-12}$)cycloalkyl(C$_{1-10}$)alkyl, aryl(C$_{1-10}$)alkyl, hetero(C$_{1-10}$)aryl(C$_{1-5}$)alkyl, (C$_{9-12}$)bicycloaryl(C$_{1-5}$)alkyl, hetero(C$_{8-12}$)bicycloaryl(C$_{1-5}$)alkyl, hetero(C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{1-10}$)aryl, (C$_{9-12}$)bicycloaryl, and hetero(C$_{4-12}$)bicycloaryl, each substituted or unsubstituted, or R$_{25'}$, R$_{26'}$, R$_{27'}$, and R$_{28'}$ are each independently absent when the atom to which it is bound forms part of a double bond; and provided that one of R$_3$ and R$_4$ is absent, and where R$_3$ is absent, the nitrogen on which R$_3$ is drawn is part of a double bond, and where R$_4$ is absent, the nitrogen on which R$_4$ is drawn is part of a double bond.

In another embodiment, the compounds of the invention consist of the formula:

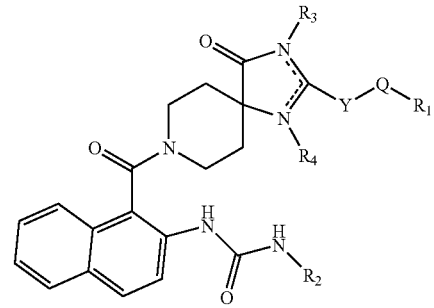

or a hydrate, solvate, ester, tautomer, enantiomer, or pharmaceutically acceptable salt thereof, wherein Y is selected from the group consisting of a bond, —CH$_2$—, —(CH$_2$)$_2$—, —NH—CH$_2$—, and —CH$_2$—NH—;

Q is selected from the group consisting of a bond, —C(O)—, —C(O)O—, —NH—, —O—, —S—, —S(O)—, and —S(O)$_2$—;

R$_1$ is selected from the group consisting of hydrogen, halo, nitro, cyano, thio, oxy, hydroxy, carbonyloxy, (C$_{1-10}$)alkoxy, (C$_{4-12}$)aryloxy, hetero(C$_{1-10}$)aryloxy, (C$_{3-12}$)cycloalkyloxy, hetero(C$_{3-12}$)cycloalkyloxy, carbonyl, oxycarbonyl, aminocarbonyl, amino, (C$_{1-10}$)alkylamino, sulfonamido, imino, sulfonyl, sulfinyl, (C$_{1-10}$)alkyl, halo(C$_{1-10}$)alkyl, hydroxy(C$_{1-10}$)alkyl, carbonyl(C$_{1-10}$)alkyl, thiocarbonyl(C$_{1-10}$)alkyl, sulfonyl(C$_{1-10}$)alkyl, sulfinyl(C$_{1-10}$)alkyl, aza(C$_{1-10}$)alkyl, (C$_{1-10}$)Oxaalkyl, (C$_{1-10}$)Oxoalkyl, imino(C$_{1-10}$)alkyl, (C$_{3-12}$)cycloalkyl(C$_{1-5}$)alkyl, hetero(C$_{3-12}$)cycloalkyl(C$_{1-10}$)alkyl, aryl(C$_{1-10}$)alkyl, hetero(C$_{1-10}$)aryl(C$_{1-5}$)alkyl, (C$_{9-12}$)bicycloaryl(C$_{1-5}$)alkyl, hetero(C$_{8-2}$)bicycloaryl(C$_{1-5}$)alkyl, hetero(C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{1-10}$)aryl, (C$_{9-12}$)bicycloaryl, and hetero(C$_{4-12}$)bicycloaryl, each substituted or unsubstituted;

R$_2$ is substituted or unsubstituted alkyl;

R$_3$ and R$_4$ are each independently selected from the group consisting of hydrogen, halo, nitro, cyano, thio, oxy, hydroxy, carbonyloxy, (C$_{1-10}$)alkoxy, (C$_{4-12}$)aryloxy, hetero(C$_{1-10}$)aryloxy, carbonyl, oxycarbonyl, aminocarbonyl, amino, (C$_{1-10}$)alkylamino, sulfonamido, imino, sulfonyl, sulfinyl, (C$_{1-10}$)alkyl, halo(C$_{1-10}$)alkyl, hydroxy(C$_{1-10}$)alkyl, carbonyl(C$_{1-10}$)alkyl, thiocarbonyl(C$_{1-10}$)alkyl, sulfonyl(C$_{1-10}$)alkyl, sulfinyl(C$_{1-10}$)alkyl, aza(C$_{1-10}$)alkyl, (C$_{1-10}$)oxaalkyl, (C$_{1-10}$)oxoalkyl, imino(C$_{1-10}$)alkyl, (C$_{3-12}$)cycloalkyl(C$_{1-5}$)alkyl, hetero(C$_{3-12}$)cycloalkyl(C$_{1-10}$)alkyl, aryl(C$_{1-10}$)alkyl, hetero(C$_{1-10}$)aryl(C$_{1-5}$)alkyl, (C$_{9-12}$)bicycloaryl(C$_{1-5}$)alkyl, hetero(C$_{8-2}$)bicycloaryl(C$_{1-5}$)alkyl, hetero(C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{1-10}$)aryl, (C$_{9-12}$)bicycloaryl, and hetero(C$_{4-12}$)bicycloaryl, each substituted or unsubstituted.

In some variations of the above embodiments and variations, when present, R$_{23}$, R$_{24}$, R$_{25}$, R$_{25'}$, R$_{26}$, R$_{26'}$, R$_{27}$, R$_{27'}$, R$_{28}$ and R$_{28'}$ are each independently selected from the group consisting of H, hydroxy, (C$_{1-6}$)alkoxy, (C$_{4-6}$)aryloxy, hetero(C$_{1-5}$)aryloxy, amino, (C$_{1-5}$)alkyl, halo(C$_{1-6}$)alkyl, hydroxy(C$_{1-6}$)alkyl, aza(C$_{1-6}$)alkyl, (C$_{1-6}$)oxaalkyl, (C$_{3-6}$)cycloalkyl(C$_{1-6}$)alkyl, hetero(C$_{1-5}$)cycloalkyl(C$_{1-6}$)alkyl, (C$_{4-6}$)aryl(C$_{1-6}$)alkyl, and hetero(C$_{1-5}$)aryl(C$_{1-6}$)alkyl, each substituted or unsubstituted; or R$_{25'}$, R$_{26'}$, R$_{27'}$, and R$_{28'}$ are each independently absent when the atom to which it is bound forms part of a double bond.

In another embodiment, the compounds of the invention consist of a formula selected from the group consisting of:

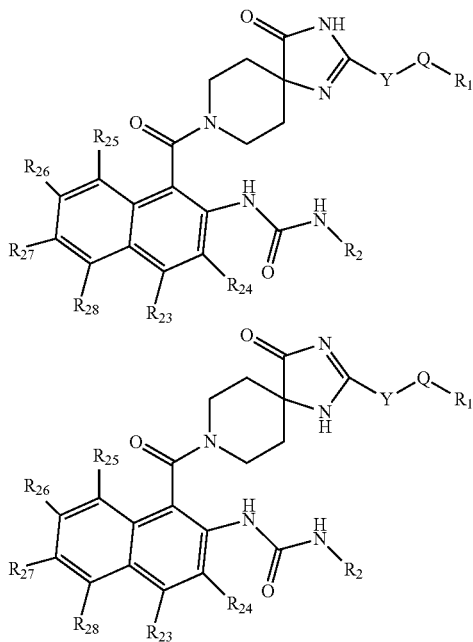

or a hydrate, solvate, ester, tautomer, enantiomer, or pharmaceutically acceptable salt thereof, wherein Y is selected from the group consisting of a bond, —$CH_2$—, —$(CH_2)_2$—, —NH—$CH_2$—, and —$CH_2$—NH—;

Q is selected from the group consisting of a bond, —C(O)—, —C(O)O—, —NH—, —O—, —S—, —S(O)—, and —$S(O)_2$—, $R_1$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, ($C_{3-12}$)cycloalkyloxy, hetero($C_{3-12}$)cycloalkyloxy, carbonyl, oxycarbonyl, aminocarbonyl, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl, and hetero($C_{4-12}$)bicycloaryl, each substituted or unsubstituted;

$R_2$ is substituted or unsubstituted alkyl; and $R_{23}$, $R_{24}$, $R_{25}$, $R_{26}$, $R_{27}$, and $R_{28}$, are each independently selected from the group consisting of H, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, aminocarbonyl, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxoalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl, and hetero($C_{4-12}$)bicycloaryl, each substituted or unsubstituted.

In some other variations, the compounds of the invention consist of a formula selected from the group consisting of:

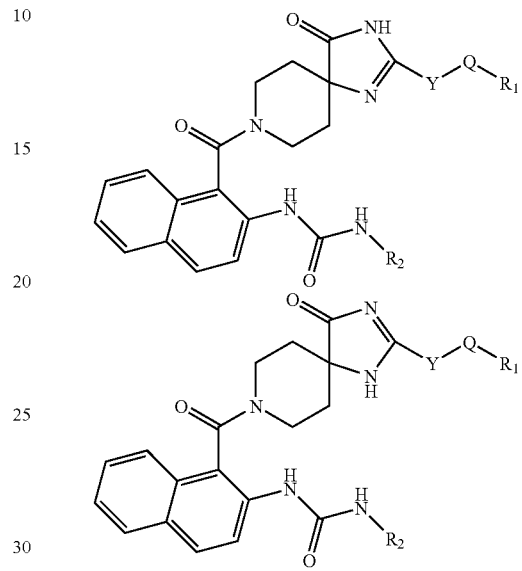

or a hydrate, solvate, ester, tautomer, enantiomer, or pharmaceutically acceptable salt thereof, wherein Y is selected from the group consisting of a bond, —$CH_2$—, —$(CH_2)_2$—, —NH—$CH_2$—, and —$CH_2$—NH—;

Q is selected from the group consisting of a bond, —C(O)—, —C(O)O—, —NH—, —O—, —S—, —S(O)—, and —$S(O)_2$—, $R_1$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, ($C_{3-12}$)cycloalkyloxy, hetero($C_{3-12}$)cycloalkyloxy, carbonyl, oxycarbonyl, aminocarbonyl, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxoalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-2}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl, and hetero($C_{4-12}$)bicycloaryl, each substituted or unsubstituted; and $R_2$ is substituted or unsubstituted alkyl.

Y

In some variations of the above embodiments of the compounds of the invention, Y is a bond. In other variations, Y is —$CH_2$—In still other variations, Y is —$(CH_2)_2$—In yet other variations, Y is —$CH_2$—NH—. In yet other variations, Y is —$CH_2$—NH—.

Q

In some variations of the above embodiments and variations of the compounds of the invention, Q is a bond. In other variations, Q is —C(O)—. In still other variations, Q is —C(O)O—. In still other variations, Q is —NH—. In still other variations, Q is —O—. In yet still other variations, Q is —S—. In yet still other variations, Q is —S(O)—. In yet still other variations, Q is —S(O)$_2$—.

R$^1$

In some variations of the above embodiments and variations of the compounds of the invention, R$_1$ is selected from the group consisting of hydrogen, halo, cyano, hydroxy, (C$_{1-10}$)alkoxy, (C$_{4-12}$)aryloxy, hetero(C$_{1-10}$)aryloxy, (C$_{3-12}$)cycloalkyloxy, hetero(C$_{3-12}$)cycloalkyloxy, amino, (C$_{1-10}$)alkylamino, (C$_{1-10}$)alkyl, halo(C$_{1-10}$)alkyl, hydroxy(C$_{1-10}$)alkyl, carbonyl(C$_{1-10}$)alkyl, aza(C$_{1-10}$)alkyl, (C$_{1-10}$)oxaalkyl, (C$_{1-10}$)oxoalkyl, imino(C$_{1-10}$)alkyl, (C$_{3-12}$)cycloalkyl(C$_{1-5}$)alkyl, hetero(C$_{3-12}$)cycloalkyl(C$_{1-10}$)alkyl, aryl(C$_{1-10}$)alkyl, hetero(C$_{1-10}$)aryl(C$_{1-5}$)alkyl, (C$_{9-12}$)bicycloaryl(C$_{1-5}$)alkyl, hetero(C$_{8-2}$)bicycloaryl(C$_{1-5}$)alkyl, hetero(C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero (C$_{1-10}$)aryl, (C$_{9-12}$)bicycloaryl, and hetero(C$_{4-12}$)bicycloaryl, each substituted or unsubstituted.

In some other variations, R$_1$ is selected from the group consisting of hydrogen, halo, cyano, hydroxyl, (C$_{1-10}$)alkoxy, (C$_{4-12}$)aryloxy, hetero(C$_{1-10}$)aryloxy, (C$_{3-12}$)cycloalkyloxy, hetero(C$_{3-12}$)cycloalkyloxy, amino, (C$_{1-10}$)alkylamino, (C$_{1-10}$)alkyl, halo(C$_{1-10}$)alkyl, (C$_{3-12}$)cycloalkyl, hetero (C$_{3-12}$)cycloalkyl, (C$_{4-12}$)aryl, and hetero(C$_{1-10}$)aryl, each substituted or unsubstituted.

In still other variations, R$_1$ is selected from the group consisting of hydrogen, hydroxyl, halo, amino, and diethylamino. In still other variations, R$_1$ is selected from the group consisting of hydrogen, hydroxyl, and halo.

In some particular variations, R$_1$ is (C$_{1-6}$)alkyl, substituted or unsubstituted. In some preferred variations, R$_1$ is selected from the group consisting of methyl, ethyl, propyl, isopropyl, isobutyl. In other preferred variations, R$_1$ is methyl. In still other preferred variations, R$_1$ is ethyl. In still other preferred variations, R$_1$ is isopropyl.

In other particular variations, R$_1$ is unsubstituted or substituted aryl or heteroaryl, each unsubstituted or substituted. In some variation, the aryl or heteroaryl is substituted with one or more substituents independently selected from the group consisting of halo, cyano, oxo, hydroxyl, methoxy, tertbutyl, cyclopropyl, —C(O)CH$_3$, —C(O)NH$_2$, —C(O)OCH$_3$, —CH$_2$NH$_2$, —CH$_2$N(CH$_3$)$_2$, —CH$_2$OH, —NHC(O)CH$_3$, and —NHS(O)$_2$CH$_3$. In some variations, the aryl or heteroaryl is selected from the group consisting of phenyl, pyridinyl, pyrazolyl, furanyl, and triazolyl, each unsubstituted or substituted. In other variations, the aryl is phenyl. In some variations, the heteroaryl is pyridinyl. In still some variations, the heteroaryl is triazolyl. Further, in some variations, the aryl or heteroaryl is substituted with one or more substituents independently selected from the group consisting of halo, cyano, oxo, hydroxyl, methoxy, tertbutyl, cyclopropyl, —C(O)CH$_3$, —C(O)NH$_2$, —C(O)OCH$_3$, —CH$_2$NH$_2$, —CH$_2$N(CH$_3$)$_2$, —CH$_2$OH, —NHC(O)CH$_3$, and —NHS(O)$_2$CH$_3$.

In other particular variations, R$_1$ is unsubstituted or substituted cycloalkyl or heterocycloalkyl. In some variations, the cycloalkyl or heterocycloalkyl is (C$_{3-6}$)cycloalkyl or hetero (C$_{1-5}$)cycloalkyl. In some variations, the (C$_{3-6}$)cycloalkyl or hetero(C$_{1-5}$)cycloalkyl is selected from the group consisting of cyclopentyl, piperidinyl, pyrrolidinyl, and cyclohexyl. In still other some variations, R$_1$ is cyclohexyl.

In still other particular variations, R$_1$ is —NR$_{29}$R$_{30}$, where R$_{29}$ and R$_{30}$ are each independently selected from the group consisting of hydrogen, (C$_{1-6}$)alkyl, aryl, heteroaryl, and (C$_{3-6}$)alicyclic. In yet other particular variations, R$_{29}$ and R$_{30}$ are each independently selected from the group consisting of hydrogen, (C$_{1-6}$)alkyl, (C$_{4-6}$)aryl, hetero(C$_{1-5}$)aryl, (C$_{3-6}$)alicyclic, and hetero(C$_{1-5}$)alicyclic.

—Y-Q-R$_1$

In some variations of the above embodiments and variations of the compounds of the invention, —Y-Q-R$_1$ is selected from the group consisting of hydrogen, —CH$_2$NH$_2$, —CH$_2$NHCH$_3$, —CH$_2$NHC(O)CH$_3$, —CH$_2$Cl, —CH$_2$NHCH$_2$CH(CH$_3$)$_2$, —CH$_2$OH, —N(CH$_2$CH$_3$)$_2$, —CH$_2$SCH$_3$, —CH$_2$S(O)$_2$CH$_3$, —(CH$_2$)$_2$C(O)OCH$_2$CH$_3$, —(CH$_2$)$_2$C(O)N(CH$_2$CH$_3$)$_2$, —CH$_2$SCH(CH$_3$)$_2$, —CH$_2$S (O)CH(CH$_3$)$_2$, —CH$_2$S(O)$_2$CH(CH$_3$)$_2$, —CH$_2$OCH$_2$CH (CH$_3$)$_2$, —(CH$_2$)$_3$CH$_3$, —CH$_2$C(O)OCH$_3$, —CH(CH$_3$)$_2$,

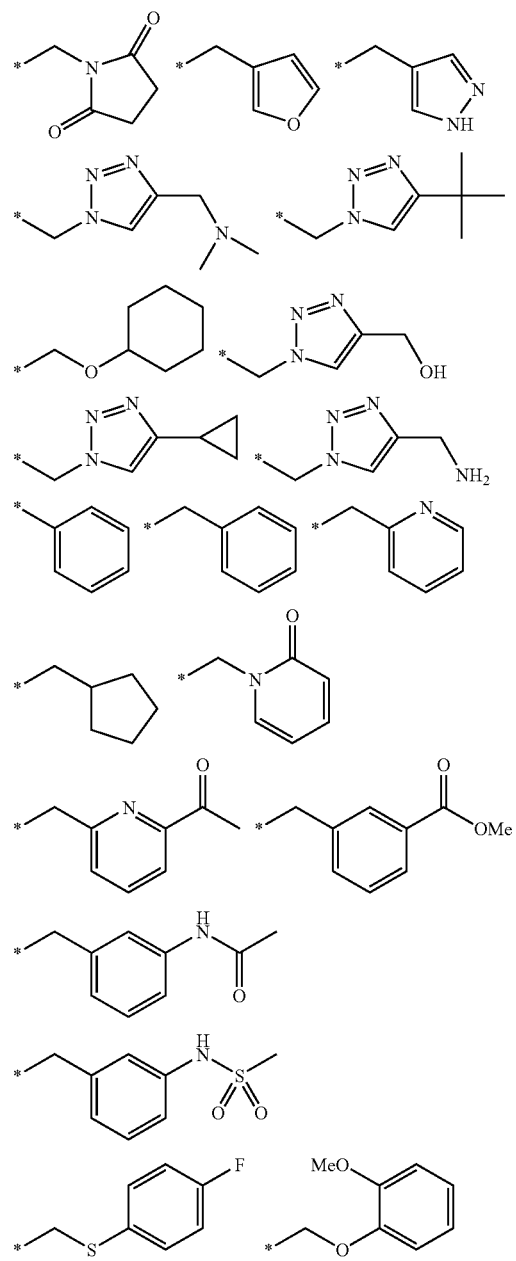

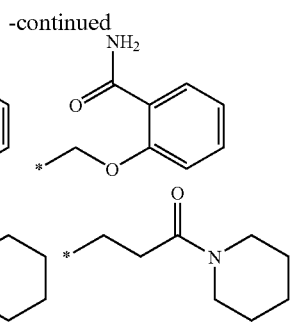

In other variations, —Y-Q-R$_1$ is selected from the group consisting of —(CH$_2$)$_2$C(O)OCH$_2$CH$_3$, —CH$_2$OCH$_2$CH(CH$_3$)$_2$, —(CH$_2$)$_3$CH$_3$, —(CH$_2$)$_2$C(O)NH$_2$, —(CH$_2$)$_2$C(O)N(CH$_2$CH$_3$)$_2$, —(CH$_2$)C(O)N(CH$_2$CH$_3$)$_2$, and

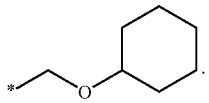

In other variations, —Y-Q-R$_1$ is selected from the group consisting of —(CH$_2$)$_2$C(O)OCH$_2$CH$_3$, —CH$_2$OCH$_2$CH(CH$_3$)$_2$, —(CH$_2$)$_3$CH$_3$, and

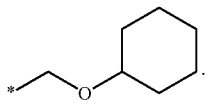

In still other variations, —Y-Q-R$_1$ is selected from the group consisting of —(CH$_2$)$_2$C(O)NH$_2$ and —(CH$_2$)C(O)N(CH$_2$CH$_3$)$_2$.

R$_2$

For some variations of the above embodiments and variations of the compounds of the invention, R$_2$ is substituted or unsubstituted (C$_{1-6}$)alkyl. In other variations, R$_2$ is substituted or unsubstituted ethyl. In still other variations, R$_2$ is unsubstituted ethyl.

R$_3$ and R$_4$

For some variations of the above embodiments and variations of the compounds of the invention, R$_3$ and R$_4$ are each independently selected from the group consisting of hydrogen, (C$_{1-10}$)alkyl, (C$_{1-10}$)azaalkyl, (C$_{1-10}$)oxaalkyl, (C$_{1-10}$)oxoalkyl, and hetero(C$_{1-10}$)alkyl, each substituted or unsubstituted, provided that one of R$_3$ and R$_4$ is absent, and where R$_3$ is absent, the nitrogen on which R$_3$ is drawn is part of a double bond, and where R$_4$ is absent, the nitrogen on which R$_4$ is drawn is part of a double bond. For other variations, R$_3$ and R$_4$ are each independently selected from the group consisting of hydrogen, (C$_{1-10}$)alkyl, (C$_{1-10}$)azaalkyl, and (C$_{1-10}$)oxaalkyl, each substituted or unsubstituted, provided that one of R$_3$ and R$_4$ is absent, and where R$_3$ is absent, the nitrogen on which R$_3$ is drawn is part of a double bond, and where R$_4$ is absent, the nitrogen on which R$_4$ is drawn is part of a double bond.

In other variations, R$_3$ and R$_4$ are each independently selected from the group consisting of hydrogen, unsubstituted (C$_{1-6}$)alkyl, and substituted (C$_{1-6}$)alkyl, provided that one of R$_3$ and R$_4$ is absent, and where R$_3$ is absent, the nitrogen on which R$_3$ is drawn is part of a double bond, and where R$_4$ is absent, the nitrogen on which R$_4$ is drawn is part of a double bond.

In still other variations, R$_3$ is hydrogen, unsubstituted or substituted (C$_{1-6}$)alkyl, and R$_4$ is absent and the nitrogen to which R$_4$ is drawn forms part of a double bond.

In yet still other variations, R$_3$ is selected from the group consisting of hydrogen, —CH$_2$C(O)N(CH$_2$CH$_3$)$_2$, —CH$_2$C(O)OCH$_3$, n-butyl, and —CH$_2$C(O)-piperidin-1-yl, and R$_4$ is absent and the nitrogen to which R$_4$ is drawn forms part of a double bond.

In yet still other variations, R$_3$ is hydrogen, and R$_4$ is absent and the nitrogen to which R$_4$ is drawn forms part of a double bond.

In yet still other variations, R$_4$ is unsubstituted or substituted (C$_{1-6}$)alkyl, and R$_3$ is absent and the nitrogen to which R$_3$ is drawn forms part of a double bond.

R$_{15}$, R$_{15'}$, R$_{16}$, R$_{16'}$, R$_{17}$, R$_{17'}$, R$_{18}$, and R$_{18'}$ For some variations of the above embodiments and variations of the compounds of the invention, R$_{15}$, R$_{16}$, R$_{17}$, and R$_{18}$, when present, are each independently selected from the group consisting of H, hydroxy, (C$_{1-10}$)alkoxy, (C$_{4-12}$)aryloxy, hetero(C$_{1-10}$)aryloxy, amino, (C$_{1-10}$)alkyl, halo(C$_{1-10}$)alkyl, hydroxy(C$_{1-10}$)alkyl, aza(C$_{1-10}$)alkyl, (C$_{1-10}$)oxaalkyl, (C$_{1-10}$)oxoalkyl, (C$_{3-12}$)cycloalkyl(C$_{1-5}$)alkyl, hetero(C$_{3-12}$)cycloalkyl(C$_{1-10}$)alkyl, aryl(C$_{1-10}$)alkyl, hetero(C$_{1-10}$)aryl(C$_{1-5}$)alkyl, and hetero(C$_{1-10}$)alkyl, each substituted or unsubstituted; and R$_{15'}$, R$_{16'}$, R$_{17'}$, and R$_{18'}$, when present, are each independently selected from the group consisting of H, hydroxy, (C$_{1-10}$)alkoxy, (C$_{4-12}$)aryloxy, hetero(C$_{1-10}$)aryloxy, amino, (C$_{1-10}$)alkyl, halo(C$_{1-10}$)alkyl, hydroxy(C$_{1-10}$)alkyl, aza(C$_{1-10}$)alkyl, (C$_{1-10}$)Oxaalkyl, (C$_{1-10}$)Oxoalkyl, (C$_{3-12}$)cycloalkyl(C$_{1-5}$)alkyl, and hetero(C$_{3-12}$)cycloalkyl(C$_{1-10}$)alkyl, aryl(C$_{1-10}$)alkyl, hetero(C$_{1-10}$)aryl(C$_{1-5}$)alkyl, hetero(C$_{1-10}$)alkyl, each substituted or unsubstituted, or R$_{15'}$, R$_{16'}$, R$_{17'}$, and R$_{18'}$ are each independently absent when the atom to which it is bound forms part of a double bond.

For other variations, R$_{15}$, R$_{16}$, R$_{17}$, and R$_{18}$, when present, are each independently selected from the group consisting of H, (C$_{1-10}$)alkoxy, (C$_{1-10}$)alkyl, halo(C$_{1-10}$)alkyl, hydroxy(C$_{1-10}$)alkyl, aza(C$_{1-10}$)alkyl, and (C$_{1-10}$)oxaalkyl, each substituted or unsubstituted; and R$_{15'}$, R$_{16'}$, R$_{17'}$, and R$_{18'}$, when present, are each independently selected from the group consisting of H, (C$_{1-10}$)alkoxy, (C$_{1-10}$)alkyl, halo(C$_{1-10}$)alkyl, hydroxy(C$_{1-10}$)alkyl, aza(C$_{1-10}$)alkyl, and (C$_{1-10}$)oxaalkyl, each substituted or unsubstituted, or R$_{15'}$, R$_{16'}$, R$_{17'}$, and R$_{18'}$ are each independently absent when the atom to which it is bound forms part of a double bond.

For some other variation, R$_{15}$, R$_{16}$, R$_{17}$, and R$_{18}$, when present, are each independently selected from the group consisting of H, (C$_{1-6}$)alkoxy, and (C$_{1-6}$)alkyl, each substituted or unsubstituted. In some other variations, R$_{15}$, R$_{16}$, R$_{17}$, and R$_{18}$, when present, are each selected from the group consisting of H, unsubstituted (C$_{1-6}$)alkyl, and substituted (C$_{1-6}$)alkyl.

In some other variations, each of R$_{15}$, R$_{16}$, R$_{17}$, and R$_{18}$ are each independently selected from the group consisting of H, unsubstituted (C$_{1-6}$)alkoxy, and substituted (C$_{1-6}$)alkoxy. In some other variations, R$_{18}$ is selected from the group consisting of H, (C$_{1-6}$)alkyl and (C$_{1-6}$)alkoxy; and each of R$_{15}$, R$_{16}$, and R$_{17}$ is H.

In other variations, R$_{18}$ is methyl and each of R$_{15}$, R$_{16}$, and R$_{17}$, is H. In other variations, R$_{18}$ is methoxy and each of R$_{15}$, R$_{16}$, and R$_{17}$, is H. In still other variations, R$_{18}$ is methoxy and each of R$_{15}$, R$_{16}$, and R$_{17}$, is H. In yet still other variations, each of R$_{15}$, R$_{16}$, R$_{17}$ and R$_{18}$ is H.

In some variations of the above embodiments and variations, none of $R_{15'}$, $R_{16'}$, $R_{17'}$, and $R_{18'}$ is absent. In still other variations, at least one of $R_{15'}$, $R_{16'}$, $R_{17'}$, and $R_{18'}$ is absent. In yet still other variations, all of $R_{15'}$, $R_{16'}$, $R_{17'}$, and $R_{18'}$ are absent.

$R_{23}, R_{24}, R_{25}, R_{25'}, R_{26}, R_{26'}, R_{27}, R_{27'}, R_{28}$ and $R_{28'}$ For some variations of the above embodiments and variations of the compounds of the invention, $R_{23}$, $R_{24}$, $R_{25}$, $R_{26}$, $R_{27}$, and $R_{28}$, when present, are each independently selected from the group consisting of H, hydroxy, $(C_{1-10})$alkoxy, $(C_{4-12})$aryloxy, hetero$(C_{1-10})$aryloxy, amino, $(C_{1-10})$alkyl, halo$(C_{1-10})$alkyl, hydroxy$(C_{1-10})$alkyl, aza$(C_{1-10})$alkyl, $(C_{1-10})$oxaalkyl, $(C_{1-10})$oxoalkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, hetero$(C_{1-10})$alkyl, each substituted or unsubstituted; and $R_{25'}$, $R_{26'}$, $R_{27'}$, and $R_{28'}$, when present, are each independently selected from the group consisting of H, hydroxy, $(C_{1-10})$alkoxy, $(C_{4-12})$aryloxy, hetero$(C_{1-10})$aryloxy, amino, $(C_{1-10})$alkyl, halo$(C_{1-10})$alkyl, hydroxy$(C_{1-10})$alkyl, aza$(C_{1-10})$alkyl, $(C_{1-10})$oxaalkyl, $(C_{1-10})$oxoalkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, and hetero$(C_{1-10})$alkyl, each substituted or unsubstituted, or $R_{25'}$, $R_{26'}$, $R_{27'}$, and $R_{28'}$ are each independently absent when the atom to which it is bound forms part of a double bond.

In some variations of the above embodiments, when present, $R_{21}$, $R_{22}$, $R_{23}$ and $R_{24}$ are each independently selected from the group consisting of H, $(C_{1-6})$alkoxy, $(C_{4-6})$aryloxy, hetero$(C_{1-5})$aryloxy, carbonyl, oxycarbonyl, aminocarbonyl, amino, $(C_{1-6})$alkylamino, sulfonamido, imino, sulfonyl, sulfinyl, $(C_{1-6})$alkyl, halo$(C_{1-6})$alkyl, hydroxy$(C_{1-6})$alkyl, carbonyl$(C_{1-6})$alkyl, thiocarbonyl$(C_{1-6})$alkyl, sulfonyl$(C_{1-6})$alkyl, sulfinyl$(C_{1-6})$alkyl, aza$(C_{1-6})$alkyl, $(C_{1-6})$oxaalkyl, $(C_{3-6})$cycloalkyl$(C_{1-6})$alkyl, hetero$(C_{1-5})$cycloalkyl$(C_{1-6})$alkyl, $(C_{4-6})$aryl$(C_{1-6})$alkyl, hetero$(C_{1-5})$aryl$(C_{1-6})$alkyl, hetero$(C_{1-6})$alkyl, $(C_{3-6})$cycloalkyl, hetero$(C_{1-5})$cycloalkyl, $(C_{4-6})$aryl, and hetero$(C_{1-5})$aryl, each substituted or unsubstituted; or $R_{21}$ and $R_{22}$, or $R_{22}$ and $R_{23}$, or $R_{23}$ and $R_{24}$, are taken together to form a ring selected from the group consisting of substituted or unsubstituted $(C_{3-6})$cycloalkyl, substituted or unsubstituted hetero$(C_{1-5})$cycloalkyl, substituted or unsubstituted $(C_{4-6})$aryl and substituted or unsubstituted hetero$(C_{1-5})$aryl.

In some particular variations, $R_{23}$, $R_{24}$, $R_{25}$, $R_{26}$, $R_{27}$, and $R_{28}$ are each independently selected from the group consisting of H, $(C_{1-10})$alkoxy, $(C_{1-10})$alkyl, halo$(C_{1-10})$alkyl, hydroxy$(C_{1-10})$alkyl, aza$(C_{1-10})$alkyl, $(C_{1-10})$oxaalkyl, $(C_{1-10})$oxoalkyl, (hetero$(C_{1-10})$alkyl, each substituted or unsubstituted, and $R_{25'}$, $R_{26'}$, $R_{27'}$, and $R_{28'}$, when present, are each independently selected from the group consisting of H, $(C_{1-10})$alkoxy, $(C_{1-10})$alkyl, halo$(C_{1-10})$alkyl, hydroxy$(C_{1-10})$alkyl, aza$(C_{1-10})$alkyl, $(C_{1-10})$Oxaalkyl, $(C_{1-10})$Oxoalkyl, (hetero$(C_{1-10})$alkyl, each substituted or unsubstituted, or $R_{25'}$, $R_{26'}$, $R_{27'}$, and $R_{28'}$ are each independently absent when the atom to which it is bound forms part of a double bond.

In some other particular variations, $R_{23}$, $R_{24}$, $R_{25}$, $R_{26}$, $R_{27}$, and $R_{28}$, when present, are each independently selected from the group consisting of H, $(C_{1-6})$alkoxy, $(C_{1-6})$alkyl, halo$(C_{1-6})$alkyl, hydroxy$(C_{1-6})$alkyl, aza$(C_{1-6})$alkyl, and $(C_{1-6})$oxaalkyl, each substituted or unsubstituted; and $R_{25'}$, $R_{26'}$, $R_{27'}$, and $R_{28'}$, when present, are each independently selected from the group consisting of H, $(C_{1-6})$alkoxy, $(C_{1-6})$alkyl, halo$(C_{1-6})$alkyl, hydroxy$(C_{1-6})$alkyl, aza$(C_{1-6})$alkyl, and $(C_{1-6})$oxaalkyl, each substituted or unsubstituted, or $R_{25'}$, $R_{26'}$, $R_{27'}$, and $R_{28'}$ are each independently absent when the atom to which it is drawn forms part of a double bond.

In some other variations, $R_{23}$, $R_{24}$, $R_{25}$, $R_{26}$, $R_{27}$, and $R_{28}$ are each independently selected from the group consisting of H, $(C_{1-6})$alkoxy, and $(C_{1-6})$alkyl, each substituted or unsubstituted. In some other variations, $R_{23}$, $R_{24}$, $R_{25}$, $R_{26}$, $R_{27}$, and $R_{28}$, when present, are each independently selected from the group consisting of H, unsubstituted $(C_{1-6})$alkoxy and substituted $(C_{1-6})$alkoxy. In some other variations, $R_{23}$, $R_{24}$, $R_{25}$, $R_{26}$, $R_{27}$, and $R_{28}$, when present, are each independently selected from the group consisting of H, unsubstituted $(C_{1-6})$alkyl and substituted $(C_{1-6})$alkyl. In some other variations, $R_{28}$ is methyl and each of $R_{23}$, $R_{24}$, $R_{25}$, $R_{26}$, and $R_{27}$ is H. In some other variations, $R_{28}$ is methoxy and each of $R_{23}$, $R_{24}$, $R_{25}$, $R_{26}$, and $R_{27}$ is H.

In some variations of the above embodiments and variations, none of $R_{25'}$, $R_{26'}$, $R_{27'}$, and $R_{28'}$ are absent. In some other variations, at least one of $R_{25'}$, $R_{26'}$, $R_{27'}$, and $R_{28}$ is absent.

A particular embodiment of the compounds of the invention is of the formula

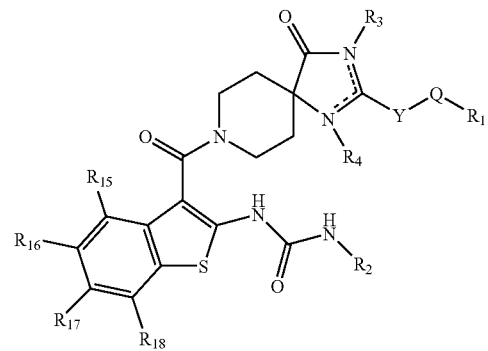

wherein

Q is selected from the group consisting of a bond, —C(O)—, —C(O)O—, —NH—, —O—, —S—, —S(O)—, and —S(O)$_2$—;

Y is selected from the group consisting of a bond, —CH$_2$—, —(CH$_2$)$_2$—, —NH—CH$_2$—, and —CH$_2$—NH—;

R$_1$ is selected from the group consisting of hydrogen, halo, cyano, hydroxyl, $(C_{1-6})$alkoxy, $(C_{4-6})$aryloxy, hetero$(C_{1-5})$aryloxy, $(C_{3-6})$cycloalkyloxy, hetero$(C_{1-5})$cycloalkyloxy, amino, $(C_{1-6})$alkylamino, $(C_{1-6})$alkyl, halo$(C_{1-6})$alkyl, $(C_{3-6})$cycloalkyl, hetero$(C_{1-5})$cycloalkyl, $(C_{4-6})$aryl, and hetero$(C_{1-5})$aryl, each substituted or unsubstituted;

R$_2$ is substituted or unsubstituted $(C_{1-4})$alkyl;

R$_3$ and R$_4$ are each independently selected from the group consisting of hydrogen, $(C_{1-6})$alkyl, $(C_{1-6})$azaalkyl, and $(C_{1-6})$oxaalkyl, each substituted or unsubstituted, provided that one of R$_3$ and R$_4$ is absent, and where R$_3$ is absent, the nitrogen on which R$_3$ is drawn is part of a double bond, and where R$_4$ is absent, the nitrogen on which R$_4$ is drawn is part of a double bond; and R$_{15}$, R$_{16}$, R$_{17}$ and R$_{18}$ are each independently selected from the group consisting of H, $(C_{1-6})$alkoxy, $(C_{1-6})$alkyl, halo$(C_{1-6})$alkyl, hydroxy$(C_{1-6})$alkyl, aza$(C_{1-6})$alkyl, and $(C_{1-6})$oxaalkyl, each substituted or unsubstituted.

In some variations of the above particular embodiment, —(Y-Q-R$_1$) is selected from the group consisting of hydrogen, —CH$_2$NH$_2$, —CH$_2$NHCH$_3$, —CH$_2$NHC(O)CH$_3$, —CH$_2$Cl, —CH$_2$NHCH$_2$CH(CH$_3$)$_2$, —CH$_2$OH, —N(CH$_2$CH$_3$)$_2$, —CH$_2$SCH$_3$, —CH$_2$S(O)$_2$CH$_3$, —(CH$_2$)$_2$C(O)OCH$_2$CH$_3$, —(CH$_2$)$_2$C(O)N(CH$_2$CH$_3$)$_2$, —CH$_2$SCH(CH$_3$)$_2$, —CH$_2$S(O)CH(CH$_3$)$_2$, —CH$_2$S(O)$_2$CH(CH$_3$)$_2$, —CH$_2$OCH$_2$CH(CH$_3$)$_2$, —(CH$_2$)$_3$CH$_3$, —CH$_2$C(O)OCH$_3$, —CH(CH$_3$)$_2$,

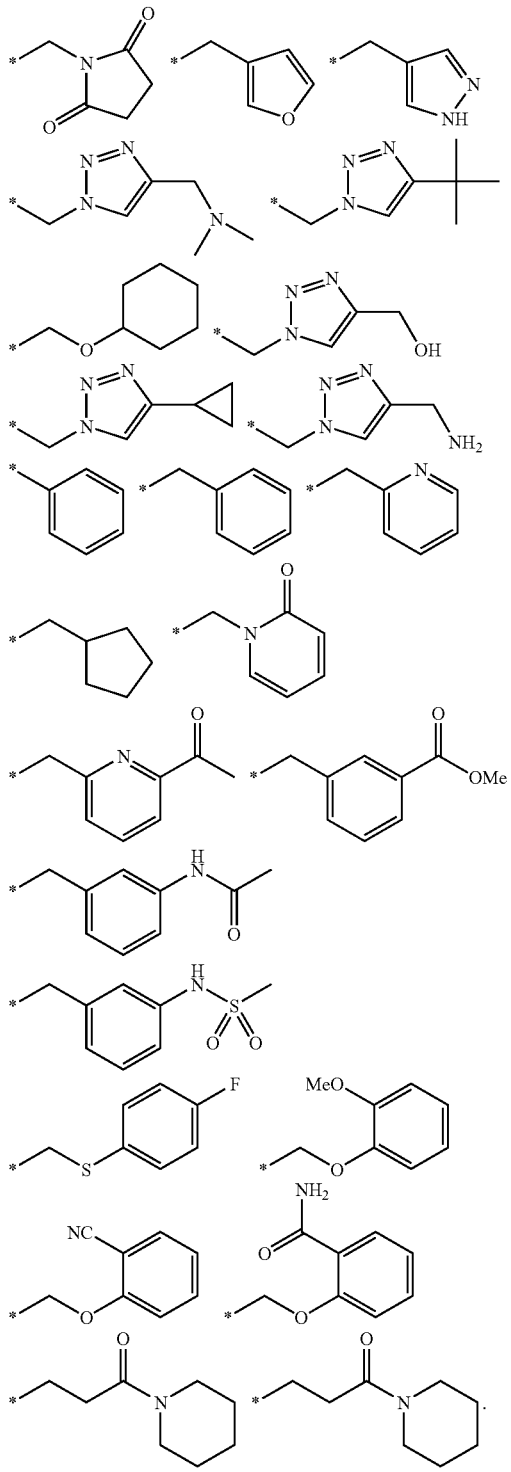

In some other variations of the above particular embodiment, —(Y-Q-R$_1$) is selected from the group consisting of hydrogen, —CH$_2$NH$_2$, —CH$_2$NHCH$_3$, —CH$_2$NHC(O)CH$_3$, —CH$_2$Cl, —CH$_2$NHCH$_2$CH(CH$_3$)$_2$, —CH$_2$OH, —N(CH$_2$CH$_3$)$_2$, —CH$_2$SCH$_3$, —CH$_2$S(O)$_2$CH$_3$, —(CH$_2$)$_2$C(O)OCH$_2$CH$_3$, —(CH$_2$)$_2$C(O)N(CH$_2$CH$_3$)$_2$, —CH$_2$SCH(CH$_3$)$_2$, —CH$_2$S(O)CH(CH$_3$)$_2$, —CH$_2$S(O)$_2$CH(CH$_3$)$_2$, —CH$_2$OCH$_2$CH(CH$_3$)$_2$, —(CH$_2$)$_3$CH$_3$, —CH$_2$C(O)OCH$_3$, —CH(CH$_3$)$_2$.

In still other variations of the above particular embodiment, —(Y-Q-R$_1$) is selected from the group consisting of

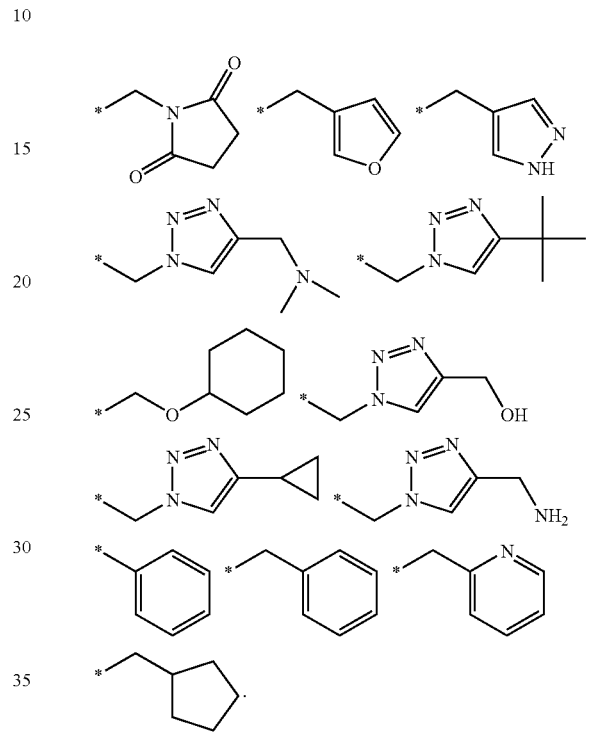

In still other variations of the above particular embodiment, —(Y-Q-R$_1$) is selected from the group consisting of

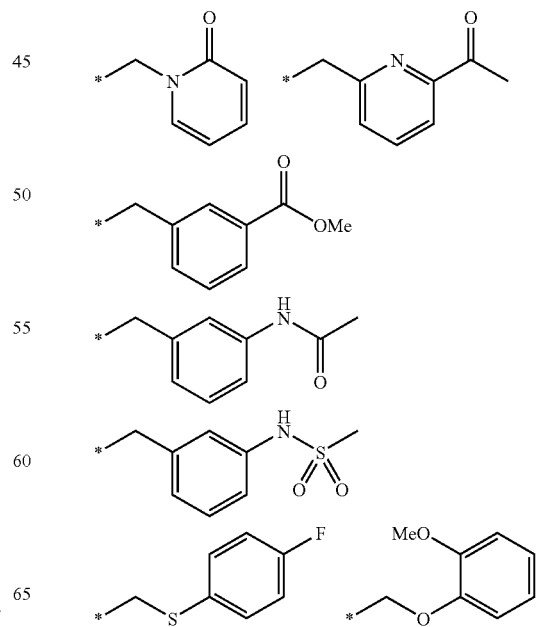

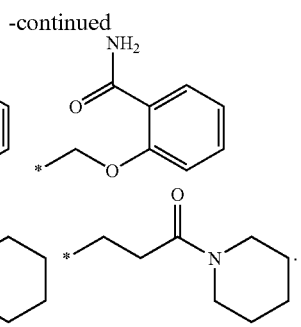

In yet still other variations, —(Y-Q-R₁) is selected from the group consisting of hydrogen, —CH₂NH₂, —CH₂OH, —CH₂NHCH₃, —CH₂NHC(O)CH₃, —CH₂NHCH₂CH(CH₃)₂, —CH₂Cl, —(CH₂)₂C(O)OCH₂CH₃, —(CH₂)₂C(O)N(CH₂CH₃)₂, benzyl, isopropyl, n-butyl, phenyl, and

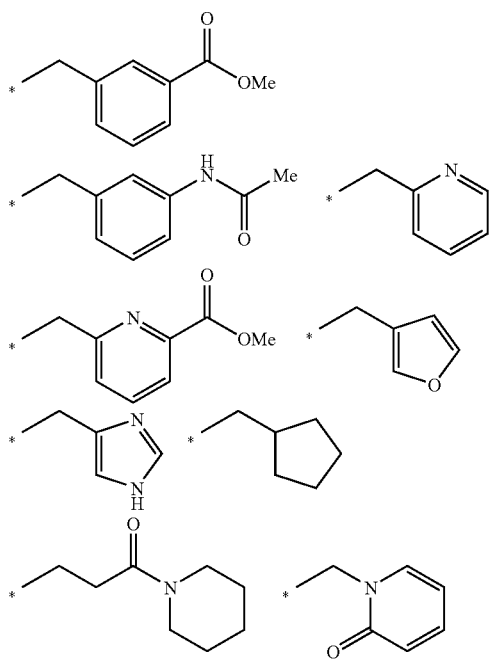

In some variations of the above particular embodiment, R₁₅, R₁₆, R₁₇, and R₁₈ are each independently selected from the group consisting of H, substituted or unsubstituted (C₁₋₆) alkoxy, and substituted or unsubstituted (C₁₋₆)alkyl.

In other variations of the above particular embodiment, R₃ and R₄ are each independently selected from the group consisting of hydrogen, and substituted or unsubstituted, (C₁₋₆) alkyl, provided that one of R₃ and R₄ is absent, and where R₃ is absent, the nitrogen on which R₃ is drawn is part of a double bond, and where R₄ is absent, the nitrogen on which R₄ is drawn is part of a double bond.

Particular examples of compounds according to the present invention include, but are not limited to, the following:

1-(3-(2-(aminomethyl)-4-oxo-1,3,8-triazaspiro[4.5]dec-1-enecarbonyl)benzo[b]thiophen-2-yl)-3-ethylurea;

N-((8-(2-(3-ethylureido)benzo[b]thiophene-3-carbonyl)-4-oxo-1,3,8-triazaspiro[4.5]dec-1-en-2-yl)methyl)acetamide;

1-ethyl-3-(3-(2-(methylthiomethyl)-4-oxo-1,3,8-triazaspiro[4.5]dec-1-enecarbonyl)benzo[b]thiophen-2-yl)urea TFA salt;

1-ethyl-3-(3-(2-(methylsulfonylmethyl)-4-oxo-1,3,8-triazaspiro[4.5]dec-1-enecarbonyl)benzo[b]thiophen-2-yl)urea TFA salt;

1-(3-(2-((2,5-dioxopyrrolidin-1-yl)methyl)-4-oxo-1,3,8-triazaspiro[4.5]dec-1-enecarbonyl)benzo[b]thiophen-2-yl)-3-ethylurea TFA salt;

1-(3-(4-amino-4-cyanopiperidine-1-carbonyl)benzo[b]thiophen-2-yl)-3-ethylurea;

4-amino-1-(2-(3-ethylureido)benzo[b]thiophene-3-carbonyl)piperidine-4-carboxamide TFA salt;

1-(3-(2-(chloromethyl)-4-oxo-1,3,8-triazaspiro[4.5]dec-1-enecarbonyl)benzo[b]thiophen-2-yl)-3-ethylurea;

1-(3-(2-(chloromethyl)-4-oxo-1,3,8-triazaspiro[4.5]dec-1-enecarbonyl)-7-methoxybenzo[b]thiophen-2-yl)-3-ethylurea TFA salt;

ethyl 3-(8-(2-(3-ethylureido)benzo[b]thiophene-3-carbonyl)-4-oxo-1,3,8-triazaspiro[4.5]dec-1-en-2-yl)propanoate;

ethyl 3-(8-(2-(3-ethylureido)-7-methoxybenzo[b]thiophene-3-carbonyl)-4-oxo-1,3,8-triazaspiro[4.5]dec-1-en-2-yl)propanoate TFA salt;

N,N-diethyl-3-(8-(2-(3-ethylureido)benzo[b]thiophene-3-carbonyl)-4-oxo-1,3,8-triazaspiro[4.5]dec-1-en-2-yl)propanamide;

1-ethyl-3-(3-(4-oxo-2-(3-oxo-3-(piperidin-1-yl)propyl)-1,3,8-triazaspiro[4.5]dec-1-enecarbonyl)benzo[b]thiophen-2-yl)urea TFA salt;

1-ethyl-3-(3-(4-oxo-1,3,8-triazaspiro[4.5]dec-1-enecarbonyl)benzo[b]thiophen-2-yl)urea TFA salt;

1-(3-(2-butyl-4-oxo-1,3,8-triazaspiro[4.5]dec-1-enecarbonyl)benzo[b]thiophen-2-yl)-3-ethylurea;

1-ethyl-3-(3-(2-isopropyl-4-oxo-1,3,8-triazaspiro[4.5]dec-2-enecarbonyl)-7-methoxybenzo[b]thiophen-2-yl)urea TFA salt;

1-(3-(2-butyl-4-oxo-1,3,8-triazaspiro[4.5]dec-1-enecarbonyl)-7-methoxybenzo[b]thiophen-2-yl)-3-ethylurea TFA salt;

1-ethyl-3-(7-methoxy-3-(4-oxo-2-phenyl-1,3,8-triazaspiro[4.5]dec-2-enecarbonyl)benzo[b]thiophen-2-yl)urea TFA salt;

methyl 2-(8-(2-(3-ethylureido)benzo[b]thiophene-3-carbonyl)-4-oxo-1,3,8-triazaspiro[4.5]dec-1-en-3-yl)acetate TFA salt;

1-(3-(3-butyl-4-oxo-1,3,8-triazaspiro[4.5]dec-1-enecarbonyl)benzo[b]thiophen-2-yl)-3-ethylurea TFA salt;

1-ethyl-3-(3-(2-((4-fluorophenylthio)methyl)-4-oxo-1,3,8-triazaspiro[4.5]dec-1-enecarbonyl)benzo[b]thiophen-2-yl)urea TFA salt;

1-ethyl-3-(3-(2-(isopropylthiomethyl)-4-oxo-1,3,8-triazaspiro[4.5]dec-1-enecarbonyl)benzo[b]thiophen-2-yl)urea TFA salt;

1-ethyl-3-(3-(2-(isopropylsulfinylmethyl)-4-oxo-1,3,8-triazaspiro[4.5]dec-1-enecarbonyl)benzo[b]thiophen-2-yl)urea TFA salt;

1-ethyl-3-(3-(2-(isopropylsulfonylmethyl)-4-oxo-1,3,8-triazaspiro[4.5]dec-1-enecarbonyl)benzo[b]thiophen-2-yl)urea TFA salt;

1-ethyl-3-(3-(2-((2-methoxyphenoxy)methyl)-4-oxo-1,3,8-triazaspiro[4.5]dec-1-enecarbonyl)benzo[b]thiophen-2-yl)urea TFA salt;

1-(3-(2-((2-cyanophenoxy)methyl)-4-oxo-1,3,8-triazaspiro[4.5]dec-1-enecarbonyl)benzo[b]thiophen-2-yl)-3-ethylurea TFA salt;

2-((8-(2-(3-ethylureido)benzo[b]thiophene-3-carbonyl)-4-oxo-1,3,8-triazaspiro[4.5]dec-1-en-2-yl)methoxy)benzamide TFA salt;

1-(3-(2-(cyclohexyloxymethyl)-4-oxo-1,3,8-triazaspiro[4.5]
    dec-1-enecarbonyl)benzo[b]thiophen-2-yl)-3-ethylurea
    TFA salt;
1-ethyl-3-(3-(2-(isopropoxymethyl)-4-oxo-1,3,8-triazaspiro
    [4.5]dec-1-enecarbonyl)benzo[b]thiophen-2-yl)urea TFA
    salt;
1-ethyl-3-(3-(2-(isobutoxymethyl)-4-oxo-1,3,8-triazaspiro
    [4.5]dec-1-enecarbonyl)benzo[b]thiophen-2-yl)urea TFA
    salt;
1-ethyl-3-(3-(2-(isobutoxymethyl)-4-oxo-1,3,8-triazaspiro
    [4.5]dec-1-enecarbonyl)-7-methoxybenzo[b]thiophen-2-
    yl)urea TFA salt;
1-(3-(2-(cyclohexyloxymethyl)-4-oxo-1,3,8-triazaspiro[4.5]
    dec-1-enecarbonyl)-7-methoxybenzo[b]thiophen-2-yl)-3-
    ethylurea TFA salt;
1-ethyl-3-(3-(4-oxo-2-((2-oxopyridin-1(2H)-yl)methyl)-1,3,
    8-triazaspiro[4.5]dec-1-enecarbonyl)benzo[b]thiophen-2-
    yl)urea TFA salt;
1-(3-(2-((4-(aminomethyl)-1H-1,2,3-triazol-1-yl)methyl)-4-
    oxo-1,3,8-triazaspiro[4.5]dec-1-enecarbonyl)benzo[b]
    thiophen-2-yl)-3-ethylurea TFA salt;
1-(3-(2-((4-((dimethylamino)methyl)-1H-1,2,3-triazol-1-yl)
    methyl)-4-oxo-1,3,8-triazaspiro[4.5]dec-1-enecarbonyl)
    benzo[b]thiophen-2-yl)-3-ethylurea TFA salt;
1-(3-(2-((4-tert-butyl-1H-1,2,3-triazol-1-yl)methyl)-4-oxo-
    1,3,8-triazaspiro[4.5]dec-1-enecarbonyl)benzo[b]
    thiophen-2-yl)-3-ethylurea TFA salt;
1-ethyl-3-(3-(2-((4-(hydroxymethyl)-1H-1,2,3-triazol-1-yl)
    methyl)-4-oxo-1,3,8-triazaspiro[4.5]dec-1-enecarbonyl)
    benzo[b]thiophen-2-yl)urea TFA salt;
1-(3-(2-((4-cyclopropyl-1H-1,2,3-triazol-1-yl)methyl)-4-
    oxo-1,3,8-triazaspiro[4.5]dec-1-enecarbonyl)benzo[b]
    thiophen-2-yl)-3-ethylurea TFA salt;
1-methyl-3-(3-(2-((methylamino)methyl)-4-oxo-1,3,8-tria-
    zaspiro[4.5]dec-1-enecarbonyl)thieno[2,3-b]pyridin-2-yl)
    urea;
1-ethyl-3-(3-(2-((isobutylamino)methyl)-4-oxo-1,3,8-tria-
    zaspiro[4.5]dec-1-enecarbonyl)-6-methylthieno[2,3-b]
    pyridin-2-yl)urea;
1-(3-(2-benzyl-4-oxo-1,3,8-triazaspiro[4.5]dec-1-enecarbo-
    nyl)benzo[b]thiophen-2-yl)-3-ethylurea;
1-ethyl-3-(3-(2-(hydroxymethyl)-4-oxo-1,3,8-triazaspiro
    [4.5]dec-1-enecarbonyl)thieno[2,3-c]pyridin-2-yl)urea;
ethylureido)benzo[b]thiophene-3-carbonyl)-4-oxo-1,3,8-
    triazaspiro[4.5]dec-1-en-2-yl)methyl)benzoate;
N-(3-((8-(2-(3-ethylureido)-7-methoxybenzo[b]thiophene-
    3-carbonyl)-4-oxo-1,3,8-triazaspiro[4.5]dec-1-en-2-yl)
    methyl)phenyl)methanesulfonamide;
N-(3-((8-(2-(3-ethylureido)benzo[b]thiophene-3-carbonyl)-
    4-oxo-1,3,8-triazaspiro[4.5]dec-1-en-2-yl)methyl)phe-
    nyl)acetamide;
1-ethyl-3-(3-(4-oxo-2-(pyridin-2-ylmethyl)-1,3,8-triaza-
    spiro[4.5]dec-1-enecarbonyl)benzo[b]thiophen-2-yl)urea;
1-(3-(2-((6-acetylpyridin-2-yl)methyl)-4-oxo-1,3,8-triaza-
    spiro[4.5]dec-1-enecarbonyl)thieno[2,3-b]pyridin-2-yl)-
    3-ethylurea;
1-(3-(2-((1H-pyrazol-4-yl)methyl)-4-oxo-1,3,8-triazaspiro
    [4.5]dec-1-enecarbonyl)benzo[b]thiophen-2-yl)-3-ethy-
    lurea;
1-ethyl-3-(3-(2-(furan-3-ylmethyl)-4-oxo-1,3,8-triazaspiro
    [4.5]dec-1-enecarbonyl)benzo[b]thiophen-2-yl)urea;
1-(3-(2-(cyclopentylmethyl)-4-oxo-1,3,8-triazaspiro[4.5]
    dec-1-enecarbonyl)benzo[b]thiophen-2-yl)-3-ethylurea;
N,N-diethyl-2-(8-(2-(3-ethylureido)-4,5,6,7-tetrahy-
    drobenzo[b]thiophene-3-carbonyl)-4-oxo-1,3,8-triaza-
    spiro[4.5]dec-1-en-3-yl)acetamide; and
1-ethyl-3-(3-(4-oxo-3-(2-oxo-2-(piperidin-1-yl)ethyl)-1,3,
    8-triazaspiro[4.5]dec-1-enecarbonyl)benzo[b]thiophen-2-
    yl)urea.

It is noted that the compounds of the present invention may be in the form of a pharmaceutically acceptable salt. It is further note that the compounds of the present invention may be in a mixture of stereoisomers, or the compound may comprise a single stereoisomer.

In another aspect, the present invention is related to a pharmaceutical composition comprising as an active ingredient a compound according to any one of the above embodiments and variations. In one embodiment, the composition is a solid formulation adapted for oral administration. In another embodiment, the composition is a liquid formulation adapted for oral administration. In yet another embodiment, the composition is a tablet. In still another embodiment, the composition is a liquid formulation adapted for parenteral administration.

In another embodiment, the pharmaceutical composition comprises a compound according to any one of the above embodiments and variations, wherein the composition is adapted for administration by a route selected from the group consisting of orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, and intrathecally.

In another aspect, the invention is related to a kit which comprises a compound of any one of the above embodiments and variations, and instructions which comprise one or more forms of information selected from the group consisting of indicating a disease state for which the composition is to be administered, storage information for the composition, dosing information and instructions regarding how to administer the composition. In one particular variation, the kit comprises the compound in a multiple dose form.

In still another aspect, the invention is related to an article of manufacture comprising a compound of any one of the above embodiments and variations and packaging materials. In one embodiment, the packaging material comprises a container for housing the compound. In another embodiment, the container comprises a label indicating one or more members of the group consisting of a disease state for which the compound is to be administered, storage information, dosing information and/or instructions regarding how to administer the compound.

In another embodiment, the article of manufacture comprises the compound in a multiple dose form.

In a further aspect, the invention is related to a therapeutic method comprising administering a compound of any one of the above embodiments and variations to a subject.

In one embodiment, the method comprises contacting ACC with a compound of any one of the above embodiments and variations. In an exemplary embodiment, ACC is a member selected from ACC1 and ACC2.

In yet another embodiment is a method of inhibiting ACC which comprises causing a compound of any one of the above embodiments and variations to be present in a subject in order to inhibit ACC in vivo. In an exemplary embodiment, ACC is a member selected from ACC1 and ACC2.

A further embodiment is a method of inhibiting ACC which comprises administering a first compound to a subject that is converted in vivo to a second compound wherein the second compound inhibits ACC in vivo, the second compound being a compound according to any one of the above embodiments and variations. In an exemplary embodiment, ACC is a member selected from ACC1 and ACC2.

Another further embodiment is a method of treating a disease state for which ACC possesses activity contributes to the pathology and/or symptomology of the disease state. In one variation, the method comprises causing a compound of any one of the above embodiments and variations to be present in a subject in a therapeutically effective amount for the disease state. In another variation, the method comprises administering a compound of any one of the above embodiments and variations to a subject, wherein the compound is present in the subject in a therapeutically effective amount for the disease state. In a further variation, the method comprises administering a first compound to a subject that is converted in vivo to a second compound wherein the second compound inhibits ACC in vivo, the second compound being a compound according to any one of the above embodiments and variations.

In one variation of the above embodiments and variations, the disease state is selected from the group consisting of metabolic syndrome (also known as insulin resistance syndrome, syndrome X), visceral obesity, hyperlipidemia, dyslipidemia, hyperglycemia, hypertension, hyperuricemia renal dysfunction, atherosclerosis, type-2 diabetes, android obesity, Cushing's disease, cognitive function, and ocular function.

In a further embodiment of the method of the invention, the ACC is an ACC1. In another variation of the method, the ACC is an ACC2.

Another aspect of the invention is directed to method of preparing the inhibitor of the invention. In one embodiment, the method comprising:

coupling a compound of the formula

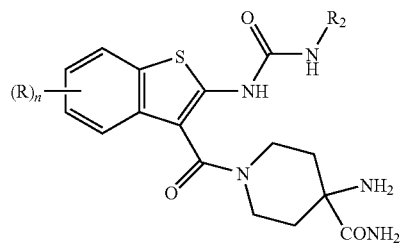

to a compound of the formula $C(Y-Q-R_1)(OEt)_3$, under conditions that form a reaction product of the formula

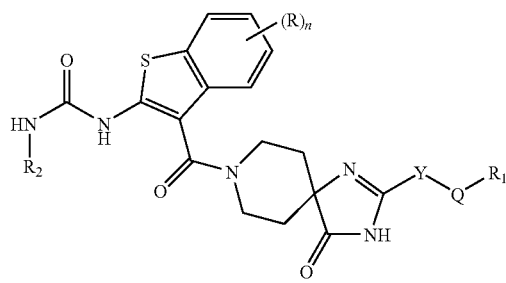

wherein
n is 4;
Y is selected from the group consisting of a bond, $-CH_2-$, $-(CH_2)_2-$, $-NH-CH_2-$, and $-CH_2-NH-$;

Q is selected from the group consisting of a bond, $-C(O)-$, $-C(O)O-$, $-NH-$, $-O-$, $-S-$, $-S(O)-$, and $-S(O)_2-$;

each R is independently selected from the group consisting of H, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted;

$R_1$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, $(C_{3-12})$cycloalkyloxy, hetero$(C_{3-12})$cycloalkyloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$Oxaalkyl, $(C_{1-10})$Oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-2})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl, and hetero$(C_{4-12})$bicycloaryl, each substituted or unsubstituted; and $R_2$ is substituted or unsubstituted alkyl.

In one variation of the preceding embodiment, $-(Y-Q-R_1)$ is selected from the group consisting of $(C_{1-6})$alkyl, halo$(C_{1-6})$alkyl, $(C_{3-6})$aryl$(C_{1-3})$alkyl, $(C_{1-6})$heteroaryl$(C_{1-3})$alkyl, $(C_{3-6})$cycloalkyl$(C_{1-13})$alkyl, and $(C_{1-16})$heterocycloalkyl$(C_{1-13})$alkyl, $(C_{3-6})$aryl, $(C_{1-16})$heteroaryl, $(C_{3-6})$cycloalkyl, and $(C_{1-6})$heterocycloalkyl, each substituted or unsubstituted.

In other variations, $-(Y-Q-R_1)$ is selected from the group consisting of hydrogen, $-CH_2NH_2$, $-CH_2NHCH_3$, $-CH_2NHC(O)CH_3$, $-CH_2Cl$, $-CH_2NHCH_2CH(CH_3)_2$, $-CH_2OH$, $-N(CH_2CH_3)_2$, $-CH_2SCH_3$, $-CH_2S(O)_2CH_3$, $-(CH_2)_2C(O)OCH_2CH_3$, $-(CH_2)_2C(O)N(CH_2CH_3)_2$, $-CH_2SCH(CH_3)_2$, $-CH_2S(O)CH(CH_3)_2$, $-CH_2S(O)_2CH(CH_3)_2$, $-CH_2OCH_2CH(CH_3)_2$, $-(CH_2)_3CH_3$, $-CH_2C(O)OCH_3$, $-CH(CH_3)_2$,

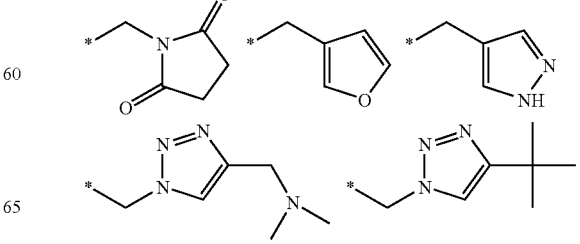

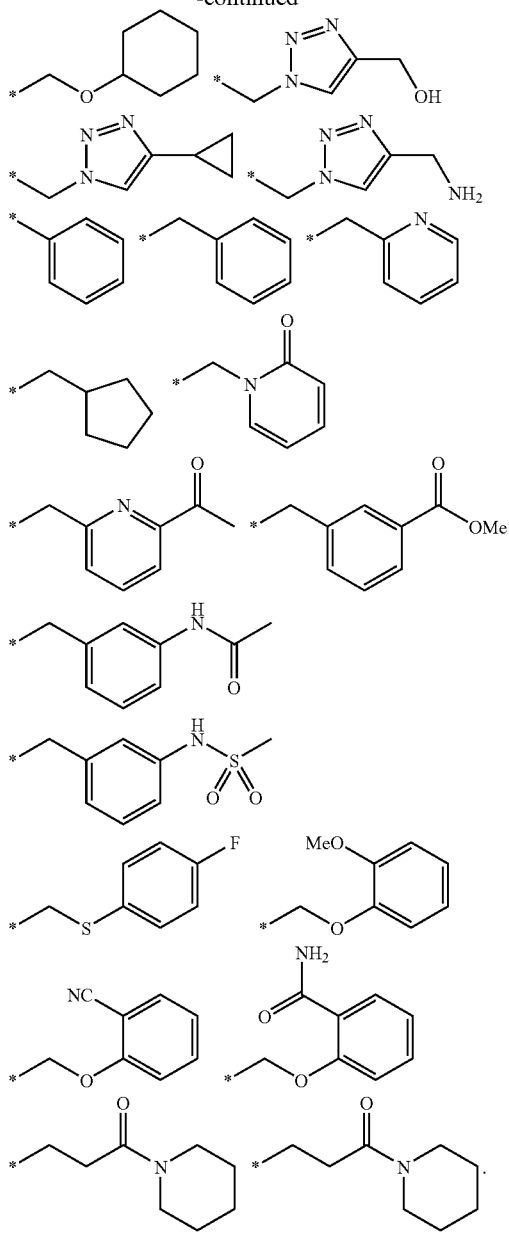

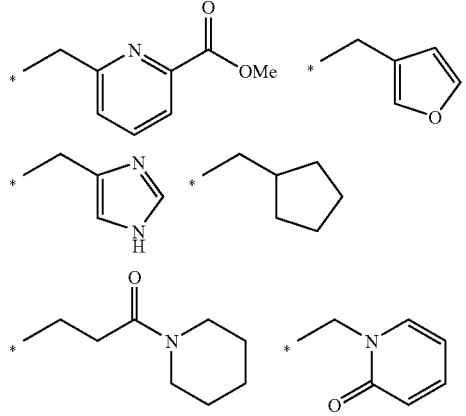

In yet another variation, —(Y-Q-R₁) is —(CH₂)ₙC(O)ORc, and the reaction product, Compound A, is of the formula Compound A

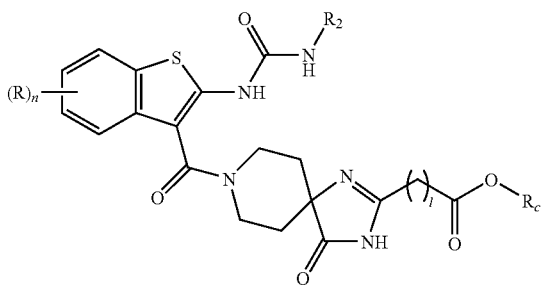

wherein n is 4;

l is 1 or 2; and $R_c$ is $(C_{1-3})$alkyl.

In still another embodiment, the method further comprising reacting Compound A with a trimethylaluminum compound of the formula Al(CH)₂—NR$_a$R$_b$ to form a compound of the formula

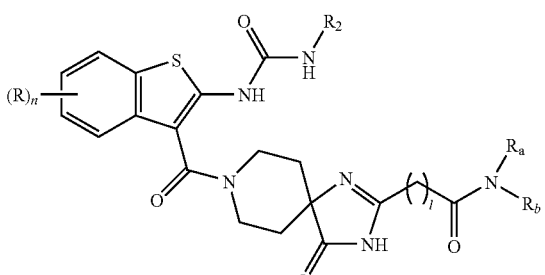

wherein

R$_a$ and R$_b$ are each independently selected from the group consisting of $(C_{1-3})$alkyl, or R$_a$ and R$_b$ are taken together to form a 5 or 6 member saturated or unsaturated heterocyclic ring.

In another variation, —(Y-Q-R₁) is selected from the group consisting of hydrogen, —CH₂NH₂, —CH₂OH, —CH₂NHCH₃, —CH₂NHC(O)CH₃, —CH₂NHCH₂CH(CH₃)₂, —CH₂Cl, —(CH₂)₂C(O)OCH₂CH₃, —(CH₂)₂C(O)N(CH₂CH₃)₂, benzyl, isopropyl, n-butyl, phenyl, and

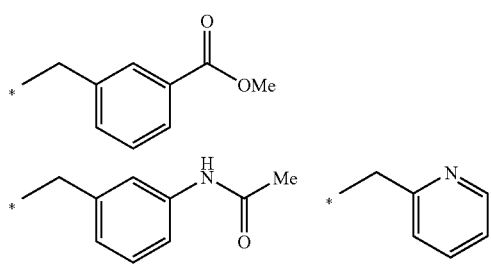

In another embodiment, the method of preparing compounds of the invention comprising:
coupling a compound of the formula

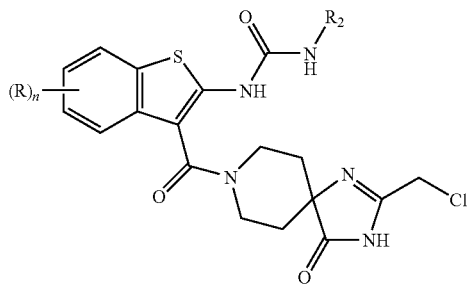

to a compound selected from the group consisting of HOR₁ and Na⁺ (OR₁)⁻, under conditions that form a product of the formula

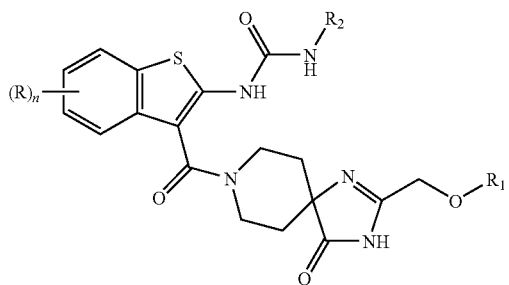

wherein
n is 4;
each R is independently selected from the group consisting of H, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl $(C_{1-10})$alkyl, aza$(C_{1-10})$alkyl, $(C_{1-10})$oxaalkyl, $(C_{1-10})$ oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero $(C_{1-10})$aryl$(C_{1-5})$alkyl, $(C_{9-12})$bicycloaryl$(C_{1-5})$alkyl, hetero $(C_{8-2})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero $(C_{3-12})$bicycloalkyl, $(C_{4-12})$aryl, hetero$(C_{1-10})$aryl, $(C_{9-12})$ bicycloaryl, and hetero$(C_{4-12})$bicycloaryl, each substituted or unsubstituted;
R₁ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, $(C_{3-12})$cycloalkyloxy, hetero$(C_{3-12})$cycloalkyloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy $(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$ cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl, and hetero$(C_{4-12})$bicycloaryl, each substituted or unsubstituted; and
R₂ is substituted or unsubstituted alkyl.

In one variation of the above embodiment and variations, R₁ is selected from the group consisting of $(C_{1-6})$alkyl, $(C_{3-6})$aryl, $(C_{1-6})$heteroaryl, $(C_{3-6})$cycloalkyl, and $(C_{1-16})$heterocycloalkyl, each unsubstituted or substituted. In another variation, R₁ is selected from the group consisting of substituted phenyl, isopropyl, isobutyl, and cyclohexyl.

In yet another embodiment, the method of preparing the inhibitor of the invention comprising:
coupling a compound of the formula

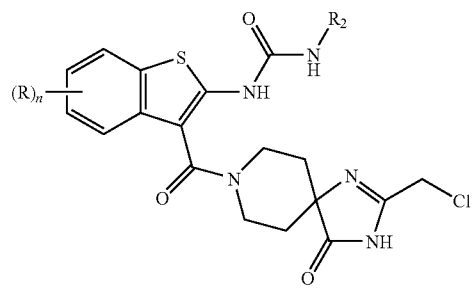

to a compound of the formula HS—R₁ under conditions that form a sulfide compound of the formula

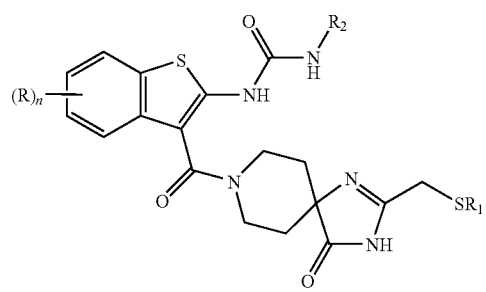

wherein
n is 4;
each R is independently selected from the group consisting of H, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl $(C_{1-10})$alkyl, aza$(C_{1-10})$alkyl, $(C_{1-10})$oxaalkyl, $(C_{1-10})$ oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero $(C_{1-10})$aryl$(C_{1-5})$alkyl, $(C_{9-12})$bicycloaryl$(C_{1-5})$alkyl, hetero $(C_{8-2})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero $(C_{3-12})$bicycloalkyl, $(C_{4-12})$aryl, hetero$(C_{1-10})$aryl, $(C_{9-12})$ bicycloaryl, and hetero$(C_{4-12})$bicycloaryl, each substituted or unsubstituted;
R₁ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, $(C_{3-12})$cycloalkyloxy, hetero$(C_{3-12})$cycloalkyloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy $(C_{1-10})$alkyl, carbonyl$(C_{1-10})$alkyl, thiocarbonyl$(C_{1-10})$alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl, and hetero($C_{4-12}$)bicycloaryl, each substituted or unsubstituted; and $R_2$ is substituted or unsubstituted alkyl.

In some variations of the immediately preceding embodiment, the method further comprising oxidizing the sulfide compound to form the corresponding sulfoxide compound of the formula:

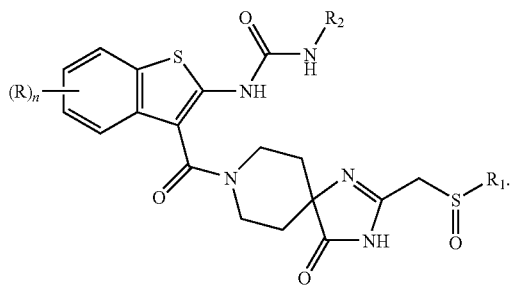

In some other variations of the immediately preceding embodiment, the method comprising further oxidizing the sulfoxide compound to form the corresponding sulfone compound of the formula:

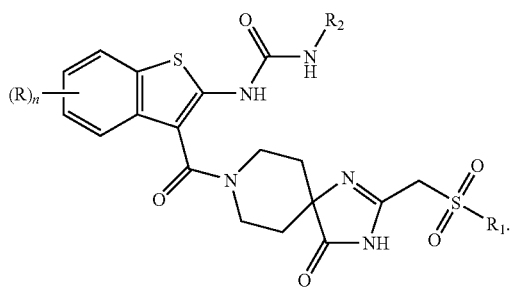

In yet another embodiment, the method of preparing compounds of the invention comprises:
coupling a compound of the formula

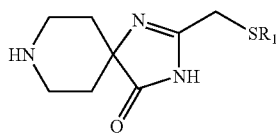

to a compound of the formula

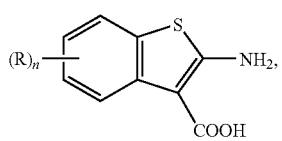

and then to a compound of the formula EtNC(O)H, under conditions that form a sulfide compound of the formula

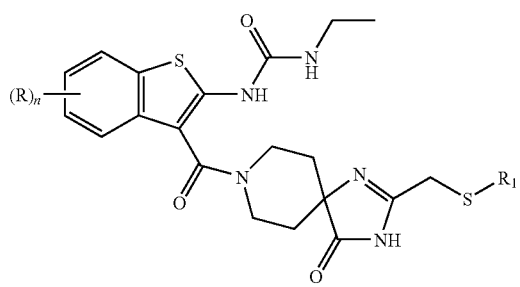

wherein
n is 4;
each R is independently selected from the group consisting of H, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, aminocarbonyl, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)Oxaalkyl, ($C_{1-10}$)Oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-2}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl, and hetero($C_{4-12}$)bicycloaryl, each substituted or unsubstituted; and $R_1$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, ($C_{3-12}$)cycloalkyloxy, hetero($C_{3-12}$)cycloalkyloxy, carbonyl, oxycarbonyl, aminocarbonyl, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)Oxaalkyl, ($C_{1-10}$)Oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl, and hetero($C_{4-12}$)bicycloaryl, each substituted or unsubstituted.

In some variations of the immediately preceding embodiment, the method further comprises oxidizing the sulfide compound to the corresponding sulfone compound of the formula:

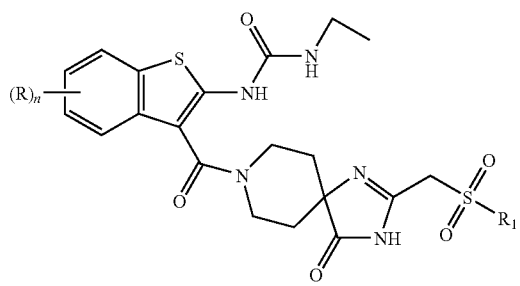

In some variation of the immediately preceding embodiment and variations, $R_1$ is selected from the group consisting of $(C_{1-6})$alkyl.

In yet another embodiment, the method of preparing compounds of the invention comprises:

coupling a compound of the formula

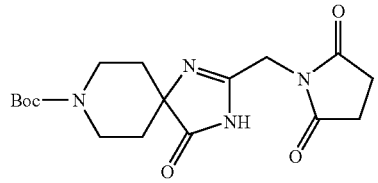

to a compound of the formula

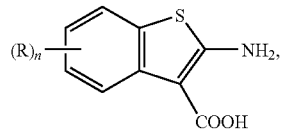

and then to a compound of the formula EtNC(O)H, under conditions that form a dioxopyrrolinyl compound of the formula

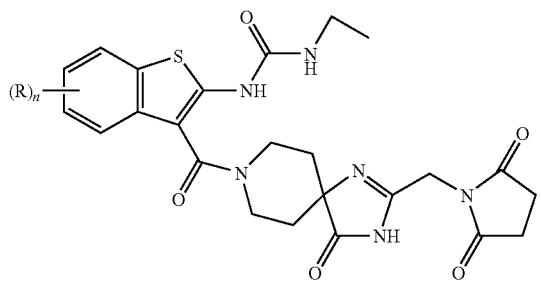

wherein n is 4;

each R is independently selected from the group consisting of H, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl $(C_{1-10})$alkyl, aza$(C_{1-10})$alkyl, $(C_{1-10})$Oxaalkyl, $(C_{1-10})$Oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero $(C_{1-10})$aryl$(C_{1-5})$alkyl, $(C_{9-12})$bicycloaryl$(C_{1-5})$alkyl, hetero $(C_{8-2})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero $(C_{3-12})$bicycloalkyl, $(C_{4-12})$aryl, hetero$(C_{1-10})$aryl, $(C_{9-12})$ bicycloaryl and hetero$(C_{4-12})$bicycloaryl, each substituted or unsubstituted.

In yet another embodiment, the method of preparing compounds of the invention comprises:

coupling an intermediate of the formula

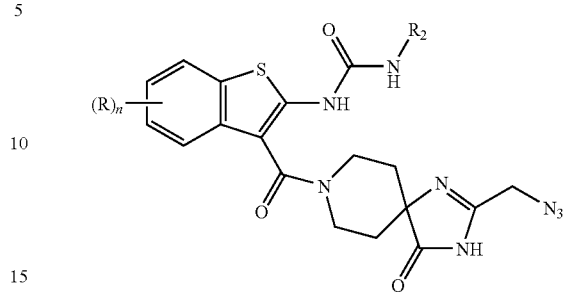

to an alkynyl compound of the formula CH≡$CR_1$ under conditions that form a triazole compound of the formula

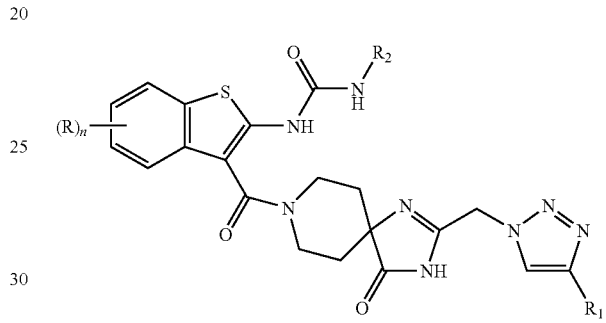

wherein n is 4;

each R is independently selected from the group consisting of H, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-2})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted; and $R_2$ is substituted or unsubstituted alkyl.

In some variations of the immediately preceding embodiment, the method further comprising forming the intermediate from a stating material of the formula

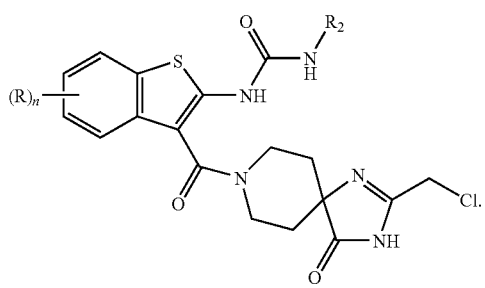

In other variations of the immediately preceding embodiment and variations of the method, $R_1$ is selected from the group consisting of hydrogen, $(C_{1-6})$alkyl, $(C_{3-6})$aryl, $(C_{1-6})$heteroaryl, $(C_{3-6})$cycloalkyl, and $(C_{1-6})$heterocycloalkyl, amino$(C_{1-6})$alkyl, each unsubstituted or substituted. In other variations, $R_1$ is selected from the group consisting of hydrogen, aminomethyl, dimethylaminomethyl, tertbutyl, hydroxylmethyl, and cyclopropyl. In still other variations $R_2$ is selected from the group consisting of methyl and ethyl.

In yet another variation of the immediately preceding embodiment and variations the intermediate is formed by
coupling a compound of the formula $(CH_3O)_3CCH_2Cl$ to a compound A of the formula

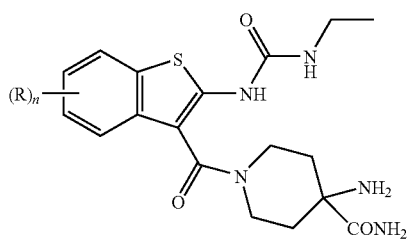

In some variations, the method further comprises forming Compound A from a compound B of the formula:

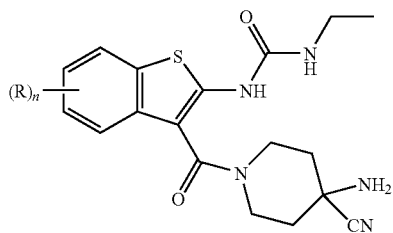

In some variations, the method further comprises forming Compound B from a compound C of the formula:

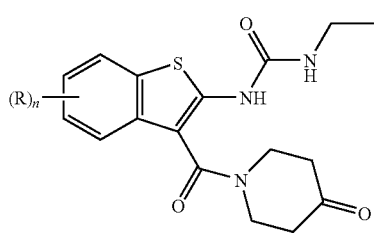

In some variations, the method further comprises forming Compound C from a compound D of the formula:

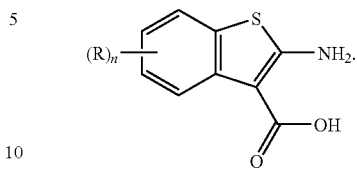

Salts, Hydrates, and Prodrugs of ACC Inhibitors

It should be recognized that the compounds of the present invention may be present and optionally administered in the form of salts, hydrates and prodrugs that are converted in vivo into the compounds of the present invention. For example, it is within the scope of the present invention to convert the compounds of the present invention into and use them in the form of their pharmaceutically acceptable salts derived from various organic and inorganic acids and bases in accordance with procedures well known in the art.

When the compounds of the present invention possess a free base form, the compounds can be prepared as a pharmaceutically acceptable acid addition salt by reacting the free base form of the compound with a pharmaceutically acceptable inorganic or organic acid, e.g., hydrohalides such as hydrochloride, hydrobromide, hydroiodide; other mineral acids and their corresponding salts such as sulfate, nitrate, phosphate, etc.; and alkyl and monoarylsulfonates such as ethanesulfonate, toluenesulfonate and benzenesulfonate; and other organic acids and their corresponding salts such as acetate, tartrate, maleate, succinate, citrate, benzoate, salicylate and ascorbate. Further acid addition salts of the present invention include, but are not limited to: adipate, alginate, arginate, aspartate, bisulfate, bisulfite, bromide, butyrate, camphorate, camphorsulfonate, caprylate, chloride, chlorobenzoate, cyclopentanepropionate, digluconate, dihydrogenphosphate, dinitrobenzoate, dodecylsulfate, fumarate, galacterate (from mucic acid), galacturonate, glucoheptonate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, iso-butyrate, lactate, lactobionate, malate, malonate, mandelate, metaphosphate, methanesulfonate, methylbenzoate, monohydrogenphosphate, 2-naphthalenesulfonate, nicotinate, nitrate, oxalate, oleate, pamoate, pectinate, persulfate, phenylacetate, 3-phenylpropionate, phosphate, phosphonate and phthalate. It should be recognized that the free base forms will typically differ from their respective salt forms somewhat in physical properties such as solubility in polar solvents, but otherwise the salts are equivalent to their respective free base forms for the purposes of the present invention.

When the compounds of the present invention possess a free acid form, a pharmaceutically acceptable base addition salt can be prepared by reacting the free acid form of the compound with a pharmaceutically acceptable inorganic or organic base. Examples of such bases are alkali metal hydroxides including potassium, sodium and lithium hydroxides; alkaline earth metal hydroxides such as barium and calcium hydroxides; alkali metal alkoxides, e.g., potassium ethanolate and sodium propanolate; and various organic bases such as ammonium hydroxide, piperidine, diethanolamine and N-methylglutamine. Also included are the aluminum salts of the compounds of the present invention. Further base salts of the present invention include, but are not limited to: copper, ferric, ferrous, lithium, magnesium, manganic, manganous, potassium, sodium and zinc salts. Organic base salts include, but are not limited to, salts of primary, secondary and tertiary amines, substituted amines including naturally occurring substituted amines, cyclic amines and basic ion exchange resins, e.g., arginine, betaine, caffeine, chloroprocaine, choline, N,N'-dibenzylethylenediamine (benzathine), dicyclohexylamine, diethanolamine, 2-diethylaminoethanol, 2-dimethylaminoethanol, ethanolamine, ethylenediamine, N-ethylmorpholine, N-ethylpiperidine, glucamine, glucosamine, histidine, hydrabamine, iso-propylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris-(hydroxymethyl)-methylamine (tromethamine). It should be recognized that the free acid forms will typically differ from their respective salt forms somewhat in physical properties such as solubility in polar solvents, but otherwise the salts are equivalent to their respective free acid forms for the purposes of the present invention.

Compounds of the present invention that comprise basic nitrogen containing groups may be quaternized with such agents as ($C_{1-4}$) alkyl halides, e.g., methyl, ethyl, iso-propyl and tert-butyl chlorides, bromides and iodides; di ($C_{1-4}$) alkyl sulfates, e.g., dimethyl, diethyl and diamyl sulfates; ($C_{10-18}$) alkyl halides, e.g., decyl, dodecyl, lauryl, myristyl and stearyl chlorides, bromides and iodides; and aryl ($C_{1-4}$) alkyl halides, e.g., benzyl chloride and phenethyl bromide. Such salts permit the preparation of both water-soluble and oil-soluble compounds of the present invention.

N-oxides of compounds according to the present invention can be prepared by methods known to those of ordinary skill in the art. For example, N-oxides can be prepared by treating an unoxidized form of the compound with an oxidizing agent (e.g., trifluoroperacetic acid, permaleic acid, perbenzoic acid, peracetic acid, meta-chloroperoxybenzoic acid, or the like) in a suitable inert organic solvent (e.g., a halogenated hydrocarbon such as dichloromethane) at approximately 0° C. Alternatively, the N-oxides of the compounds can be prepared from the N-oxide of an appropriate starting material.

Prodrug derivatives of compounds according to the present invention can be prepared by modifying substituents of compounds of the present invention that are then converted in vivo to a different substituent. It is noted that in many instances, the prodrugs themselves also fall within the scope of the range of compounds according to the present invention. For example, prodrugs can be prepared by reacting a compound with a carbamylating agent (e.g., 1,1-acyloxyalkylcarbonochloridate, para-nitrophenyl carbonate, or the like) or an acylating agent. Further examples of methods of making prodrugs are described in Saulnier et al. (1994), *Bioorganic and Medicinal Chemistry Letters*, Vol. 4, p. 1985.

Protected derivatives of compounds of the present invention can also be made. Examples of techniques applicable to the creation of protecting groups and their removal can be found in P. G. M. Wuts and T. W. Greene in "*Greene's Protective Groups in Organic Synthesis*" 4th edition, John Wiley and Sons, 2007.

Compounds of the present invention may also be conveniently prepared, or formed during the process of the invention, as solvates (e.g., hydrates). Hydrates of compounds of the present invention may be conveniently prepared by recrystallization from an aqueous/organic solvent mixture, using organic solvents such as dioxin, tetrahydrofuran or methanol.

A "pharmaceutically acceptable salt", as used herein, is intended to encompass any compound according to the present invention that is utilized in the form of a salt thereof, especially where the salt confers on the compound improved pharmacokinetic properties as compared to the free form of compound or a different salt form of the compound. The pharmaceutically acceptable salt form may also initially confer desirable pharmacokinetic properties on the compound that it did not previously possess, and may even positively affect the pharmacodynamics of the compound with respect to its therapeutic activity in the body. An example of a pharmacokinetic property that may be favorably affected is the manner in which the compound is transported across cell membranes, which in turn may directly and positively affect the absorption, distribution, biotransformation and excretion of the compound. While the route of administration of the pharmaceutical composition is important, and various anatomical, physiological and pathological factors can critically affect bioavailability, the solubility of the compound is usually dependent upon the character of the particular salt form thereof, which it utilized. One of skill in the art will appreciate that an aqueous solution of the compound will provide the most rapid absorption of the compound into the body of a subject being treated, while lipid solutions and suspensions, as well as solid dosage forms, will result in less rapid absorption of the compound.

Uses for the Compounds of the Invention

Compounds of the invention are ACC inhibitors useful in the treatment, control and/or prevention of metabolic diseases and conditions that are mediated by abnormal fatty acid metabolism. These diseases and conditions include obesity, an overweight condition, hypertriglyceridemia, hyperlipidemia, hypoalphalipoproteinemia, metabolic syndrome, diabetes mellitus (especially Type II), hyperinsulinemia, impaired glucose tolerance, insulin resistance, diabetic complication, atherosclerosis, hypertension, coronary heart disease, hypercholesterolemia, stroke, polycystic ovary disease, cerebrovascular disease and congestive heart failure. In particularly, metabolic syndrome, atherosclerosis, and non-insulin dependent diabetes mellitus (NIDDM).

Metabolic syndrome (aka insulin resistance syndrome, syndrome X) is a common clinical disorder that is defined as the presence of increased insulin concentrations in association with other disorders including visceral obesity, hyperlipidemia and dyslipidemia, hyperglycemia, hypertension, and sometimes hyperuricemia and renal dysfunction. Recent studies have suggested that abnormal fatty acid metabolism may be at the core of metabolic syndrome. It is now well established that the development of insulin resistance and type 2 diabetics are tightly associated with excess intramyocellular triacylglyceride (TAG) in nonadipose tissues such as in skeletal muscle, liver and pancreas. Krissak et al., *Diabetologia* 1999, 42:113-6; Hulver, M. W. et al., *Am J Physiol Endocrinol Metab* 2003; 284:E741-7; Sinha R. et al., *Diabetes* 2002; 51:1022-7. The precise mechanism of how increased intracellular lipid content exacerbates whole body insulin sensitivity is unclear at present but it has been postulated that increased long chain fatty acyl-CoAs, ceramide or diacylglycerol, whose contents are proportional to the accumulation of intramyocellular triglyceride, antagonizes metabolic actions of insulin, reduces muscle glucose uptake and inhibits hepatic glucose production. Sinha R. et al., *Diabetes* 2002; 51:1022-7; Friedman J. *Nature* 2002; 415:268-9). As muscle is the primary site of metabolic action of insulin, the development of muscle insulin resistance along with liver insulin resistance are thus inherently linked to the development of whole body insulin resistance.

Inhibiting the activity of acetyl CoA carboxylase (ACC) would reduce the production of malonyl-CoA from acetyl-CoA. Malonyl-CoA plays an important role in the overall fatty acid metabolism: malonyl-CoA is an intermediate utilized by fatty acid synthase for de novo lipogenesis, and it also acts as a potent allosteric inhibitor of carnitine palmitoyltransferase 1 (CPT1), a mitochondrial membrane protein that shuttles long chain fatty acyl CoAs into the mitochondria for β-oxidization. Ruderman N. and Prentki M. *Nat Rev Drug Discov* 2004; 3: 340-51. A small molecule inhibitor of ACC would thus limit de novo lipid synthesis and increase muscle and liver fat oxidation; thus reduce the accumulation of long chain fatty acids.

The compounds of the invention are also useful for the prophylaxis or treatment of atherosclerosis, a disease of the arteries. The pathological sequence leading to atherosclerosis and occlusive heart disease is well known. The earliest stage in this sequence is the formation of "fatty streaks" in the carotid, coronary and cerebral arteries and in the aorta. These lesions are yellow in color due to the presence of lipid deposits found principally within smooth-muscle cells and in macrophages of the intima layer of the arteries and aorta. Further, it is postulated that most of the cholesterol found within the fatty streaks, in turn, gives rise to development of the "fibrous plaque," which consists of accumulated intimal smooth muscle cells laden with lipid and surrounded by extra-cellular lipid, collagen, elastin and proteoglycans. These cells plus matrix form a fibrous cap that covers a deeper deposit of cell debris and more extracellular lipid. The lipid is primarily free and esterified cholesterol. The fibrous plaque forms slowly, and is likely in time to become calcified and necrotic, advancing to the "complicated lesion," which accounts for the arterial occlusion and tendency toward mural thrombosis and arterial muscle spasm that characterize advanced atherosclerosis. The ACC inhibitors reduce the formation of the fatty streaks and lower the chance of atherosclerosis.

Combination Therapy

The ACC inhibitors according to the present invention may have a therapeutic additive or synergistic effect with a wide variety of therapeutic agents. Combination therapies that comprise one or more compounds of the present invention with one or more other therapeutic agents can be used, for example, to: 1) enhance the therapeutic effect(s) of the one or more compounds of the present invention and/or the one or more other therapeutic agents; 2) reduce the side effects exhibited by the one or more compounds of the present invention and/or the one or more other therapeutic agents; and/or 3) reduce the effective dose of the one or more compounds of the present invention and/or the one or more other therapeutic agents. It is noted that combination therapy is intended to cover when agents are administered before or after each other (sequential therapy) as well as when the agents are administered at the same time.

Examples of such therapeutic agents that may be used in combination with ACC inhibitors include, but are not limited to, antiatherosclerosis agents, a diabetes treating agents, obesity treating agents, and cardiovascular agents.

Antiatherosclerosis agents being contemplated for combination therapy with the compounds of the invention include, but are not limited to, lipase inhibitors, HMG-CoA reductase inhibitors, HMG-CoA synthase inhibitors, HMG-CoA reductases, gene expression inhibitors, HMG-CoA synthase gene expression inhibitors, microsomal triglyceride transfer protein (MTP)/Apo B secretion inhibitors, cholesterol ester transfer protein (CETP) inhibitors, bile acid absorption inhibitors, cholesterol absorption inhibitors, cholesterol synthesis inhibitors, squalene synthetase inhibitors, squalene epoxidase inhibitors, squalene cyclase inhibitors, combined squalene epoxidase/squalene cyclase inhibitors, fibrates, niacin, PPAR agonists, ion-exchange resins, antioxidants, acyl-CoA:cholesterol acyl transferase (ACAT) inhibitors, bile acid sequestrants, antiplatelet agents, antithrombotic agents or estrogen receptor modulators. HMG-CoA reductases and CETP inhibitors are preferred antiatherosclerosis agents for use with the compounds of the invention. Examples of HMG-CoA reductase inhibitor which may be used with the compounds of the invention include lovastatin, rosuvastatin, itavastatin, simvastatin, pravastatin, fluvastatin, atorvastatin (and its hemicalcium salt) or rivastatin.

Diabetes treating agent being contemplated for combination therapy with the compounds of the invention include, but are not limited to, aldose reductase inhibitors, glucocorticoid receptor antagonists, glycogenolysis inhibitors, glycogen phosphorylase inhibitors, sorbitol dehydrogenase inhibitors, insulin, insulin analogs, insulinotropin, sulfonylureas, sulfonylureas analogs, biguanides, imidazolines, insulin secretagogues, linogliride, glitazones, glucosidase inhibitors, acarbose, miglitol, emiglitate, voglibose, camiglibose, β-agonists, phosphodiesterase inhibitors (e.g., PDE5 or PDE11), vanadate, vanadium complexes (e.g. Naglivan®), peroxovanadium complexes, amylin antagonists, amylase inhibitors, glucagon antagonists, gluconeogenesis inhibitors, somatostatin analogs, antilipolytic agents, nicotinic acid, acipimox, pramlintide (Symlin™), nateglinide, activators of AMP-activated protein kinase, PPARδ agonists, duel PPARα or/PPAR-δ agonists, protein kinase C-B inhibitors, PTP1B inhibitors, glycogen synthase kinase-3 inhibitors, GLP-1 agonists or soluble guanylate cyclase (sGc) activators. Specific diabetes treating agents include, but are not limited to, chlorpropamide, glibenclamide, tolbutamide, tolazamide, acetohexamide, Glypizide®, glimepiride, repaglinide, meglitinide, metformin, phenformin, buformin, midaglizole, isaglidole, deriglidole, idazoxan, efaroxan, fluparoxan, ciglitazone, pioglitazone, englitazone, darglitazone, clomoxir or etomoxir.

Obesity treating agent being contemplated for combination therapy with the compounds of the invention include, but are not limited to, phenylpropanolamine, ephedrine, pseudoephedrine, phentermine, a neuropeptide Y antagonist, a β-adrenergic receptor agonist, a cholecystokinin-A agonist, a monoamine reuptake inhibitor, a sympathomimetic agent, a serotonin modulator, a dopamine agonist, a melanocortin receptor modulator, a cannabinoid receptor antagonist, a melanin concentrating hormone antagonist, leptin, a leptin analog, a leptin receptor agonist, a galanin antagonist, a lipase inhibitor, a phosphatase 1B inhibitor, a bombesin agonist, dehydroepiandrosternone or analogs thereof, thyroxine, a thyromimetic agent, dehydroepiandrosterone or an analog thereof, a glucocorticoid receptor modulator, an orexin receptor antagonist, a urocortin binding protein antagonist, a glucagon-like peptide-1 receptor agonist, an eating behavior modifying agent, a ciliary neurotrophic factor, a neurokinin receptor antagonist, a noradrenalin transport modulator or a dopamine transport modulator. Specific examples of obesity treating agents include orlistat, sibutramine or bromocriptine.

Cardiovascular agents being contemplated for combination therapy with the compounds of the invention include, but are not limited to, calcium channel blockers, angiotensin converting enzyme (ACE) inhibitors or diuretics.

Compositions Comprising ACC Inhibitors

A wide variety of compositions and administration methods may be used in conjunction with the compounds of the present invention. Such compositions may include, in addition to the compounds of the present invention, conventional pharmaceutical excipients, and other conventional, pharmaceutically inactive agents. Additionally, the compositions may include active agents in addition to the compounds of the present invention. These additional active agents may include additional compounds according to the invention, and/or one or more other pharmaceutically active agents.

The compositions may be in gaseous, liquid, semi-liquid or solid form, formulated in a manner suitable for the route of administration to be used. For oral administration, capsules and tablets are typically used. For parenteral administration, reconstitution of a lyophilized powder, prepared as described herein, is typically used.

Compositions comprising compounds of the present invention may be administered or coadministered orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, or intrathecally. The compounds and/or compositions according to the invention may also be administered or coadministered in slow release dosage forms.

The ACC inhibitors and compositions comprising them may be administered or coadministered in any conventional dosage form. Co-administration in the context of this invention is intended to mean the administration of more than one therapeutic agent, one of which includes an ACC inhibitor, in the course of a coordinated treatment to achieve an improved clinical outcome. Such co-administration may also be coextensive, that is, occurring during overlapping periods of time.

Solutions or suspensions used for parenteral, intradermal, subcutaneous, or topical application may optionally include one or more of the following components: a sterile diluent, such as water for injection, saline solution, fixed oil, polyethylene glycol, glycerine, propylene glycol or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; agents for the adjustment of tonicity such as sodium chloride or dextrose, and agents for adjusting the acidity or alkalinity of the composition, such as alkaline or acidifying agents or buffers like carbonates, bicarbonates, phosphates, hydrochloric acid, and organic acids like acetic and citric acid. Parenteral preparations may optionally be enclosed in ampules, disposable syringes or single or multiple dose vials made of glass, plastic or other suitable material.

When compounds according to the present invention exhibit insufficient solubility, methods for solubilizing the compounds may be used. Such methods are known to those of skill in this art, and include, but are not limited to, using cosolvents, such as dimethylsulfoxide (DMSO), using surfactants, such as TWEEN, or dissolution in aqueous sodium bicarbonate. Derivatives of the compounds, such as prodrugs of the compounds may also be used in formulating effective pharmaceutical compositions.

Upon mixing or adding compounds according to the present invention to a composition, a solution, suspension, emulsion or the like may be formed. The form of the resulting composition will depend upon a number of factors, including the intended mode of administration, and the solubility of the compound in the selected carrier or vehicle. The effective concentration needed to ameliorate the disease being treated may be empirically determined.

Compositions according to the present invention are optionally provided for administration to humans and animals in unit dosage forms, such as tablets, capsules, pills, powders, dry powders for inhalers, granules, sterile parenteral solutions or suspensions, and oral solutions or suspensions, and oil-water emulsions containing suitable quantities of the compounds, particularly the pharmaceutically acceptable salts, preferably the sodium salts, thereof. The pharmaceutically therapeutically active compounds and derivatives thereof are typically formulated and administered in unit-dosage forms or multiple-dosage forms. Unit-dose forms, as used herein, refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoules and syringes individually packaged tablet or capsule. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pint or gallons. Hence, multiple dose form is a multiple of unit-doses that are not segregated in packaging.

In addition to one or more compounds according to the present invention, the composition may comprise: a diluent such as lactose, sucrose, dicalcium phosphate, or carboxymethylcellulose; a lubricant, such as magnesium stearate, calcium stearate and talc; and a binder such as starch, natural gums, such as gum acaciagelatin, glucose, molasses, polyvinylpyrrolidine, celluloses and derivatives thereof, povidone, crospovidones and other such binders known to those of skill in the art. Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to form a solution or suspension. If desired, the pharmaceutical composition to be administered may also contain minor amounts of auxiliary substances such as wetting agents, emulsifying agents, or solubilizing agents, pH buffering agents and the like, for example, acetate, sodium citrate, cyclodextrine derivatives, sorbitan monolaurate, triethanolamine sodium acetate, triethanolamine oleate, and other such agents. Actual methods of preparing such dosage forms are known in the art, or will be apparent, to those skilled in this art; for example, see Remington: The Science and Practices of Pharmacy, Lippincott Williams, and Wilkins Publisher, $21^{st}$ edition, 2005. The composition or formulation to be administered will, in any event, contain a sufficient quantity of an inhibitor of the present invention to reduce ACC activity in vivo, thereby treating the disease state of the subject.

Dosage forms or compositions may optionally comprise one or more compounds according to the present invention in the range of 0.005% to 100% (weight/weight) with the balance comprising additional substances such as those described herein. For oral administration, a pharmaceutically acceptable composition may optionally comprise any one or more commonly employed excipients, such as, for example pharmaceutical grades of mannitol, lactose, starch, magnesium stearate, talcum, cellulose derivatives, sodium crosscarmellose, glucose, sucrose, magnesium carbonate, sodium saccharin, talcum. Such compositions include solutions, suspensions, tablets, capsules, powders, dry powders for inhalers and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparing these formulations are known to those skilled in the art. The compositions may optionally contain 0.01%-100% (weight/weight) of one or more ACC inhibitors, optionally 0.1-95%, and optionally 1-95%.

Salts, preferably sodium salts, of the inhibitors may be prepared with carriers that protect the compound against rapid elimination from the body, such as time release formulations or coatings. The formulations may further include other active compounds to obtain desired combinations of properties.

A. Formulations for Oral Administration

Oral pharmaceutical dosage forms may be as a solid, gel or liquid. Examples of solid dosage forms include, but are not limited to tablets, capsules, granules, and bulk powders. More specific examples of oral tablets include compressed, chewable lozenges and tablets that may be enteric-coated, sugar-coated or film-coated. Examples of capsules include hard or soft gelatin capsules. Granules and powders may be provided in non-effervescent or effervescent forms. Each may be combined with other ingredients known to those skilled in the art.

In certain embodiments, compounds according to the present invention are provided as solid dosage forms, preferably capsules or tablets. The tablets, pills, capsules, troches and the like may optionally contain one or more of the following ingredients, or compounds of a similar nature: a binder; a diluent; a disintegrating agent; a lubricant; a glidant; a sweetening agent; and a flavoring agent.

Examples of binders that may be used include, but are not limited to, microcrystalline cellulose, gum tragacanth, glucose solution, acacia mucilage, gelatin solution, sucrose, and starch paste.

Examples of lubricants that may be used include, but are not limited to, talc, starch, magnesium or calcium stearate, lycopodium and stearic acid.

Examples of diluents that may be used include, but are not limited to, lactose, sucrose, starch, kaolin, salt, mannitol, and dicalcium phosphate.

Examples of glidants that may be used include, but are not limited to, colloidal silicon dioxide.

Examples of disintegrating agents that may be used include, but are not limited to, crosscarmellose sodium, sodium starch glycolate, alginic acid, corn starch, potato starch, bentonite, methylcellulose, agar and carboxymethylcellulose.

Examples of coloring agents that may be used include, but are not limited to, any of the approved certified water-soluble FD and C dyes, mixtures thereof, and water insoluble FD and C dyes suspended on alumina hydrate.

Examples of sweetening agents that may be used include, but are not limited to, sucrose, lactose, mannitol and artificial sweetening agents such as sodium cyclamate and saccharin, and any number of spray-dried flavors.

Examples of flavoring agents that may be used include, but are not limited to, natural flavors extracted from plants such as fruits and synthetic blends of compounds that produce a pleasant sensation, such as, but not limited to peppermint and methyl salicylate.

Examples of wetting agents that may be used include, but are not limited to, propylene glycol monostearate, sorbitan monooleate, diethylene glycol monolaurate, and polyoxyethylene lauryl ether.

Examples of anti-emetic coatings that may be used include, but are not limited to, fatty acids, fats, waxes, shellac, ammoniated shellac and cellulose acetate phthalates.

Examples of film coatings that may be used include, but are not limited to, hydroxyethylcellulose, sodium carboxymethylcellulose, polyethylene glycol 4000 and cellulose acetate phthalate.

If oral administration is desired, the salt of the compound may optionally be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it may optionally additionally comprise a liquid carrier such as a fatty oil. In addition, dosage unit forms may optionally additionally comprise various other materials that modify the physical form of the dosage unit, for example, coatings of sugar and other enteric agents.

Compounds according to the present invention may also be administered as a component of an elixir, suspension, syrup, wafer, sprinkle, chewing gum or the like. A syrup may optionally comprise, in addition to the active compounds, sucrose as a sweetening agent and certain preservatives, dyes and colorings and flavors.

The compounds of the present invention may also be mixed with other active materials that do not impair the desired action, or with materials that supplement the desired action, such as antacids, H2 blockers, and diuretics. For example, if a compound is used for treating asthma or hypertension, it may be used with other bronchodilators and antihypertensive agents, respectively.

Examples of pharmaceutically acceptable carriers that may be included in tablets comprising compounds of the present invention include, but are not limited to binders, lubricants, diluents, disintegrating agents, coloring agents, flavoring agents, and wetting agents. Enteric-coated tablets, because of the enteric-coating, resist the action of stomach acid and dissolve or disintegrate in the neutral or alkaline intestines. Sugar-coated tablets may be compressed tablets to which different layers of pharmaceutically acceptable substances are applied. Film-coated tablets may be compressed tablets that have been coated with polymers or other suitable coating. Multiple compressed tablets may be compressed tablets made by more than one compression cycle utilizing the pharmaceutically acceptable substances previously mentioned. Coloring agents may also be used in tablets. Flavoring and sweetening agents may be used in tablets, and are especially useful in the formation of chewable tablets and lozenges.

Examples of liquid oral dosage forms that may be used include, but are not limited to, aqueous solutions, emulsions, suspensions, solutions and/or suspensions reconstituted from non-effervescent granules and effervescent preparations reconstituted from effervescent granules.

Examples of aqueous solutions that may be used include, but are not limited to, elixirs and syrups. As used herein, elixirs refer to clear, sweetened, hydroalcoholic preparations. Examples of pharmaceutically acceptable carriers that may be used in elixirs include, but are not limited to solvents. Particular examples of solvents that may be used include glycerin, sorbitol, ethyl alcohol and syrup. As used herein, syrups refer to concentrated aqueous solutions of a sugar, for example, sucrose. Syrups may optionally further comprise a preservative.

Emulsions refer to two-phase systems in which one liquid is dispersed in the form of small globules throughout another liquid. Emulsions may optionally be oil-in-water or water-in-oil emulsions. Examples of pharmaceutically acceptable carriers that may be used in emulsions include, but are not limited to non-aqueous liquids, emulsifying agents and preservatives.

Examples of pharmaceutically acceptable substances that may be used in non-effervescent granules, to be reconstituted into a liquid oral dosage form, include diluents, sweeteners and wetting agents.

Examples of pharmaceutically acceptable substances that may be used in effervescent granules, to be reconstituted into a liquid oral dosage form, include organic acids and a source of carbon dioxide.

Coloring and flavoring agents may optionally be used in all of the above dosage forms.

Particular examples of preservatives that may be used include glycerin, methyl and propylparaben, benzoic add, sodium benzoate and alcohol.

Particular examples of non-aqueous liquids that may be used in emulsions include mineral oil and cottonseed oil.

Particular examples of emulsifying agents that may be used include gelatin, acacia, tragacanth, bentonite, and surfactants such as polyoxyethylene sorbitan monooleate.

Particular examples of suspending agents that may be used include sodium carboxymethylcellulose, pectin, tragacanth, Veegum and acacia. Diluents include lactose and sucrose. Sweetening agents include sucrose, syrups, glycerin and artificial sweetening agents such as sodium cyclamate and saccharin.

Particular examples of wetting agents that may be used include propylene glycol monostearate, sorbitan monooleate, diethylene glycol monolaurate, and polyoxyethylene lauryl ether.

Particular examples of organic acids that may be used include citric and tartaric acid.

Sources of carbon dioxide that may be used in effervescent compositions include sodium bicarbonate and sodium carbonate. Coloring agents include any of the approved certified water soluble FD and C dyes, and mixtures thereof.

Particular examples of flavoring agents that may be used include natural flavors extracted from plants such fruits, and synthetic blends of compounds that produce a pleasant taste sensation.

For a solid dosage form, the solution or suspension, in for example propylene carbonate, vegetable oils or triglycerides, is preferably encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. Nos. Re 28,819 and 4,358, 603.

B. Injectables, Solutions, and Emulsions

The present invention is also directed to compositions designed to administer the compounds of the present invention by parenteral administration, generally characterized by subcutaneous, intramuscular or intravenous injection. Injectables may be prepared in any conventional form, for example as liquid solutions or suspensions, solid forms suitable for solution or suspension in liquid prior to injection, or as emulsions.

Examples of excipients that may be used in conjunction with injectables according to the present invention include, but are not limited to water, saline, dextrose, glycerol or ethanol. The injectable compositions may also optionally comprise minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins. Implantation of a slow-release or sustained-release system, such that a constant level of dosage is maintained (see, e.g., U.S. Pat. No. 3,710,795) is also contemplated herein. The percentage of active compound contained in such parenteral compositions is highly dependent on the specific nature thereof, as well as the activity of the compound and the needs of the subject.

Parenteral administration of the formulations includes intravenous, subcutaneous and intramuscular administrations. Preparations for parenteral administration include sterile solutions ready for injection, sterile dry soluble products, such as the lyophilized powders described herein, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

When administered intravenously, examples of suitable carriers include, but are not limited to physiological saline or phosphate buffered saline (PBS), and solutions containing thickening and solubilizing agents, such as glucose, polyethylene glycol, and polypropylene glycol and mixtures thereof.

Examples of pharmaceutically acceptable carriers that may optionally be used in parenteral preparations include, but are not limited to aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles that may optionally be used include Sodium Chloride Injection, Ringers Injection, Isotonic Dextrose Injection, Sterile Water Injection, Dextrose and Lactated Ringers Injection.

Examples of nonaqueous parenteral vehicles that may optionally be used include fixed oils of vegetable origin, cottonseed oil, corn oil, sesame oil and peanut oil.

Antimicrobial agents in bacteriostatic or fungistatic concentrations may be added to parenteral preparations, particularly when the preparations are packaged in multiple-dose containers and thus designed to be stored and multiple aliquots to be removed. Examples of antimicrobial agents that may be used include phenols or cresols, mercurials, benzyl alcohol, chlorobutanol, methyl and propyl p-hydroxybenzoic acid esters, thimerosal, benzalkonium chloride and benzethonium chloride.

Examples of isotonic agents that may be used include sodium chloride and dextrose. Examples of buffers that may be used include phosphate and citrate. Examples of antioxidants that may be used include sodium bisulfate. Examples of local anesthetics that may be used include procaine hydrochloride. Examples of suspending and dispersing agents that may be used include sodium carboxymethylcellulose, hydroxypropyl methylcellulose and polyvinylpyrrolidone. Examples of emulsifying agents that may be used include Polysorbate 80 (TWEEN 80). A sequestering or chelating agent of metal ions includes EDTA.

Pharmaceutical carriers may also optionally include ethyl alcohol, polyethylene glycol and propylene glycol for water miscible vehicles and sodium hydroxide, hydrochloric acid, citric acid or lactic acid for pH adjustment.

The concentration of an inhibitor in the parenteral formulation may be adjusted so that an injection administers a pharmaceutically effective amount sufficient to produce the desired pharmacological effect. The exact concentration of an inhibitor and/or dosage to be used will ultimately depend on the age, weight and condition of the patient or animal as is known in the art.

Unit-dose parenteral preparations may be packaged in an ampoule, a vial or a syringe with a needle. All preparations for parenteral administration should be sterile, as is known and practiced in the art.

Injectables may be designed for local and systemic administration. Typically a therapeutically effective dosage is formulated to contain a concentration of at least about 0.1% w/w up to about 90% w/w or more, preferably more than 1% w/w of the ACC inhibitor to the treated tissue(s). The inhibitor may be administered at once, or may be divided into a number of smaller doses to be administered at intervals of time. It is understood that the precise dosage and duration of treatment will be a function of the location of where the composition is parenterally administered, the carrier and other variables that may be determined empirically using known testing protocols or by extrapolation from in vivo or in vitro test data. It is to be noted that concentrations and dosage values may also vary with the age of the individual treated. It is to be further understood that for any particular subject, specific dosage regimens may need to be adjusted over time according to the individual need and the professional judgment of the person administering or supervising the administration of the formulations. Hence, the concentration ranges set forth herein are intended to be exemplary and are not intended to limit the scope or practice of the claimed formulations.

The ACC inhibitor may optionally be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the disease state and may be empirically determined.

C. Lyophilized Powders

The compounds of the present invention may also be prepared as lyophilized powders, which can be reconstituted for administration as solutions, emulsions and other mixtures. The lyophilized powders may also be formulated as solids or gels.

Sterile, lyophilized powder may be prepared by dissolving the compound in a sodium phosphate buffer solution containing dextrose or other suitable excipient. Subsequent sterile filtration of the solution followed by lyophilization under standard conditions known to those of skill in the art provides the desired formulation. Briefly, the lyophilized powder may optionally be prepared by dissolving dextrose, sorbitol, fructose, corn syrup, xylitol, glycerin, glucose, sucrose or other suitable agent, about 1-20%, preferably about 5 to 15%, in a suitable buffer, such as citrate, sodium or potassium phosphate or other such buffer known to those of skill in the art at, typically, about neutral pH. Then, a ACC inhibitor is added to the resulting mixture, preferably above room temperature, more preferably at about 30-35° C., and stirred until it dissolves. The resulting mixture is diluted by adding more buffer to a desired concentration. The resulting mixture is sterile filtered or treated to remove particulates and to insure sterility, and apportioned into vials for lyophilization. Each vial may contain a single dosage or multiple dosages of the inhibitor.

D. Formulation for Topical Administration

The compounds of the present invention may also be administered as topical mixtures. Topical mixtures may be used for local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The ACC inhibitors may be formulated as aerosols for topical application, such as by inhalation (see, U.S. Pat. Nos. 4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will typically have diameters of less than 50 microns, preferably less than 10 microns.

The inhibitors may also be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the ACC inhibitor alone or in combination with other pharmaceutically acceptable excipients can also be administered.

E. Formulations for Other Routes of Administration

Depending upon the disease state being treated, other routes of administration, such as topical application, transdermal patches, and rectal administration, may also be used. For example, pharmaceutical dosage forms for rectal administration are rectal suppositories, capsules and tablets for systemic effect. Rectal suppositories are used herein mean solid bodies for insertion into the rectum that melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax, (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The typical weight of a rectal suppository is about 2 to 3 gm. Tablets and capsules for rectal administration may be manufactured using the same pharmaceutically acceptable substance and by the same methods as for formulations for oral administration.

F. Examples of Formulations

The following are particular examples of oral, intravenous and tablet formulations that may optionally be used with compounds of the present invention. It is noted that these formulations may be varied depending on the particular compound being used and the indication for which the formulation is going to be used.

| ORAL FORMULATION | |
|---|---|
| Compound of the Present Invention | 10-100 mg |
| Citric Acid Monohydrate | 105 mg |
| Sodium Hydroxide | 18 mg |
| Flavoring | |
| Water | q.s. to 100 mL |

| INTRAVENOUS FORMULATION | |
|---|---|
| Compound of the Present Invention | 0.1-10 mg |
| Dextrose Monohydrate | q.s. to make isotonic |
| Citric Acid Monohydrate | 1.05 mg |
| Sodium Hydroxide | 0.18 mg |
| Water for Injection | q.s. to 1.0 mL |

| TABLET FORMULATION | |
|---|---|
| Compound of the Present Invention | 1% |
| Microcrystalline Cellulose | 73% |
| Stearic Acid | 25% |
| Colloidal Silica | 1%. |

Dosage, Host and Safety

The compounds of the present invention are stable and can be used safely. In particular, the compounds of the present invention are useful as ACC inhibitors for a variety of subjects (e.g., humans, non-human, mammals, and non-mammals).

The optimal dose may vary depending upon such conditions as, for example, the type of subject, the body weight of the subject, on the severity of the condition, the route of administration, and specific properties of the particular compound being used. Generally, acceptable and effective daily doses are amounts sufficient to effectively slow or eliminate the condition being treated. Typically, the daily dose for oral administration to an adult (body weight of about 60 kg) is about 1 to 1000 mg, about 3 to 300 mg, or about 10 to 200 mg. It will be appreciated that the daily dose can be given in a single administration or in multiple (e.g., 2 or 3) portions a day.

Kits and Articles of Manufacture Comprising ACC Inhibitors

The invention is also directed to kits and other articles of manufacture for treating diseases associated with ACC. It is noted that diseases are intended to cover all conditions for which ACC inhibitors possess activity that contributes to the pathology and/or symptomology of the condition.

In one embodiment, a kit is provided that comprises a composition comprising at least one inhibitor of the present invention in combination with instructions. The instructions may indicate the disease state for which the composition is to be administered, storage information, dosing information and/or instructions regarding how to administer the composition. The kit may also comprise packaging materials. The packaging material may comprise a container for housing the composition. The kit may also optionally comprise additional components, such as syringes for administration of the composition. The kit may comprise the composition in single or multiple dose forms.

In another embodiment, an article of manufacture is provided that comprises a composition comprising at least one inhibitor of the present invention in combination with packaging materials. The packaging material may comprise a container for housing the composition. The container may optionally comprise a label indicating the disease state for which the composition is to be administered, storage information, dosing information and/or instructions regarding how to administer the composition. The kit may also optionally comprise additional components, such as syringes for administration of the composition. The kit may comprise the composition in single or multiple dose forms.

It is noted that the packaging material used in kits and articles of manufacture according to the present invention may form a plurality of divided containers such as a divided bottle or a divided foil packet. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container that is employed will depend on the exact dosage form involved, for example a conventional cardboard box would not generally be used to hold a liquid suspension. It is feasible that more than one container can be used together in a single package to market a single dosage form. For example, tablets may be contained in a bottle that is in turn contained within a box. Typically the kit includes directions for the administration of the separate components. The kit form is particularly advantageous when the separate components are preferably administered in different dosage forms (e.g., oral, topical, transdermal and parenteral), are administered at different dosage intervals, or when titration of the individual components of the combination is desired by the prescribing physician.

One particular example of a kit according to the present invention is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of individual tablets or capsules to be packed or may have the size and shape to accommodate multiple tablets and/or capsules to be packed. Next, the tablets or capsules are placed in the recesses accordingly and the sheet of relatively stiff material is sealed against the plastic foil at the face of the foil which is opposite from the direction in which the recesses were formed. As a result, the tablets or capsules are individually sealed or collectively sealed, as desired, in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

Another specific embodiment of a kit is a dispenser designed to dispense the daily doses one at a time in the order of their intended use. Preferably, the dispenser is equipped with a memory-aid, so as to further facilitate compliance with the regimen. An example of such a memory-aid is a mechanical counter that indicates the number of daily doses that has been dispensed. Another example of such a memory-aid is a battery-powered micro-chip memory coupled with a liquid crystal readout, or audible reminder signal which, for example, reads out the date that the last daily dose has been taken and/or reminds one when the next dose is to be taken.

Preparation of ACC Inhibitors

Synthetic Schemes for Compounds of the Present Invention

Various methods may be developed for synthesizing compounds according to the present invention. The following reaction schemes may be used for the preparation of the compounds according to the present invention. Representative methods for synthesizing these compounds are provided in the Examples. It should be appreciated that a variety of different solvents, temperatures and other reaction conditions can be varied to optimize the yields of the reactions. It should also be appreciated that compounds of the present invention may also be synthesized by other synthetic routes that others may devise.

A synthetic route for producing compounds of the present invention is shown in Scheme 1. Aminocarboxy heterocycloalkyl compounds 1A (e.g., N,N'-protected 4-amino-4-carboxypiperidine) may be coupled to ammonia or an alkylamine 1B to form the corresponding carboxamide 1C and deprotected by hydrogenolysis of the benzyloxycarbonyl protecting group to yield 1D. Cyclocondensation with a chloroalkyl compound 1E (e.g., 2-chloro-1,1,1-trimethoxyethane) would afford the chloroalkyl substituted spiroheterocyclic imidazolone 1F. Substitution reaction of 1F with a primary amine 1G would afford the aminoalkyl imidazolone 1H. Alternatively, substitution reaction of 1F with ammonia followed by an acid chloride 1I would afford the corresponding amide 1J.

Removal of the tert-butyl carbamate protecting group of 1H and 1J with TFA would afford the corresponding free spiropiperidines. Coupling of a carboxylic acid 1K to the free spiropiperidines would afford the corresponding final compounds 1L and 1M.

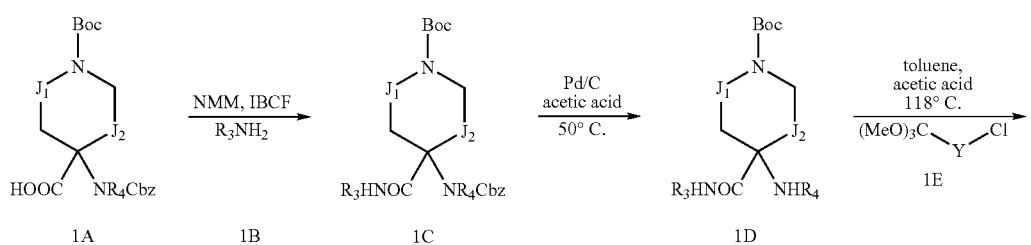

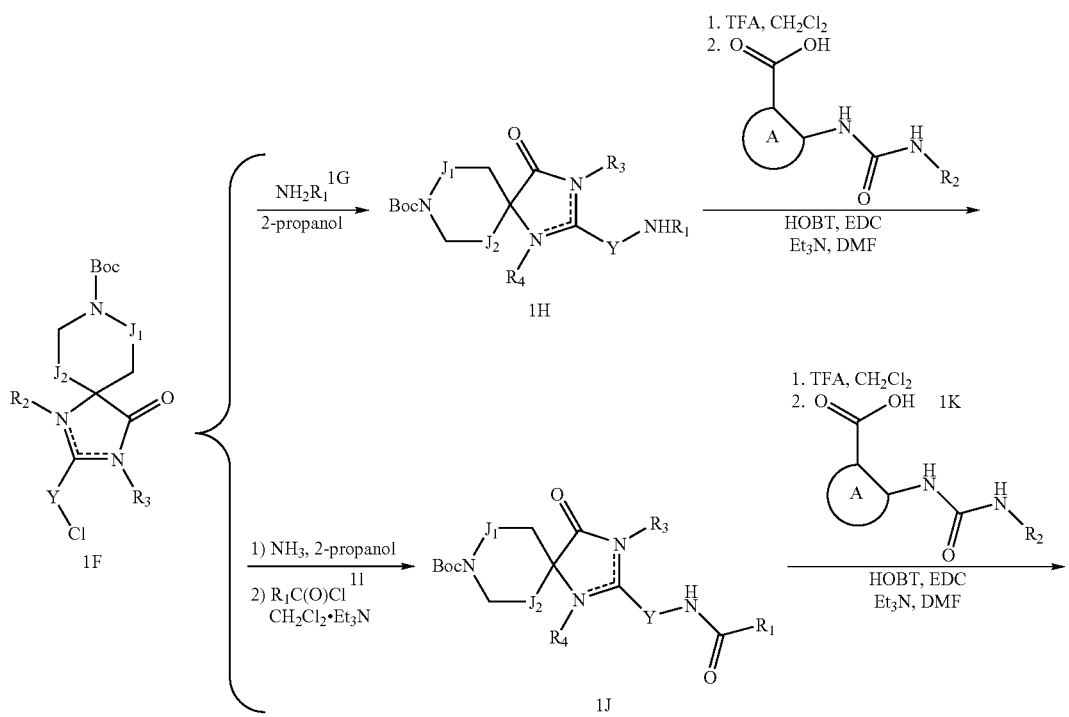

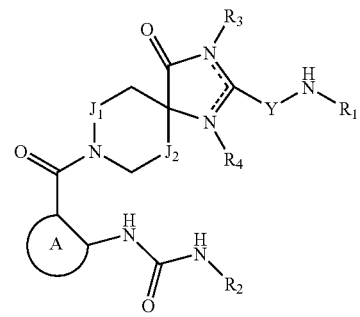

1L

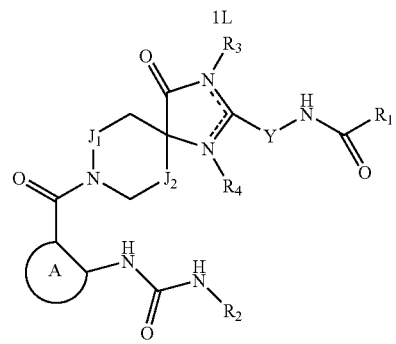

1M

Other compounds in this invention could be synthesized using tert-butyl 2-(chloromethyl)-4-oxo-1,3,8-triazaspiro[4.5]dec-1-ene-8-carboxylate (1F, Scheme 1) as an intermediate as outlined in Scheme 2. 1F could be first converted to pyrrolidine-2,5-dione 2B or an alkyl thioether derivative 2D by nucleophilic substitution of the chloride with pyrrolidine-2,5-dione 2A or a sodium thiolate 2C, respectively. Subsequently removal of the tert-butyl carbamate protecting group with TFA would afford the free spiropiperidine 2B or 2D. Coupling of a carboxylic acid 2E with the free spiropiperidine would afford the corresponding amides; this could then be converted to the final urea 2F or 2G by treatment with an alkyl isocyanate in the presence of pyridine. In the case of an alkyl thioether 2G, the product could be further reacted with Oxone® to obtain the corresponding alkyl sulfone 2H.

Scheme 2

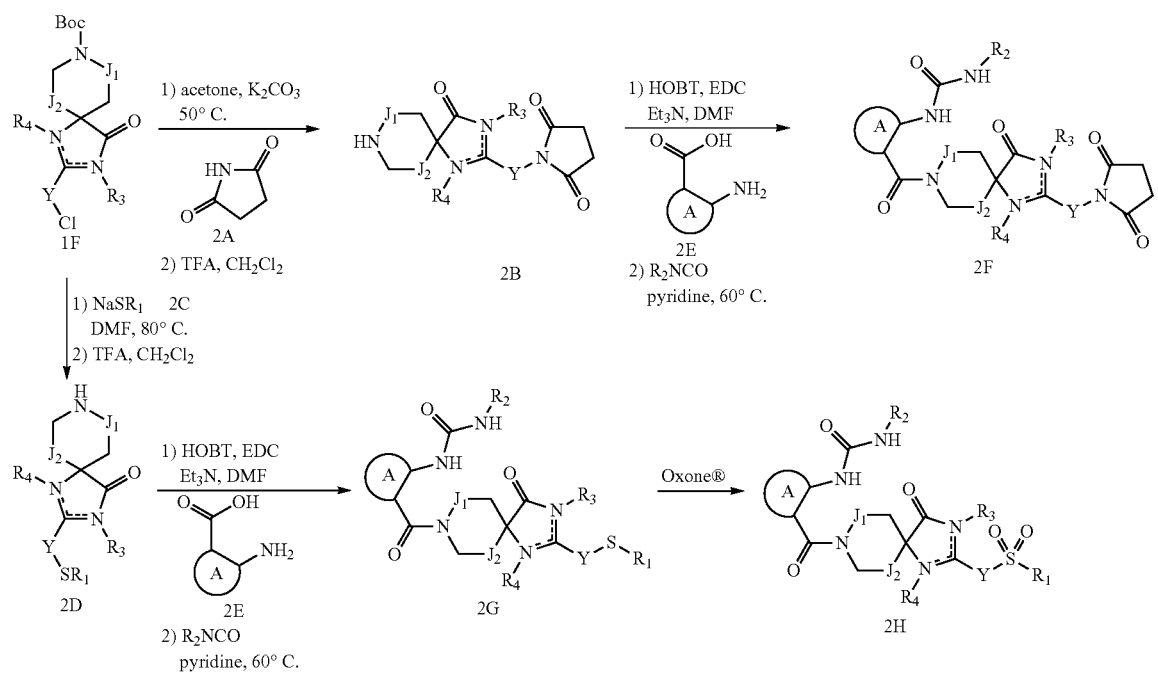

Alternatively, compounds of the invention could be synthesized from intermediates as shown in Scheme 3 below. Coupling of a carboxylic acid 3A to a cyclic ketone 3B (e.g., 4-piperidone) followed by urea formation would afford oxopiperidinamide 3C. Formation of the amino-cyanopiperidinamide 3E could be achieved with alkyl ammonium chloride 3D, potassium cyanide and aqueous ammonium hydroxide. The cyano substituted compound 3E can be converted to the corresponding carboxamide 3F by reacting with sodium hydroxide and hydrogen peroxide. Reacting the carboxamide 3F with 2-chloro-1,1-trimethoxyalkane 3G would afford the chloroalkyl spiropiperidinyl imidazolone intermediate 3H.

Scheme 3

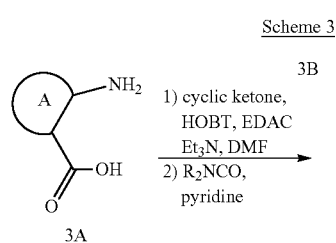

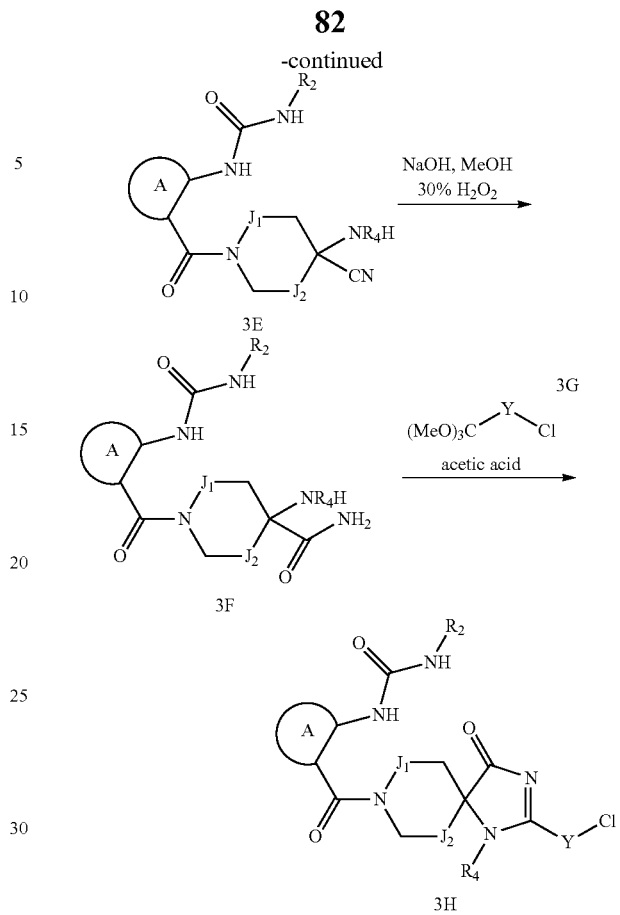

The carboxamide intermediate 3F (see Scheme 3) could be used as in Scheme 4 to prepare other compounds of this invention. Reaction of an orthoester $4A^1$ or $4A^2$ with the carboxamide would provide the corresponding spiropiperidinyl imidazolones, 4B and 4E, respectively. The spiropiperidinyl imidazolone ethyl ester 4B could provide access to various amides 4D via trimethylaluminum and the corresponding amine 4C. Substitution could also occur at the nitrogen site of 4E when $R_4$ is H via an alkyl bromide 4F and NaH to give 4G.

Scheme 4

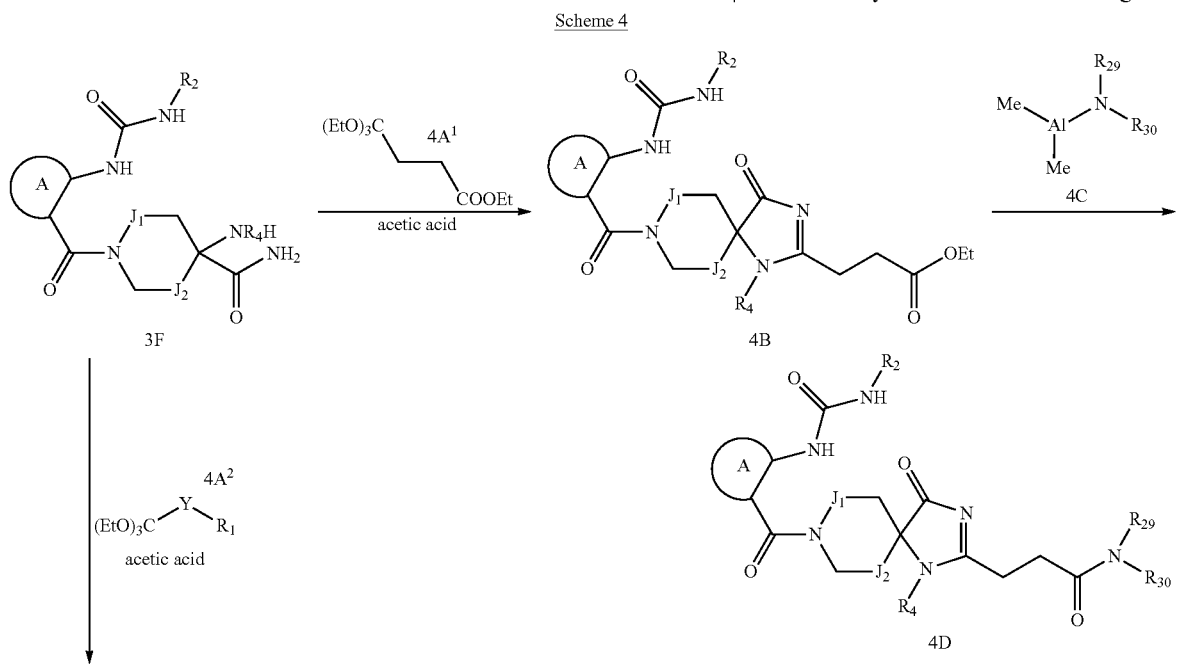

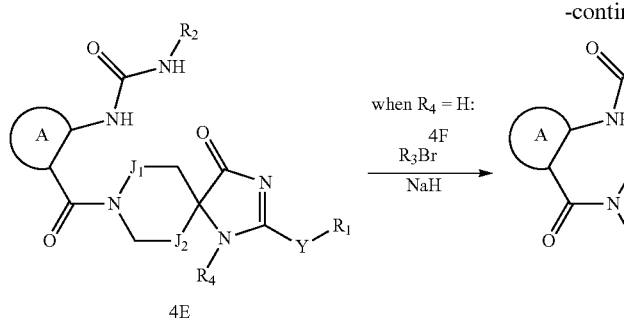
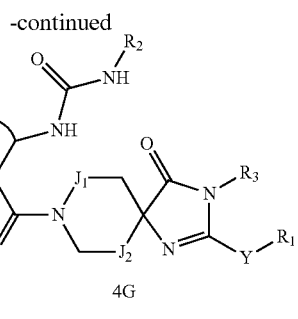

Thioether, sulfoxide and sulfone compounds of the invention could be synthesized from the chloroalkyl intermediate 3H (see Scheme 3) by nucleophilic substitution of the 3H as described in Scheme 5. The resulting thioether 5B could also be oxidized to furnish the desired sulfoxide 5C or sulfone 5D.

Scheme 5

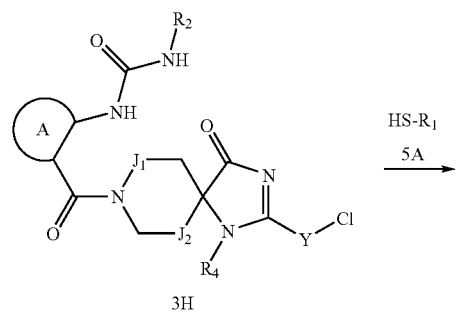

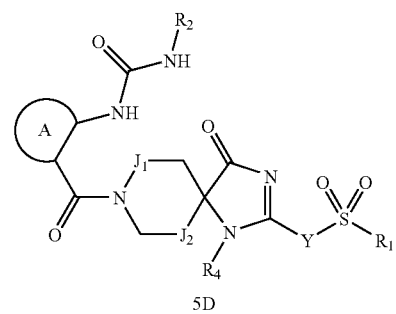

Aryl ether 6B and alkyl or cycloalkyl ether 6D compounds of this invention could be synthesized from a chloromethyl intermediate 3H (see Scheme 3) by nucleophilic substitution as described in Scheme 6. For example, spiropiperidinyl imidazolone aryl ether 6B could be synthesized from using the corresponding phenolic 6A, and spiropiperidinyl imidazolone alkyl ether 6D could be synthesized from the corresponding sodium alkoxide 6C.

Scheme 6

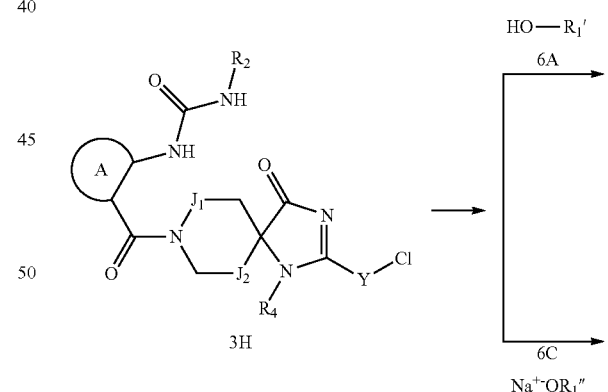

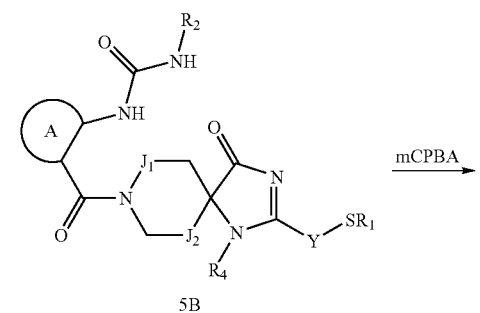

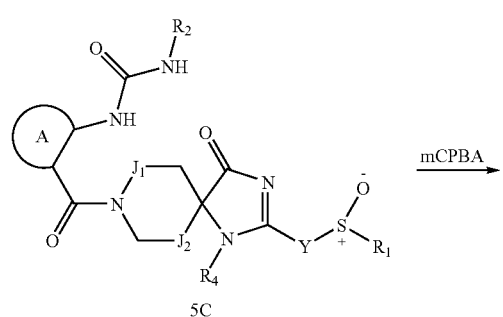

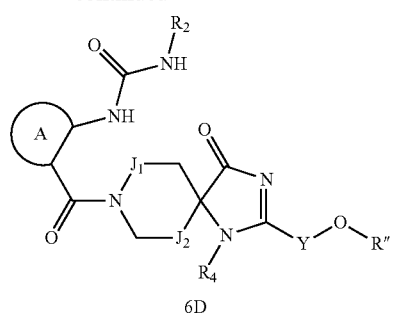

6D $R_1'$ is the aryl component of $R_1$ as defined in the application
$R_1''$ is the cycloalkyl or alkyl component of $R_1$ as defined in the application Spiropiperidinyl imidazolone triazoles 7B compound of the invention could be synthesized from a chloromethyl intermediate 3H (see Scheme 3) via azide 7A, followed by cyclizing with the corresponding alkynes as described in Scheme 7.

Scheme 7

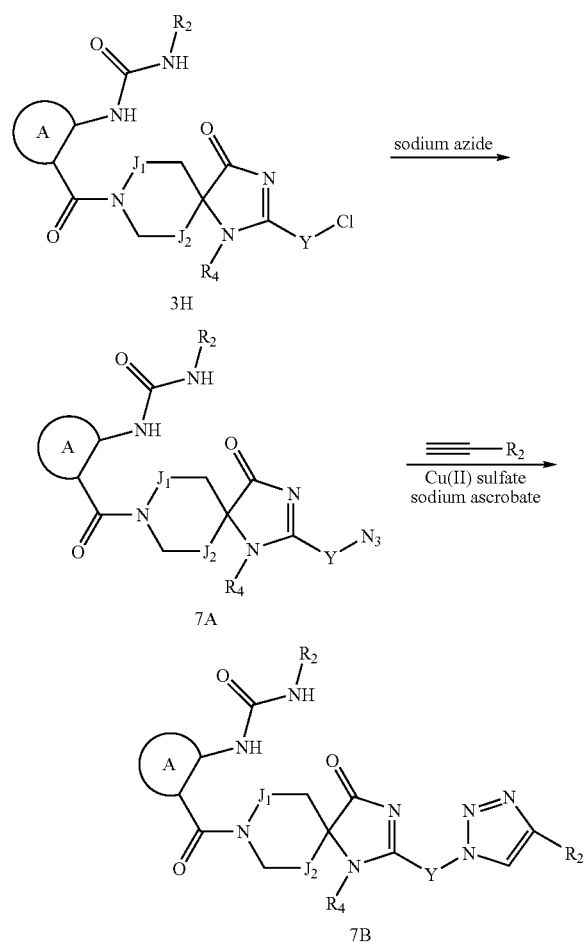

Pyridone compound such as 8A could be synthesized from a chloromethyl intermediate 3H (see Scheme 3) by nucleophilic substitution as described in Scheme 8.

Scheme 8

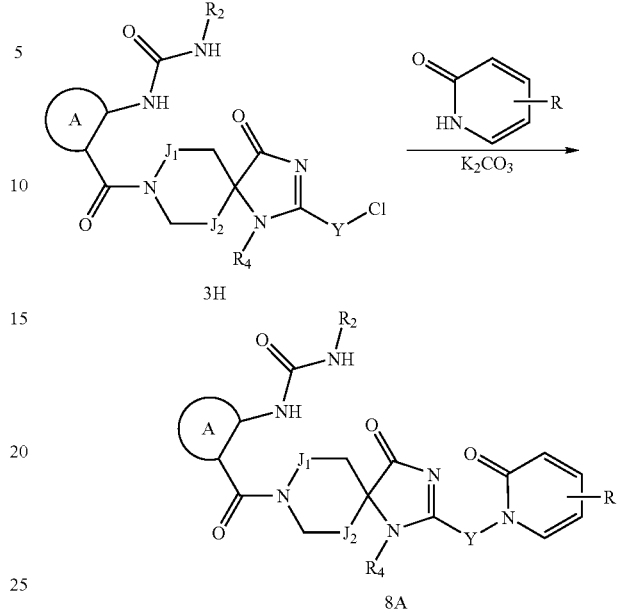

In each of the above reaction procedures or schemes, the various substituents may be selected from among the various substituents otherwise taught herein.

General Procedures

It will be readily recognized that certain compounds according to the present invention have atoms with linkages to other atoms that confer a particular stereochemistry to the compound (e.g., chiral centers). It is recognized that synthesis of compounds according to the present invention may result in the creation of mixtures of different stereoisomers (i.e., enantiomers and diastereomers). Unless a particular stereochemistry is specified, recitation of a compound is intended to encompass all of the different possible stereoisomers.

Compounds according to the present invention can also be prepared as their individual stereoisomers by reacting a racemic mixture of the compound with an optically active resolving agent to form a pair of diastereoisomeric compounds, separating the diastereomers and recovering the optically pure enantiomer. While resolution of enantiomers can be carried out using covalent diastereomeric derivatives of compounds, dissociable complexes are preferred (e.g., crystalline diastereoisomeric salts).

Compounds according to the present invention can also be prepared as a pharmaceutically acceptable acid addition salt by reacting the free base form of the compound with a pharmaceutically acceptable inorganic or organic acid. Alternatively, a pharmaceutically acceptable base addition salt of a compound can be prepared by reacting the free acid form of the compound with a pharmaceutically acceptable inorganic or organic base. Inorganic and organic acids and bases suitable for the preparation of the pharmaceutically acceptable salts of compounds are set forth in the definitions section of this application. Alternatively, the salt forms of the compounds can be prepared using salts of the starting materials or intermediates.

The free acid or free base forms of the compounds can be prepared from the corresponding base addition salt or acid addition salt form. For example, a compound in an acid addition salt form can be converted to the corresponding free base by treating with a suitable base (e.g., ammonium hydroxide solution, sodium hydroxide, and the like). A compound in a base addition salt form can be converted to the corresponding free acid by treating with a suitable acid (e.g., hydrochloric acid, etc).

The N-oxides of compounds according to the present invention can be prepared by methods known to those of ordinary skill in the art. For example, N-oxides can be prepared by treating an unoxidized form of the compound with an oxidizing agent (e.g., trifluoroperacetic acid, permaleic acid, perbenzoic acid, peracetic acid, meta-chloroperoxybenzoic acid, or the like) in a suitable inert organic solvent (e.g., a halogenated hydrocarbon such as dichloromethane) at approximately 0° C. Alternatively, the N-oxides of the compounds can be prepared from the N-oxide of an appropriate starting material.

Compounds in an unoxidized form can be prepared from N-oxides of compounds by treating with a reducing agent (e.g., sulfur, sulfur dioxide, triphenyl phosphine, lithium borohydride, sodium borohydride, phosphorus trichloride, tribromide, or the like) in an suitable inert organic solvent (e.g., acetonitrile, ethanol, aqueous dioxane, or the like) at 0 to 80° C.

Prodrug derivatives of the compounds can be prepared by methods known to those of ordinary skill in the art (e.g., for further details see Saulnier et al. (1994), *Bioorganic and Medicinal Chemistry Letters*, Vol. 4, p. 1985). For example, appropriate prodrugs can be prepared by reacting a non-derivatized compound with a suitable carbamylating agent (e.g., 1,1-acyloxyalkylcarbonochloridate, para-nitrophenyl carbonate, or the like).

Protected derivatives of the compounds can be made by methods known to those of ordinary skill in the art. A detailed description of the techniques applicable to the creation of protecting groups and their removal can be found in P. G. M. Wuts and T. W. Greene, "*Greene's Protecting Groups in Organic Synthesis*", 4$^{th}$ edition, John Wiley & Sons, Inc. 2007.

Compounds according to the present invention may be conveniently prepared, or formed during the process of the invention, as solvates (e.g., hydrates). Hydrates of compounds of the present invention may be conveniently prepared by recrystallization from an aqueous/organic solvent mixture, using organic solvents such as dioxin, tetrahydrofuran or methanol.

As used herein the symbols and conventions used in these processes, schemes and examples are consistent with those used in the contemporary scientific literature, for example, the Journal of the American Chemical Society or the Journal of Biological Chemistry. Standard single-letter or three-letter abbreviations are generally used to designate amino acid residues, which are assumed to be in the L-configuration unless otherwise noted. Unless otherwise noted, all starting materials were obtained from commercial suppliers and used without further purification. Specifically, the following abbreviations may be used in the examples and throughout the specification:

| | |
|---|---|
| μL (microliters) | Ac (acetyl) |
| atm (atmosphere) | ATP (Adenosine Triphophatase) |
| BOC (tert-butyloxycarbonyl) | BOP (bis(2-oxo-3-oxazolidinyl)phosphinic chloride) |
| BSA (Bovine Serum Albumin) | CBZ (benzyloxycarbonyl) |
| CDI (1,1-carbonyldiimidazole) | DCC (dicyclohexylcarbodiimide) |
| DCE (dichloroethane) | DCM (dichloromethane) |
| DMAP (4-dimethylaminopyridine) | DME (1,2-dimethoxyethane) |
| DMF (N,N-dimethylformamide) | DMPU (N,N'-dimethylpropyleneurea) |
| DMSO (dimethylsulfoxide) | EDCI (ethylcarbodiimide hydrochloride) |
| EDTA (Ethylenediaminetetraacetic acid) | Et (ethyl) |
| Et$_2$O (diethyl ether) | EtOAc (ethyl acetate) |
| FMOC (9-fluorenylmethoxycarbonyl) | g (grams) |
| hr (hour) | HOAc or AcOH (acetic acid) |
| HOBT (1-hydroxybenzotriazole) | HOSu (N-hydroxysuccinimide) |
| HPLC (high pressure liquid chromatography) | Hz (Hertz) |
| i.v. (intravenous) | IBCF (isobutyl chloroformate) |
| i-PrOH (isopropanol) | L (liters) |
| M (molar) | mCPBA (meta-chloroperbenzoic acid) |
| Me (methyl) | MeOH (methanol) |
| mg (milligrams) | MHz (megahertz) |
| min (minutes) | mL (milliliters) |
| mM (millimolar) | mmol (millimoles) |
| mol (moles) | MOPS (Morpholinepropanesulfonic acid) |
| mp (melting point) | NaOAc (sodium acetate) |
| OMe (methoxy) | psi (pounds per square inch) |
| RP (reverse phase) | RT (ambient temperature) |
| SPA (Scintillation Proximity Assay) | TBAF (tetra-n-butylammonium fluoride) |
| TBS (t-butyldimethylsilyl) | tBu (tert-butyl) |
| TEA (triethylamine) | TFA (trifluoroacetic acid) |
| TFAA (trifluoroacetic anhydride) | THF (tetrahydrofuran) |
| TIPS (triisopropylsilyl) | TLC (thin layer chromatography) |
| TMS (trimethylsilyl) | TMSE (2-(trimethylsilyl)ethyl) |
| Tr (retention time) | Brij35 (polyoxyethyleneglycol dodecyl ether) |

All references to ether or Et$_2$O are to diethyl ether; and brine refers to a saturated aqueous solution of NaCl. Unless otherwise indicated, all temperatures are expressed in ° C. (degrees Centigrade). All reactions are conducted under an inert atmosphere at RT unless otherwise noted.

$^1$H NMR spectra were recorded on a Bruker Avance 400. Chemical shifts are expressed in parts per million (ppm). Coupling constants are in units of Hertz (Hz). Splitting patterns describe apparent multiplicities and are designated as s (singlet), d (doublet), t (triplet), q (quartet), m (multiplet), br (broad).

Low-resolution mass spectra (MS) and compound purity data were acquired on a Waters ZQ LC/MS single quadrupole system equipped with electrospray ionization (ESI) source, UV detector (220 and 254 nm), and evaporative light scattering detector (ELSD). Thin-layer chromatography was performed on 0.25 mm E. Merck silica gel plates (60F-254), visualized with UV light, 5% ethanolic phosphomolybdic acid, Ninhydrin orp-anisaldehyde solution. Flash column chromatography was performed on silica gel (230-400 mesh, Merck).

The starting materials and reagents used in preparing these compounds are either available from commercial suppliers such as the Aldrich Chemical Company (Milwaukee, Wis.), Bachem (Torrance, Calif.), Sigma (St. Louis, Mo.), or may be prepared by methods well known to a person of ordinary skill in the art, following procedures described in such standard references as Fieser and Fieser's Reagents for Organic Synthesis, vols. 1-23, John Wiley and Sons, New York, N.Y., 2006; Rodd's Chemistry of Carbon Compounds, vols. 1-5 and supps., Elsevier Science Publishers, 1998; Organic Reactions, vols. 1-68, John Wiley and Sons, New York, N.Y., 2007; March J.: Advanced Organic Chemistry, 5th ed., 2001, John Wiley and Sons, New York, N.Y.; and Larock: Comprehensive Organic Transformations, $2^{nd}$ edition, John Wile and Sons, New York, 1999. The entire disclosures of all documents cited throughout this application are incorporated herein by reference.

Various methods for separating mixtures of different stereoisomers are known in the art. For example, a racemic mixture of a compound may be reacted with an optically active resolving agent to form a pair of diastereoisomeric compounds. The diastereomers may then be separated in order to recover the optically pure enantiomers. Dissociable complexes may also be used to resolve enantiomers (e.g., crystalline diastereoisomeric salts). Diastereomers typically have sufficiently distinct physical properties (e.g., melting points, boiling points, solubilities, reactivity, etc.) and can be readily separated by taking advantage of these dissimilarities. For example, diastereomers can typically be separated by chromatography or by separation/resolution techniques based upon differences in solubility. A more detailed description of techniques that can be used to resolve stereoisomers of compounds from their racemic mixture can be found in Jean Jacques, Andre Collet, and Samuel H. Wilen, Enantiomers, Racemates and Resolutions, John Wiley & Sons, Inc. (1981).

Diastereomers have distinct physical properties (e.g., melting points, boiling points, solubilities, reactivity, etc.) and can be readily separated by taking advantage of these dissimilarities. The diastereomers can be separated by chromatography or, preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques, Andre Collet, and Samuel H. Wilen, Enantiomers, Racemates and Resolutions, John Wiley & Sons, Inc. (1981).

Chiral components can be separated and purified using any of a variety of techniques known to those skilled in the art. For example, chiral components can be purified using supercritical fluid chromatography (SFC). In one particular variation, chiral analytical SFC/MS analyses are conducted using a Berger analytical SFC system (AutoChem, Newark, Del.) which consists of a Berger SFC dual pump fluid control module with a Berger FCM 1100/1200 supercritical fluid pump and FCM 1200 modifier fluid pump, a Berger TCM 2000 oven, and an Alcott 718 autosampler. The integrated system can be controlled by BI-SFC Chemstation software version 3.4. Detection can be accomplished with a Waters ZQ 2000 detector operated in positive mode with an ESI interface and a scan range from 200-800 Da with 0.5 second per scan. Chromatographic separations can be performed on a ChiralPak AD-H, ChiralPak AS-H, ChiralCel OD-H, or ChiralCel OJ-H column (5p, 4.6×250 mm; Chiral Technologies, Inc. West Chester, Pa.) with 10 to 40% methanol as the modifier and with or without ammonium acetate (10 mM). Any of a variety of flow rates can be utilized including, for example, 1.5 or 3.5 mL/min with an inlet pressure set at 100 bar. Additionally, a variety of sample injection conditions can be used including, for example, sample injections of either 5 or 10 L in methanol at 0.1 mg/mL in concentration.

In another variation, preparative chiral separations are performed using a Berger MultiGram II SFC purification system. For example, samples can be loaded onto a ChiralPak AD column (21×250 mm, 10μ). In particular variations, the flow rate for separation can be 70 mL/min, the injection volume up to 2 mL, and the inlet pressure set at 130 bar. Stacked injections can be applied to increase the efficiency.

Descriptions of the syntheses of particular compounds according to the present invention based on the above reaction schemes and variations thereof are set forth in the Example section.

Assaying the Biological Activity of the Compounds of the Invention

The inhibitory effect of the compound of the invention on ACC may be evaluated by a variety of in vitro and in vivo binding assays and functional assays, e.g., Harwood H J Jr. et al., *J Biol Chem.* 2003, 278(39):37099-111; Liu Y. et al. *Assay Drug Dev Technol.* 2007, 5(2):225-35; and Seethala R. et al., *Anal Biochem.* 2006, 358(2):257-65.

Provided in Example A is an in vitro enzymatic ACC activity assay for activity against ACC. The binding affinity of the test compound to ACC1 or ACC2 is determined by the changes in absorbance (at 620 nm); the absorbance is proportional to the fraction of bound inhibitor. It should be noted that a variety of other expression systems and hosts are also suitable for the expression of ACC, as would be readily appreciated by one of skill in the art.

Using the procedure described in Example A, some of the exemplified compounds were shown to have ACC inhibitory activity at an $IC_{50}$ of less than 10 μM, some others less than about 1 μM. The $IC_{50}$ values of the exemplified compounds of the present invention are given in Table 1.

EXAMPLE

The present invention is further exemplified, but not limited by, the following examples that describe the synthesis of particular compounds according to the invention. It will be readily recognized that certain compounds according to the present invention have atoms with linkages to other atoms that confer a particular stereochemistry to the compound (e.g., chiral centers). It is recognized that synthesis of compounds according to the present invention may result in the creation of mixtures of different stereoisomers (i.e., enantiomers and diastereomers). Unless a particular stereochemis-

Example 1

Preparation of 1-(3-(2-(aminomethyl)-4-oxo-1,3,8-triazaspiro[4.5]dec-1-enecarbonyl)benzo[b]thiophen-2-yl)-3-ethylurea (1)

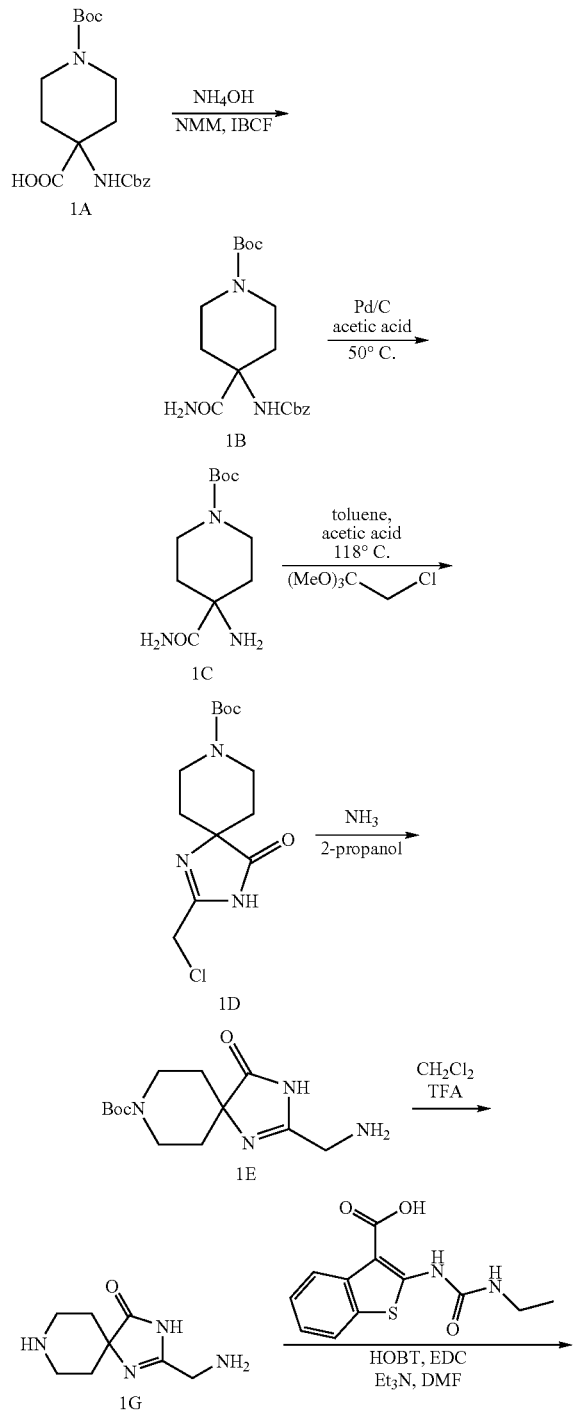

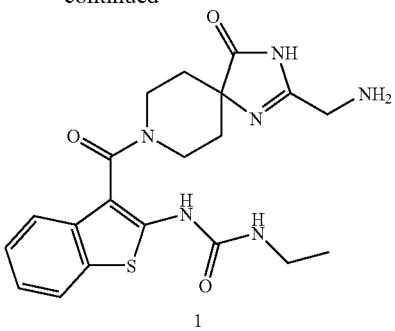

A solution 4-(benzyloxycarbonylamino)-1-(tert-butoxycarbonyl)piperidine-4-carboxylic acid (1A, 2.0 g, 1.0 equivalent) in DME (0.5 M) was treated with NMM (1.0 equivalent) and IBCF (1.0 equivalent) at −15° C. After 10 min, aqueous ammonia (1.5 equivalents) was added. The reaction mixture was stirred at room temperature for 1.5 hr. The reaction was complete as determined by LCMS analysis and then partitioned between ethyl acetate and water. The organics were subsequently washed with brine, then dried over $Na_2SO_4$, filter, and the volatiles removed under reduced pressure. The residue was purified by crystallization from diethyl ether to afford the tert-butyl 4-(benzyloxycarbonylamino)-4-carbamoylpiperidine-1-carboxylate (1B, 70%).

1B (1.0 equivalent) and a catalytic amount of acetic acid in MeOH (0.05M) was passed through H-cube hydrogenator equipped with Pd/C cartridge at 50° C. The methanol in the reaction mixture was then removed under reduced pressure, and the product was washed with cold ether twice to afford the tert-butyl 4-amino-4-carbamoylpiperidine-1-carboxylate (1C, 90%).

1C (0.3M) was added 2-chloro-1,1,1-trimethoxyethane (4.0 equivalents) and acetic acid (2.0 equivalents). The mixture was stirred for 12 hr at 118° C. Solvent was removed under reduced pressure and the residue was purified by crystallization from cold diethyl ether to afford tert-butyl 2-(chloromethyl)-4-oxo-1,3,8-triazaspiro[4.5]dec-1-ene-8-carboxylate (1D, 67%).

1D in a seal tube was added 2.0 M ammonia in 2-propanol (0.04M). Excess ammonia gas was bubbled in and the mixture was heated at 60° C. for 12 hr. The reaction was complete as determined by LCMS analysis. After removal of solvent; the residue tert-butyl 2-(aminomethyl)-4-oxo-1,3,8-triazaspiro[4.5]dec-1-ene-8-carboxylate (1E) was used without further purification. ESI-MS: m/z 283.1 $(M+H)^+$.

For deprotection, 1E (1.0 equivalent) was dissolved in $CH_2Cl_2$ at 0° C., and slowly treated with a 1.6:1 solution of $CH_2Cl_2$/TFA (2:1 final ratio, 0.15 M). The reaction was completed in 30 minutes at 0° C. as determined by LCMS analysis. The volatiles were removed under reduced pressure to yield the respective 2-(aminomethyl)-1,3,8-triazaspiro[4.5]dec-1-en-4-one (1G) as TFA salts which were used without further purification. ESI-MS: m/z 183.1 $(M+H)^+$.

The title compound 1 may be prepared from the intermediate 1G by the following prophetic route:

Solution of 1G (1.0 equivalent), 2-(3-ethylureido)benzo[b]thiophene-3-carboxylic acid (1I, 1.25 equivalents), DMF (0.14 M), EDC (1.25 equivalents), and HOBT (1.25 equivalents) is added triethylamine (1.0 equivalent) at room temperature. After stirring for 12 hr, the reaction is complete as determined by LCMS analysis. The reaction mixture is then partitioned between ethyl acetate and water and the separated organics is dried over $Na_2SO_4$, filtered, and concentrated under reduced pressure. Purification by preparatory LCMS provides the title compound, 1-(3-(2-(aminomethyl)-4-oxo-1,3,8-triazaspiro[4.5]dec-1-enecarbonyl)benzo[b]thiophen-2-yl)-3-ethylurea (1).

Example 2

Preparation of and N-((8-(2-(3-ethylureido)benzo[b]thiophene-3-carbonyl)-4-oxo-1,3,8-triazaspiro[4.5]dec-1-en-2-yl)methyl)acetamide (2)

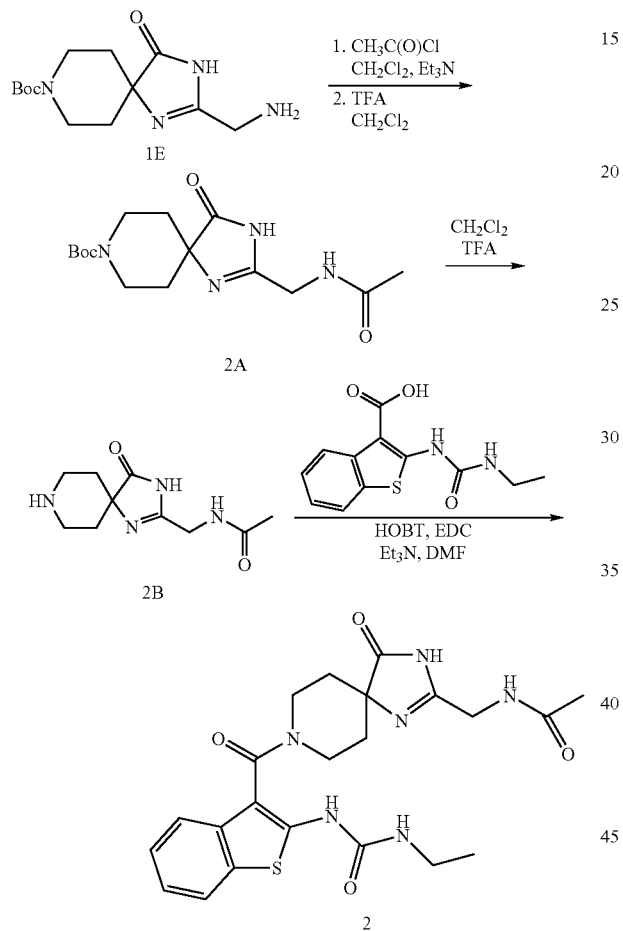

tert-Butyl 2-(aminomethyl)-4-oxo-1,3,8-triazaspiro[4.5]dec-1-ene-8-carboxylate (1E) in CH$_2$Cl$_2$ (150 mg, 0.05 M), prepared by the procedure of Example 1, was added Et$_3$N and acetyl chloride at −45° C. The reaction was complete after 20 minutes at −30° C. as determined by LCMS analysis, and then partitioned between ethyl acetate and water. The organics were subsequently washed with NaHCO$_3$ and brine, dried over Na$_2$SO$_4$, filtered and concentrated under reduced pressure. The residue was passed thorough a pad of silica to afford the tert-butyl 2-(acetamidomethyl)-4-oxo-1,3,8-triazaspiro[4.5]dec-1-ene-8-carboxylate (2A, 87%).

For deprotection, 2A (1.0 equivalent) was dissolved in CH$_2$Cl$_2$ at 0° C., and slowly treated with a 1.6:1 solution of CH$_2$Cl$_2$/TFA (2:1 final ratio, 0.15 M). The reaction was completed in 30 minutes at 0° C. as determined by LCMS analysis. The volatiles were removed under reduced pressure to yield N-((4-oxo-1,3,8-triazaspiro[4.5]dec-1-en-2-yl)methyl) acetamide (2B) as TFA salts which were used without further purification. ESI-MS: m/z 225.1 (M+H)$^+$.

The title compound 2 may be prepared from the intermediate 1G by the following prophetic route:

Solutions each of 2B (1.0 equivalent), 2-(3-ethylureido)benzo[b]thiophene-3-carboxylic acid (2C, 1.25 equivalents), DMF (0.14 M), EDC (1.25 equivalents), and HOBT (1.25 equivalents) is added triethylamine (1.0 equivalent) at room temperature. After stirring for 12 hr, the reaction is complete as determined by LCMS analysis. The reaction mixture is then partitioned between ethyl acetate and water and the separated organics is dried over Na$_2$SO$_4$, filtered, and concentrated under reduced pressure. Purification by preparatory LCMS provides N-((8-(2-(3-ethylureido)benzo[b]thiophene-3-carbonyl)-4-oxo-1,3,8-triazaspiro[4.5]dec-1-en-2-yl)methyl)acetamide (2), respectively.

Example 3

Preparation of 1-ethyl-3-(3-(2-(methylthiomethyl)-4-oxo-1,3,8-triazaspiro[4.5]dec-1-enecarbonyl)benzo[b]thiophen-2-yl)urea TFA salt (3)

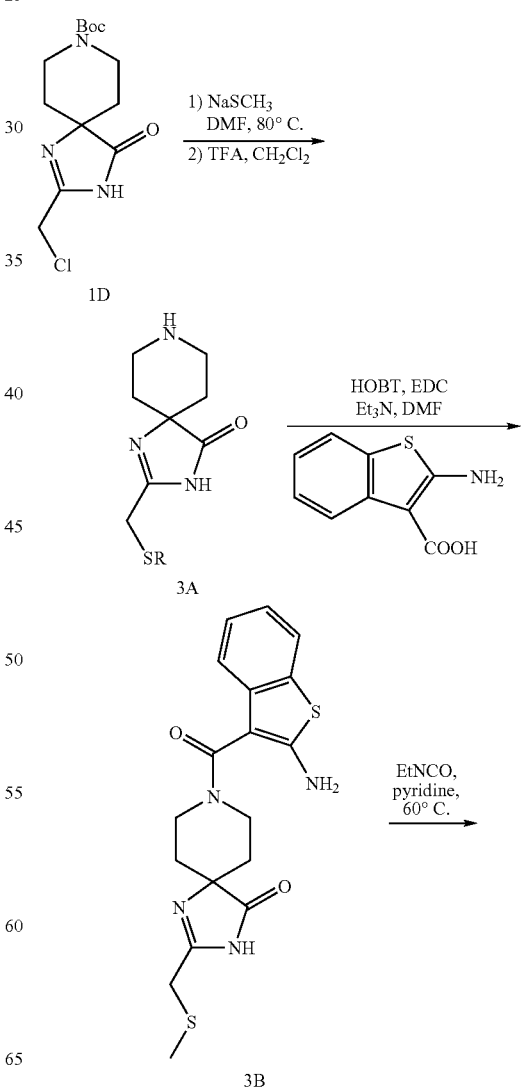

95
-continued

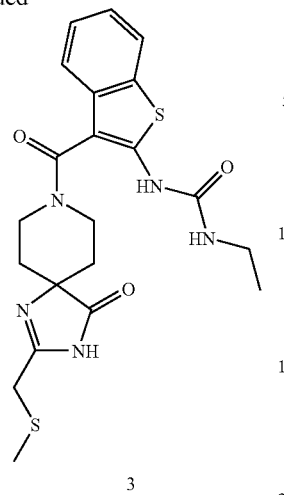

3 tert-Butyl 2-(chloromethyl)-4-oxo-1,3,8-triazaspiro[4.5] dec-1-ene-8-carboxylate (1D, 500 mg, 1.0 equivalent) prepared by the procedure of Example 1 and a sodium methanethiolate (1.5 equivalents) in DMF (0.17M) were heated to 80° C. for 1 hr. After the reaction was complete based on LCMS analysis, the crude product was purified by preparatory LCMS to provide the N-protected spiroimidazolone which (1.0 equivalent) was dissolved in $CH_2Cl_2$ at 0° C., and was slowly treated with a 1.6:1 solution of $CH_2Cl_2$/TFA (2:1 final ratio, 0.15 M). The deprotection reaction was complete in 2 hrs at 0° C. as determined by LCMS analysis. The volatiles were removed under reduced pressure and yielded 2-(methylthiomethyl)-1,3,8-triazaspiro[4.5]dec-1-en-4-one (3A) as TFA salts and was used without further purification. ESI-MS: m/z 214.1.1 $(M+H)^+$.

A solution of 3A (1.0 equivalent) in DMF (0.12 M) along with a 2-aminobenzo[b]thiophene-3-carboxylic acid (1.0 equivalent) was treated with EDC (1.0 equivalent), HOBt (1.0 equivalent) and $Et_3N$ (2.0 equivalents) at rt. The reaction mixture was stirred until the reaction was complete as determined by LCMS analysis and then partitioned between ethyl acetate and water. Organic layers were washed with brine and dried over $Na_2SO_4$, and volatiles removed under reduced pressure. Residue purified by LCMS to afford 8-(2-aminobenzo[b]thiophene-3-carbonyl)-2-(methylthiomethyl)-1,3,8-triazaspiro[4.5]dec-1-en-4-one (2B).

A solution of 3B (1.0 equivalent), and ethyl isocyanate (1.1 equivalents), and pyridine (0.11 M) were prepared in a sealed tube and warmed to 60° C. for 12 hrs. The reaction mixture was then cooled to rt, the volatiles removed under reduced pressure, and the residue purified by LCMS to afford 1-ethyl-3-(3-(2-(methylthiomethyl)-4-oxo-1,3,8-triazaspiro[4.5] dec-1-enecarbonyl)benzo[b]thiophen-2-yl)urea (3). Two rotamers observed (ratio 3:2).

First rotamer: $^1$H NMR (400 MHz, Acetone) δ ppm, 1.14 (q, J=3.37 Hz, 3 H), 1.45 (d, J=12.63 Hz, 2 H), 1.86-1.95 (m, 2 H), 2.13 (s, 3 H), 3.23-3.33 (m, 2 H), 3.44 (s, 2 H), 3.47-3.64 (m, 2 H), 4.05 (br. s., 2 H), 6.94 (br. s., 1 H), 7.16-7.27 (m, 1 H), 7.32-7.43 (m, 1 H), 7.53 (d, J=7.83 Hz, 1 H), 7.78 (d, J=7.83 Hz, 1 H), 9.29 (s, 1 H) 9.91 (br. s., 1 H); ESI-MS: m/z 459.1 $(M+H)^+$.

Second rotamer: $^1$H NMR (400 MHz, Acetone) δ ppm, 1.20 (t, J=7.20 Hz, 3 H), 1.50-1.58 (m, 2 H), 1.80 (br. s., 2 H), 2.11 (s, 3 H), 3.22-3.33 (m, 2 H), 3.42 (s, 2 H), 3.46-3.65 (m, 2 H), 4.05 (br. s., 2 H), 6.82 (br. s., 1 H), 7.17-7.26 (m, 1 H), 7.32-7.42 (m, 1 H), 7.62 d, J=8.08 Hz, 1 H), 7.78 (d, J=7.83 Hz, 1 H), 9.07 (s, 1 H), 9.91 (br. s., 1 H); ESI-MS: m/z 459.1 $(M+H)^+$.

96

Example 4

Preparation of 1-ethyl-3-(3-(2-(methylsulfonylmethyl)-4-oxo-1,3,8-triazaspiro[4.5]dec-1-enecarbonyl)benzo[b]thiophen-2-yl)urea TFA salt (4)

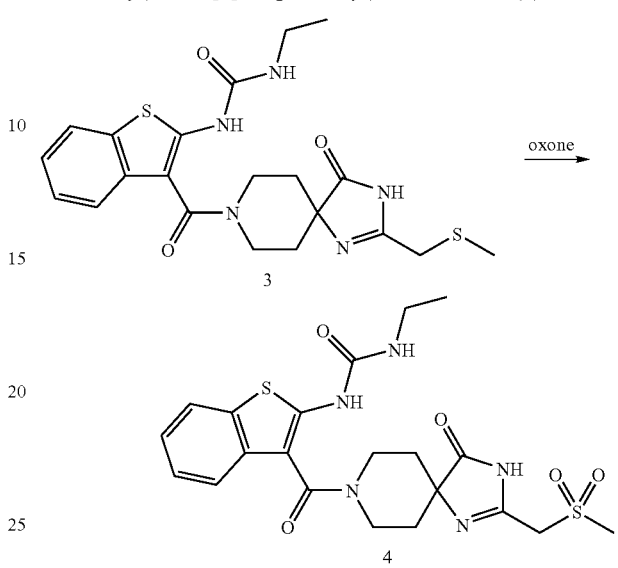

Compound 3 was prepared as described in Example 3. To a solution of Compound 3 in solution (90 mg, 1.0 equivalent) in MeOH (0.03M) at 0° C. was added a solution of Oxone® (1.5 equivalents) in water (0.1M). The mixture was stirred at room temperature for 1.5 hr then warmed to 30° C. for 1.5 hr. The mixture was filtered and purified by LCMS to afford the 1-ethyl-3-(3-(2-(methylsulfonylmethyl)-4-oxo-1,3,8-triazaspiro[4.5]dec-1-enecarbonyl)benzo[b]thiophen-2-yl)urea (4, 30%) in which two rotamers were observed (ratio 3:2).

First rotamer: $^1$H NMR (400 MHz, Acetone) δ ppm, 0.09 (t, J=6.95 Hz, 3 H), 0.51 (br. s., 2 H), 0.85 (br. s., 2 H), 2.07 (s, 2 H), 2.14-2.21 (m, 2 H), 2.48-2.56 (m, 2 H), 3.03 (br. s., 2 H), 6.10-6.18 (m, 1 H), 6.22-6.30 (m, 1 H), 6.37 (d, J=7.83 Hz, 1 H), 6.65 (d, J=7.83 Hz, 1 H);). ESI-MS: m/z 491.1 $(M+H)^+$.

Second rotamer: $^1$H NMR (400 MHz, Acetone) δ ppm, 0.09 (t, J=6.95 Hz, 3 H), 0.66 (br. s, 2 H), 0.98 (br. s, 2 H), 2.05 (s, 2 H), 2.14-2.21 (m, 2 H), 2.48-2.56 (m, 2 H), 3.03 (br. s., 2 H), 6.10-6.18 (m, 1 H), 6.22-6.30 (m, 1 H), 6.48 (d, J=8.08 Hz, 1 H), 6.65 (d, J=7.83 Hz, 1 H). ESI-MS: m/z 491.1 $(M+H)^+$.

Example 5

Preparation of 1-(3-(2-((2,5-dioxopyrrolidin-1-yl) methyl)-4-oxo-1,3,8-triazaspiro[4.5]dec-1-enecarbonyl)benzo[b]thiophen-2-yl)-3-ethylurea TFA salt (5)

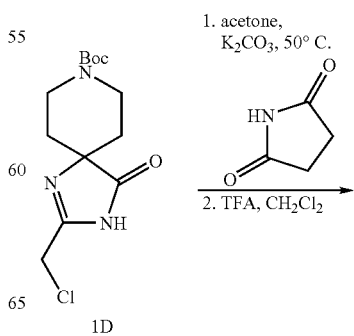

1D

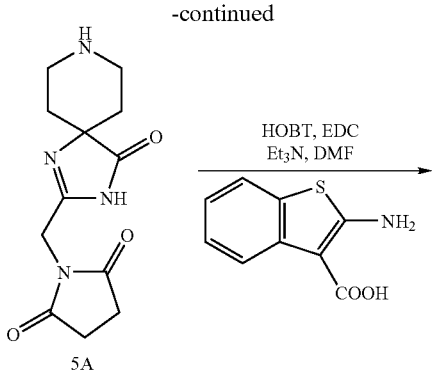

The volatiles were removed under reduced pressure to yield 1-((4-oxo-1,3,8-triazaspiro[4.5]dec-1-en-2-yl)methyl)pyrrolidine-2,5-dione (5A) as a TFA salts which was used without further purification. ESI-MS: m/z 265.1 (M+H)⁺.

5A (1.0 equivalent) in DMF (0.12 M) along with a 2-aminobenzo[b]thiophene-3-carboxylic acid (1.0 equivalent) was treated with EDC (1.0 equivalent), HOBt (1.0 equivalent) and Et₃N (2.0 equivalents) at rt. The reaction mixture was stirred until the reaction was complete as determined by LCMS analysis and then partitioned between ethyl acetate and water. Organic layers were washed with brine and dried over Na₂SO₄, and volatiles removed under reduced pressure. Residue purified by LCMS to afford 1-((8-(2-aminobenzo[b]thiophene-3-carbonyl)-4-oxo-1,3,8-triazaspiro[4.5]dec-1-en-2-yl)methyl)pyrrolidine-2,5-dione (5B).

A solution of 5B (1.0 equivalent), and ethyl isocyanate (1.1 equivalents), and pyridine (0.11 M) were prepared in a sealed tube and warmed to 60° C. for 12 hrs. The reaction mixture was then cooled to rt, the volatiles removed under reduced pressure, and the residue purified by LCMS to afford 1-(3-(2-((2,5-dioxopyrrolidin-1-yl)methyl)-4-oxo-1,3,8-triazaspiro[4.5]dec-1-enecarbonyl)benzo[b]thiophen-2-yl)-3-ethylurea (5, 31%). Two rotamers observed (ratio 1:1).

First rotamer: ¹H NMR (400 MHz, Acetone) δ ppm, 1.12 (td, J=7.26, 5.18 Hz, 3 H), 1.69 (br. s., 2 H), 1.82 (br. s., 2 H), 1.91-1.99 (m, 2 H), 3.21-3.32 (m, 2 H), 3.58-3.68 (m, 2H), 3.71-3.81 (m, 2 H), 3.90-4.05 (m, 2 H), 4.75 (br. s., 2 H), 6.92 (br. s., 1 H), 7.20 (t, J=7.58 Hz, 1 H), 7.33 (t, J=7.58 Hz, 1 H), 7.58 (d, J=7.83 Hz, 1 H), 7.76 (dd, J=7.58, 3.79 Hz, 1 H), 9.25 (s, 1 H); ESI-MS: m/z 510.1 (M+H)⁺.

Second rotamer: ¹H NMR (400 MHz, Acetone) δ ppm, 1.12 (td, J=7.26, 5.18 Hz, 3H), 1.65 (br. s., 2 H), 1.82 (br. s., 2 H), 1.91-1.99 (m, 2 H), 3.21-3.32 (m, 2 H), 3.58-3.68 (m, 2 H), 3.71-3.81 (m, 2 H), 3.90-4.05 (m, 2 H), 4.62 (s, 2 H), 6.52 (br. s., 1 H), 7.20 (t, J=7.58 Hz, 1 H), 7.33 (t, J=7.58 Hz, 1 H), 7.54 (d, J=8.08 Hz, 1 H), 7.76 (dd, J=7.58, 3.79 Hz, 1 H), 8.81 (s, 1 H); ESI-MS: m/z 510.1 (M+H)⁺.

Example 6

Preparation of 1-(3-(4-amino-4-cyanopiperidine-1-carbonyl)benzo[b]thiophen-2-yl)-3-ethylurea (6)

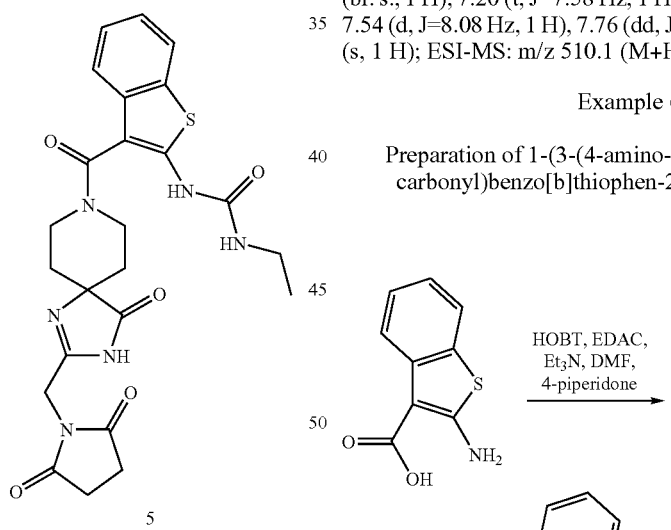

tert-Butyl 2-(chloromethyl)-4-oxo-1,3,8-triazaspiro[4.5]dec-1-ene-8-carboxylate (1D, 300 mg, 1.0 equivalent) prepared by the procedure of Example 1, pyrrolidine-2,5-dione (1.5 equivalents) and K₂CO₃ (1.5 equivalents) in acetone (0.09 M) were heated to 50° C. for 48 hrs. The mixture was then filtered and solvent was removed under reduced pressure. Purification by preparatory LCMS provided a protected product (23%). Deprotection was achieved by dissolving the protect product (1.0 equivalent) in CH₂Cl₂ at 0° C., and the solution was slowly treated with a 1.6:1 solution of CH₂Cl₂/TFA (2:1 final ratio, 0.15 M). The deprotection reaction was complete in 2 hrs at 0° C. as determined by LCMS analysis.

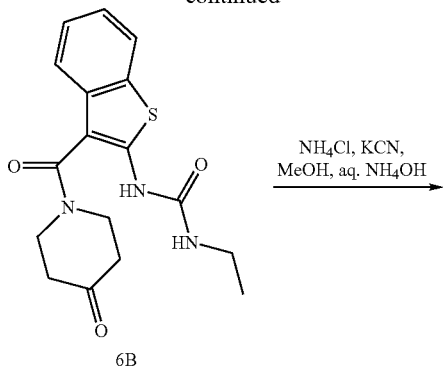

6B

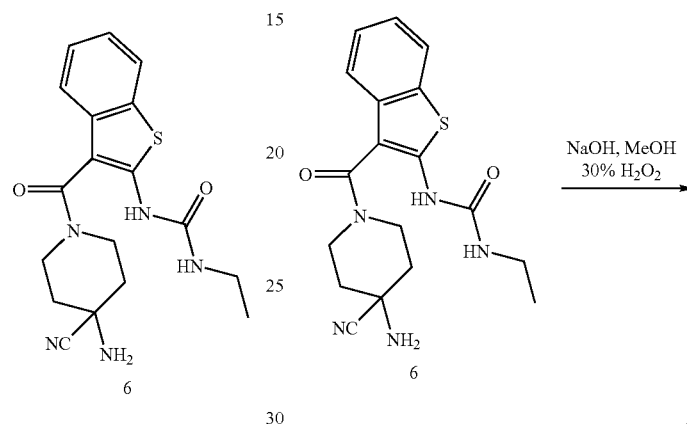

A solution of 2-aminobenzo[b]thiophene-3-carboxylic acid (1.0 g, 1.0 equivalent) and 4-piperidone (1.0 equivalent) in DMF (0.33 M) was treated with EDC (1.0 equivalent), HOBt (1.0 equivalent) and Et$_3$N (2.0 equivalents) at rt. The reaction mixture was stirred until the reaction was complete as determined by LCMS analysis and then partitioned between ethyl acetate and water. Organic layers were washed with saturated aqueous NaHCO$_3$ and brine, dried over Na$_2$SO$_4$, and volatiles removed under reduced pressure. Residue was purified by SiO$_2$ chromatography (5%-10% MeOH/ CH$_2$Cl$_2$ gradient) to afford the 1-(2-aminobenzo[b] thiophene-3-carbonyl)piperidin-4-one (6A, 84%).

A solution of 6A (1.0 equivalent) and ethyl isocyanate (3.0 equivalents), and pyridine (0.21 M) was prepared in a sealed tube and warmed to 80° C. for 8 hrs. The reaction mixture was then cooled to rt, the volatiles removed under reduced pressure, and the residue purified by SiO$_2$ chromatography (5%- 10% MeOH/CH$_2$Cl$_2$ gradient) to afford the 1-ethyl-3-(3-(4- oxopiperidine-1-carbonyl)benzo[b]thiophen-2-yl)urea (6B, 85%).

A solution of 6B (1.0 equivalent) in MeOH (0.06M), was slowly added NH$_4$Cl (1.2 equivalents) and 30% aq. NH$_3$OH (0.06M) and stirred at room temperature for 30 minutes. The mixture was cooled at 0° C., and KCN was added in portions. After 12 hrs, 80% of MeOH was removed under reduced pressure, and then replaced MeOH with diethyl ether at 0° C. Filtered crystallized solid and washed crystals with cold diethyl ether twice to afford the 1-(3-(4-amino-4-cyanopiperidine-1-carbonyl)benzo[b]thiophen-2-yl)-3-ethylurea (6, 79%). Two rotamers observed (ratio 1:1).

First rotamer: $^1$H NMR (400 MHz, CHLOROFORM-d) δ ppm, 0.94 (t, J=7.71 Hz, 3H), 1.83-1.95 (m, 2 H), 2.11 (br. s., 2 H), 3.12-3.21 (m, 2 H), 3.48 (dd, J=11.12, 2.78 Hz, 2 H), 4.03 (br. s., 2 H), 7.19-7.26 (m, 1 H), 7.30-7.44 (m, 2 H), 7.74 (d, J=7.83 Hz, 1 H), 9.39 (br. s., 1 H); ESI-MS: m/z 371.1 (M+H)$^+$.

Second rotamer: 0.86 (t, J=6.95 Hz, 3 H), 1.83-1.95 (m, 2 H), 2.11 (br. s., 2 H), 3.03-3.11 (m, 2 H), 3.48 (dd, J=11.12, 2.78 Hz, 2 H), 4.03 (br. s., 2 H), 7.19-7.26 (m, 1 H), 7.30-7.44 (m, 2 H), 7.74 (d, J=7.83 Hz, 1 H), 9.39 (br. s., 1 H); ESI-MS: m/z 371.1 (M+H)$^+$.

Example 7

Preparation of 4-amino-1-(2-(3-ethylureido)benzo[b] thiophene-3-carbonyl)piperidine-4-carboxamide TFA salt (7)

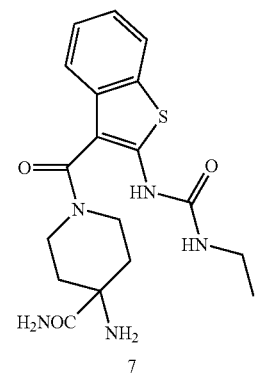

7

1-(3-(4-Amino-4-cyanopiperidine-1-carbonyl)benzo[b] thiophen-2-yl)-3-ethylurea (6 (Example 6), 730 mg, 1.0 equivalent) was dissolved in MeOH (0.11 M) at 0° C. and to which was added an aqueous 20% w/v NaOH. Then the mixture was cooled to −5° C., and 30% wt H$_2$O$_2$ was added drop wise, then it was warmed to 10° C. over 30 minutes. The reaction mixture was then partitioned between ethyl acetate and water and the separated organics was washed with brine and dried over Na$_2$SO$_4$, filtered, and concentrated under reduced pressure. The residue was crystallized from ice cold diethyl ether, and the crystals was washed with ether twice to afford the 4-amino-1-(2-(3-ethylureido)benzo[b]thiophene-3-carbonyl)piperidine-4-carboxamide (7, free base, 52%). Compound 7 freebase (1.0 equivalent) was dissolved in a solution of 0.05% TFA in CH$_2$Cl$_2$ (0.01 M), and subsequently removed the CH$_2$Cl$_2$ under reduced pressure to result the TFA salt of the carboximide. Two rotamers observed (ratio 1.3:1).

First rotamer: $^1$H NMR (400 MHz, MeOD) δ ppm, 1.17 (td, J=7.14, 3.41 Hz, 3 H), 1.93 (s, 2 H), 2.37 (dd, J=14.02, 6.44 Hz, 2 H), 3.25 (q, J=7.16 Hz, 2 H), 3.49 (dd, J=13.64, 11.12 Hz, 2 H), 4.05 (br. s., 2 H), 7.25 (dd, J=15.28, 1.14 Hz, 1 H), 7.33-7.42 (m, 1 H), 7.46 (d, J=7.83 Hz, 1 H), 7.75 (dd, J=7.83, 2.53 Hz, 1 H); ESI-MS: m/z 389.1 (M+H)$^+$.

Second rotamer: $^1$H NMR (400 MHz, MeOD) δ ppm, 1.17 (td, J=7.14, 3.41 Hz, 3 H), 1.93 (s, 2 H), 2.37 (dd, J=14.02, 6.44 Hz, 2 H), 3.25 (q, J=7.16 Hz, 2 H), 3.49 (dd, J=13.64, 11.12 Hz, 2 H), 4.05 (br. s., 2 H), 7.25 (dd, J=15.28, 1.14 Hz, 1 H), 7.33-7.42 (m, 1 H), 7.65 (d, J=7.83 Hz, 1 H), 7.75 (dd, J=7.83, 2.53 Hz, 1 H); ESI-MS: m/z 389.1 (M+H)$^+$.

Example 8

Preparation of 1-(3-(2-(chloromethyl)-4-oxo-1,3,8-triazaspiro[4.5]dec-1-enecarbonyl)benzo[b]thiophen-2-yl)-3-ethylurea (8)

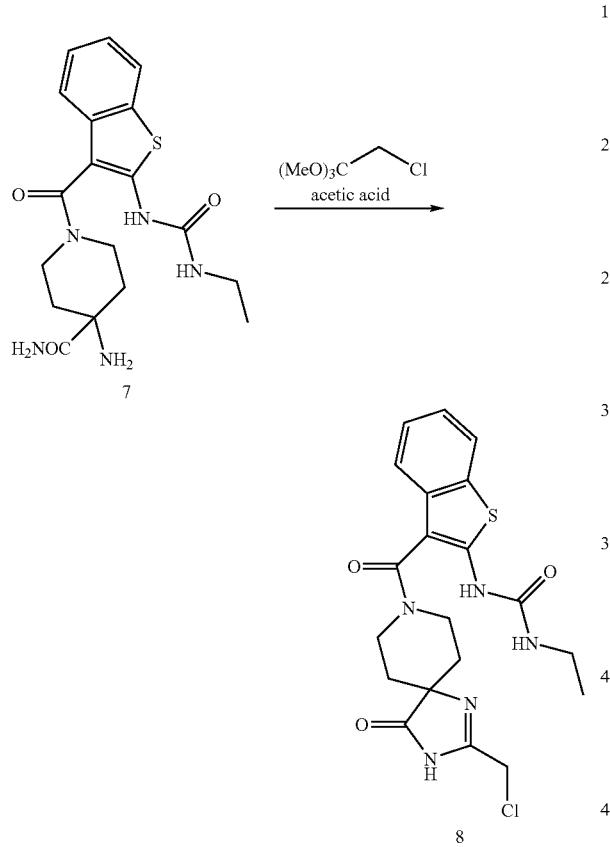

To 4-Amino-1-(2-(3-ethylureido)benzo[b]thiophene-3-carbonyl)piperidine-4-carboxamide TFA salt (7 (Example 7), 300 mg, 1.0 equivalent), 2-chloro-1,1,1-trimethoxyethane (4.0 equivalents) and acetic acid (0.07 M) was added, and then the mixture was heated to 60° C. for 1 hr. The volatiles was removed under reduced pressure and the residue was purified by SiO$_2$ chromatography (5%-10% MeOH/CH$_2$Cl$_2$ gradient) to afford 1-(3-(2-(chloromethyl)-4-oxo-1,3,8-triazaspiro[4.5]dec-1-enecarbonyl)benzo[b]thiophen-2-yl)-3-ethylurea (8, 65%). Two rotamers observed (ratio 3:2).

First rotamer: $^1$H NMR (400 MHz, CHLOROFORM-d) δ ppm, 1.10 (dt, J=11.18, 7.29 Hz, 3 H), 1.56 (br. s., 2 H), 1.98 (br. s., 2 H), 3.27 (dd, J=19.45, 5.56 Hz, 2 H), 3.64 (t, J=1.37 Hz, 2 H), 4.07 (br. s., 2 H), 4.34 (s, 2 H), 6.40 (t, J=5.18 Hz, 1 H), 7.21 (m, 1 H), 7.29-7.50 (m, 2 H), 7.68-7.77 (m, 1 H) 9.47 (br. s., 1 H); ESI-MS: m/z 447.1 (M+H)$^+$.

Second rotamer: $^1$H NMR (400 MHz, CHLOROFORM-d) δ ppm, 1.10 (dt, J=11.18, 7.29 Hz, 3 H), 1.69 (br. s., 2 H), 1.90 (br. s., 2 H), 3.27 (dd, J=19.45, 5.56 Hz, 2 H), 3.64 (t, J=11.37 Hz, 2 H), 4.07 (br. s., 2 H), 4.30 (s, 2 H), 6.35 (t, J=5.31 Hz, 1 H), 7.17-7.25 (m, 1 H), 7.29-7.50 (m, 2 H), 7.68-7.77 (m, 1 H), 9.35 (br. s., 1 H); ESI-MS: m/z 447.1 (M+H)$^+$.

Example 9

Preparation of 1-(3-(2-(chloromethyl)-4-oxo-1,3,8-triazaspiro[4.5]dec-1-enecarbonyl)-7-methoxybenzo[b]thiophen-2-yl)-3-ethylurea TFA salt (9)

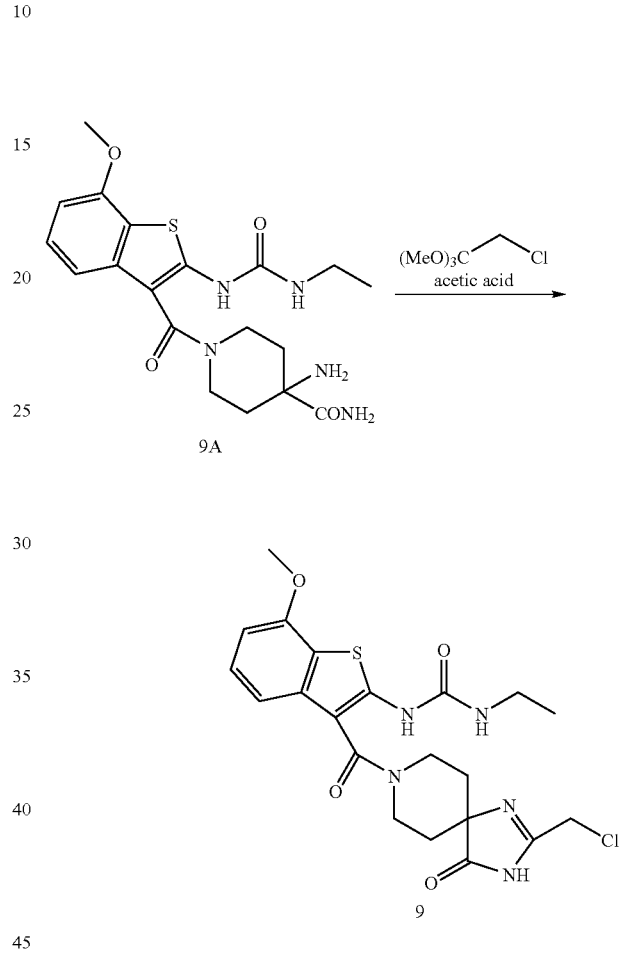

4-Amino-1-(2-(3-ethylureido)-7-methoxybenzo[b]thiophene-3-carbonyl)piperidine-4-carboxamide (9A) was prepared according to the method of Example 7 except 2-amino-7-methoxybenzo[b]thiophene-3-carboxylic acid was used.

The title compound was then prepared from 9A by a procedure analogous to that described in Example 8. Two rotamers observed (ratio 1:1)

First rotamer: $^1$H NMR (400 MHz, MeOD) δ ppm, 1.18 (m, 3 H) 1.58 (br. s., 2 H) 1.94 (br. s, 2 H) 3.47-3.69 (m, 4 H) 3.97 (s, 3 H) 4.35-4.43 (m, 2 H) 6.77-6.82 (m, 1 H) 7.17 (d, J=7.83 Hz, 1 H) 7.28-7.38 (m, 1 H); ESI-MS: m/z 478.0 (M+H)$^+$.

Second rotamer: $^1$H NMR (400 MHz, MeOD) δ ppm 1.18 (m, 3 H) 1.58 (br. s., 2 H) 1.94 (br. s, 2 H) 3.47-3.69 (m, 2 H) 3.97 (s, 3 H) 4.35-4.43 (m, 2 H) 6.77-6.82 (m, 1 H) 7.07 (d, J=7.83 Hz, 1 H) 7.28-7.38 (m, 1 H); ESI-MS: m/z 478.0 (M+H)$^+$.

Example 10

Preparation of ethyl 3-(8-(2-(3-ethylureido)benzo[b]thiophene-3-carbonyl)-4-oxo-1,3,8-triazaspiro[4.5]dec-1-en-2-yl)propanoate (10)

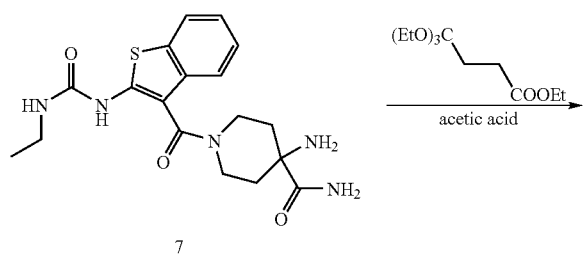

4-Amino-1-(2-(3-ethylureido)benzo[b]thiophene-3-carbonyl)piperidine-4-carboxamide (7, 100 mg, 1.0 equivalent) as prepared in Example 7 was dissolved in toluene (0.09 M) and DMF (0.26 M), and to which acetic acid (2.0 equivalents), and ethyl 4,4,4-triethoxybutanoate (4.0 equivalents) were added and the reaction mixture was heated to 85° C. for 9 hrs. The reaction mixture was then partitioned between ethyl acetate and water and the separated organics was washed with brine and dried over $Na_2SO_4$, filtered, and concentrated under reduced pressure. The residue was purified by $SiO_2$ chromatography (5%-10% $MeOH/CH_2Cl_2$ gradient) to afford ethyl 3-(8-(2-(3-ethylureido)benzo[b]thiophene-3-carbonyl)-4-oxo-1,3,8-triazaspiro[4.5]dec-1-en-2-yl)propanoate (10, 65%). Two rotamers observed (ratio 1.3:1).

First rotamer: $^1H$ NMR (400 MHz, MeOD) δ ppm, 1.18 (td, J=7.20, 4.55 Hz, 3 H), 1.85 (br. s., 2 H), 2.03 (br. s., 2 H), 2.89 (q, J=6.82 Hz, 2 H), 3.01 (dd, J=9.47, 6.95 Hz, 2 H), 3.27 (dd, J=7.33, 4.80 Hz, 2 H), 3.58-3.73 (m, 2 H), 4.07 (br. s., 2 H), 4.15 (qd, J=7.12, 3.41 Hz, 2 H), 7.24 (t, J=7.58 Hz, 1 H), 7.35 (td, J=8.34, 1.52 Hz, 1 H), 7.46 (d, J=7.83 Hz, 1 H), 7.74 (d, J=1.01 Hz, 1 H); ESI-MS: m/z 499.1 $(M+H)^+$.

Second rotamer: $^1H$ NMR (400 MHz, MeOD) δ ppm, 1.25 (td, J=7.07, 3.03 Hz, 3 H), 1.85 (br. s., 2 H), 2.03 (br. s., 2 H), 2.89 (q, J=6.82 Hz, 2 H), 3.01 (dd, J=9.47, 6.95 Hz, 2 H), 3.27 (dd, J=7.33, 4.80 Hz, 2 H), 3.58-3.73 (m, 2 H), 4.07 (br. s., 2 H), 4.15 (qd, J=7.12, 3.41 Hz, 2 H), 7.24 (t, J=7.58 Hz, 1 H), 7.35 (td, J=8.34, 1.52 Hz, 1 H), 7.53 (d, J=8.08 Hz, 1 H), 7.74 (d, J=1.01 Hz, 1 H); ESI-MS: m/z 499.1 $(M+H)^+$.

Example 11

Preparation of ethyl 3-(8-(2-(3-ethylureido)-7-methoxybenzo[b]thiophene-3-carbonyl)-4-oxo-1,3,8-triazaspiro[4.5]dec-1-en-2-yl)propanoate TFA salt (11)

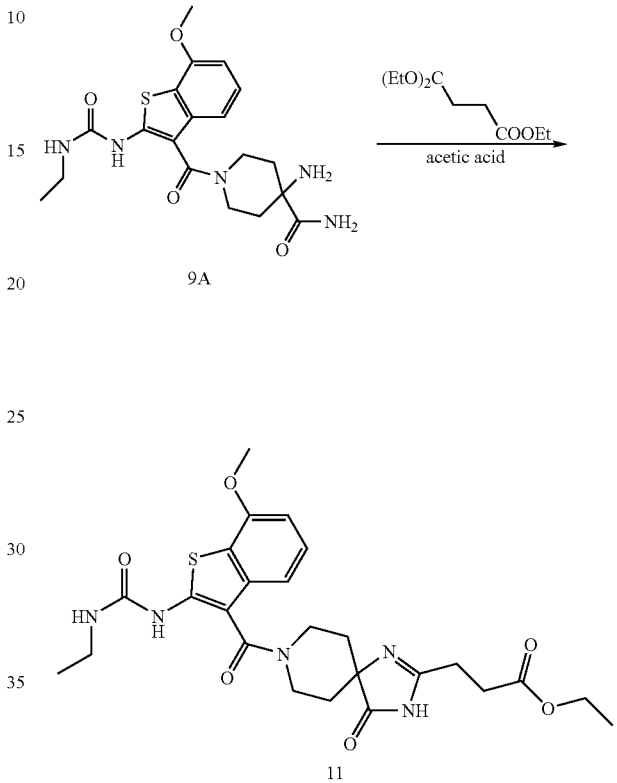

The title compound was prepared by a procedure analogous to that of Example 10 except that 4-amino-1-(2-(3-ethylureido)-7-methoxybenzo[b]thiophene-3-carbonyl)piperidine-4-carboxamide (9A) prepared by the method of Example 9 was used. Two rotamers were observed (ratio 1:1.3).

First rotamer: $^1H$ NMR (400 MHz, MeOD) δ ppm 1.14-1.22 (m, 3 H) 1.21-1.30 (m, 3 H) 1.77 (br. s., 2 H) 1.99 (br. s, 2 H) 2.89 (s, 4 H) 3.22-3.34 (m, 2 H) 3.61 (br. s., 2 H) 3.97 (s, 3 H) 4.09-4.19 (m, 2 H) 6.77-6.83 (m, 1 H) 7.15 (d, J=8.08 Hz, 1 H) 7.27-7.39 (m, 1 H). ESI-MS: m/z 530.2 $(M+H)^+$.

Second rotamer: $^1H$ NMR (400 MHz, MeOD-d) δ ppm 1.14-1.22 (m, 3 H) 1.21-1.30 (m, 3 H) 1.77 (br. s., 2 H) 1.99 (br. s, 2 H) 2.89 (s, 4 H) 3.22-3.34 (m, 2 H) 3.61 (br. s., 2H) 3.97 (s, 3 H) 4.09-4.19 (m, 2 H) 6.77-6.83 (m, 1 H) 7.07 (d, J=8.08 Hz, 1 H) 7.27-7.39 (m, 1 H). ESI-MS: m/z 530.2 $(M+H)^+$.

Example 12

Preparation of N,N-diethyl-3-(8-(2-(3-ethylureido)benzo[b]thiophene-3-carbonyl)-4-oxo-1,3,8-triazaspiro[4.5]dec-1-en-2-yl)propanamide (12)

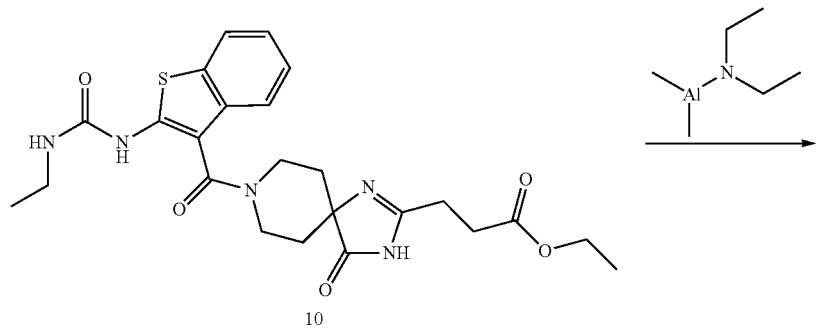

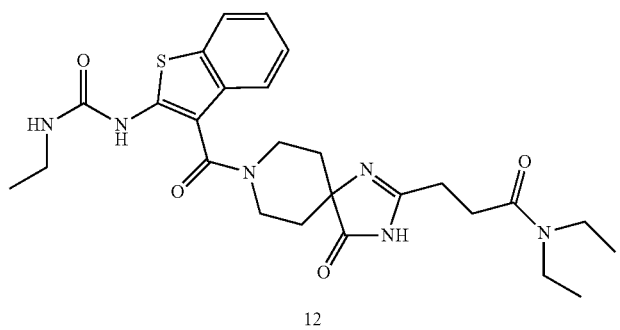

To a 2.0 M hexane solution of (diethylamino)dimethylaluminum (3.2 equivalents) in dry benzene (0.26 M) was cooled to −15° C., a solution of ethyl 3-(8-(2-(3-ethylureido)benzo[b]thiophene-3-carbonyl)-4-oxo-1,3,8-triazaspiro[4.5]dec-1-en-2-yl)propanoate (10 (Example 10), 12 mg, 1.0 equivalent) in THF (0.16M) was added; the mixture was heated to 80° C. for 6 hrs. The mixture was cooled in an ice bath; then a saturated aqueous Rochelle's solution was added and stirred for 1 hr, then partitioned between ethyl acetate and water and the separated organics was washed with brine and dried over $Na_2SO_4$, filtered, and concentrated under reduced pressure. The residue was purified by preparatory LCMS to afford N,N-diethyl-3-(8-(2-(3-ethylureido)benzo[b]thiophene-3-carbonyl)-4-oxo-1,3,8-triazaspiro[4.5]dec-1-en-2-yl)propanamide (10, 20%). Two rotamers observed (ratio 1.3:1).

First rotamer: $^1$H NMR (400 MHz, MeOD) δ ppm, 1.12-1.27 (m, 9 H), 1.78 (d, J=4.04 Hz, 2 H), 2.00 (br. s., 2 H), 2.94 (br. s., 4 H), 3.23-3.29 (m, 2 H), 3.33-3.45 (m, 4 H), 3.60 (br. s., 2 H), 4.09 (br. s., 2 H), 7.18-7.27 (m, 1 H), 7.30-7.41 (m, 1 H), 7.45 (d, J=7.83 Hz 1 H), 7.74 (d, J=7.83 Hz, 1 H). ESI-MS: m/z 526.2 (M+H)$^+$.

Second rotamer: $^1$H NMR (400 MHz, MeOD) δ ppm, 1.12-1.27 (m, 9 H), 1.78 (d, J=4.04 Hz, 2 H), 2.00 (br. s., 2 H), 2.94 (br. s, 4 H), 3.23-3.29 (m, 2 H), 3.33-3.45 (m, 4 H), 3.60 (br. s, 2 H), 4.09 (br. s, 2 H), 7.18-7.27 (m, 1 H), 7.30-7.41 (m, 1 H), 7.54 (d, J=8.08 Hz 1 H), 7.74 (d, J=7.83 Hz, 1 H). ESI-MS: m/z 526.2 (M+H)$^+$.

Example 13

Preparation of 1-ethyl-3-(3-(4-oxo-2-(3-oxo-3-(piperidin-1-yl)propyl)-1,3,8-triazaspiro[4.5]dec-1-enecarbonyl)benzo[b]thiophen-2-yl)urea TFA salt (13)

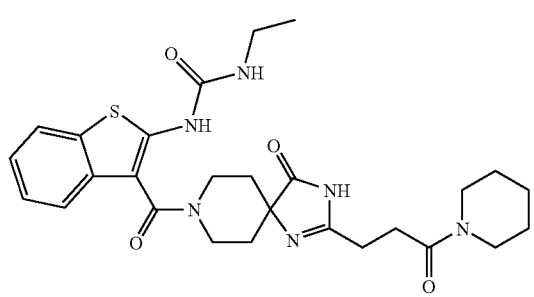

The title compound was prepared by a procedure analogous to Example 12 except dimethyl(piperidin-1-yl)aluminum was used. Two rotamers was observed (ratio 1.3:1).

First rotamer: $^1$H NMR (400 MHz, MeOD) δ ppm, 1.12-1.21 (m, 3 H), 1.51 (br. s., 2H) 1.57-1.72 (m, 4 H), 1.93 (d, J=1.01 Hz, 2 H), 2.04 (br. s., 2 H), 2.99-3.05 (m, 4 H), 3.27 (q, 2 H), 3.48 (dd, J=9.85, 5.31 Hz, 4 H), 3.61 (br. s., 2 H), 4.07 (br. s., 2 H), 7.23 (dd, J=15.16, 1.01 Hz, 1 H), 7.36 (dt, J=12.63, 7.58 Hz, 1 H), 7.46 (d, J=7.83 Hz, 1 H), 7.75 (d, J=8.08 Hz, 1 H). ESI-MS: m/z 538.2 (M+H)$^+$.

Second rotamer: $^1$H NMR (400 MHz, MeOD) δ ppm, 1.12-1.21 (m, 3 H), 1.51 (br. s., 2 H) 1.57-1.72 (m, 4 H), 1.93 (d, J=1.01 Hz, 2 H), 2.04 (br. s., 2 H), 2.99-3.05 (m, 4 H), 3.27 (q, 2 H), 3.48 (dd, J=9.85, 5.31 Hz, 4 H), 3.61 (br. s., 2 H), 4.07 (br. s., 2 H), 7.23 (dd, J=15.16, 1.01 Hz, 1 H), 7.36 (dt, J=12.63, 7.58 Hz, 1 H), 7.53 (d, J=8.08 Hz, 1 H), 7.75 (d, J=8.08 Hz, 1 H). ESI-MS: m/z 538.2 (M+H)$^+$.

Example 14

Preparation of 1-ethyl-3-(3-(4-oxo-1,3,8-triazaspiro [4.5]dec-1-enecarbonyl)benzo[b]thiophen-2-yl)urea TFA salt (14)

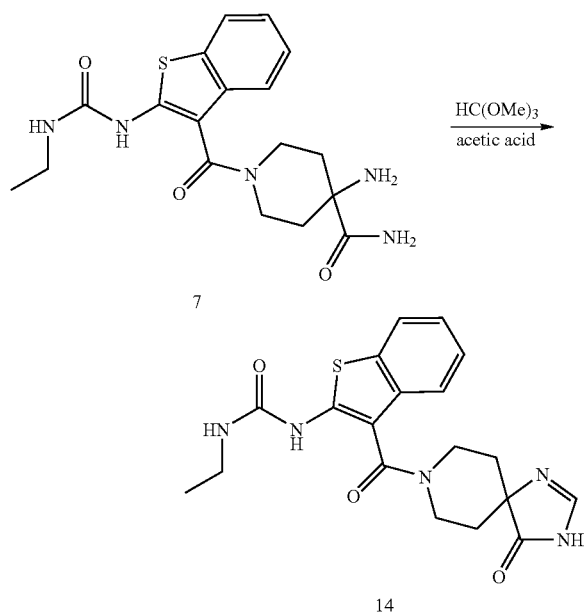

4-Amino-1-(2-(3-ethylureido)benzo[b]thiophene-3-carbonyl)piperidine-4-carboxamide (7, 100 mg) prepared in Example 7 was dissolved in toluene (0.05 M), and to which acetic acid (2.0 equivalents) and trimethoxymethane (4.0 equivalents) were added and the reaction mixture was heated to 65° C. for 5 hr. The solvent was removed under vacuum, and the mixture was filtered and purified by LCMS to afford the title compound 14 (50%) as a TFA salt. Two rotamers were observed (ratio 1:1).

First rotamer: $^1$H NMR (400 MHz, MeOH-d$_4$) δ ppm, 1.14-1.21 (m, 3 H), 1.76 (br. s., 2 H), 1.99 (br. s., 2 H), 3.26 (dd, J=7.07, 5.56 Hz, 2 H), 3.60 (t, J=10.48 Hz, 2 H), 4.10 (br. s., 2 H), 7.23 (dd, J=15.16, 1.01 Hz, 1 H), 7.36 (dt, J=10.61, 7.58 Hz, 1 H), 7.46 (d, J=8.08 Hz, 1H), 7.74 (d, J=7.83 Hz, 1 H), 8.82 (s, 1 H). ESI-MS: m/z 399.1 (M+H)$^+$.

Second rotamer: $^1$H NMR (400 MHz, MeOH-d$_4$) δ ppm, 1.14-1.21 (m, 3 H), 1.76 (br. s., 2 H), 1.99 (br. s., 2 H), 3.26 (dd, J=7.07, 5.56 Hz, 2 H), 3.60 (t, J=10.48 Hz, 2 H), 4.10 (br. s., 2 H), 7.23 (dd, J=15.16, 1.01 Hz, 1 H), 7.36 (dt, J=10.61, 7.58 Hz, 1 H), 7.55 (d, J=8.08 Hz, 1 H), 7.74 (d, J=7.83 Hz, 1 H), 8.67 (s, 1 H). ESI-MS: m/z 399.1 (M+H)$^+$.

Example 15

Preparation of 1-(3-(2-butyl-4-oxo-1,3,8-triazaspiro [4.5]dec-1-enecarbonyl)benzo[b]thiophen-2-yl)-3-ethylurea (15)

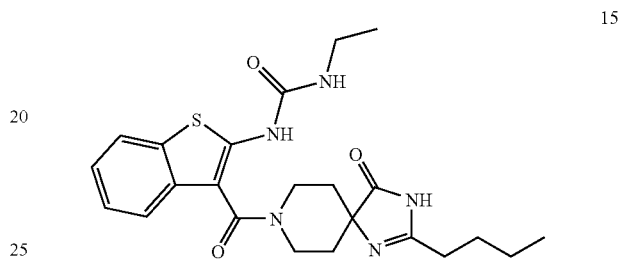

The title compound was prepared by a procedure analogous to Example 14 except 1,1,1-triethoxypentane was used. Two rotamers were observed (ratio 3:1).

First rotamer: $^1$H NMR (400 MHz, CHLOROFORM-d) δ ppm, 0.87-0.97 (m, 6 H), 1.02 (t, J=7.20 Hz, 3 H), 1.38 (dt, J=14.72, 7.42 Hz, 2 H), 1.50 (d, J=12.38 Hz, 2 H), 1.58-1.72 (m, 2 H), 1.79 (br. s., 2 H), 2.39-2.52 (m, 2 H), 3.11-3.27 (m, 2 H), 3.67 (t, J=11.12 Hz, 2 H), 4.13 (br. s., 2 H), 5.99 (s, 1 H), 7.21 (q, J=7.16 Hz, 1 H), 7.31 (t, J=7.71 Hz, 1 H), 7.41 (d, J=8.08 Hz, 1 H), 7.68-7.75 (m, 1 H), 9.14 (br. s., 1 H), 9.44 (br. s., 1 H). ESI-MS: m/z 455.2 (M+H)$^+$.

Second rotamer: $^1$H NMR (400 MHz, CHLOROFORM-d) δ ppm, 0.87-0.97 (m, 6H), 1.02 (t, J=7.20 Hz, 3 H), 1.38 (dt, J=14.72, 7.42 Hz, 2 H), 1.50 (d, J=12.38 Hz, 2 H), 1.58-1.72 (m, 2 H), 1.91 (br. s., 2 H), 2.39-2.52 (m, 2 H), 3.11-3.27 (m, 2 H), 3.67 (t, J=11.12 Hz, 2H), 4.13 (br. s., 2 H), 5.77 (br. s., 1 H), 7.21 (q, J=7.16 Hz, 1 H), 7.31 (t, J=7.71 Hz, 1 H), 7.50 (d, J=8.08 Hz, 1 H), 7.68-7.75 (m, 1 H), 8.85 (br. s., 1 H), 9.31 (br. s., 1 H). ESI-MS: m/z 455.2 (M+H)$^+$.

Example 16

Preparation of 1-ethyl-3-(3-(2-isopropyl-4-oxo-1,3, 8-triazaspiro[4.5]dec-2-enecarbonyl)-7-methoxybenzo[b]thiophen-2-yl)urea TFA salt (16)

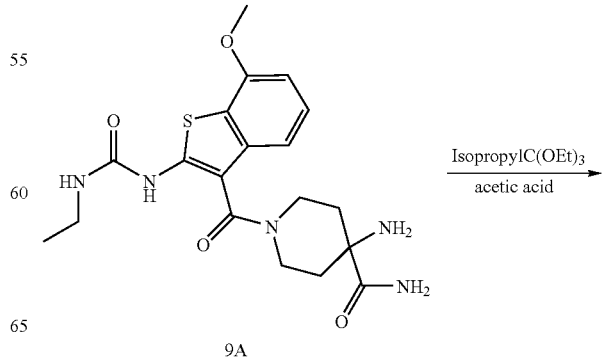

-continued

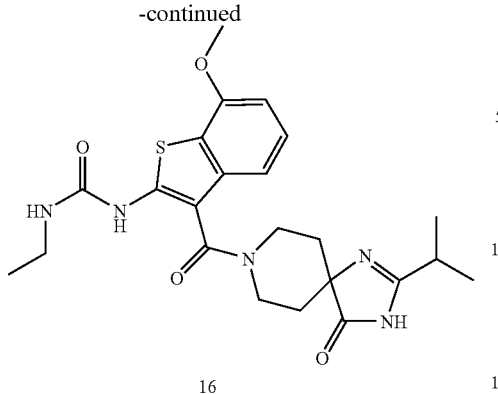

16

4-Amino-1-(2-(3-ethylureido)-7-methoxybenzo[b]thiophene-3-carbonyl)piperidine-4-carboxamide (9A) was prepared according to the method of Example 7 except 2-amino-7-methoxybenzo[b]thiophene-3-carboxylic acid was used.

The title compound was then prepared using a procedure analogous to Example 14 using 1,1,1-triethoxy-2-methylisopropane. Two rotamers were observed (ratio 1:1.3).

First rotamer: $^1$H NMR (400 MHz, MeOD) δ ppm 1.13-1.24 (m, 3 H) 1.36 (d, J=7.07 Hz, 6 H) 1.82 (br. s., 2 H) 2.00 (br. s., 2 H) 2.83-3.08 (m, 1 H) 3.20-3.37 (m, 2 H) 3.59-3.81 (m, 2 H) 3.91-4.10 (m, 5 H) 6.72-6.85 (m, 1 H) 7.14 (d, 1 H) 7.25-7.42 (m, 1 H). ESI-MS: m/z 472.2 (M+H)$^+$.

second rotamer: $^1$H NMR (400 MHz, MeOD) δ ppm 1.13-1.24 (m, 3 H) 1.36 (d, J=7.07 Hz, 6 H) 1.82 (br. s, 2 H) 2.00 (br. s., 2 H) 2.83-3.08 (m, 1 H) 3.20-3.37 (m, 2 H) 3.59-3.81 (m, 2 H) 3.91-4.10 (m, 5 H) 6.72-6.85 (m, 1 H) 7.08 (d, 1 H) 7.25-7.42 (m, 1 H). ESI-MS: m/z 472.2 (M+H)$^+$.

Example 17

Preparation of 1-(3-(2-butyl-4-oxo-1,3,8-triazaspiro[4.5]dec-1-enecarbonyl)-7-methoxybenzo[b]thiophen-2-yl)-3-ethylurea TFA salt (17)

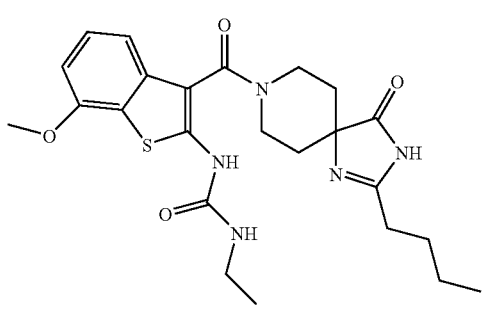

17

The title compound was prepared by a procedure analogous to Example 14 except 1,1,1-triethoxypentane was used. Two rotamers were observed (ratio 1:1).

First rotamer: $^1$H NMR (400 MHz, MeOD) δ ppm first rotamer: 0.99 (m, 3 H) 1.18 (m, 3 H) 1.39-1.52 (m, 2 H) 1.66-1.85 (m, 4 H) 1.94-2.08 (m, 2 H) 2.62-2.75 (m, 2 H) 3.22-3.34 (m, 2 H) 3.62 (br. s., 2 H) 3.97 (s, 3 H) 4.06 (br. s., 2 H) 6.77-6.83 (m, 1 H) 7.14 (d, J=7.83 Hz, 1H) 7.27-7.38 (m, 1 H). ESI-MS: m/z 486.2 (M+H)$^+$.

Second rotamer: $^1$H NMR (400 MHz, MeOD) δ ppm 0.94-1.03 (m, 3 H) 1.13-1.23 (m, 3 H) 1.39-1.52 (m, 2 H) 1.66-1.85 (m, 4 H) 1.94-2.08 (m, 2 H) 2.62-2.75 (m, 2 H) 3.22-3.34 (m, 2 H) 3.62 (br. s., 2 H) 3.97 (s, 3 H) 4.06 (br. s., 2 H) 6.77-6.83 (m, 1 H) 7.07 (d, J=7.83 Hz, 1 H), 7.27-7.38 (m, 1 H). ESI-MS: m/z 486.2 (M+H)$^+$.

Example 18

Preparation of 1-ethyl-3-(7-methoxy-3-(4-oxo-2-phenyl-1,3,8-triazaspiro[4.5]dec-2-enecarbonyl)benzo[b]thiophen-2-yl)urea TFA salt (18)

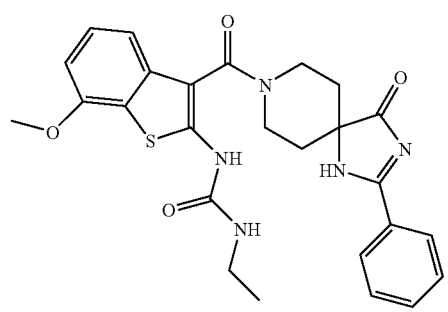

18

The title compound was prepared by a procedure analogous to Example 14 except (triethoxymethyl)benzene was used. $^1$H NMR (400 MHz, MeOD) δ ppm 1.13-1.24 (m, 3 H) 1.88 (br. s, 3 H) 2.08 (br. s, 2 H) 3.20-3.35 (m, 2 H) 3.79 (br. s., 2 H) 3.97 (s, 3 H) 4.11 (br. s., 1 H) 6.73-6.84 (m, 1 H) 7.12 (d, J=8.08 Hz, 1 H) 7.18 (d, J=8.08 Hz, 1 H) 7.27-7.41 (m, 1 H) 7.56-7.68 (m, 1 H) 7.69-7.80 (m, 1 H) 7.98 (dd, J=8.21, 1.39 Hz, 1 H) 8.02 (dd, J=8.46, 1.39 Hz, 1 H). ESI-MS: m/z 506.2 (M+H)$^+$.

Example 19

Preparation of methyl 2-(8-(2-(3-ethylureido)benzo[b]thiophene-3-carbonyl)-4-oxo-1,3,8-triazaspiro[4.5]dec-1-en-3-yl)acetate TFA salt (19)

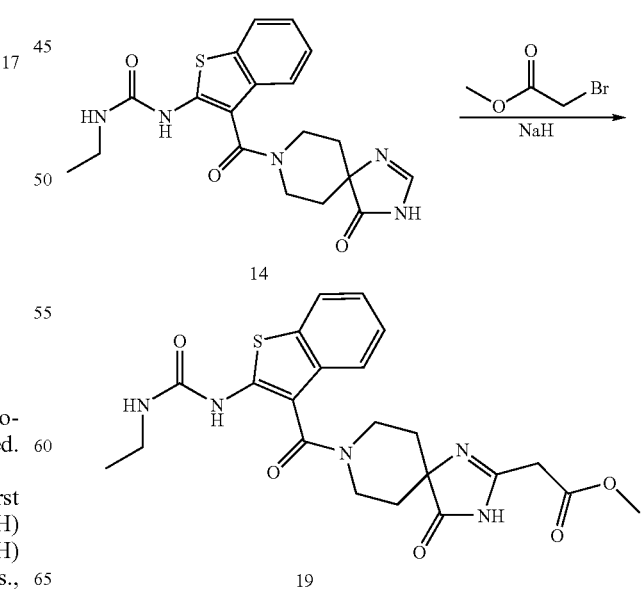

14

19

To a solution of 1-ethyl-3-(3-(4-oxo-1,3,8-triazaspiro[4.5]dec-1-enecarbonyl)benzo[b]thiophen-2-yl)urea (14 (Example 14), 20 mg, 1.0 equivalent) in DMF (0.13 M) prepared as described in Example 14 was added a 60% NaH (1.2 equivalents), and this was stirred at room temperature for 20 minutes, and then methyl 2-bromoacetate was added (1.2 equivalents). This mixture was heated at 50° C. for 4 hrs, and the reaction was complete as determined by LCMS analysis, the reaction mixture was washed with water, brine, dried over MgSO$_4$, filtered, and the volatiles removed under reduced pressure. The residue was purified by LCMS to afford the title compound (19, 42%). Two rotamers were observed (ratio 1:1). ESI-MS: m/z 455.2 (M+H)$^+$.

First rotamer: $^1$H NMR (400 MHz, MeOH-d$_4$) δ ppm, 1.17 (tt, J=7.29, 2.56 Hz, 3 H), 1.61 (br. s., 2 H), 1.93 (br. s., 2 H), 3.26 (dt, J=7.33, 2.65 Hz, 2 H), 3.55-3.68 (m, 2 H), 3.75 (t, J=2.15 Hz, 3 H), 4.11 (br. s., 2 H), 4.38 (t, J=2.15 Hz, 2 H), 7.17-7.27 (m, 1H), 7.31-7.41 (m, 1 H), 7.55 (d, J=8.08 Hz, 1 H), 7.74 (d, J=7.83 Hz, 1 H), 8.13 (d, J=5.81 Hz, 1 H).

Second rotamer: $^1$H NMR (400 MHz, MeOH-d$_4$) δ ppm, 1.17 (tt, J=7.29, 2.56 Hz, 3H), 1.61 (br. s., 2 H), 1.93 (br. s., 2 H), 3.26 (dt, J=7.33, 2.65 Hz, 2 H), 3.55-3.68 (m, 2 H), 3.75 (t, J=2.15 Hz, 3 H), 4.11 (br. s., 2 H), 4.38 (t, J=2.15 Hz, 2 H), 7.17-7.27 (m, 1 H), 7.31-7.41 (m, 1 H), 7.46 (d, J=8.08 Hz, 1 H), 7.74 (d, J=7.83 Hz, 1 H), 8.13 (d, J=5.81 Hz, 1 H). ESI-MS: m/z 471.1 (M+H)$^+$.

Example 20

Preparation of 1-(3-(3-butyl-4-oxo-1,3,8-triazaspiro[4.5]dec-1-enecarbonyl)benzo[b]thiophen-2-yl)-3-ethylurea TFA salt (20)

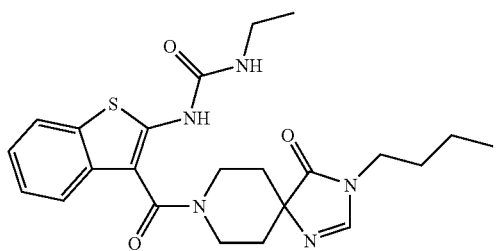

20

The title compound was prepared by a procedure analogous to Example 19 except 1,1,1-triethoxypentane was used. Two rotamers were observed (ratio 1:1).

First rotamer: $^1$H NMR (400 MHz, MeOD-d$_4$) δ ppm, 0.95 (td, J=7.33, 1.77 Hz, 3H), 1.18 (q, J=7.07 Hz, 3 H), 1.32 (dt, J=14.84, 7.36 Hz, 2 H), 1.56-1.69 (m, 4 H), 1.93 (br. s., 2 H), 3.22-3.29 (m, 2 H), 3.52-3.66 (m, 4 H), 4.13 (br. s., 2 H), 7.23 (td, J=7.58, 3.54 Hz, 1H), 7.35 (t, J=7.71 Hz, 1 H), 7.56 (d, J=8.08 Hz, 1 H), 7.74 (d, J=7.83 Hz, 1 H), 8.42 (s, 1 H). ESI-MS: m/z 455.2 (M+H)$^+$.

Second rotamer: $^1$H NMR (400 MHz, MeOD-d$_4$) δ ppm, 0.95 (td, J=7.33, 1.77 Hz, 3H), 1.18 (q, J=7.07 Hz, 3 H), 1.32 (dt, J=14.84, 7.36 Hz, 2 H), 1.56-1.69 (m, 4 H), 1.93 (br. s., 2 H), 3.22-3.29 (m, 2 H), 3.52-3.66 (m, 4 H), 4.13 (br. s., 2 H), 7.23 (td, J=7.58, 3.54 Hz, 1H), 7.35 (t, J=7.71 Hz, 1 H), 7.46 (d, J=8.08 Hz, 1 H), 7.74 (d, J=7.83 Hz, 1 H), 8.34 (s, 1 H). ESI-MS: m/z 455.2 (M+H)$^+$.

Example 21

Preparation of 1-ethyl-3-(3-(2-((4-fluorophenylthio)methyl)-4-oxo-1,3,8-triazaspiro[4.5]dec-1-enecarbonyl)benzo[b]thiophen-2-yl)urea TFA salt (21)

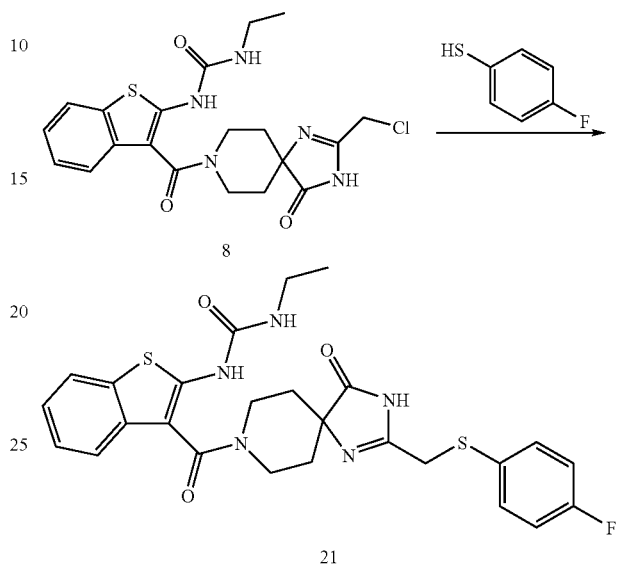

To a solution of 1-(3-(2-(chloromethyl)-4-oxo-1,3,8-triazaspiro[4.5]dec-1-enecarbonyl)benzo[b]thiophen-2-yl)-3-ethylurea (8 (Example 8), 15 mg, 1.0 equivalent) in DMF (0.04 M) was added 4-fluorobenzenethiol and heated to 80° C. for 1 hr. The mixture was filtered and purified by LCMS to afford 1-ethyl-3-(3-(2-((4-fluorophenylthio)methyl)-4-oxo-1,3,8-triazaspiro[4.5]dec-1-enecarbonyl)benzo[b]thiophen-2-yl)urea (21, 56%) as a TFA salt. $^1$H NMR (400 MHz, MeOD), δ ppm 1.18 (td, J=7.20, 2.78 Hz, 3 H), 1.36 (br. s., 2 H), 1.79 (br. s., 2H), 3.23-3.28 (m, 4 H), 3.43 (t, J=10.99 Hz, 2 H), 4.04 (br. s., 2 H), 7.09 (t, J=8.34 Hz, 2 H), 7.23 (t, J=7.58 Hz, 1 H), 7.31-7.43 (m, 2 H), 7.48-7.57 (m, 2 H), 7.73 (d, J=7.83 Hz, 1 H). ESI-MS: m/z 539.1 (M+H)$^+$.

Example 22

Preparation of 1-ethyl-3-(3-(2-(isopropylthiomethyl)-4-oxo-1,3,8-triazaspiro[4.5]dec-1-enecarbonyl)benzo[b]thiophen-2-yl)urea TFA salt (22)

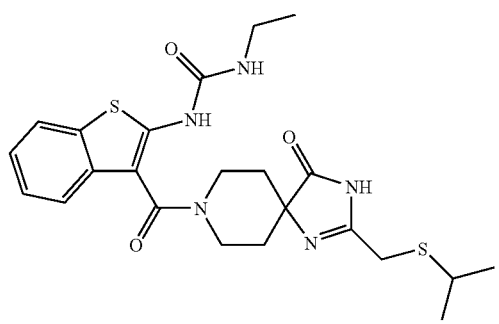

The title compound was prepared by the procedure analogous to Example 21 except sodium propane-2-thiolate was used. Two rotamers were observed (ratio 1:1).

First rotamer: $^1$H NMR (400 MHz, MeOD) δ ppm, 1.19 (td, J=7.33, 4.04 Hz, 3 H), 1.30 (dd, J=6.69, 4.17 Hz, 6 H), 1.71 (br. s., 2 H), 1.94 (br. s., 2 H), 2.95-3.08 (m, 1 H), 3.24-3.30 (m, 4 H), 3.59-3.72 (m, 2 H), 4.07 (br. s., 2 H), 7.24 (dt, J=15.16, 1.52 Hz, 1 H), 7.37 (qd, J=8.21, 1.14 Hz, 1 H), 7.47 (d, J=8.08 Hz, 1 H), 7.75 (d, J=8.08 Hz, 1 H). ESI-MS: m/z 487.1 (M+H)$^+$.

Second rotamer: 1.19 (td, J=7.33, 4.04 Hz, 3 H), 1.30 (dd, J=6.69, 4.17 Hz, 6 H), 1.71 (br. s., 2 H), 1.94 (br. s, 2 H), 2.95-3.08 (m, 1 H), 3.24-3.30 (m, 4 H), 3.59-3.72 (m, 2 H), 4.07 (br. s., 2 H), 7.24 (dt, J=15.16, 1.52 Hz, 1 H), 7.37 (qd, J=8.21, 1.14 Hz, 1 H), 7.55 (d, J=8.08 Hz, 1 H), 7.75 (d, J=8.08 Hz, 1 H). ESI-MS: m/z 487.1 (M+H)$^+$.

Example 23

Preparation of 1-ethyl-3-(3-(2-(isopropylsulfinylmethyl)-4-oxo-1,3,8-triazaspiro[4.5]dec-1-enecarbonyl)benzo[b]thiophen-2-yl)urea TFA salt (23)

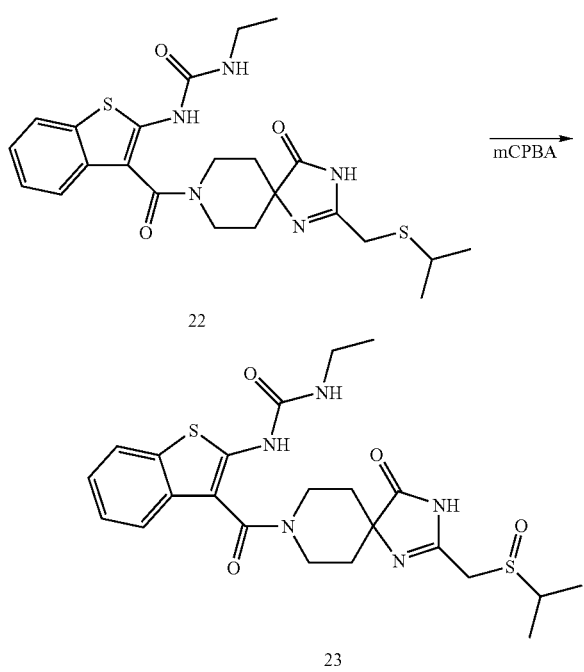

To a solution of 1-ethyl-3-(3-(2-(isopropylthiomethyl)-4-oxo-1,3,8-triazaspiro[4.5]dec-1-enecarbonyl)benzo[b]thiophen-2-yl)urea TFA salt (22 (Example 22), 10 mg, 1.0 equivalent) in CH$_2$Cl$_2$ at 0° C., mCPBA (1.0 equivalent) was added to obtain the crude sulfoxide after 1 hr. The crude product mixture was filtered and the residue was purified by LCMS to afford the title compound (23, 55%). Two rotamers were observed (ratio 1:1).

First rotamer: $^1$H NMR (400 MHz, MeOD) δ ppm: 1.13-1.22 (m, J=7.26, 7.26, 5.31, 2.15 Hz, 3 H), 1.32-1.38 (m, 6 H), 1.61 (br. s., 2 H), 1.93 (br. s., 2 H), 3.05-3.18 (m, 1 H), 3.23-3.29 (m, 4 H), 3.59 (m, 2 H), 4.09 (br. s., 2 H), 7.18-7.26 (m, 1 H), 7.31-7.40 (m, 1 H), 7.55 (d, J=8.08 Hz, 1 H), 7.73 (d, J=8.08 Hz, 1 H). ESI-MS: m/z 503.1 (M+H)$^+$.

Second rotamer: $^1$H NMR (400 MHz, MeOD) δ ppm: 1.13-1.22 (m, J=7.26, 7.26, 5.31, 2.15 Hz, 3 H), 1.32-1.38 (m, 6 H), 1.61 (br. s., 2 H), 1.93 (br. s., 2 H), 3.05-3.18 (m, 1 H), 3.23-3.29 (m, 4 H), 3.59 (m, 2 H), 4.09 (br. s., 2 H), 7.18-7.26 (m, 1 H), 7.31-7.40 (m, 1 H), 7.45 (d, J=8.08 Hz, 1 H), 7.73 (d, J=8.08 Hz, 1 H). ESI-MS: m/z 503.1 (M+H)$^+$.

Example 24

Preparation of 1-ethyl-3-(3-(2-(isopropylsulfonylmethyl)-4-oxo-1,3,8-triazaspiro[4.5]dec-1-enecarbonyl)benzo[b]thiophen-2-yl)urea TFA salt (24)

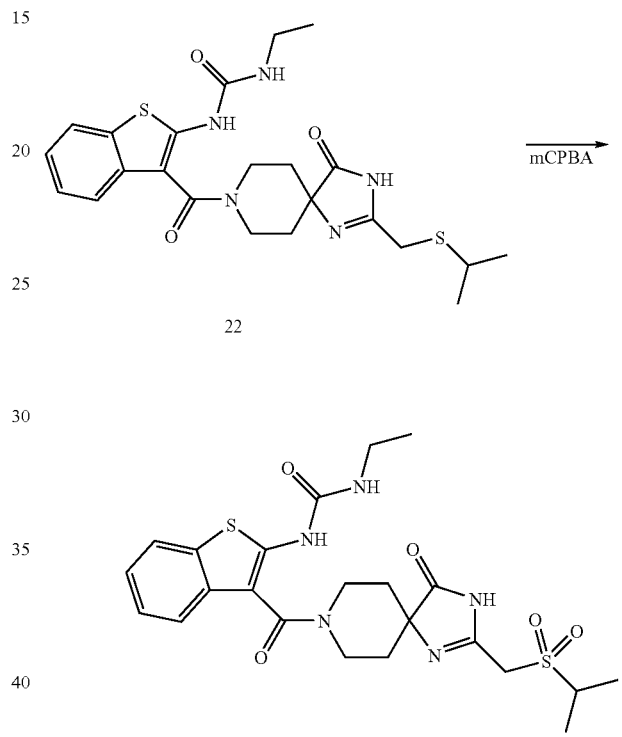

To a solution of 1-ethyl-3-(3-(2-(isopropylthiomethyl)-4-oxo-1,3,8-triazaspiro[4.5]dec-1-enecarbonyl)benzo[b]thiophen-2-yl)urea TFA salt (22 (Example 22), 10 mg, 1.0 equivalent) in CH$_2$Cl$_2$ at 0° C., mCPBA (2.0 equivalents) was added to obtain the sulfone crude product after 1 hr. The crude product mixture was filtered and the residue was purified by LCMS to afford the title compound (24, 45%). Two rotamers were observed (ratio 1:1).

First rotamer: $^1$H NMR (400 MHz, MeOD) δ ppm, 1.15 (td, J=6.63, 1.89 Hz, 3 H), 1.38-1.44 (m, 6 H), 1.58 (br. s., 2 H), 1.94 (br. s, 2 H), 3.22-3.29 (m, 4 H), 3.43-3.51 (m, 1H), 3.53-3.65 (m, 1 H), 4.14 (br. s., 2 H), 7.19-7.27 (m, 1 H), 7.36 (q, J=8.34 Hz, 1 H), 7.55 (d, J=8.08 Hz, 1 H), 7.73 (d, J=8.08 Hz, 1 H). ESI-MS: m/z 519.1 (M+H)$^+$.

Second rotamer: $^1$H NMR (400 MHz, MeOD) δ ppm, 1.15 (td, J=6.63, 1.89 Hz, 3 H), 1.38-1.44 (m, 6 H), 1.58 (br. s., 2 H), 1.94 (br. s., 2 H), 3.22-3.29 (m, 4 H), 3.43-3.51 (m, 1H), 3.53-3.65 (m, 1 H), 4.14 (br. s., 2 H), 7.19-7.27 (m, 1 H), 7.36 (q, J=8.34 Hz, 1 H), 7.45 (d, J=8.08 Hz, 1 H), 7.73 (d, J=8.08 Hz, 1 H). ESI-MS: m/z 519.1 (M+H)$^+$.

Example 25

Preparation of 1-ethyl-3-(3-(2-((2-methoxyphenoxy)methyl)-4-oxo-1,3,8-triazaspiro[4.5]dec-1-enecarbonyl)benzo[b]thiophen-2-yl)urea TFA salt (25)

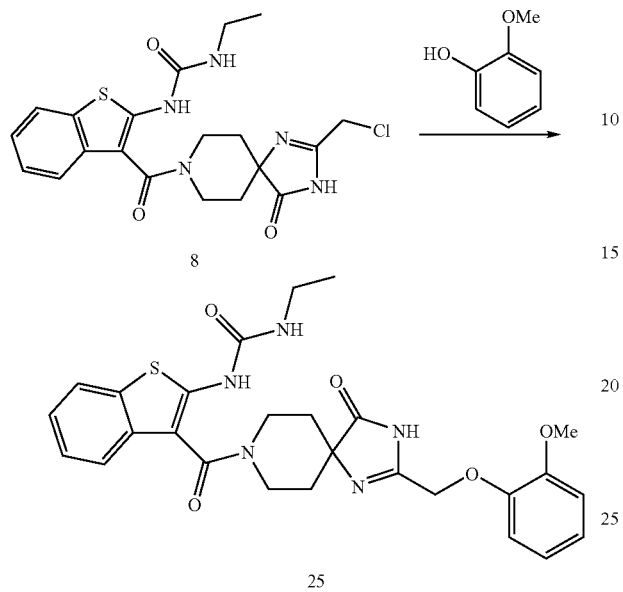

To a solution of 1-(3-(2-(chloromethyl)-4-oxo-1,3,8-triazaspiro[4.5]dec-1-enecarbonyl)benzo[b]thiophen-2-yl)-3-ethylurea (8 (Example 8), 25 mg, 1.0 equivalent) in MeOH (0.045 M) was added $K_2CO_3$ (4.0 equivalents), and 2-methoxyphenol (4.0 equivalents). The mixture was heated to 63° C. for 8 hrs and then partitioned between ethyl acetate and water and the separated organics was washed with brine and dried over $Na_2SO_4$, filtered, and concentrated under reduced pressure. The residue was purified by preparatory LCMS to afford 25 (50%). Two rotamers were observed (ratio 1:1).

First rotamer: $^1$H NMR (400 MHz, MeOD) δ ppm, 1.12-1.21 (m, 3 H), 1.68 (br. s., 2H), 1.93 (br. s., 2 H), 3.26 (q, 2H), 3.56-3.68 (m, 2 H), 3.85 (d, J=4.04 Hz, 3 H), 4.09 (br. s., 2H), 4.98 (dd, 2 H), 7.00-7.10 (m, 3 H), 7.18-7.26 (m, 1 H), 7.30-7.40 (m, 1 H), 7.54 (d, J=7.58 Hz, 1 H), 7.73 (d, J=7.83 Hz, 1 H). ESI-MS: m/z 535.21 (M+H)$^+$.

Second rotamer: $^1$H NMR (400 MHz, MeOD) δ ppm, 1.12-1.21 (m, 3 H), 1.68 (br. s., 2 H), 1.93 (br. s., 2 H), 3.26 (q, 2 H), 3.56-3.68 (m, 2 H), 3.85 (d, J=4.04 Hz, 3 H), 4.09 (br. s., 2 H), 4.98 (dd, 2 H), 7.00-7.10 (m, 3 H), 7.18-7.26 (m, 1 H), 7.30-7.40 (m, 1 H), 7.45 (d, J=7.83 Hz, 1 H), 7.73 (d, J=7.83 Hz, 1 H); ESI-MS: m/z 535.21 (M+H)$^+$.

Example 26

Preparation of 1-(3-(2-((2-cyanophenoxy)methyl)-4-oxo-1,3,8-triazaspiro[4.5]dec-1-enecarbonyl)benzo[b]thiophen-2-yl)-3-ethylurea TFA salt (26)

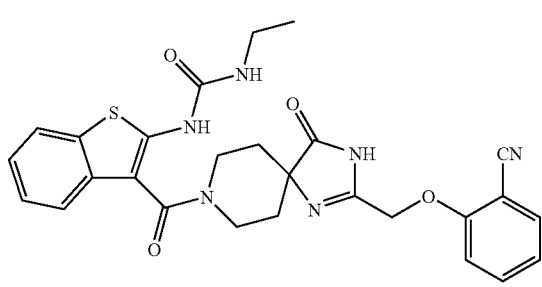

The title compound was prepared by a procedure analogous to Example 25 except that 2-hydroxybenzonitrile was used. $^1$H NMR (400 MHz, MeOD) δ ppm 1.12-1.22 (m, 3 H), 1.94 (br. s., 2 H), 2.13 (br. s., 2 H), 3.22-3.29 (m, 4 H), 3.91 (br. s., 2 H), 4.06 (br. s., 2 H), 7.23 (t, J=7.20 Hz, 1 H), 7.32-7.41 (m, 2 H), 7.52 (q, 2 H), 7.67 (t, J=7.83 Hz, 1 H), 7.74 (d, J=7.83 Hz, 1 H), 7.97 (t, J=6.95 Hz, 1 H). ESI-MS: m/z 530.1 (M+H)$^+$.

Example 27

Preparation of 2-((8-(2-(3-ethylureido)benzo[b]thiophene-3-carbonyl)-4-oxo-1,3,8-triazaspiro[4.5]dec-1-en-2-yl)methoxy)benzamide TFA salt (27)

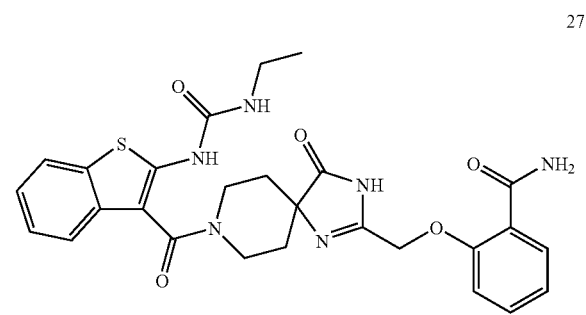

The title compound was prepared by a procedure analogous to Example 25 except that 2-hydroxybenzamide was used. Two rotamers were observed (ratio 3:2).

First rotamer: $^1$H NMR (400 MHz, MeOD) δ ppm, 1.12-1.22 (m, 3 H), 1.54 (br. s., 2H), 1.93 (br. s., 2 H), 3.23-3.29 (m, 2 H), 3.51-3.63 (m, 2 H), 4.06 (br. s., 2 H), 5.15 (s, 2 H), 7.12 (t, J=7.58 Hz, 1 H), 7.18 (d, J=8.34 Hz, 1 H), 7.20-7.26 (m, 1 H), 7.37 (td, J=7.64, 4.67 Hz, 1 H), 7.46-7.54 (m, 2 H), 7.73 (d, J=8.08 Hz, 1 H), 7.87 (dd, J=13.39, 7.83 Hz, 1 H). ESI-MS: m/z 548.1 (M+H)$^+$.

Second rotamer: $^1$H NMR (400 MHz, MeOD) δ ppm, 1.12-1.22 (m, 3 H), 1.54 (br. s., 2 H), 1.93 (br. s., 2 H), 3.23-3.29 (m, 2 H), 3.51-3.63 (m, 2 H), 4.06 (br. s., 2 H), 5.13 (s, 2H), 7.12 (t, J=7.58 Hz, 1 H), 7.18 (d, J=8.34 Hz, 1 H), 7.20-7.26 (m, 1 H), 7.37 (td, J=7.64, 4.67 Hz, 1 H), 7.50-7.54 (m, 1 H), 7.56 (d, J=8.08 Hz, 1 H), 7.73 (d, J=8.08 Hz, 1 H), 7.87 (dd, J=13.39, 7.83 Hz, 1 H). ESI-MS: m/z 548.1 (M+H)$^+$.

Example 28

Preparation of 1-(3-(2-(cyclohexyloxymethyl)-4-oxo-1,3,8-triazaspiro[4.5]dec-1-enecarbonyl)benzo[b]thiophen-2-yl)-3-ethylurea TFA salt (28)

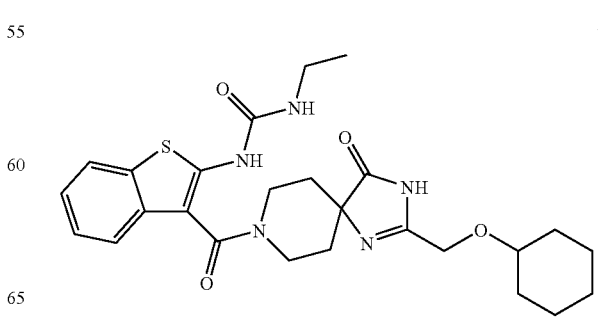

The title compound was prepared by a procedure analogous to Example 25 except cyclohexanol was used. Two rotamers were observed (ratio 3:2).

First rotamer: $^1$H NMR (400 MHz, CHLOROFORM-d) δ ppm, first rotamer: 1.18-1.36 (m, 3 H), 1.49-1.61 (m, 4 H), 1.66-1.80 (m, 4 H), 1.91 (d, J=2.78 Hz, 4 H), 3.12-3.27 (m, 2 H), 3.33-3.42 (m, 1 H), 3.56-3.70 (m, 4 H), 4.13 (br. s., 2 H), 4.37 (s, 2 H), 5.82 (br. s., 1H), 7.21 (q, J=7.33 Hz, 1 H), 7.26-7.38 (m, 1 H), 7.40 (d, J=8.08 Hz, 1 H), 7.72 (d, J=8.08 Hz, 1 H), 8.68 (s, 1 H), 9.42 (br. s., 1 H). ESI-MS: m/z 511.2 (M+H)$^+$.

Second rotamer: $^1$H NMR (400 MHz, MeOD) δ ppm, 1.18-1.36 (m, 3 H), 1.49-1.61 (m, 4 H), 1.66-1.80 (m, 4 H), 1.91 (d, J=2.78 Hz, 4 H), 3.12-3.27 (m, 2 H), 3.33-3.42 (m, 1H), 3.56-3.70 (m, 4 H), 4.13 (br. s., 2 H), 4.34 (s, 2 H), 5.73 (br. s., 1 H), 7.21 (q, J=7.33 Hz, 1H), 7.26-7.38 (m, 1 H), 7.51 (d, J=8.08 Hz, 1 H), 7.72 (d, J=8.08 Hz, 1 H), 8.59 (s, 1 H), 9.33 (br. s., 1 H). ESI-MS: m/z 511.2 (M+H)$^+$.

Example 29

Preparation of 1-ethyl-3-(3-(2-(isopropoxymethyl)-4-oxo-1,3,8-triazaspiro[4.5]dec-1-enecarbonyl)benzo[b]thiophen-2-yl)urea TFA salt (29)

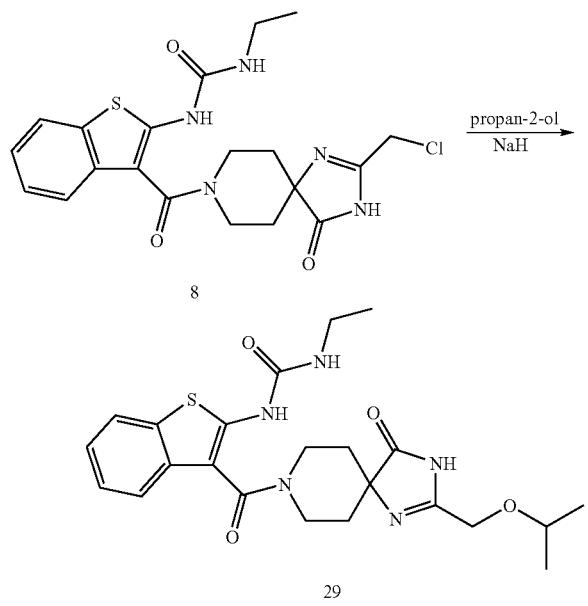

To a 60% dispersion NaH (15.0 equivalent), isopropanol (0.02 M) was added at room temperature and stirred for 10 minutes, and then 1-(3-(2-(chloromethyl)-4-oxo-1,3,8-triazaspiro[4.5]dec-1-enecarbonyl)benzo[b]thiophen-2-yl)-3-ethylurea (8 (Example 8), 10 mg, 1.0 equivalent) in isopropanol (0.2 M) was added. The mixture was heated to 50° C. for 4 hrs and quenched with water, and the residue was purified by LCMS to afford Compound 29 (60%). Two rotamers were observed (ratio 1:1).

First rotamer: $^1$H NMR (400 MHz, DMSO-d$_6$) δ ppm, 1.09 (td, J=7.14, 4.67 Hz, 3 H), 1.14 (dd, J=6.06, 3.54 Hz, 6 H), 1.51 (br. s., 2 H), 1.73 (br. s., 2 H), 3.11-3.20 (m, 2 H), 3.48 (br. s., 4 H), 3.68 (dd, J=11.75, 5.94 Hz, 1 H), 4.30 (s, 2 H), 7.17-7.23 (m, 1 H), 7.30-7.36 (m, 1 H), 7.46 (d, J=8.08 Hz, 1 H), 7.81 (d, J=8.08 Hz, 1 H), 9.35 (s, 1 H). ESI-MS: m/z 471.1 (M+H)$^+$.

Second rotamer: $^1$H NMR (400 MHz, DMSO-d$_6$) δ ppm, 1.09 (td, J=7.14, 4.67 Hz, 3H), 1.14 (dd, J=6.06, 3.54 Hz, 6 H), 1.51 (br. s., 2 H), 1.73 (br. s., 2 H), 3.11-3.20 (m, 2 H), 3.48 (br. s., 4 H), 3.68 (dd, J=11.75, 5.94 Hz, 1 H), 4.27 (s, 2 H), 7.17-7.23 (m, 1 H), 7.30-7.36 (m, 1 H), 7.41 (d, J=8.08 Hz, 1 H), 7.81 (d, J=8.08 Hz, 1 H), 9.25 (s, 1 H). ESI-MS: m/z 471.1 (M+H)$^+$.

Example 30

Preparation of 1-ethyl-3-(3-(2-(isobutoxymethyl)-4-oxo-1,3,8-triazaspiro[4.5]dec-1-enecarbonyl)benzo[b]thiophen-2-yl)urea TFA salt (30)

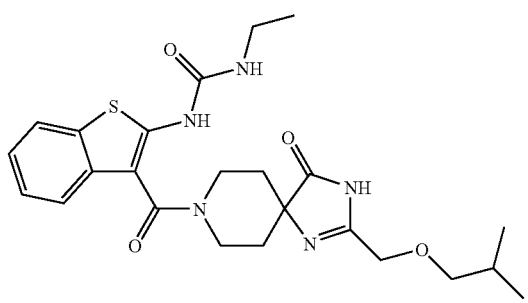

The title compound was prepared by a procedure analogous to Example 29 except isobutanol was used. Two rotamers were observed (ratio 1:1).

First rotamer: $^1$H NMR (400 MHz, DMSO-d$_6$) δ ppm, 0.82-0.90 (m, 6 H), 1.09 (td, J=7.20, 4.55 Hz, 3 H), 1.51 (br. s., 2 H), 1.72 (br. s., 2 H), 1.79-1.88 (m, 1 H), 3.10-3.20 (m, 2H), 3.25 (dd, J=6.44, 3.92 Hz, 2 H), 3.38-3.48 (m, 2 H), 3.48-3.57 (m, 2 H), 4.31 (s, 2 H), 7.16-7.23 (m, 1 H), 7.29-7.38 (m, 1 H), 7.46 (d, J=8.08 Hz, 1 H), 7.81 (d, J=7.83 Hz, 1 H), 9.36 (s, 1 H). ESI-MS: m/z 485.2 (M+H)$^+$.

Second rotamer: $^1$H NMR (400 MHz, DMSO-d$_6$) δ ppm, 0.82-0.90 (m, 6 H), 1.09 (td, J=7.20, 4.55 Hz, 3 H), 1.51 (br. s., 2 H), 1.72 (br. s., 2 H), 1.79-1.88 (m, 1 H), 3.10-3.20 (m, 2 H), 3.25 (dd, J=6.44, 3.92 Hz, 2 H), 3.38-3.48 (m, 2 H), 3.48-3.57 (m, 2 H), 4.28 (s, 2H), 7.16-7.23 (m, 1 H), 7.29-7.38 (m, 1 H), 7.41 (d, J=8.08 Hz, 1 H), 7.81 (d, J=7.83 Hz, 1 H), 9.25 (s, 1 H). ESI-MS: m/z 485.2 (M+H)$^+$.

Example 31

Preparation of 1-ethyl-3-(3-(2-(isobutoxymethyl)-4-oxo-1,3,8-triazaspiro[4.5]dec-1-enecarbonyl)-7-methoxybenzo[b]thiophen-2-yl)urea TFA salt (31)

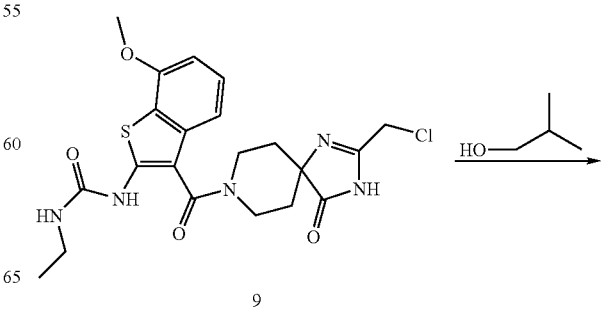

-continued

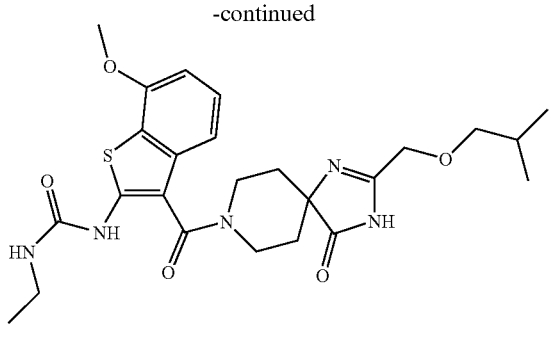

31

The title compound was prepared by coupling isobutanol to 1-(3-(2-(chloromethyl)-4-oxo-1,3,8-triazaspiro[4.5]dec-1-enecarbonyl)-7-methoxybenzo[b]thiophen-2-yl)-3-ethylurea (9, Example 9) by a procedure analogous to Example 29. Two rotamers were observed (ratio 1:1)

First rotamer: $^1$H NMR (400 MHz, DMSO-d$_6$) δ ppm, 0.81-0.94 (m, 6 H) 1.08 (m, J=7.14, 4.93 Hz, 3 H) 1.44 (br. s., 2 H) 1.70 (br. s., 2 H) 1.76-1.89 (m, 2 H) 2.46-2.57 (m, 2 H) 3.09-3.20 (m, 2 H) 3.23 (m, 2 H) 3.92 (s, 3 H) 4.23 (s, 1 H) 6.75-6.84 (m, 1 H) 6.99-7.15 (m, 1 H) 7.22-7.38 (m, 1 H) 9.21 (s, 1 H) 9.33 (s, 1 H). ESI-MS: m/z 516.4 (M+H)$^+$.

Second rotamer: $^1$H NMR (400 MHz, DMSO-d$_6$) δ ppm, 0.81-0.94 (m, 6 H) 1.08 (td, J=7.14, 4.93 Hz, 3 H) 1.44 (br. s., 2 H) 1.70 (br. s., 2 H) 1.76-1.89 (m, 2 H) 2.46-2.57 (m, 2 H) 3.09-3.20 (m, 2 H) 3.23 (m, 2 H) 3.92 (s, 3 H) 4.23 (s, 1 H) 6.75-6.84 (m, 1 H) 6.99-7.15 (m, 1 H) 7.22-7.38 (m, 1 H) 9.21 (s, 1 H), 9.33 (s, 1 H). ESI-MS: m/z 516.4 (M+H)$^+$.

Example 32

Preparation of 1-(3-(2-(cyclohexyloxymethyl)-4-oxo-1,3,8-triazaspiro[4.5]dec-1-enecarbonyl)-7-methoxybenzo[b]thiophen-2-yl)-3-ethylurea TFA salt (32)

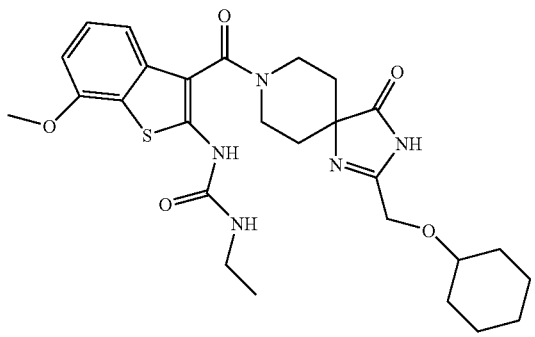

32

The title compound was prepared according to the procedure of Example 31 except that cyclohexanol was used. Two rotamers were observed (ratio 1:1)

First rotamer: $^1$H NMR (400 MHz, MeOD) δ ppm first rotamer: 1.14-1.22 (m, 3 H) 1.24-1.45 (m, 2 H) 1.50-1.69 (m, 4 H) 1.72-1.81 (m, 3 H) 1.86-2.01 (m, 4 H) 3.10-3.15 (m, 1 H) 3.39-3.45 (m, 2 H) 3.46-3.49 (m, 1 H) 3.54-3.72 (m, 3 H) 4.39 (s, 3 H) 4.42 (s, 3 H) 6.76-6.83 (m, 1 H) 7.15 (d, J=8 Hz, 1 H) 7.31 (s, 1 H). ESI-MS: m/z 542.1 (M+H)$^+$.

Second rotamer: $^1$H NMR (400 MHz, MeOD) δ ppm 1.14-1.22 (m, 3 H) 1.24-1.45 (m, 2 H) 1.50-1.69 (m, 4 H) 1.72-1.81 (m, 3 H) 1.86-2.01 (m, 4 H) 3.10-3.15 (m, 0 H) 3.39-3.45 (m, 2 H) 3.46-3.49 (m, 0 H) 3.54-3.72 (m, 3 H) 4.39 (s, 3 H) 4.42 (s, 3 H) 6.76-6.83 (m, 1 H) 7.08 (d, J=8 Hz, 1 H) 7.31 (s, 1 H). ESI-MS: m/z 542.1 (M+H)$^+$.

Example 33

Preparation of 1-ethyl-3-(3-(4-oxo-2-((2-oxopyridin-1(2 H)-yl)methyl)-1,3,8-triazaspiro[4.5]dec-1-enecarbonyl)benzo[b]thiophen-2-yl)urea TFA salt (33)

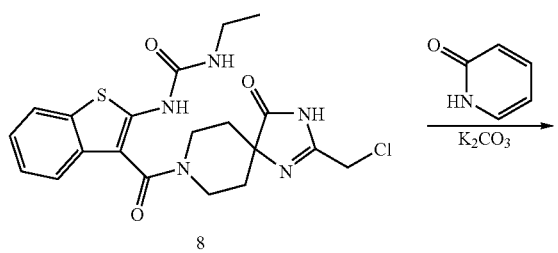

8

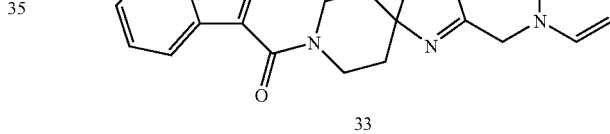

33

To a solution of 1-(3-(2-(chloromethyl)-4-oxo-1,3,8-triazaspiro[4.5]dec-1-enecarbonyl)benzo[b]thiophen-2-yl)-3-ethylurea (8, (Example 8), 40 mg, 1.0 equivalent) in MeOH (0.045 M) was added K$_2$CO$_3$ (4.0 equivalents), and 2-methoxyphenol (4.0 equivalents). The mixture was heated to 63° C. for 8 hrs and then partitioned between ethyl acetate and water and the separated organics was washed with brine and dried over Na$_2$SO$_4$, filtered, and concentrated under reduced pressure. The residue was purified by preparatory LCMS to afford 31 (50%). Two rotamers were observed (ratio 3:2).

First rotamer: $^1$H NMR (400 MHz, MeOD) δ ppm, 1.13-1.23 (m, 3 H), 1.62 (br. s., 2H), 1.93 (br. s., 2 H), 3.20-3.29 (m, 4 H), 3.51-3.64 (m, 2 H), 4.05 (br. s., 2 H), 6.40-6.48 (m, 1 H), 6.58 (dd, J=8.84, 5.31 Hz, 1 H), 7.22 (q, 1 H), 7.34 (q, 1 H), 7.42 (d, J=7.33 Hz, 1 H), 7.56-7.63 (m, 1 H), 7.68 (td, J=6.95, 2.02 Hz, 1 H), 7.73 (d, J=8.08 Hz, 1 H). ESI-MS: m/z 506.1 (M+H)$^+$.

Second rotamer: $^1$H NMR (400 MHz, MeOD) δ ppm, 1.13-1.23 (m, 3 H), 1.62 (br. s., 2 H), 1.93 (br. s., 2 H), 3.20-3.29 (m, 4 H), 3.51-3.64 (m, 2 H), 4.05 (br. s., 2 H), 6.40-6.48 (m, 1 H), 6.58 (dd, J=8.84, 5.31 Hz, 1 H), 7.22 (q, 1 H), 7.34 (q, 1 H), 7.53 (d, J=8.08 Hz, 1 H), 7.56-7.63 (m, 1 H), 7.68 (td, J=6.95, 2.02 Hz, 1 H), 7.73 (d, J=8.08 Hz, 1 H). ESI-MS: m/z 506.1 (M+H)$^+$.

Example 34

Preparation of 1-(3-(2-((4-(aminomethyl)-1H-1,2,3-triazol-1-yl)methyl)-4-oxo-1,3,8-triazaspiro[4.5]dec-1-enecarbonyl)benzo[b]thiophen-2-yl)-3-ethylurea TFA salt (34)

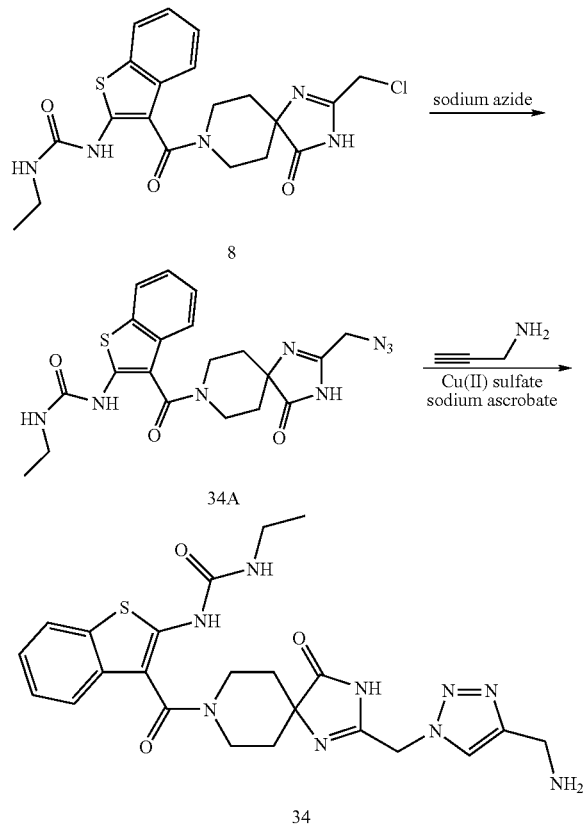

A solution of 1-(3-(2-(chloromethyl)-4-oxo-1,3,8-triazaspiro[4.5]dec-1-enecarbonyl)benzo[b]thiophen-2-yl)-3-ethylurea (8 (Example 8), 25 mg, 1.0 equivalent) in DMF (0.11 M) was added sodium azide (10.0 equivalents) and stirred for 30 min at room temperature. Then the mixture was partitioned between ethyl acetate and water, and the separated organics was washed with brine and dried over Na$_2$SO$_4$, filtered, and concentrated under reduced pressure to afford 1-(3-(2-(azidomethyl)-4-oxo-1,3,8-triazaspiro[4.5]dec-1-enecarbonyl)benzo[b]thiophen-2-yl)-3-ethylurea (34A) in quantitative yield.

A solution of 34A (1.0 equivalent) in THF (0.11 M) and water (0.11 M) was added prop-2-yn-1-amine (10.0 equivalents), sodium ascorbate (0.5 equivalent) pre-dissolved in water (0.22), and copper sulfate pentahydrate (0.2 equivalent) pre-dissolved in water (0.09 M), and the mixture was stirred at room temperature until the reaction was complete as determined by LCMS analysis. The mixture was then partitioned between ethyl acetate and water. Organic layers were washed and brine, dried over Na$_2$SO$_4$, and volatiles removed under reduced pressure. The residue was purified by LCMS to afford 1-(3-(2-((4-(aminomethyl)-1H-1,2,3-triazol-1-yl)methyl)-4-oxo-1,3,8-triazaspiro[4.5]dec-1-enecarbonyl)benzo[b]thiophen-2-yl)-3-ethylurea (23, 34%). Two rotamers were observed (ratio 3:2).

First rotamer: $^1$H NMR (400 MHz, DMSO-d$_6$) δ ppm, 1.07 (dd, J=7.83, 6.06 Hz, 3H), 1.44 (br. s., 2 H), 1.70 (br. s., 2 H), 3.10-3.20 (m, 2 H), 3.28-3.40 (m, 2 H), 3.74 (br. s., 2H), 4.18 (dd, 2 H), 5.53 (s, 2 H), 7.15 (br. s., 1 H), 7.16-7.23 (m, 1 H), 7.25-7.48 (m, 3 H), 7.81 (d, J=7.83 Hz, 1 H), 8.21 (d, J=3.03 Hz, 1 H), 8.32 (br. s., 2 H), 9.36 (s, 1 H). ESI-MS: m/z 509.2 (M+H)$^+$.

Second rotamer: $^1$H NMR (400 MHz, DMSO-d$_6$) δ ppm, 1.07 (dd, J=7.83, 6.06 Hz, 3H), 1.44 (br. s., 2 H), 1.70 (br. s, 2 H), 3.10-3.20 (m, 2 H), 3.28-3.40 (m, 2 H), 3.74 (br. s., 2H), 4.18 (dd, 2 H), 5.53 (s, 2 H), 7.03 (br. s., 1 H), 7.16-7.23 (m, 1 H), 7.25-7.48 (m, 3 H), 7.81 (d, J=7.83 Hz, 1 H), 8.21 (d, J=3.03 Hz, 1 H), 8.32 (br. s., 2 H), 9.26 (s, 1 H). ESI-MS: m/z 509.2 (M+H)$^+$.

Example 35

Preparation of 1-(3-(2-((4-((dimethylamino)methyl)-1H-1,2,3-triazol-1-yl)methyl)-4-oxo-1,3,8-triazaspiro[4.5]dec-1-enecarbonyl)benzo[b]thiophen-2-yl)-3-ethylurea TFA salt (35)

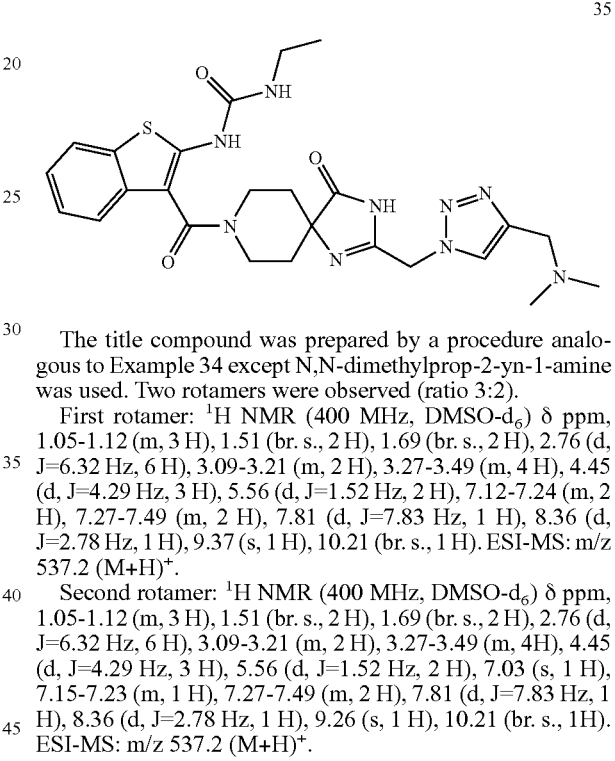

The title compound was prepared by a procedure analogous to Example 34 except N,N-dimethylprop-2-yn-1-amine was used. Two rotamers were observed (ratio 3:2).

First rotamer: $^1$H NMR (400 MHz, DMSO-d$_6$) δ ppm, 1.05-1.12 (m, 3 H), 1.51 (br. s., 2 H), 1.69 (br. s., 2 H), 2.76 (d, J=6.32 Hz, 6 H), 3.09-3.21 (m, 2 H), 3.27-3.49 (m, 4 H), 4.45 (d, J=4.29 Hz, 3 H), 5.56 (d, J=1.52 Hz, 2 H), 7.12-7.24 (m, 2 H), 7.27-7.49 (m, 2 H), 7.81 (d, J=7.83 Hz, 1 H), 8.36 (d, J=2.78 Hz, 1 H), 9.37 (s, 1 H), 10.21 (br. s., 1 H). ESI-MS: m/z 537.2 (M+H)$^+$.

Second rotamer: $^1$H NMR (400 MHz, DMSO-d$_6$) δ ppm, 1.05-1.12 (m, 3 H), 1.51 (br. s., 2 H), 1.69 (br. s., 2 H), 2.76 (d, J=6.32 Hz, 6 H), 3.09-3.21 (m, 2 H), 3.27-3.49 (m, 4 H), 4.45 (d, J=4.29 Hz, 3 H), 5.56 (d, J=1.52 Hz, 2 H), 7.03 (s, 1 H), 7.15-7.23 (m, 1 H), 7.27-7.49 (m, 2 H), 7.81 (d, J=7.83 Hz, 1 H), 8.36 (d, J=2.78 Hz, 1 H), 9.26 (s, 1 H), 10.21 (br. s., 1H). ESI-MS: m/z 537.2 (M+H)$^+$.

Example 36

Preparation of 1-(3-(2-((4-tert-butyl-1H-1,2,3-triazol-1-yl)methyl)-4-oxo-1,3,8-triazaspiro[4.5]dec-1-enecarbonyl)benzo[b]thiophen-2-yl)-3-ethylurea TFA salt (36)

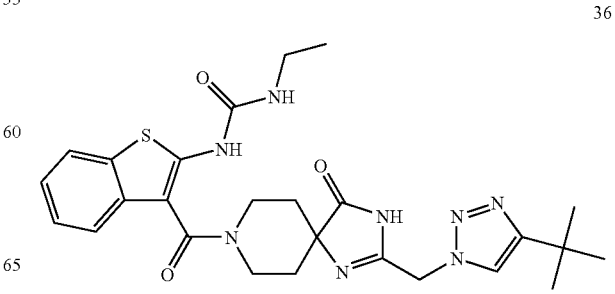

The title compound was prepared by a procedure analogous to Example 34 except 3,3-dimethylbut-1-yne was used. ¹H NMR (400 MHz, DMSO-d₆) δ ppm 1.07 (td, J=7.14, 5.43 Hz, 3H), 1.28 (d, J=2.02 Hz, 9 H), 1.50 (br. s., 2 H), 1.68 (br. s., 2 H), 2.29-2.34 (m, 1 H) 2.64-2.68 (m, 1 H), 3.15 (dd, J=9.09, 3.28 Hz, 2 H), 3.41-3.46 (m, 2H), 5.36 (br. s., 2 H), 7.14-7.21 (m, 2H), 7.28-7.47 (m, 3 H), 7.79 (d, J=8.08 Hz, 1 H), 7.89 (d, J=1.52 Hz, 1 H), 9.34 (m, 1 H). ESI-MS: m/z 536.2 (M+H)⁺.

Example 37

Preparation of 1-ethyl-3-(3-(2-((4-(hydroxymethyl)-1 H-1,2,3-triazol-1-yl)methyl)-4-oxo-1,3,8-triazaspiro[4.5]dec-1-enecarbonyl)benzo[b]thiophen-2-yl)urea TFA salt (37)

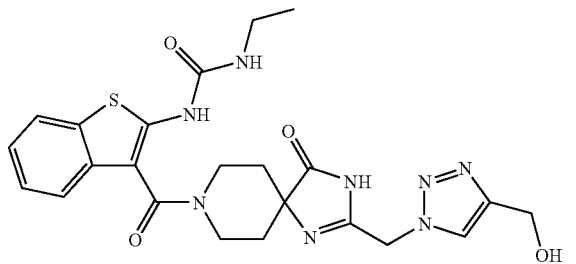

The title compound was prepared by a procedure analogous to Example 34 except prop-2-yn-1-ol was used. Two rotamers were observed (ratio 1:1).

First rotamer: ¹H NMR (400 MHz, DMSO-d₆) δ ppm, 1.08 (td, J=7.20, 5.56 Hz, 3 H), 1.40-1.53 (m, 2 H), 1.68 (br. s., 2 H), 3.15 (ddd, J=7.20, 4.93, 4.80 Hz, 2 H), 3.29-3.40 (m, 2H), 3.40-3.51 (m, 2 H), 4.54 (d, J=2.53 Hz, 2 H), 5.44 (s, 2 H), 7.09 (t, J=5.81 Hz, 1 H), 7.19 (td, J=7.26, 4.17 Hz, 1 H), 7.29-7.37 (m, 2 H), 7.43 (dd, J=15.79, 7.96 Hz, 1 H), 7.80 (d, J=7.83 Hz, 1 H), 8.02 (d, J=1.52 Hz, 1 H), 9.35 (s, 1 H). ESI-MS: m/z 510.1 (M+H)⁺.

Second rotamer: ¹H NMR (400 MHz, DMSO-d₆) δ ppm, 1.08 (td, J=7.20, 5.56 Hz, 3H), 1.40-1.53 (m, 2 H), 1.68 (br. s., 2 H), 3.15 (ddd, J=7.20, 4.93, 4.80 Hz, 2 H), 3.29-3.40 (m, 2 H), 3.40-3.51 (m, 2 H), 4.54 (d, J=2.53 Hz, 2 H), 5.44 (s, 2 H), 7.09 (t, J=5.81 Hz, 1 H), 7.19 (td, J=7.26, 4.17 Hz, 1 H), 7.29-7.37 (m, 2 H), 7.43 (dd, J=15.79, 7.96 Hz, 1 H), 7.80 (d, J=7.83 Hz, 1 H), 8.02 (d, J=1.52 Hz, 1 H), 9.19 (s, 1 H). ESI-MS: m/z 510.1 (M+H)⁺.

Example 38

Preparation of 1-(3-(2-((4-cyclopropyl-1 H-1,2,3-triazol-1-yl)methyl)-4-oxo-1,3,8-triazaspiro[4.5]dec-1-enecarbonyl)benzo[b]thiophen-2-yl)-3-ethylurea TFA salt (Compound 38)

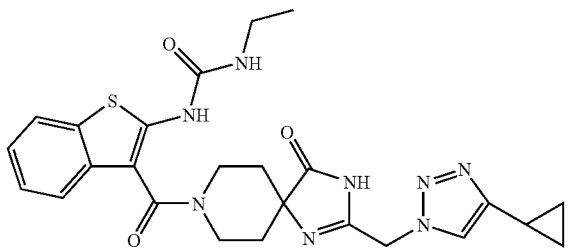

The title compound was prepared by a procedure analogous to Example 34 except ethynylcyclopropane was used. Two rotamers were observed (ratio 1:1).

First rotamer: ¹H NMR (400 MHz, DMSO-d₆) δ ppm, 0.68-0.76 (m, 2 H), 0.86-0.95 (m, 2 H), 1.02-1.12 (m, 3 H), 1.47 (br. s., 2 H), 1.68 (br. s., 2 H), 1.96 (br. s., 1 H), 3.15 (br. s., 2 H), 3.29-3.47 (m, 4 H), 5.37 (s, 2 H), 7.08 (br. s., 1 H), 7.15-7.23 (m, 1 H), 7.28-7.38 (m, 1 H), 7.38-7.47 (m, 1 H), 7.80 (d, J=7.58 Hz, 1 H), 7.87 (d, J=2.78 Hz, 1 H), 9.35 (s, 1 H). ESI-MS: m/z 520.2 (M+H)⁺.

Second rotamer: 0.68-0.76 (m, 2 H), 0.86-0.95 (m, 2 H), 1.02-1.12 (m, 3 H), 1.47 (br. s., 2 H), 1.68 (br. s., 2 H), 1.96 (br. s., 1 H), 3.15 (br. s., 2 H), 3.29-3.47 (m, 4 H), 5.37 (s, 2H), 7.08 (br. s., 1 H), 7.15-7.23 (m, 1 H), 7.28-7.38 (m, 1 H), 7.38-7.47 (m, 1 H), 7.80 (d, J=7.58 Hz, 1 H), 7.87 (d, J=2.78 Hz, 1 H), 9.20 (s, 1 H). ESI-MS: m/z 520.2 (M+H)⁺.

The above reaction schemes, and variations thereof, can be used to prepare the following:

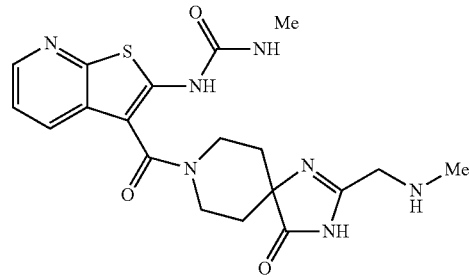

1-methyl-3-(3-(2-((methylamino)methyl)-4-oxo-1,3,8-triazaspiro[4.5]dec-1-enecarbonyl)thieno[2,3-b]pyridin-2-yl)urea

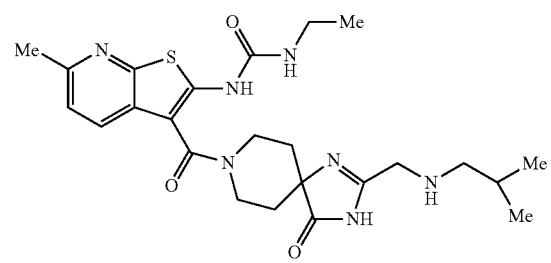

1-ethyl-3-(3-(2-((isobutylamino)methyl)-4-oxo-1,3,8-triazaspiro[4.5]dec-1-enecarbonyl)-6-methylthieno[2,3-b]pyridin-2-yl)urea

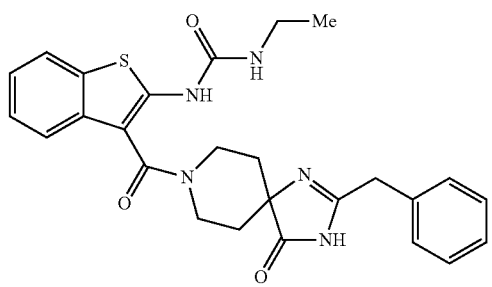

1-(3-(2-benzyl-4-oxo-1,3,8-triazaspiro[4.5]dec-1-enecarbonyl)benzo[b]thiophen-2-yl)-3-ethylurea

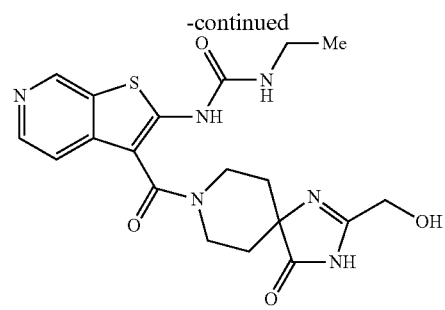

1-ethyl-3-(3-(2-(hydroxymethyl)-4-oxo-1,3,8-triazaspiro[4.5]dec-1-enecarbonyl)thieno[2,3-c]pyridin-2-yl)urea

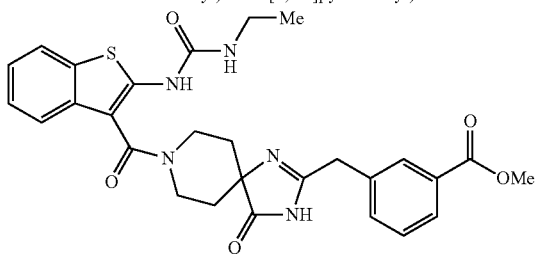

methyl 3-((8-(2-(3-ethylureido)benzo[b]thiophene-3-carbonyl)-4-oxo-1,3,8-triazaspiro[4.5]dec-1-en-2-yl)methyl)benzoate

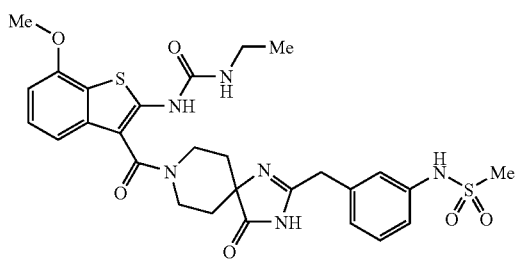

N-(3-((8-(2-(3-ethylureido)-7-methoxybenzo[b]thiophene-3-carbonyl)-4-oxo-1,3,8-triazaspiro[4.5]dec-1-en-2-yl)methyl)phenyl)methanesulfonamide

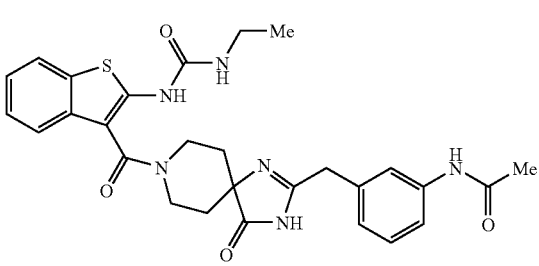

N-(3-((8-2-(3-ethylureido)benzo[b]thiophene-3-carbonyl)-4-oxo-1,3,8-triazaspiro[4.5]dec-1-en-2-yl)methyl)phenyl)acetamide

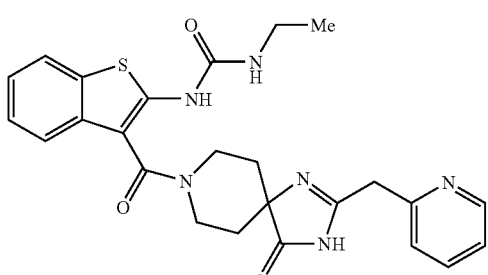

1-ethyl-3-(3-(4-oxo-2-(pyridin-2-ylmethyl)-1,3,8-triazaspiro[4.5]dec-1-enecarbonyl)benzo[b]thiophen-2-yl)urea

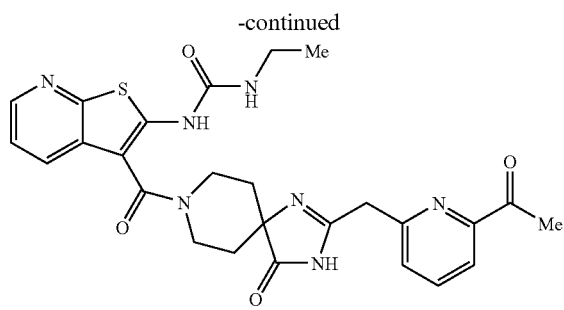

1-(3-(2-((6-acetylpridin-2-yl)methyl)-4-oxo-1,3,8-triazasprio[4.5]dec-1-enecarbonyl)thieno[2,3-b]pyridin-2-yl)-3-ethylurea

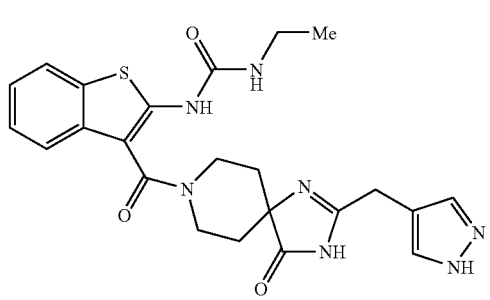

1-(3-(2-((1H-pyrazol-4-yl)methyl)-4-oxo-1,3,8-triazaspiro[4.5]dec-1-enecarbonyl)benzo[b]thiophen-2-yl)-3-ethylurea

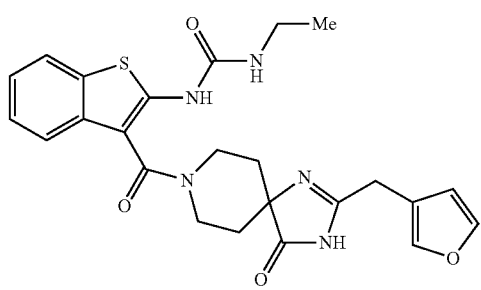

1-ethyl-3-(3-(2-(furan-3-ylmethyl)-4-oxo-1,3,8-triazaspiro[4.5]dec-1-enecarbonyl)benzo[b]thiophen-2-yl)urea

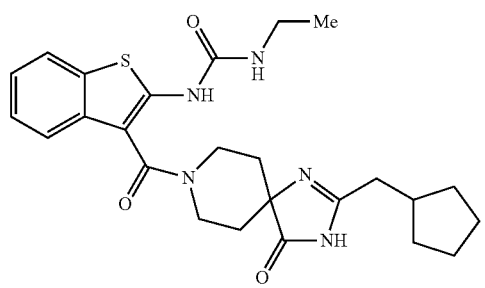

1-(3-(2-(cyclopentylmethyl)-4-oxo-1,3,8-triazaspiro[4.5]dec-1-enecarbonyl)benzo[b]thiophen-2-yl)-3-ethylurea

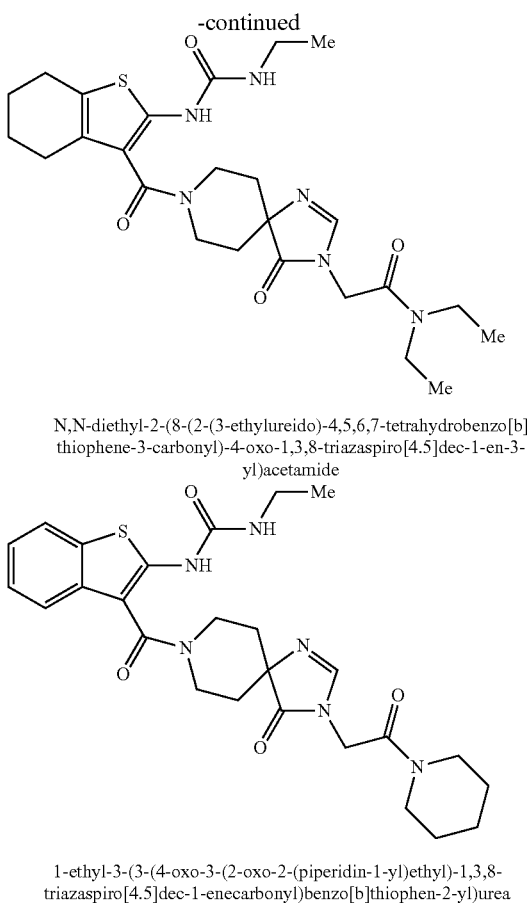

N,N-diethyl-2-(8-(2-(3-ethylureido)-4,5,6,7-tetrahydrobenzo[b]thiophene-3-carbonyl)-4-oxo-1,3,8-triazaspiro[4.5]dec-1-en-3-yl)acetamide 1-ethyl-3-(3-(4-oxo-3-(2-oxo-2-(piperidin-1-yl)ethyl)-1,3,8-triazaspiro[4.5]dec-1-enecarbonyl)benzo[b]thiophen-2-yl)urea Example A Enzyme Binding Assay for Hsp90 Inhibitors A. Purification of Human ACC1

Human ACC1 cDNA was amplified from human liver cDNA by polymerase chain reaction using primers; 5'AAAAGTCGACCCACCATGGATGAACCT-TCTCCCTTGGCCC3' (SEQ ID NO: 1) and 5'AAAAGCG-GCCGCCTACGTAGAAGGGGAGTCCATAGTG3' (SEQ ID NO: 2). The amplified DNA fragment was digested by restriction enzyme SalI and NotI, and cloned into pFAST-BacHTc (Invitrogen). This plasmid DNA was used for preparation of recombinant vaculovirus with BAC-TO-BAC Baculovirus Expression System (Invitrogen).

SF-9 cells were infected with the vaculovirus and cultured at 27° C. for 3 days. Harvested cells were homogenized in buffer A (25 mM HEPES (pH7.5), 130 mM NaCl, 1 mM EDTA, 25 mM sodium glycerophosphate, 1 mM sodium orthovanadate, 10% glycerol, complete protease inhibitor), and subjected to ultracentrifuge at 185700×g for 50 min at 4° C. ACC1 protein with 6×His-tag at the N-terminal was purified from the supernatant using Ni-NTA Super Flow Gel (QIAGEN). Eluted protein was dialysed against buffer B (50 mM HEPES (pH 7.5), 300 mM NaCl, 10 mM MgCl$_2$, 10 mM tripotassium citrate, 2 mM dithiothreitol) and concentrated using Vivaspin20 ultrafiltration tube (Sartorius).

B. Purification of Human ACC2

Human ACC2 cDNA except coding region for mitochondria localization sequence was amplified from human skeletal muscle cDNA by polymerase chain reaction using primers; 5'CCAGGTCGACCCGCCAACGGGACTGGGA-CACAAGG3' (SEQ ID NO: 3) and 5'CGCACTCT-CAGTTTCCCGGATTCCC3' (SEQ ID NO: 4). The amplified DNA fragment was digested by SalI and AflIII, and cloned into pFAST-BacHTa (Invitrogen). Preparation of recombinant vaculovirus, infection of the virus to SF-9 cells and purification of recombinant ACC2 protein with 6×His-tag at the N-terminal were performed in the same method as described above.

C. Measurement of ACC Activity

Malachite green solution was prepared by mixing 100 mL of solution A (0.12% malachite green in 5N H$_2$SO$_4$), 25 mL of solution B (7.5% ammonium molybdate) and 2 mL of solution C (11% TWEEN-20).

ACC1 was diluted to 8 µg/mL in reaction buffer (50 mM HEPES pH7.5, 10 mM MgCl$_2$, 10 mM tripotassium citrate, 2 mM DTT, 0.75 mg/mL fatty acid free BSA) and 10 µL diluted enzyme solution was pored into each well of 384-well clear bottom plate. Test compound was diluted in the reaction buffer and 5 µL of the compound solution was added into each well, and the mixture was incubated at 30° C. for 60 minutes. Reaction was initiated by addition of 5 µL substrate solution (50 mM KHCO$_3$, 200 µM ATP, 200 µM acetyl-CoA). After incubation at 30° C. for 20 minutes, reaction was terminated by addition of 5 µL malachite green solution and absorbance at 620 nm was measured.

ACC2 was diluted to 6.4 µg/mL in reaction buffer, and the activity was measured by the same method as described for ACC1.

Percent activity at each concentration of compound was calculated from the following equation:

$$\frac{Abs_{(enzyme+inhibitor)} - AvgAbs_{(no\ enzyme)}}{AvgAbs_{(no\ inhibitor)} - AvgAbs_{(no\ enzyme)}} \times 100$$

where Abs is absorbance, Avg is average.

Data were subjected to nonlinear regression analysis using GraphPad Prism Software (GraphPad Software Inc.) to obtain IC$_{50}$ values. Enzymatic activities of selected compounds are reported in TABLE 1.

TABLE 1

| Compound | ACC1 (µM) | ACC2 (µM) |
|---|---|---|
| 3 | 1-10 | 1-10 |
| 4 | >10 | 1-10 |
| 5 | >10 | >10 |
| 6 | >10 | >10 |
| 7 | >10 | >10 |
| 8 | >10 | 1-10 |
| 9 | 1-10 | 1-10 |
| 10 | 1-10 | 1-10 |
| 11 | <1 | <1 |
| 12 | 1-10 | 1-10 |
| 13 | 1-10 | <1 |
| 14 | >10 | >10 |
| 15 | 1-10 | <1 |
| 16 | 1-10 | <1 |
| 17 | <1 | <1 |
| 18 | 1-10 | <1 |
| 19 | >10 | 1-10 |
| 20 | >10 | 1-10 |
| 21 | 1-10 | 1-10 |
| 22 | 1-10 | <1 |
| 23 | >10 | <1 |
| 24 | 1-10 | <1 |

TABLE 1-continued

| Compound | ACC1 (μM) | ACC2 (μM) |
|---|---|---|
| 25 | 1-10 | <1 |
| 26 | >10 | <1 |
| 27 | >10 | <1 |
| 28 | 1-10 | <1 |
| 29 | 1-10 | 1-10 |
| 30 | 1-10 | <1 |
| 31 | <1 | <1 |
| 32 | <1 | <1 |

TABLE 1-continued

| Compound | ACC1 (μM) | ACC2 (μM) |
|---|---|---|
| 33 | >10 | 1-10 |
| 34 | >10 | >10 |
| 35 | >10 | 1-10 |
| 36 | 1-10 | <1 |
| 37 | >10 | 1-10 |
| 38 | 1-10 | <1 |

What is claimed is:
1. A compound consisting of the formula:

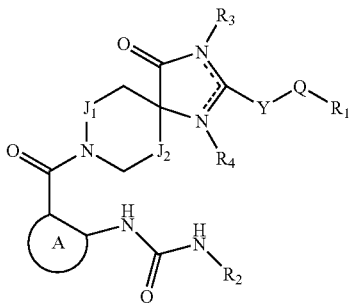

or a tautomer, or pharmaceutically acceptable salt thereof, wherein $J_1$ and $J_2$ are each $(CH_2)$—;

Y is selected from the group consisting of a bond, —$CH_2$—, —$(CH_2)_2$—, —NH—$CH_2$—, and —$CH_2$—NH—;

Q is selected from the group consisting of a bond, —C(O)—, —C(O)O—, —NH—, —O—, —S—, —S(O)—, and —S(O)$_2$—;

A is selected from the group consisting of five or six membered, substituted or unsubstituted aryl and heteroaryl, where the substituents on adjacent ring atoms of the aryl or heteroaryl may be taken together to form a five or six membered, substituted or unsubstituted, saturated, unsaturated or aromatic ring;

$R_1$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, $(C_{3-12})$cycloalkyloxy, hetero$(C_{3-12})$cycloalkyloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl, and hetero$(C_{4-12})$bicycloaryl, each substituted or unsubstituted;

$R_2$ is substituted or unsubstituted alkyl;

$R_3$ and $R_4$ are each independently selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl, and hetero$(C_{4-12})$bicycloaryl, each substituted or unsubstituted, and provided that one of $R_3$ and $R_4$ is absent, and where $R_3$ is absent, the nitrogen on which $R_3$ is drawn is part of a double bond, and where $R_4$ is absent, the nitrogen on which $R_4$ is drawn is part of a double bond.

2. The compound according to claim 1 consisting of the formula:

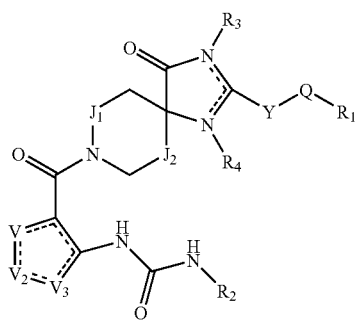

wherein the ring comprising $V_1$, $V_2$ and $V_3$ is selected from the group of substituted or unsubstituted aryl and substituted or unsubstituted heteroaryl;

$V_1$ is $CR_{11}$, $NR_{11}$, N, O, or S;
$V_2$ is $CR_{12}$, $NR_{12}$, N, O, or S;
$V_3$ is $CR_{13}$, $NR_{13}$, N, O, or S;

wherein $R_{11}$, $R_{12}$ and $R_{13}$ are each independently selected from the group consisting of H, $(C_{1-6})$alkoxy, $(C_{4-6})$aryloxy, hetero$(C_{1-5})$aryloxy, carbonyl, oxycarbonyl, aminocarbonyl, amino, $(C_{1-6})$alkylamino, sulfonamido, imino, sulfonyl, sulfinyl, $(C_{1-6})$alkyl, halo$(C_{1-6})$alkyl, hydroxy$(C_{1-6})$alkyl, carbonyl$(C_{1-6})$alkyl, thiocarbonyl$(C_{1-6})$alkyl, sulfonyl$(C_{1-6})$alkyl, sulfinyl$(C_{1-6})$alkyl, aza$(C_{1-6})$alkyl, $(C_{1-6})$oxaalkyl, $(C_{3-6})$cycloalkyl$(C_{1-5})$alkyl, hetero$(C_{1-5})$cycloalkyl$(C_{1-6})$alkyl, $(C_{4-6})$aryl$(C_{1-6})$alkyl, hetero$(C_{1-5})$aryl$(C_{1-5})$alkyl, hetero$(C_{1-6})$alkyl, $(C_{3-6})$cycloalkyl, hetero$(C_{1-5})$cycloalkyl, $(C_{4-6})$aryl, and hetero$(C_{1-5})$aryl, each substituted or unsubstituted; or $R_{11}$ and $R_{12}$, or $R_{12}$ and $R_{13}$, are taken together to form a ring selected from the group consisting of substituted or unsubstituted $(C_{3-6})$cycloalkyl, substituted or unsubstituted hetero$(C_{1-5})$cycloalkyl, substituted or unsubstituted $(C_{4-6})$aryl and substituted or unsubstituted hetero$(C_{1-5})$aryl.

3. The compound according to claim 2 consisting of the formula:

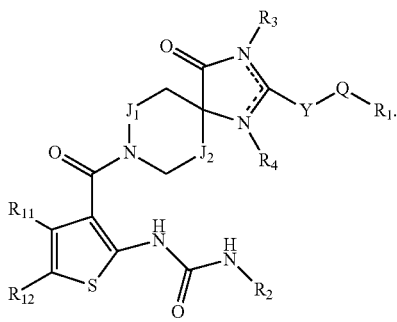

4. The compound according to claim 2 consisting of the formula:

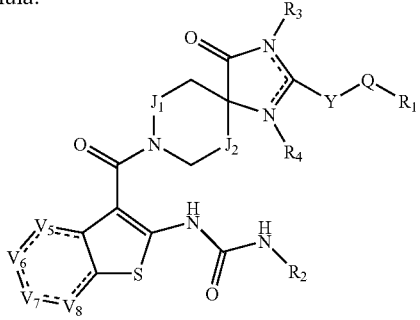

wherein
 $V_5$ is $CR_{15}R_{15'}$, $NR_{15'}$, O, or S,
 $V_6$ is $CR_{16}R_{16'}$, $NR_{16'}$, O, or S,
 $V_7$ is $CR_{17}R_{17'}$, $NR_{17'}$, O, or S,
 $V_8$ is $CR_{18}R_{18'}$, $NR_{18'}$, O, or S,
  where
   $R_{15}$, $R_{15'}$, $R_{16}$, $R_{16'}$, $R_{17}$, $R_{17'}$, $R_{18}$ and $R_{18'}$ are each independently selected from the group consisting of H, hydroxy, $(C_{1-6})$alkoxy, $(C_{4-6})$aryloxy, and hetero$(C_{1-5})$aryloxy, amino, $(C_{1-6})$alkyl, halo$(C_{1-6})$alkyl, hydroxy$(C_{1-6})$alkyl, aza$(C_{1-6})$alkyl, $(C_{1-6})$oxaalkyl, $(C_{3-6})$cycloalkyl$(C_{1-6})$alkyl, hetero$(C_{1-5})$cycloalkyl$(C_{1-6})$alkyl, $(C_{4-6})$aryl$(C_{1-6})$alkyl, and hetero$(C_{1-5})$aryl$(C_{1-6})$alkyl, each substituted or unsubstituted, or $R_{15'}$, $R_{16'}$, $R_{17'}$, and $R_{18'}$ are each independently absent when the atom to which it is bound forms part of a double bond.

5. The compound according to claim 4 consisting of the formula:

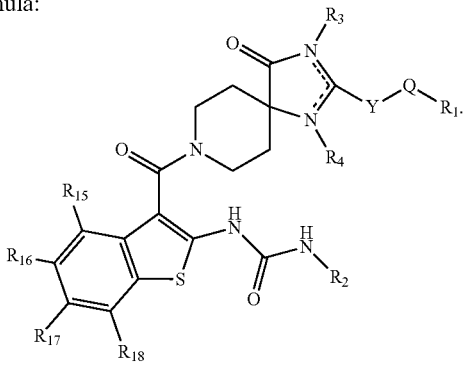

6. The compound according to claim 1 consisting of the formula:

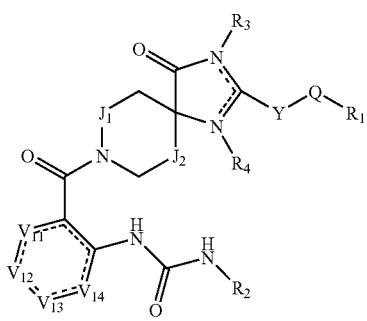

wherein
 the ring comprising $V_{11}$, $V_{12}$, $V_{13}$ and $V_{14}$ is selected from the group of substituted or unsubstituted aryl and substituted or unsubstituted heteroaryl, where
 $V_{11}$ is $CR_{21}$ or N,
 $V_{12}$ is $CR_{22}$ or N,
 $V_{13}$ is $CR_{23}$ or N,
 $V_{14}$ is $CR_{24}$ or N,
  wherein
   $R_{21}$, $R_{22}$, $R_{23}$ and $R_{24}$ are each independently selected from the group consisting of H, hydroxyl, $(C_{1-6})$alkoxy, $(C_{4-6})$aryloxy, hetero$(C_{1-5})$aryloxy, carbonyl, oxycarbonyl, aminocarbonyl, amino, $(C_{1-6})$alkylamino, sulfonamido, imino, sulfonyl, sulfinyl, $(C_{1-6})$alkyl, halo$(C_{1-6})$alkyl, hydroxy$(C_{1-6})$alkyl, carbonyl$(C_{1-6})$alkyl, thiocarbonyl$(C_{1-6})$alkyl, sulfonyl$(C_{1-6})$alkyl, sulfinyl$(C_{1-6})$alkyl, aza$(C_{1-6})$alkyl, $(C_{1-6})$oxaalkyl, $(C_{3-6})$cycloalkyl$(C_{1-6})$alkyl, hetero$(C_{1-5})$cycloalkyl$(C_{1-6})$alkyl, $(C_{4-6})$aryl$(C_{1-6})$alkyl, hetero$(C_{1-5})$aryl$(C_{1-6})$alkyl, hetero$(C_{1-6})$alkyl, $(C_{3-6})$cycloalkyl, hetero$(C_{1-5})$cycloalkyl, $(C_{4-6})$aryl, and hetero$(C_{1-5})$aryl, each substituted or unsubstituted; or $R_{21}$ and $R_{22}$, or $R_{22}$ and $R_{23}$, or $R_{23}$ and $R_{24}$, are taken together to form a ring selected from the group consisting of substituted or unsubstituted $(C_{3-6})$cycloalkyl, substituted or unsubstituted hetero$(C_{1-5})$cycloalkyl, substituted or unsubstituted $(C_{4-6})$aryl and substituted or unsubstituted hetero$(C_{1-5})$aryl.

7. The compound according to claim 6 consisting of the formula:

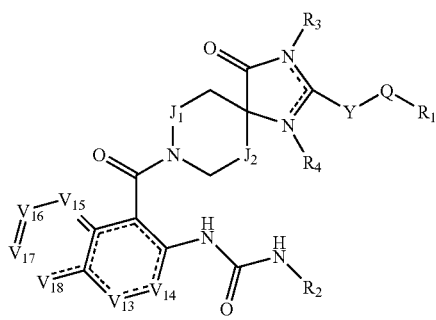

wherein
 $V_{13}$ is $CR_{23}$ or N,
 $V_{14}$ is $CR_{24}$ or N,
 $V_{15}$ is $CR_{25}R_{25'}$, $NR_{25'}$, O, or S,
 $V_{16}$ is $CR_{26}R_{26'}$, $NR_{26'}$, O, or S,
 $V_{17}$ is $CR_{27}R_{27'}$, $NR_{27'}$, O, or S,
 $V_{18}$ is $CR_{28}R_{28'}$, $NR_{28'}$, O, or S,
  where
   $R_{23}$, $R_{24}$, $R_{25}$, $R_{25'}$, $R_{26}$, $R_{26'}$, $R_{27}$, $R_{27'}$, $R_{28}$ and $R_{28'}$ are each independently selected from the group consisting of H, hydroxy, $(C_{1-6})$alkoxy, $(C_{4-6})$aryloxy, hetero$(C_{1-5})$aryloxy, amino, $(C_{1-6})$alkyl, halo$(C_{1-6})$alkyl, hydroxy$(C_{1-6})$alkyl, aza$(C_{1-6})$alkyl, $(C_{1-6})$oxaalkyl, $(C_{3-6})$cycloalkyl$(C_{1-6})$alkyl, hetero$(C_{1-5})$cycloalkyl$(C_{1-6})$alkyl, $(C_{4-6})$aryl$(C_{1-6})$alkyl, and hetero$(C_{1-5})$aryl$(C_{1-6})$alkyl, each substituted or unsubstituted; or $R_{25'}$, $R_{26'}$, $R_{27'}$, and $R_{28'}$ are each independently absent when the atom to which it is bound forms part of a double bond.

8. The compound according to claim 6 consisting of the formula:

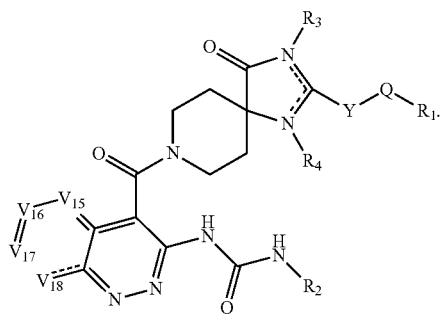

9. The compound according to claim 6 consisting of the formula:

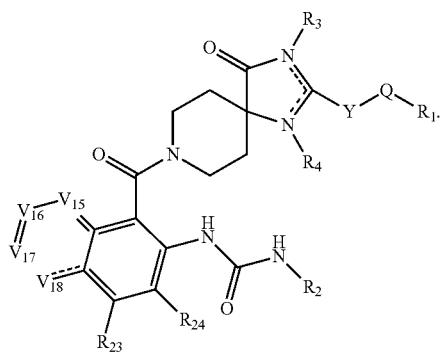

10. The compound according to claim 6 consisting of the formula:

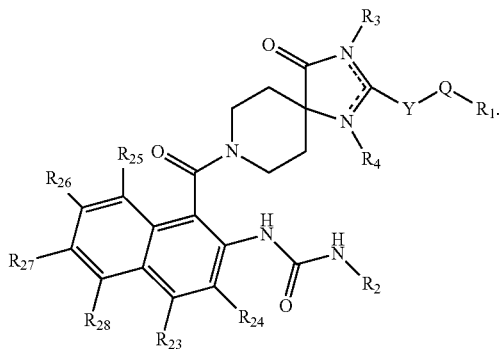

11. The compound according to claim 6 consisting of the formula:

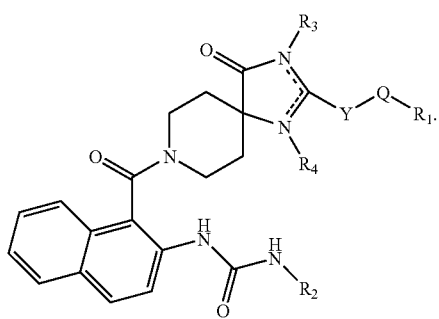

12. The compound according to claim 1, wherein $R_1$ is selected from the group consisting of hydrogen, halo, cyano, hydroxyl, $(C_{1-6})$alkoxy, $(C_{4-12})$aryloxy, hetero$(C_{4-12})$aryloxy, $(C_{3-12})$cycloalkyloxy, hetero$(C_{3-12})$cycloalkyloxy, amino, $(C_{1-6})$alkylamino, $(C_{1-6})$alkyl, halo$(C_{1-6})$alkyl, $(C_{3-12})$cycloalkyl, hetero$(C_{3-12})$cycloalkyl, $(C_{4-12})$aryl, and hetero$(C_{1-10})$aryl, each substituted or unsubstituted.

13. The compound according to claim 1, wherein $R_1$ is selected from the group consisting of hydrogen, hydroxyl, and halo.

14. The compound according to claim 1, wherein $R_1$ is $(C_{1-6})$alkyl, substituted or unsubstituted.

15. The compound according to claim 1, wherein $R_1$ is selected from the group consisting of aryl and heteroaryl, each unsubstituted or substituted with one or more substituents independently selected from the group consisting of halo, cyano, oxo, hydroxyl, methoxy, tertbutyl, cyclopropyl, —C(O)CH$_3$, —C(O)NH$_2$, —C(O)OCH$_3$, —CH$_2$NH$_2$, —CH$_2$N(CH$_3$)$_2$, —CH$_2$OH, —NHC(O)CH$_3$, and —NHS(O)$_2$CH$_3$.

16. The compound according to claim 15, wherein the aryl or heteroaryl is selected from the group consisting of phenyl, pyridinyl, pyrazolyl, furanyl, and triazolyl, each unsubstituted or substituted with said one or more substituents.

17. The compound according to claim 1, wherein $R_1$ is unsubstituted or substituted $(C_{1-6})$cycloalkyl or hetero$(C_{1-6})$cycloalkyl.

18. The compound according to claim 17, wherein $R_1$ is unsubstituted or substituted cyclopentyl, cyclohexyl, piperidinyl, and pyrrolidinyl.

19. The compound according to claim 1, wherein $R_1$ is —NR$_{29}$R$_{30}$, where R$_{29}$ and R$_{30}$ are each independently selected from the group consisting of hydrogen, $(C_{1-6})$alkyl, $(C_{4-6})$aryl, hetero$(C_{1-5})$aryl, $(C_{3-6})$alicyclic, and hetero$(C_{1-5})$alicyclic.

20. The compound according to claim 1, wherein —Y-Q-R$_1$ is selected from the group consisting of hydrogen, —CH$_2$NH$_2$, —CH$_2$NHCH$_3$, —CH$_2$NHC(O)CH$_3$, —CH$_2$Cl, —CH$_2$NHCH$_2$CH(CH$_3$)$_2$, —CH$_2$OH, —N(CH$_2$CH$_3$)$_2$, —CH$_2$SCH$_3$, —CH$_2$S(O)$_2$CH$_3$, —(CH$_2$)$_2$C(O)OCH$_2$CH$_3$, —(CH$_2$)$_2$C(O)N(CH$_2$CH$_3$)$_2$, —CH$_2$SCH(CH$_3$)$_2$, —CH$_2$S(O)CH(CH$_3$)$_2$, —CH$_2$S(O)$_2$CH(CH$_3$)$_2$, —CH$_2$OCH$_2$CH(CH$_3$)$_2$, —(CH$_2$)$_3$CH$_3$, —CH$_2$C(O)OCH$_3$, —CH(CH$_3$)$_2$,

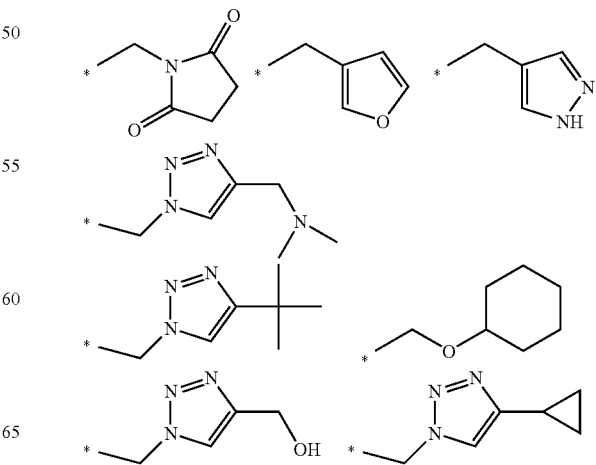

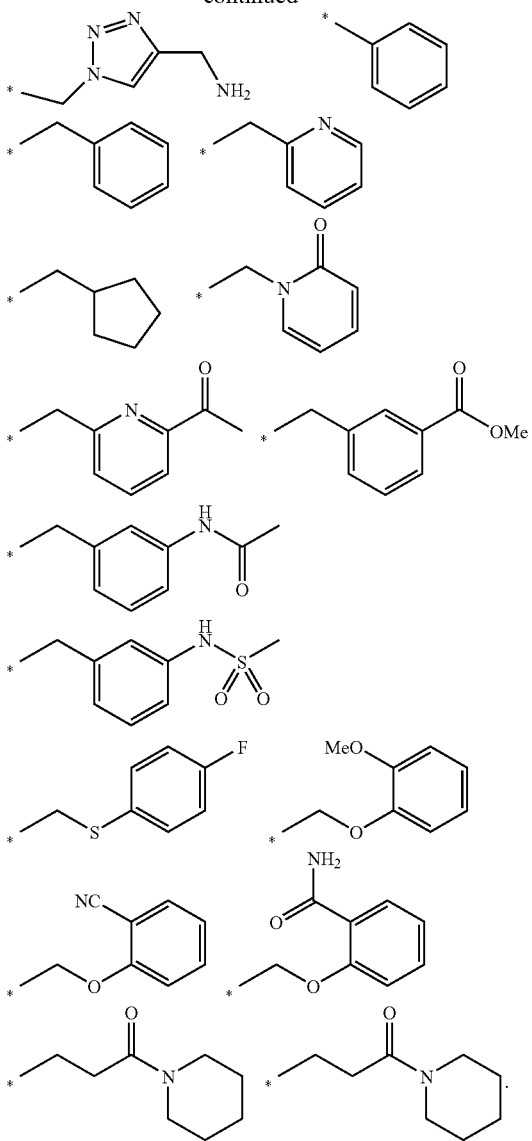

21. The compound according to claim 20, wherein —Y-Q-R₁ is selected from the group consisting of —(CH₂)₂C(O)OCH₂CH₃, —CH₂OCH₂CH(CH₃)₂, —(CH₂)₃CH₃, —(CH₂)₂C(O)NH₂, —(CH₂)₂C(O)N(CH₂CH₃)₂, —(CH₂)C(O)N(CH₂CH₃)₂, and

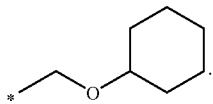

22. The compound according to claim 1, wherein R₂ is substituted or unsubstituted (C₁₋₆)alkyl.

23. The compound according to claim 1, wherein R₃ and R₄ are each independently selected from the group consisting of hydrogen, (C₁₋₆)alkyl, (C₁₋₆)azaalkyl, and (C₁₋₆)oxaalkyl, each substituted or unsubstituted, provided that one of R₃ and R₄ is absent, and where R₃ is absent, the nitrogen on which R₃ is drawn is part of a double bond, and where R₄ is absent, the nitrogen on which R₄ is drawn is part of a double bond.

24. The compound according to claim 23, wherein R₃ or R₄ are each independently selected from the group consisting of hydrogen, —CH₂C(O)N(CH₂CH₃)₂, —CH₂C(O)OCH₃, n-butyl, and —CH₂C(O)-piperidin-1-yl.

25. The compound according to claim 4, wherein

R₁₅, R₁₆, R₁₇, and R₁₈, when present, are each independently selected from the group consisting of H, (C₁₋₁₀)alkoxy, (C₁₋₁₀)alkyl, halo(C₁₋₁₀)alkyl, hydroxy(C₁₋₁₀)alkyl, aza(C₁₋₁₀)alkyl, and (C₁₋₁₀)oxaalkyl, each substituted or unsubstituted; and R₁₅', R₁₆', R₁₇', and R₁₈', when present, are each independently selected from the group consisting of H, (C₁₋₁₀)alkoxy, (C₁₋₁₀)alkyl, halo(C₁₋₁₀)alkyl, hydroxy(C₁₋₁₀)alkyl, aza(C₁₋₁₀)alkyl, (C₁₋₁₀)oxaalkyl, each substituted or unsubstituted, or R₁₅', R₁₆', R₁₇', and R₁₈' are each independently absent when the atom to which it is bound forms part of a double bond.

26. The compound according to claim 4, wherein R₁₈ is selected from the group consisting of H, (C₁₋₆)alkyl and (C₁₋₆)alkoxy; and each of R₁₅, R₁₆, and R₁₇ is H.

27. The compound according to claim 7, wherein

R₂₃, R₂₄, R₂₅, R₂₆, R₂₇, and R₂₈, when present, are each independently selected from the group consisting of H, (C₁₋₆)alkoxy, (C₁₋₆)alkyl, halo(C₁₋₆)alkyl, hydroxy(C₁₋₆)alkyl, aza(C₁₋₆)alkyl, and (C₁₋₆)oxaalkyl, each substituted or unsubstituted; and R₂₅', R₂₆', R₂₇', and R₂₈', when present, are each independently selected from the group consisting of H, (C₁₋₆)alkoxy, (C₁₋₆)alkyl, halo(C₁₋₆)alkyl, hydroxy(C₁₋₆)alkyl, aza(C₁₋₆)alkyl, and (C₁₋₆)oxaalkyl, each substituted or unsubstituted, or R₂₅', R₂₆', R₂₇', and R₂₈' are each independently absent when the atom to which it is drawn forms part of a double bond.

28. A compound consisting of the formula:

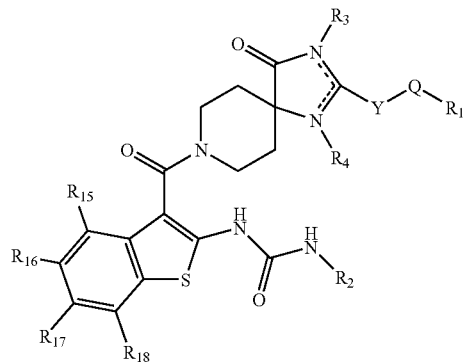

wherein

Q is selected from the group consisting of a bond, —C(O)—, —C(O)O—, —NH—, —O—, —S—, —S(O)—, and —S(O)₂—;

Y is selected from the group consisting of a bond, —CH₂—, —(CH₂)₂—, —NH—CH₂—, and —CH₂—NH—;

R₁ is selected from the group consisting of hydrogen, halo, cyano, hydroxyl, (C₁₋₆)alkoxy, (C₄₋₆)aryloxy, hetero(C₁₋₅)aryloxy, (C₃₋₆)cycloalkyloxy, hetero(C₁₋₅)cycloalkyloxy, amino, (C₁₋₆)alkylamino, (C₁₋₆)alkyl, halo(C₁₋₆)alkyl, (C₃₋₆)cycloalkyl, hetero(C₁₋₅)cycloalkyl, (C₄₋₆)aryl, and hetero(C₁₋₅)aryl, each substituted or unsubstituted;

R₂ is substituted or unsubstituted (C₁₋₄)alkyl;

R₃ and R₄ are each independently selected from the group consisting of hydrogen, (C$_{1-6}$)alkyl, (C$_{1-6}$) azaalkyl, and (C$_{1-6}$)oxaalkyl, each substituted or unsubstituted, provided that one of R₃ and R₄ is absent, and where R₃ is absent, the nitrogen on which R₃ is drawn is part of a double bond, and where R₄ is absent, the nitrogen on which R₄ is drawn is part of a double bond; and R$_{15}$, R$_{16}$, R$_{17}$ and R$_{18}$ are each independently selected from the group consisting of H, (C$_{1-6}$)alkoxy, (C$_{1-6}$) alkyl, halo (C$_{1-6}$)alkyl, hydroxy(C$_{1-6}$)alkyl, aza(C$_{1-6}$) alkyl, and (C$_{1-6}$)oxaalkyl, each substituted or unsubstituted.

29. The compound according to claim 28, wherein —(Y-Q-R₁) is selected from the group consisting of hydrogen, —CH₂NH₂, —CH₂NHCH₃, —CH₂NHC(O)CH₃, —CH₂Cl, —CH₂NHCH₂CH(CH₃)₂, —CH₂OH, —N(CH₂CH₃)₂, —CH₂SCH₃, —CH₂S(O)₂CH₃, —(CH₂)₂C(O)OCH₂CH₃, —(CH₂)₂C(O)N(CH₂CH₃)₂, —CH₂SCH(CH₃)₂, —CH₂S(O)CH(CH₃)₂, —CH₂S(O)₂CH(CH₃)₂, —CH₂OCH₂CH(CH₃)₂, —(CH₂)₃CH₃, —CH₂C(O)OCH₃, —CH(CH₃)₂,

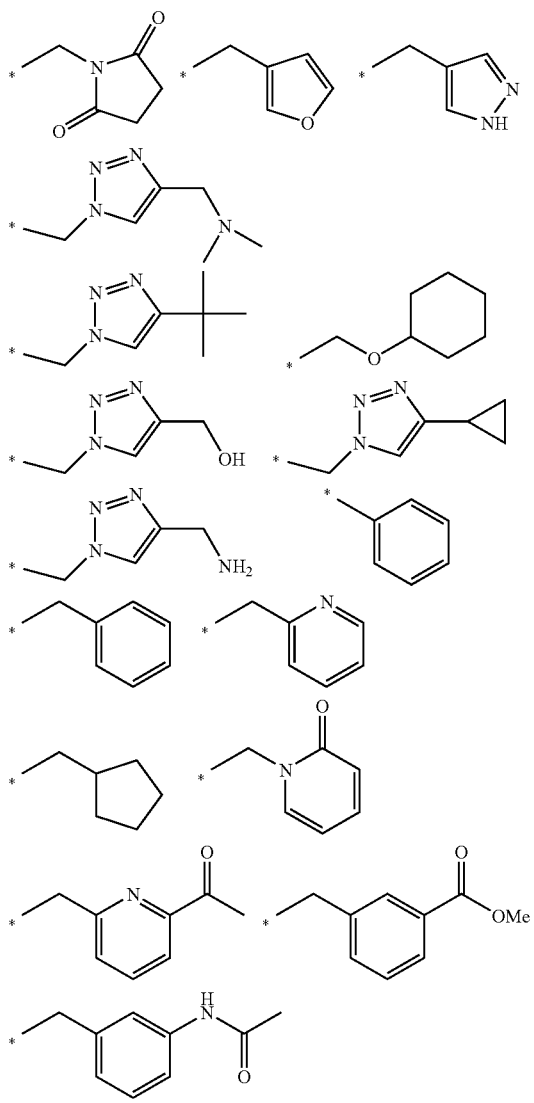

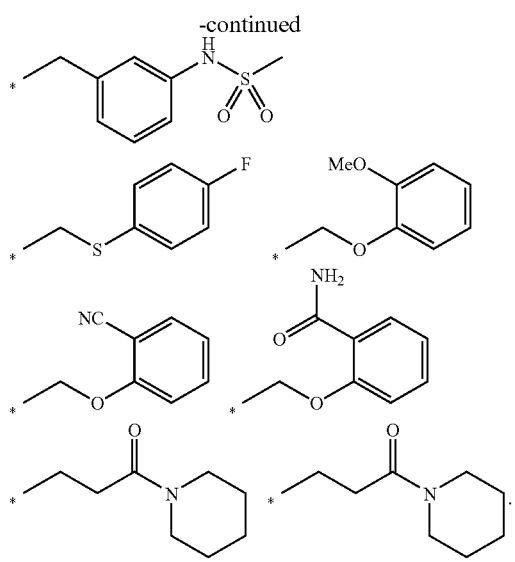

30. The compound according to claim 29, wherein R$_{15}$, R$_{16}$, R$_{17}$, and R$_{18}$ are each independently selected from the group consisting of H, substituted or unsubstituted (C$_{1-6}$) alkoxy, and substituted or unsubstituted (C$_{1-6}$)alkyl.

31. The compound according to claim 30, wherein R₃ and R₄ are each independently selected from the group consisting of hydrogen, and substituted or unsubstituted, (C$_{1-6}$)alkyl, provided that one of R₃ and R₄ is absent, and where R₃ is absent, the nitrogen on which R₃ is drawn is part of a double bond, and where R₄ is absent, the nitrogen on which R₄ is drawn is part of a double bond.

32. A compound, or a tautomer, or pharmaceutically acceptable salt thereof, selected from the group consisting of:
1-(3-(2-(aminomethyl)-4-oxo-1,3,8-triazaspiro[4.5]dec-1-enecarbonyl)benzo[b]thiophen-2-yl)-3-ethylurea;
N-((8-(2-(3-ethylureido)benzo[b]thiophene-3-carbonyl)-4-oxo-1,3,8-triazaspiro[4.5]dec-1-en-2-yl)methyl)acetamide;
1-ethyl-3-(3-(2-(methylthiomethyl)-4-oxo-1,3,8-triazaspiro[4.5]dec-1-enecarbonyl)benzo[b]thiophen-2-yl)urea;
1-ethyl-3-(3-(2-(methylsulfonylmethyl)-4-oxo-1,3,8-triazaspiro[4.5]dec-1-enecarbonyl)benzo[b]thiophen-2-yl)urea;
1-(3-(2-((2,5-dioxopyrrolidin-1-yl)methyl)-4-oxo-1,3,8-triazaspiro[4.5]dec-1-enecarbonyl)benzo[b]thiophen-2-yl)-3-ethylurea;
1-(3-(4-amino-4-cyanopiperidine-1-carbonyl)benzo[b] thiophen-2-yl)-3-ethylurea;
4-amino-1-(2-(3-ethylureido)benzo[b]thiophene-3-carbonyl)piperidine-4-carboxamide;
1-(3-(2-(chloromethyl)-4-oxo-1,3,8-triazaspiro[4.5]dec-1-enecarbonyl)benzo[b]thiophen-2-yl)-3-ethylurea;
1-(3-(2-(chloromethyl)-4-oxo-1,3,8-triazaspiro[4.5]dec-1-enecarbonyl)-7-methoxybenzo[b]thiophen-2-yl)-3-ethylurea;
ethyl 3-(8-(2-(3-ethylureido)benzo[b]thiophene-3-carbonyl)-4-oxo-1,3,8-triazaspiro[4.5]dec-1-en-2-yl)propanoate;
ethyl 3-(8-(2-(3-ethylureido)-7-methoxybenzo[b] thiophene-3-carbonyl)-4-oxo-1,3,8-triazaspiro[4.5] dec-1-en-2-yl)propanoate;
N,N-diethyl-3-(8-(2-(3-ethylureido)benzo[b]thiophene-3-carbonyl)-4-oxo-1,3,8-triazaspiro[4.5]dec-1-en-2-yl) propanamide;

1-ethyl-3-(3-(4-oxo-2-(3-oxo-3-(piperidin-1-yl)propyl)-1,3,8-triazaspiro[4.5]dec-1-enecarbonyl)benzo[b]thiophen-2-yl)urea;
1-ethyl-3-(3-(4-oxo-1,3,8triazaspiro[4.5]dec-1-enecarbonyl)benzo[b]thiophen-2-yl)urea;
1-(3-(2-butyl-4-oxo-1,3,8-triazaspiro[4.5]dec-1-enecarbonyl)benzo[b]thiophen-2-yl)-3 -ethylurea;
1-ethyl-3-(3-(2-isopropyl-4-oxo-1,3,8-triazaspiro[4.5]dec-2-enecarbonyl)-7 -methoxybenzo[b]thiophen-2-yl)urea;
1-(3-(2-butyl-4-oxo-1,3,8-triazaspiro[4.5]dec-1-enecarbonyl)-7-methoxybenzo[b]thiophen-2-yl)-3-ethylurea;
1-ethyl-3-(7-methoxy-3-(4-oxo-2-phenyl-1,3,8-triazaspiro[4.5]dec-2 -enecarbonyl)benzo[b]thiophen-2-yl)urea;
methyl 2-(8-(2-(3-ethylureido)benzo[b]thiophene-3-carbonyl)-4-oxo-1,3,8 -triazaspiro[4.5]dec-1-en-3-yl)acetate;
1-(3-(3-butyl-4-oxo-1,3,8-triazaspiro[4.5]dec-1-enecarbonyl)benzo[b]thiophen-2-yl)-3 -ethylurea;
1-ethyl-3-(3-(2-((4-fluorophenylthio)methyl)-4-oxo-1,3,8triazaspiro[4.5]dec-1 -enecarbonyl)benzo[b]thiophen-2-yl)urea;
1-ethyl-3-(3-(2-(isopropylthiomethyl)-4-oxo-1,3,8-triazaspiro[4.5]dec-1 -enecarbonyl)benzo[b]thiophen-2-yl)urea;
1-ethyl-3-(3-(2-(isopropylsulfinylmethyl)-4-oxo-1,3,8triazaspiro[4.5]dec-1 -enecarbonyl)benzo[b]thiophen-2-yl)urea;
1-ethyl-3-(3-(2-(isopropylsulfonylmethyl)-4-oxo-1,3,8triazaspiro[4.5]dec-1 -enecarbonyl)benzo[b]thiophen-2-yl)urea;
1-ethyl-3-(3-(2((2-methoxyphenoxy)methyl)-4-oxo-1,3,8-triazaspiro[4.5]dec-1 -enecarbonyl)benzo[b]thiophen-2-yl)urea;
1-(3-(2((2-cyanophenoxy)methyl)-4-oxo-1,3,8triazaspiro[4.5]dec-1 -enecarbonyl)benzo[b]thiophen-2-yl)-3-ethylurea;
2-((8-(2-(3-ethylureido)benzo[b]thiophene-3-carbonyl)-4-oxo-1,3,8-triazaspiro[4.5]dec -1-en-2-yl)methoxy)benzamide;
1-(3-(2-(cyclohexyloxymethyl)-4-oxo-1,3,8-triazaspiro[4.5]dec-1 -enecarbonyl)benzo[b]thiophen-2-yl)-3-ethylurea;
1-ethyl-3-(3-(2-(isopropoxymethyl)-4-oxo-1,3,8-triazaspiro[4.5]dec-1 -enecarbonyl)benzo[b]thiophen-2-yl)urea;
1-ethyl-3-(3-(2-(isobutoxymethyl)-4-oxo-1,3,8triazaspiro[4.5]dec-1 -enecarbonyl)benzo[b]thiophen-2-yl)urea;
1-ethyl-3-(3-(2-(isobutoxymethyl)-4-oxo-1,3,8triazaspiro[4.5]dec-1-enecarbonyl)-7 -methoxybenzo[b]thiophen-2-yl)urea;
1-(3-(2-(cyclohexyloxymethyl)-4-oxo-1,3,8-triazaspiro[4.5]dec-1-enecarbonyl)-7 -methoxybenzo[b]thiophen-2-yl)-3-ethylurea;
1-ethyl-3-(3-(4-oxo-2-((2oxopyridin-1(2H)-yl)methyl)1,3,8triazaspiro[4.5]dec-1 -enecarbonyl)benzo[b]thiophen-2-yl)urea;
1-(3-(2-((4-(aminomethyl)-1H-1,2,3-triazol-1-yl)methyl)-4-oxo-1,3,8triazaspiro[4.5]dec -1-enecarbonyl)benzo[b]thiophen-2-yl)-3-ethylurea ;
1-(3-(2-((4-((dimethylamino)methyl)-1H-1,2,3-triazol-1-yl)methyl)-4-oxo-1,3,8 -triazaspiro[4.5]dec-1-enecarbonyl)benzo[b]thiophen-2-yl)-3-ethylurea ;
1-(3-(2((4-tert-butyl-1H-1,2,3-triazol-1-yl)methyl)-4-oxo-1,3,8-triazaspiro[4.5]dec-1 -enecarbonyl)benzo[b]thiophen-2-yl)-3-ethylurea;
1-ethyl-3-(3-(2((4-(hydroxymethyl)-1H-1,2,3-triazol-1-yl)methyl)-4-oxo-1,3,8 -triazaspiro[4.5]dec-1-enecarbonyl)benzo[b]thiophen-2-yl)urea;
1-(3-(2-((4-cyclopropyl-1H1,2,3triazol-1-yl)methyl)-4-oxo-1,3,8triazaspiro[4.5]dec-1 -enecarbonyl)benzo[b]thiophen-2-yl)-3-ethylurea;
1-methyl-3-(3-(2-((methylamino)methyl)-4-oxo-1,3,8triazaspiro[4.5]dec-1 -enecarbonyl)thieno[2,3-b]pyridin-2-yl)urea;
1-ethyl-3-(3-(2-((isobutylamino)methyl)-4-oxo-1,3,8-triazaspiro[4.5]dec-1-enecarbonyl) -6-methylthieno[2,3-b]pyridin-2-yl)urea;
1-(3-(2-benzyl-4-oxo-1,3,8triazaspiro[4.5]dec-1-enecarbonyl)benzo[b]thiophen-2-yl)-3 -ethylurea;
1-ethyl-3-(3-(2-(hydroxymethyl)-4-oxo-1,3,8-triazaspiro[4.5]dec-1 -enecarbonyl)thieno[2,3-c]pyridin-2-yl)urea;
ethylureido)benzo[b]thiophene-3-carbonyl)-4-oxo-1,3,8-triazaspiro[4.5]dec-1-en-2 -yl1)methyl)benzoate;
N-(3-((8-(2-(3-ethylureido)-7-methoxybenzo[b]thiophene-3-carbonyl)-4-oxo-1,3,8 -triazaspiro[4.5]dec-1-en-2-yl)methyl)phenyl)methanesulfonamide;
N-(3-((8-(2-(3-ethylureido)benzo[b]thiophene-3-carbonyl)-4-oxo-1,3,8 -triazaspiro[4.5]dec-1-en-2-yl)methyl)phenyl)acetamide;
1-ethyl-3-(3-(4-oxo-2-(pyridin-2-ylmethyl)-1,3,8-triazaspiro[4.5]dec-1 -enecarbonyl)benzo[b]thiophen-2-yl)urea;
1-(3-(2-((6-acetylpyridin-2-yl)methyl)-4-oxo-1,3,8-triazaspiro[4.5]dec-1 -enecarbonyl)thieno[2,3-b]pyridin-2-yl)-3-ethylurea;
1-(3-(2-((1H-pyrazol-4-yl)methyl)-4-oxo-1,3,8-triazaspiro[4.5]dec-1 -enecarbonyl)benzo[b]thiophen-2-yl)-3-ethylurea;
1-ethyl-3-(3-(2-(furan-3-ylmethyl)-4-oxo-1,3,8-triazaspiro[4.5]dec-1 -enecarbonyl)benzo[b]thiophen-2-yl)urea;
1-(3-(2-(cyclopentylmethyl)-4-oxo-1,3,8-triazaspiro[4.5]dec-1 -enecarbonyl)benzo[b]thiophen-2-yl)-3-ethylurea;
N,N-diethyl-2-(8-(2-(3-ethylureido)-4,5,6,7-tetrahydrobenzo[b]thiophene-3-carbonyl)-4 -oxo-1,3,8-triazaspiro[4.5]dec-1-en-3-yl)acetamide; and
1-ethyl-3-(3-(4-oxo-3-(2-oxo-2-(piperidin-1-yl)ethyl)-1,3,8-triazaspiro[4.5]dec-1 -enecarbonyl)benzo[b]thiophen-2-yl)urea.

33. The compound according to claim 1, wherein the compound is in the form of a pharmaceutically acceptable salt.

34. The compound according to claim 1, wherein the compound is present in a mixture of stereoisomers.

35. The compound according to claim 1, wherein the compound comprises a single stereoisomer.

36. A pharmaceutical composition comprising a compound according to claim 1 and one or more pharmaceutically acceptable excipients.

37. The pharmaceutical composition according to claim 36, wherein the composition is adapted for administration by a route selected from the group consisting of orally, parenterally, intraperitoneally, intravenously, intraarterially, transdermally, sublingually, intramuscularly, rectally, transbuccally, intranasally, liposomally, via inhalation, vaginally, intraoccularly, via local delivery, subcutaneously, intraadiposally, intraarticularly, and intrathecally.

* * * * *

SEQUENCE LISTING

<160> NUMBER OF SEQ ID NOS: 4

<210> SEQ ID NO 1
<211> LENGTH: 40
<212> TYPE: DNA
<213> ORGANISM: Artificial
<220> FEATURE:
<223> OTHER INFORMATION: Synthetic Primers

<400> SEQUENCE: 1
aaaagtcgac ccaccatgga tgaaccttct cccttggccc     40

<210> SEQ ID NO 2
<211> LENGTH: 37
<212> TYPE: DNA
<213> ORGANISM: Artificial
<220> FEATURE:
<223> OTHER INFORMATION: Synthetic Primers

<400> SEQUENCE: 2
aaaagcggcc gcctacgtag aaggggagtc catagtg     37

<210> SEQ ID NO 3
<211> LENGTH: 35
<212> TYPE: DNA
<213> ORGANISM: Artificial Sequence
<220> FEATURE:
<223> OTHER INFORMATION: Synthetic Primers

<400> SEQUENCE: 3
ccaggtcgac ccgccaacgg gactgggaca caagg     35

<210> SEQ ID NO 4
<211> LENGTH: 25
<212> TYPE: DNA
<213> ORGANISM: Artificial
<220> FEATURE:
<223> OTHER INFORMATION: Synthetic Primers

<400> SEQUENCE: 4
cgcactctca gtttcccgga ttccc     25